US009644025B2

(12) United States Patent
Black et al.

(10) Patent No.: US 9,644,025 B2
(45) Date of Patent: May 9, 2017

(54) IMMUNOTHERAPY REGIMES DEPENDENT ON APOE STATUS

(75) Inventors: Ronald Black, Berwyn, PA (US); Lars Ekman, La Jolla, CA (US); Ivan Lieberburg, Berkeley, CA (US); Michael Grundman, San Diego, CA (US); James Callaway, San Diego, CA (US); Keith M. Gregg, Goodyear, AZ (US); Jack Steven Jacobsen, Ramsey, NJ (US); Davinder Gill, Andover, MA (US); Lioudmila Tchistiakova, Andover, MA (US); Angela Widom, Acton, MA (US)

(73) Assignees: WYETH LLC, Madison, NJ (US); JANSSEN SCIENCES IRELAND UC, County Cork (IE)

( * ) Notice: Subject to any disclaimer, the term of this patent is extended or adjusted under 35 U.S.C. 154(b) by 862 days.

(21) Appl. No.: 12/738,396

(22) PCT Filed: Oct. 17, 2008

(86) PCT No.: PCT/US2008/080382
§ 371 (c)(1),
(2), (4) Date: Jun. 24, 2010

(87) PCT Pub. No.: WO2009/052439
PCT Pub. Date: Apr. 23, 2009

(65) Prior Publication Data
US 2010/0266505 A1    Oct. 21, 2010

Related U.S. Application Data

(60) Provisional application No. 60/999,423, filed on Oct. 17, 2007, provisional application No. 61/083,827, filed on Jul. 25, 2008.

(51) Int. Cl.
*A61K 39/395* (2006.01)
*C07K 16/18* (2006.01)
*C07K 16/28* (2006.01)
*G06Q 99/00* (2006.01)
*A61K 39/00* (2006.01)

(52) U.S. Cl.
CPC .......... *C07K 16/18* (2013.01); *C07K 16/2896* (2013.01); *G06Q 99/00* (2013.01); *A61K 2039/505* (2013.01); *C07K 2317/24* (2013.01); *C07K 2317/34* (2013.01); *C07K 2317/56* (2013.01); *C07K 2317/71* (2013.01); *C07K 2317/732* (2013.01); *C07K 2317/734* (2013.01); *C07K 2317/77* (2013.01)

(58) Field of Classification Search
CPC  C07K 2317/71; C07K 16/18; C07K 2317/24; C07K 2317/56; A61K 39/3955; A61K 2039/505
See application file for complete search history.

(56) References Cited

U.S. PATENT DOCUMENTS

| | | |
|---|---|---|
| 4,666,829 A | 5/1987 | Glenner et al. |
| 4,713,366 A | 12/1987 | Stevens |
| 4,816,397 A | 3/1989 | Boss et al. |
| 4,816,567 A | 3/1989 | Cabilly et al. |
| 4,879,213 A | 11/1989 | Fox et al. |
| 4,883,666 A | 11/1989 | Sabel et al. |
| 4,912,206 A | 3/1990 | Goldgaber et al. |
| 4,966,753 A | 10/1990 | McMichael |
| 5,004,697 A | 4/1991 | Pardridge |
| 5,057,540 A | 10/1991 | Kensil et al. |
| 5,096,706 A | 3/1992 | Flint |
| 5,187,153 A | 2/1993 | Cordell et al. |
| 5,192,753 A | 3/1993 | McGeer et al. |
| 5,208,036 A | 5/1993 | Eppstein et al. |
| 5,220,013 A | 6/1993 | Ponte et al. |
| 5,225,539 A | 7/1993 | Winter |
| 5,227,159 A | 7/1993 | Miller |
| 5,231,000 A | 7/1993 | Majocha et al. |
| 5,231,170 A | 7/1993 | Averback |
| 5,245,015 A | 9/1993 | Fung et al. |
| 5,258,498 A | 11/1993 | Huston et al. |
| 5,262,332 A | 11/1993 | Selkoe |
| 5,270,165 A | 12/1993 | Van Nostrand et al. |
| 5,278,049 A | 1/1994 | Baker et al. |
| 5,358,708 A | 10/1994 | Patel |
| 5,385,887 A | 1/1995 | Yim et al. |
| 5,387,742 A | 2/1995 | Cordell |
| 5,417,986 A | 5/1995 | Reid et al. |
| 5,434,170 A | 7/1995 | Andrulis, Jr. |
| 5,441,870 A | 8/1995 | Seubert et al. |

(Continued)

FOREIGN PATENT DOCUMENTS

| | | |
|---|---|---|
| AU | 707083 | 7/1999 |
| EP | 285 159 A1 | 10/1988 |

(Continued)

OTHER PUBLICATIONS

Greaves P et al. Posterior reversible encephalopathy syndrome following anti-lymphocyte globulin treatment for severe aplastic anaemia. Br J Haematol. Aug. 2006; 134(3):251.*
Raber J et al. ApoE geneotype accounts for the vast majority of AD risk and AD pathology. Neurobiol. Aging, 2004; 25:641-50.*
Lemere et al. (2006) Amyloid-beta immunotherapy for the prevention and treatment of Alzheimer disease: lessons from mice, monkeys, and humans. Rejuvenation Res. 9(1):77-84.*
Klafki H-W et al. (2006) Therapeutic approaches to Alzheimer's disease. Brain, 129:2840-2855.*
Wang Y-J et al. (2006) Clearance of amyloid-beta in Alzheimer's disease: progress, problems and perspectives. Drug Discovery Today, 11(19/20):931-938.*
U.S. Appl. No. 09/201,430, Office Action mailed May 10, 2000.
U.S. Appl. No. 09/201,430, Office Action mailed Dec. 21, 1999.

(Continued)

*Primary Examiner* — Kimberly A Ballard
(74) *Attorney, Agent, or Firm* — Alston & Bird LLP

(57) ABSTRACT

The invention provides methods of immunotherapy of Alzheimer's and similar diseases in which the regime administered to a patient depends on the ApoE genotype of the patient.

27 Claims, 18 Drawing Sheets

(56) References Cited

U.S. PATENT DOCUMENTS

| | | |
|---|---|---|
| 5,464,823 A | 11/1995 | Lehrer et al. |
| 5,470,951 A | 11/1995 | Roberts |
| 5,472,693 A | 12/1995 | Gourlie et al. |
| 5,514,548 A | 5/1996 | Krebber et al. |
| 5,530,101 A | 6/1996 | Queen et al. |
| 5,571,499 A | 11/1996 | Hafler et al. |
| 5,571,500 A | 11/1996 | Hafler et al. |
| 5,576,184 A | 11/1996 | Better et al. |
| 5,583,112 A | 12/1996 | Kensil et al. |
| 5,585,089 A | 12/1996 | Queen et al. |
| 5,585,100 A | 12/1996 | Mond et al. |
| 5,589,154 A | 12/1996 | Anderson |
| 5,593,846 A | 1/1997 | Schenk et al. |
| 5,601,827 A | 2/1997 | Collier et al. |
| 5,605,811 A | 2/1997 | Seubert et al. |
| 5,612,486 A | 3/1997 | McConlogue et al. |
| 5,618,920 A | 4/1997 | Robinson et al. |
| 5,620,844 A | 4/1997 | Neurath et al. |
| 5,622,701 A | 4/1997 | Berg |
| 5,624,821 A | 4/1997 | Winter et al. |
| 5,624,937 A | 4/1997 | Reel et al. |
| 5,641,473 A | 6/1997 | Hafler et al. |
| 5,641,474 A | 6/1997 | Hafler et al. |
| 5,645,820 A | 7/1997 | Hafler et al. |
| 5,648,260 A | 7/1997 | Winter et al. |
| 5,652,334 A | 7/1997 | Roberts |
| 5,677,425 A | 10/1997 | Bodmer et al. |
| 5,679,348 A | 10/1997 | Nesburn et al. |
| 5,688,651 A | 11/1997 | Solomon |
| 5,693,761 A | 12/1997 | Queen et al. |
| 5,693,762 A | 12/1997 | Queen et al. |
| 5,702,906 A | 12/1997 | Rosenthal |
| 5,721,130 A | 2/1998 | Seubert et al. |
| 5,723,130 A | 3/1998 | Hancock et al. |
| 5,731,284 A | 3/1998 | Williams |
| 5,733,547 A | 3/1998 | Weiner et al. |
| 5,733,548 A | 3/1998 | Restifo et al. |
| 5,736,142 A | 4/1998 | Sette et al. |
| 5,744,132 A | 4/1998 | Warne et al. |
| 5,744,368 A | 4/1998 | Goldgaber et al. |
| 5,750,349 A | 5/1998 | Suzuki et al. |
| 5,750,361 A | 5/1998 | Prusiner et al. |
| 5,753,624 A | 5/1998 | McMichael et al. |
| 5,766,846 A | 6/1998 | Schlossmacher et al. |
| 5,770,700 A | 6/1998 | Webb et al. |
| 5,773,007 A | 6/1998 | Penney et al. |
| 5,776,468 A | 7/1998 | Hauser et al. |
| 5,780,587 A | 7/1998 | Potter |
| 5,786,180 A | 7/1998 | Konig et al. |
| 5,798,102 A | 8/1998 | McMichael et al. |
| 5,817,626 A | 10/1998 | Findeis et al. |
| 5,824,322 A | 10/1998 | Balasubramanian |
| 5,837,268 A | 11/1998 | Potter et al. |
| 5,837,473 A | 11/1998 | Maggio et al. |
| 5,837,672 A | 11/1998 | Schenk et al. |
| 5,846,533 A | 12/1998 | Prusiner |
| 5,849,298 A | 12/1998 | Weiner et al. |
| 5,851,996 A | 12/1998 | Kline |
| 5,854,204 A | 12/1998 | Findeis et al. |
| 5,854,215 A | 12/1998 | Findeis et al. |
| 5,858,981 A | 1/1999 | Schreiber et al. |
| 5,859,205 A | 1/1999 | Adair et al. |
| 5,866,129 A | 2/1999 | Chang et al. |
| 5,869,046 A | 2/1999 | Presta et al. |
| 5,869,054 A | 2/1999 | Weiner et al. |
| 5,869,093 A | 2/1999 | Weiner et al. |
| 5,877,399 A | 3/1999 | Hsiao et al. |
| 5,891,991 A | 4/1999 | Wasco et al. |
| 5,895,654 A | 4/1999 | Hartford et al. |
| 5,910,427 A | 6/1999 | Mikayama |
| 5,935,927 A | 8/1999 | Vitek et al. |
| 5,955,079 A | 9/1999 | Mond et al. |
| 5,955,317 A | 9/1999 | Suzuki et al. |
| 5,958,883 A | 9/1999 | Snow |
| 5,985,242 A | 11/1999 | Findeis et al. |
| 5,989,566 A | 11/1999 | Cobb et al. |
| 5,994,083 A | 11/1999 | Felici et al. |
| 6,015,662 A | 1/2000 | Hackett et al. |
| 6,022,859 A | 2/2000 | Kiessling et al. |
| 6,054,297 A | 4/2000 | Carter et al. |
| 6,057,098 A | 5/2000 | Buechler et al. |
| 6,057,367 A | 5/2000 | Stamler et al. |
| 6,096,318 A | 8/2000 | Stevens et al. |
| 6,114,133 A | 9/2000 | Seubert et al. |
| 6,121,022 A | 9/2000 | Presta et al. |
| 6,150,091 A | 11/2000 | Pandolfo et al. |
| 6,165,745 A | 12/2000 | Ward et al. |
| 6,175,057 B1 | 1/2001 | Mucke et al. |
| 6,180,370 B1 | 1/2001 | Queen et al. |
| 6,194,551 B1 | 2/2001 | Idusogie et al. |
| 6,210,671 B1 | 4/2001 | Co |
| 6,218,506 B1 | 4/2001 | Krafft et al. |
| 6,261,569 B1 | 7/2001 | Comis et al. |
| 6,262,335 B1 | 7/2001 | Hsiao et al. |
| 6,267,958 B1 | 7/2001 | Andya et al. |
| 6,270,757 B1 | 8/2001 | Warne |
| 6,277,375 B1 | 8/2001 | Ward |
| 6,284,221 B1 | 9/2001 | Schenk et al. |
| 6,284,533 B1 | 9/2001 | Thomas |
| 6,294,171 B2 | 9/2001 | McMichael |
| 6,303,567 B1 | 10/2001 | Findeis et al. |
| 6,331,440 B1 | 12/2001 | Nordstedt et al. |
| 6,339,068 B1 | 1/2002 | Krieg et al. |
| 6,372,716 B1 | 4/2002 | Bush et al. |
| 6,399,314 B1 | 6/2002 | Krishnamurthy |
| 6,407,213 B1 | 6/2002 | Carter et al. |
| 6,417,178 B1 | 7/2002 | Klunk et al. |
| 6,432,710 B1 | 8/2002 | Boss, Jr. et al. |
| 6,528,624 B1 | 3/2003 | Idusogie et al. |
| 6,538,124 B1 | 3/2003 | Idusogie et al. |
| 6,548,640 B1 | 4/2003 | Winter |
| 6,562,341 B2 | 5/2003 | Prusiner et al. |
| 6,582,945 B1 | 6/2003 | Raso |
| 6,610,493 B1 | 8/2003 | Citron et al. |
| 6,632,927 B2 | 10/2003 | Adair et al. |
| 6,639,055 B1 | 10/2003 | Carter et al. |
| 6,710,226 B1 | 3/2004 | Schenk |
| 6,713,450 B2 | 3/2004 | Frangione et al. |
| 6,727,349 B1 | 4/2004 | LaRosa et al. |
| 6,743,427 B1 | 6/2004 | Schenk |
| 6,750,324 B1 | 6/2004 | Schenk et al. |
| 6,761,888 B1 | 7/2004 | Schenk |
| 6,787,129 B1 | 9/2004 | Klein et al. |
| 6,787,138 B1 | 9/2004 | Schenk |
| 6,787,139 B1 | 9/2004 | Schenk |
| 6,787,140 B1 | 9/2004 | Schenk |
| 6,787,143 B1 | 9/2004 | Schenk |
| 6,787,144 B1 | 9/2004 | Schenk |
| 6,787,523 B1 | 9/2004 | Schenk |
| 6,787,637 B1 | 9/2004 | Schenk et al. |
| 6,808,712 B2 | 10/2004 | Schenk |
| 6,818,218 B2 | 11/2004 | Schenk |
| 6,824,780 B1 | 11/2004 | Devaux et al. |
| 6,866,849 B2 | 3/2005 | Schenk |
| 6,866,850 B2 | 3/2005 | Schenk |
| 6,875,434 B1 | 4/2005 | Schenk |
| 6,890,535 B1 | 5/2005 | Schenk |
| 6,905,686 B1 | 6/2005 | Schenk |
| 6,913,745 B1 | 7/2005 | Schenk |
| 6,923,964 B1 | 8/2005 | Schenk |
| 6,933,368 B2 | 8/2005 | Co et al. |
| 6,936,698 B2 | 8/2005 | Taylor |
| 6,946,135 B2 | 9/2005 | Schenk |
| 6,962,707 B2 | 11/2005 | Schenk |
| 6,962,984 B2 | 11/2005 | Ishiwata et al. |
| 6,972,127 B2 | 12/2005 | Schenk |
| 6,982,084 B2 | 1/2006 | Schenk |
| 7,014,855 B2 | 3/2006 | Schenk |
| 7,112,661 B1 | 9/2006 | Miller |
| 7,147,851 B1 | 12/2006 | Ponath et al. |
| 7,179,892 B2 | 2/2007 | Basi et al. |
| 7,189,819 B2 | 3/2007 | Basi et al. |
| 7,195,761 B2 | 3/2007 | Holtzman et al. |
| 7,256,273 B2 | 8/2007 | Basi et al. |

(56) References Cited

U.S. PATENT DOCUMENTS

| | | |
|---|---|---|
| 7,575,880 B1 | 8/2009 | Schenk et al. |
| 7,582,733 B2 | 9/2009 | Basi et al. |
| 7,588,766 B1 | 9/2009 | Schenk |
| 7,625,560 B2 | 12/2009 | Basi et al. |
| 7,635,473 B2 | 12/2009 | Warne et al. |
| 7,790,856 B2 | 9/2010 | Schenk |
| 7,871,615 B2 | 1/2011 | Basi et al. |
| 7,893,214 B2 | 2/2011 | Schenk |
| 7,906,626 B2 | 3/2011 | Raso |
| 7,928,203 B2 | 4/2011 | Schenk et al. |
| 8,689,528 B1 | 4/2014 | Gaspari et al. |
| 2001/0018053 A1 | 8/2001 | McMichael |
| 2001/0021769 A1 | 9/2001 | Prusiner |
| 2002/0009445 A1 | 1/2002 | Du et al. |
| 2002/0058267 A1 | 5/2002 | Ozenberger et al. |
| 2002/0077288 A1 | 6/2002 | Frangione |
| 2002/0086847 A1 | 7/2002 | Chain |
| 2002/0094335 A1 | 7/2002 | Chalifour et al. |
| 2002/0102261 A1 | 8/2002 | Raso |
| 2002/0132268 A1 | 9/2002 | Chang et al. |
| 2002/0133001 A1 | 9/2002 | Gefter et al. |
| 2002/0136718 A1 | 9/2002 | Raso |
| 2002/0160394 A1 | 10/2002 | Wu |
| 2002/0162129 A1 | 10/2002 | Lannfelt |
| 2002/0168377 A1 | 11/2002 | Schaetzl |
| 2002/0187157 A1 | 12/2002 | Jensen et al. |
| 2002/0197258 A1 | 12/2002 | Ghanbari et al. |
| 2003/0009104 A1 | 1/2003 | Hyman et al. |
| 2003/0039645 A1 | 2/2003 | Adair et al. |
| 2003/0054484 A1 | 3/2003 | Fong et al. |
| 2003/0068316 A1 | 4/2003 | Klein et al. |
| 2003/0068325 A1 | 4/2003 | Wang |
| 2003/0073655 A1 | 4/2003 | Chain |
| 2003/0092145 A1 | 5/2003 | Jira et al. |
| 2003/0135035 A1 | 7/2003 | Shannon |
| 2003/0147882 A1 | 8/2003 | Solomon et al. |
| 2003/0165496 A1 | 9/2003 | Basi et al. |
| 2003/0166557 A1 | 9/2003 | Minna et al. |
| 2003/0166558 A1 | 9/2003 | Frangione et al. |
| 2003/0202972 A1 | 10/2003 | Andya et al. |
| 2003/0207828 A1 | 11/2003 | Ishiwata et al. |
| 2004/0043418 A1 | 3/2004 | Holtzman et al. |
| 2004/0081657 A1 | 4/2004 | Schenk |
| 2004/0082762 A1 | 4/2004 | Basi et al. |
| 2004/0087777 A1 | 5/2004 | Basi et al. |
| 2004/0171815 A1 | 9/2004 | Schenk et al. |
| 2004/0171816 A1 | 9/2004 | Schenk et al. |
| 2004/0197324 A1 | 10/2004 | Jun et al. |
| 2004/0213800 A1 | 10/2004 | Seubert et al. |
| 2004/0219146 A1 | 11/2004 | Schenk |
| 2004/0241164 A1 | 12/2004 | Bales et al. |
| 2004/0247590 A1 | 12/2004 | Schenk et al. |
| 2004/0247591 A1 | 12/2004 | Schenk et al. |
| 2004/0247612 A1 | 12/2004 | Wang |
| 2004/0265301 A1 | 12/2004 | Schenk et al. |
| 2004/0265308 A1 | 12/2004 | Schenk |
| 2004/0265919 A1 | 12/2004 | Vanderstichlele et al. |
| 2005/0013815 A1 | 1/2005 | Schenk |
| 2005/0019328 A1 | 1/2005 | Schenk |
| 2005/0019330 A1 | 1/2005 | Schenk |
| 2005/0048049 A1 | 3/2005 | Schenk |
| 2005/0059591 A1 | 3/2005 | Schenk et al. |
| 2005/0059802 A1 | 3/2005 | Schenk et al. |
| 2005/0090648 A1 | 4/2005 | Tsurushita et al. |
| 2005/0118651 A1 | 6/2005 | Basi et al. |
| 2005/0123534 A1 | 6/2005 | Adair et al. |
| 2005/0123544 A1 | 6/2005 | Schenk et al. |
| 2005/0136054 A1 | 6/2005 | Adair et al. |
| 2005/0142132 A1 | 6/2005 | Schenk et al. |
| 2005/0147613 A1 | 7/2005 | Raso |
| 2005/0152878 A1 | 7/2005 | Solomon et al. |
| 2005/0158304 A1 | 7/2005 | Schenk et al. |
| 2005/0163788 A1 | 7/2005 | Schenk |
| 2005/0169925 A1 | 8/2005 | Bardroff et al. |
| 2005/0191292 A1 | 9/2005 | Schenk |
| 2005/0191314 A1 | 9/2005 | Schenk |
| 2005/0196399 A1 | 9/2005 | Schenk et al. |
| 2005/0214222 A1 | 9/2005 | McKinnon et al. |
| 2005/0249725 A1 | 11/2005 | Schenk et al. |
| 2005/0249727 A1 | 11/2005 | Schenk |
| 2005/0255122 A1 | 11/2005 | Schenk |
| 2006/0019850 A1 | 1/2006 | Korzenski et al. |
| 2006/0029611 A1 | 2/2006 | Schenk |
| 2006/0034858 A1 | 2/2006 | Schenk |
| 2006/0057701 A1 | 3/2006 | Rosenthal et al. |
| 2006/0099206 A1 | 5/2006 | Sinacore |
| 2006/0121038 A9 | 6/2006 | Schenk et al. |
| 2006/0153772 A1 | 7/2006 | Jacobsen |
| 2006/0160161 A1 | 7/2006 | Pavlikova et al. |
| 2006/0182321 A1 | 8/2006 | Hu et al. |
| 2006/0188512 A1 | 8/2006 | Yednock et al. |
| 2006/0193850 A1 | 8/2006 | Warne et al. |
| 2006/0198851 A1 | 9/2006 | Basi et al. |
| 2006/0210557 A1 | 9/2006 | Luisi et al. |
| 2006/0210964 A1 | 9/2006 | Hyslop et al. |
| 2006/0234912 A1 | 10/2006 | Wang et al. |
| 2006/0240486 A1 | 10/2006 | Johnson-Wood et al. |
| 2006/0257396 A1 | 11/2006 | Jacobsen |
| 2006/0280743 A1 | 12/2006 | Basi et al. |
| 2007/0021454 A1 | 1/2007 | Coburn et al. |
| 2007/0072307 A1 | 3/2007 | Godavarti et al. |
| 2007/0082367 A1 | 4/2007 | Godavarti et al. |
| 2007/0134762 A1 | 6/2007 | Arumugham et al. |
| 2007/0154480 A1 | 7/2007 | Schenk et al. |
| 2007/0161088 A1 | 7/2007 | Arumugham et al. |
| 2007/0196375 A1 | 8/2007 | Tobinick |
| 2007/0238154 A1 | 10/2007 | Basi et al. |
| 2008/0031954 A1 | 2/2008 | Paris et al. |
| 2008/0050367 A1 | 2/2008 | Basi et al. |
| 2008/0096818 A1 | 4/2008 | Schenk et al. |
| 2008/0145373 A1 | 6/2008 | Arumugham |
| 2008/0219931 A1 | 9/2008 | Klunk et al. |
| 2008/0221306 A1 | 9/2008 | Basi |
| 2008/0227718 A1 | 9/2008 | Schenk |
| 2008/0227719 A1 | 9/2008 | Schenk |
| 2008/0279873 A1 | 11/2008 | Seubert |
| 2008/0281082 A1 | 11/2008 | Basi |
| 2008/0292625 A1 | 11/2008 | Schroeter |
| 2008/0299074 A1 | 12/2008 | Arumugham |
| 2009/0069544 A1 | 3/2009 | Basi |
| 2009/0142270 A1 | 6/2009 | Schroeter et al. |
| 2009/0155256 A1 | 6/2009 | Black et al. |
| 2009/0191231 A1 | 7/2009 | Schenk |
| 2009/0297511 A1 | 12/2009 | Schenk |
| 2010/0221187 A1 | 9/2010 | Lieberburg et al. |
| 2010/0266505 A1 | 10/2010 | Black |
| 2011/0142824 A1* | 6/2011 | Burbidge et al. .......... 424/133.1 |
| 2011/0229413 A1 | 9/2011 | Lieberburg et al. |
| 2012/0070379 A1 | 3/2012 | Black et al. |
| 2013/0058869 A1 | 3/2013 | Schenk et al. |
| 2014/0227274 A1 | 8/2014 | Schenk |

FOREIGN PATENT DOCUMENTS

| | | |
|---|---|---|
| EP | 0 391 714 A2 | 10/1990 |
| EP | 451 700 A1 | 10/1991 |
| EP | 506 785 B1 | 10/1992 |
| EP | 276 723 B1 | 12/1993 |
| EP | 613007 A2 | 2/1994 |
| EP | 616 814 A1 | 3/1994 |
| EP | 597 101 A1 | 5/1994 |
| EP | 0 613 007 A2 | 8/1994 |
| EP | 613 007 A2 | 8/1994 |
| EP | 620 276 A1 | 10/1994 |
| EP | 626 390 A1 | 11/1994 |
| EP | 666 080 A1 | 8/1995 |
| EP | 359 783 B1 | 11/1995 |
| EP | 683 234 A1 | 11/1995 |
| EP | 440 619 B1 | 1/1996 |
| EP | 758 248 B1 | 2/1997 |
| EP | 758 901 B1 | 2/1997 |
| EP | 526 511 B1 | 5/1997 |
| EP | 782 859 A1 | 7/1997 |
| EP | 783 104 A1 | 7/1997 |

(56) References Cited

FOREIGN PATENT DOCUMENTS

| | | |
|---|---:|---|
| EP | 594 607 B1 | 8/1997 |
| EP | 0 783 104 | 9/1997 |
| EP | 752 886 B1 | 1/1998 |
| EP | 845 270 A1 | 6/1998 |
| EP | 863 211 A1 | 9/1998 |
| EP | 868 918 A2 | 10/1998 |
| EP | 652 962 B1 | 12/1998 |
| EP | 911 036 A2 | 4/1999 |
| EP | 561 087 B1 | 8/1999 |
| EP | 639 081 B1 | 11/1999 |
| EP | 1 172 378 A1 | 1/2002 |
| EP | 1 481 992 A2 | 12/2004 |
| EP | 1 481 992 A3 | 12/2004 |
| EP | 921 189 B1 | 1/2005 |
| EP | 1 033 998 B1 | 10/2005 |
| EP | 1 185 298 B1 | 6/2009 |
| EP | 1 690 547 B1 | 7/2009 |
| EP | 1 321 166 B1 | 1/2011 |
| EP | 1524994 B1 | 4/2011 |
| EP | 1160256 B2 | 11/2011 |
| EP | 1994937 B1 | 11/2011 |
| EP | 1842859 B1 | 1/2013 |
| EP | 1950991 B1 | 3/2013 |
| GB | 2 220 211 A | 1/1990 |
| GB | 2 335 192 A | 9/1999 |
| JP | 62-267297 A | 11/1987 |
| JP | 07-132033 A | 5/1995 |
| JP | 7-165799 A | 6/1995 |
| JP | 09/208485 | 8/1997 |
| JP | 9215492 | 8/1997 |
| JP | 9208485 A | 12/1997 |
| JP | 9119929 A | 6/1999 |
| WO | WO 87/02671 A1 | 5/1987 |
| WO | WO 87/06838 A1 | 11/1987 |
| WO | WO 88/07089 A1 | 9/1988 |
| WO | WO 88/10120 A1 | 12/1988 |
| WO | WO 89/01343 A1 | 2/1989 |
| WO | WO 89/03687 A1 | 5/1989 |
| WO | WO 89/06242 A1 | 7/1989 |
| WO | WO 89/06689 A1 | 7/1989 |
| WO | WO 90/05142 A1 | 5/1990 |
| WO | WO 90/07861 A1 | 7/1990 |
| WO | WO 90/12870 A1 | 11/1990 |
| WO | WO 90/12871 A1 | 11/1990 |
| WO | WO 90/14837 A1 | 12/1990 |
| WO | WO 90/14840 A1 | 12/1990 |
| WO | WO 91/08760 A1 | 6/1991 |
| WO | WO 91/09967 A1 | 7/1991 |
| WO | WO 91/10741 A1 | 7/1991 |
| WO | WO 91/12816 A1 | 9/1991 |
| WO | WO 91/16819 A1 | 11/1991 |
| WO | WO 91/16928 A1 | 11/1991 |
| WO | WO 91/17271 A1 | 11/1991 |
| WO | WO 91/19795 A1 | 12/1991 |
| WO | WO 91/19810 A1 | 12/1991 |
| WO | WO 92/01047 A1 | 1/1992 |
| WO | WO 92/01059 A1 | 1/1992 |
| WO | WO 92/05793 A1 | 4/1992 |
| WO | WO 92/06187 A1 | 4/1992 |
| WO | WO 92/06708 A1 | 4/1992 |
| WO | WO 92/07944 A1 | 5/1992 |
| WO | WO 92/13069 A1 | 8/1992 |
| WO | WO 92/15330 A1 | 9/1992 |
| WO | WO 92/19267 A1 | 11/1992 |
| WO | WO 92/22653 A1 | 12/1992 |
| WO | WO 93/02189 A1 | 2/1993 |
| WO | WO 93/04194 A1 | 3/1993 |
| WO | WO 93/12227 A1 | 6/1993 |
| WO | WO 93/14200 A1 | 7/1993 |
| WO | WO 93/15760 A1 | 8/1993 |
| WO | WO 93/16724 A1 | 9/1993 |
| WO | WO 93/21950 A1 | 11/1993 |
| WO | WO 94/00153 A1 | 1/1994 |
| WO | WO 94/01772 A1 | 1/1994 |
| WO | WO 94/03208 A1 | 2/1994 |
| WO | WO 94/03615 A1 | 2/1994 |
| WO | WO 94/05311 A1 | 3/1994 |
| WO | WO 94/09364 A1 | 4/1994 |
| WO | WO 94/09823 A1 | 5/1994 |
| WO | WO 94/10569 A1 | 5/1994 |
| WO | WO 94/16731 A1 | 8/1994 |
| WO | WO 94/17197 A1 | 8/1994 |
| WO | WO 94/21288 A1 | 9/1994 |
| WO | WO 94/28412 A1 | 12/1994 |
| WO | WO 94/29459 A1 | 12/1994 |
| WO | WO 94/29531 | 12/1994 |
| WO | WO 95/04151 A2 | 2/1995 |
| WO | WO 95/05393 A2 | 2/1995 |
| WO | WO 95/05849 A1 | 3/1995 |
| WO | WO 95/05853 A1 | 3/1995 |
| WO | WO 95/06407 A1 | 3/1995 |
| WO | WO 95/07301 A1 | 3/1995 |
| WO | WO 95/07707 A1 | 3/1995 |
| WO | WO 95/08999 A1 | 4/1995 |
| WO | WO 95/11008 A2 | 4/1995 |
| WO | WO 95/11311 A1 | 4/1995 |
| WO | WO 95/11994 A1 | 5/1995 |
| WO | WO 95/12815 A1 | 5/1995 |
| WO | WO 95/17085 A1 | 6/1995 |
| WO | WO 95/23166 A1 | 8/1995 |
| WO | WO 95/23860 A2 | 9/1995 |
| WO | WO 95/31996 A1 | 11/1995 |
| WO | WO 96/01126 A1 | 1/1996 |
| WO | WO 96/03144 A1 | 2/1996 |
| WO | WO 96/08565 A2 | 3/1996 |
| WO | WO 96/14061 A1 | 5/1996 |
| WO | WO 96/15799 A1 | 5/1996 |
| WO | WO 96/18900 A1 | 6/1996 |
| WO | WO 96/22373 A1 | 7/1996 |
| WO | WO 96/25435 A1 | 8/1996 |
| WO | WO 96/28471 A1 | 9/1996 |
| WO | WO 96/29421 A1 | 9/1996 |
| WO | WO 96/33739 A1 | 10/1996 |
| WO | WO 96/37621 A2 | 11/1996 |
| WO | WO 96/39176 A1 | 12/1996 |
| WO | WO 96/39834 A1 | 12/1996 |
| WO | WO 96/40895 A1 | 12/1996 |
| WO | WO 97/03192 A3 | 1/1997 |
| WO | WO 97/05164 A1 | 2/1997 |
| WO | WO 97/08320 A1 | 3/1997 |
| WO | WO 97/10505 A1 | 3/1997 |
| WO | WO 97/13855 A1 | 4/1997 |
| WO | WO 97/17613 A1 | 5/1997 |
| WO | WO 97/18855 A1 | 5/1997 |
| WO | WO 97/21728 A1 | 6/1997 |
| WO | WO 97/36913 A1 | 7/1997 |
| WO | WO 97/28816 A1 | 8/1997 |
| WO | WO 97/32017 A1 | 9/1997 |
| WO | WO 97/36601 A1 | 10/1997 |
| WO | WO 97/37031 A1 | 10/1997 |
| WO | WO 97/40147 A1 | 10/1997 |
| WO | WO 98/02462 A1 | 1/1998 |
| WO | WO 98/04720 A1 | 2/1998 |
| WO | WO 98/05350 A1 | 2/1998 |
| WO | WO 98/07850 A2 | 2/1998 |
| WO | WO 98/08098 A2 | 2/1998 |
| WO | WO 98/08868 A1 | 3/1998 |
| WO | WO 98/22120 A1 | 5/1998 |
| WO | WO 98/33815 A1 | 8/1998 |
| WO | WO 98/39303 A1 | 9/1998 |
| WO | WO 98/44955 A1 | 10/1998 |
| WO | WO 98/46642 A1 | 10/1998 |
| WO | WO 98/56418 A1 | 12/1998 |
| WO | WO 99/00150 A2 | 1/1999 |
| WO | WO 99/06066 A2 | 2/1999 |
| WO | WO 99/06587 A2 | 2/1999 |
| WO | WO 99/10008 A1 | 3/1999 |
| WO | WO 99/27911 A1 | 6/1999 |
| WO | WO 99/27944 A1 | 6/1999 |
| WO | WO 99/27949 A1 | 6/1999 |
| WO | WO 99/06545 A2 | 11/1999 |
| WO | WO 99/58564 A1 | 11/1999 |
| WO | WO 99/58572 | 11/1999 |
| WO | WO 99/60021 A2 | 11/1999 |

(56) References Cited

FOREIGN PATENT DOCUMENTS

| | | |
|---|---|---|
| WO | WO 99/60024 A1 | 11/1999 |
| WO | WO 00/20027 A2 | 4/2000 |
| WO | WO 00/23082 A1 | 4/2000 |
| WO | WO 00/26238 A2 | 5/2000 |
| WO | WO 00/43039 A1 | 7/2000 |
| WO | WO 00/43049 A1 | 7/2000 |
| WO | WO 00/68263 A2 | 11/2000 |
| WO | WO 00/72870 A1 | 12/2000 |
| WO | WO 00/72876 A2 | 12/2000 |
| WO | WO 00/72876 A3 | 12/2000 |
| WO | WO 00/72880 A2 | 12/2000 |
| WO | WO 00/72880 A3 | 12/2000 |
| WO | WO 00/77178 A1 | 12/2000 |
| WO | WO 01/05355 A2 | 1/2001 |
| WO | WO 01/10900 A2 | 2/2001 |
| WO | WO 01/18169 A3 | 3/2001 |
| WO | WO 01/39796 A2 | 6/2001 |
| WO | WO 01/42306 A2 | 6/2001 |
| WO | WO 01/62284 A2 | 8/2001 |
| WO | WO 01/62801 A2 | 8/2001 |
| WO | WO 01/77167 A2 | 10/2001 |
| WO | WO 01/78777 A2 | 10/2001 |
| WO | WO 01/90182 A2 | 11/2001 |
| WO | WO 02/03911 A2 | 1/2002 |
| WO | WO 02/21141 A2 | 3/2002 |
| WO | WO 02/34777 A1 | 5/2002 |
| WO | WO 02/34878 A2 | 5/2002 |
| WO | WO 02/46237 A2 | 6/2002 |
| WO | WO 02/46237 A3 | 6/2002 |
| WO | WO 02/060481 A1 | 8/2002 |
| WO | WO 02/088306 A2 | 11/2002 |
| WO | WO 02/088307 A2 | 11/2002 |
| WO | WO 02/096457 A2 | 12/2002 |
| WO | WO 02/096937 A2 | 12/2002 |
| WO | WO 03/009817 A2 | 2/2003 |
| WO | WO 03/015691 A2 | 2/2003 |
| WO | WO 03/016466 A2 | 2/2003 |
| WO | WO 03/016467 A2 | 2/2003 |
| WO | WO 03/016467 A3 | 2/2003 |
| WO | WO 03/020212 A2 | 3/2003 |
| WO | WO 03/039485 A2 | 5/2003 |
| WO | WO 03/051374 A2 | 6/2003 |
| WO | WO 03/072036 A2 | 9/2003 |
| WO | WO 03/072036 A3 | 9/2003 |
| WO | WO 03/074081 A1 | 9/2003 |
| WO | WO 03/077858 A2 | 9/2003 |
| WO | WO 03/077858 A3 | 9/2003 |
| WO | WO 03/104437 A2 | 12/2003 |
| WO | WO 03/105894 A1 | 12/2003 |
| WO | WO 2004/13172 A2 | 2/2004 |
| WO | WO 2004/13172 A3 | 2/2004 |
| WO | WO 2004/015140 A1 | 2/2004 |
| WO | WO 2004/016282 A1 | 2/2004 |
| WO | WO 2004/029629 | 4/2004 |
| WO | WO 2004/031400 A2 | 4/2004 |
| WO | WO 2004/044204 A2 | 5/2004 |
| WO | WO 2004/044204 A3 | 5/2004 |
| WO | WO 2004/055164 A2 | 7/2004 |
| WO | WO 2004/069182 A2 | 8/2004 |
| WO | WO 2004/069182 A3 | 8/2004 |
| WO | WO 2004/071408 A2 | 8/2004 |
| WO | WO 2004/080419 A2 | 9/2004 |
| WO | WO 2004/080419 A3 | 9/2004 |
| WO | WO 2004/108895 A2 | 12/2004 |
| WO | WO 2004/108895 A3 | 12/2004 |
| WO | WO 2005/014041 A2 | 2/2005 |
| WO | WO 2005/026211 A2 | 3/2005 |
| WO | WO 2005/026211 A3 | 3/2005 |
| WO | WO 2005/035753 A1 | 4/2005 |
| WO | WO 2005/058940 A2 | 6/2005 |
| WO | WO 2005/058941 A2 | 6/2005 |
| WO | WO 2005/090315 A1 | 9/2005 |
| WO | WO 2006/014381 A2 | 2/2006 |
| WO | WO 2006/032653 A2 | 3/2006 |
| WO | WO 2006/042158 A2 | 4/2006 |
| WO | WO 2006/066049 A2 | 6/2006 |
| WO | WO 2006/066171 A1 | 6/2006 |
| WO | WO 2006/081587 A2 | 8/2006 |
| WO | WO 2006/081587 A3 | 8/2006 |
| WO | WO 2006/083689 A2 | 8/2006 |
| WO | WO 2006/121656 A2 | 11/2006 |
| WO | WO 2008/011348 A2 | 1/2008 |
| WO | WO 2008/114801 A1 | 9/2008 |
| WO | WO 2008/131298 A2 | 10/2008 |
| WO | WO 2008/131298 A3 | 10/2008 |
| WO | WO 2009/017467 A1 | 2/2009 |
| WO | WO 2009/052439 A2 | 4/2009 |
| WO | WO 2010/033861 A1 | 3/2010 |
| WO | WO 2010/044803 A1 | 4/2010 |
| WO | WO 2011/106732 A1 | 9/2011 |
| WO | WO 2011/133919 A1 | 10/2011 |

OTHER PUBLICATIONS

U.S. Appl. No. 09/204,838, Office Action mailed Mar. 17, 2000.
U.S. Appl. No. 09/322,289, Office Action mailed Sep. 29, 2000.
U.S. Appl. No. 09/497,553, Office Action mailed Oct. 3, 2003.
U.S. Appl. No. 09/580,015, Office Action mailed Feb. 11, 2002.
U.S. Appl. No. 09/580,018, Office Action mailed Mar. 12, 2002.
U.S. Appl. No. 09/580,019, Office Action mailed Mar. 12, 2002.
U.S. Appl. No. 09/723,544, Office Action mailed Sep. 23, 2002.
U.S. Appl. No. 09/723,760, Office Action mailed Mar. 12, 2002.
U.S. Appl. No. 09/723,765, Office Action mailed Mar. 12, 2002.
U.S. Appl. No. 09/723,766, Office Action mailed Mar. 5, 2002.
U.S. Appl. No. 09/723,766, Office Action mailed Jun. 11, 2002.
U.S. Appl. No. 09/724,273, Office Action mailed Jul. 2, 2002.
U.S. Appl. No. 09/724,273, Office Action mailed Nov. 8, 2005.
U.S. Appl. No. 09/724,288, Office Action mailed Mar. 12, 2002.
U.S. Appl. No. 09/724,288, Office Action mailed May 3, 2004.
U.S. Appl. No. 09/724,319, Office Action mailed Jul. 21, 2003.
U.S. Appl. No. 09/724,495, Office Action mailed Mar. 13, 2003.
U.S. Appl. No. 09/724,495, Office Action mailed Sep. 24, 2002.
U.S. Appl. No. 09/724,551, Office Action mailed Jul. 2, 2002.
U.S. Appl. No. 09/724,552, Office Action mailed May 6, 2002.
U.S. Appl. No. 09/724,567, Office Action mailed Mar. 27, 2002.
U.S. Appl. No. 09/724,575, Office Action mailed Mar. 27, 2002.
U.S. Appl. No. 09/724,921, Office Action mailed Apr. 30, 2002.
U.S. Appl. No. 09/724,929, Office Action mailed Mar. 22, 2002.
U.S. Appl. No. 09/724,940, Office Action mailed Mar. 13, 2003.
U.S. Appl. No. 09/724,953, Office Action mailed Mar. 26, 2002.
U.S. Appl. No. 09/724,961, Office Action mailed Mar. 12, 2002.
U.S. Appl. No. 09/979,701, Office Action mailed Feb. 15, 2005.
U.S. Appl. No. 09/979,701, Office Action mailed Sep. 15, 2005.
U.S. Appl. No. 09/979,952, Office Action mailed Aug. 7, 2003.
U.S. Appl. No. 09/980,568, Office Action mailed May 29, 2003.
U.S. Appl. No. 10/010,942, Office Action mailed Sep. 24, 2003.
U.S. Appl. No. 10/232,030, Office Action mailed Dec. 2, 2004.
U.S. Appl. No. 10/388,214, Office Action mailed May 31, 2005.
U.S. Appl. No. 10/388,389, Office Action mailed Nov. 22, 2005.
U.S. Appl. No. 10/429,216, Office Action mailed Dec. 28, 2005.
U.S. Appl. No. 10/544,093, Office Action mailed Jun. 16, 2008.
U.S. Appl. No. 10/625,854, Office Action mailed Nov. 10, 2005.
U.S. Appl. No. 10/703,713, Office Action mailed Nov. 5, 2004.
U.S. Appl. No. 10/704,070, Office Action mailed Nov. 5, 2004.
U.S. Appl. No. 10/771,174, Office Action mailed Sep. 14, 2006.
U.S. Appl. No. 10/777,792, Office Action mailed Mar. 2, 2006.
U.S. Appl. No. 10/788,666, Office Action mailed Jan. 12, 2005.
U.S. Appl. No. 10/789,273, Office Action mailed Sep. 22, 2006.
U.S. Appl. No. 10/822,968, Office Action mailed Mar. 22, 2006.
U.S. Appl. No. 10/823,463, Office Action mailed Feb. 4, 2005.
U.S. Appl. No. 10/828,548, Office Action mailed Feb. 4, 2005.
U.S. Appl. No. 10/828,548, Office Action mailed Sep. 29, 2005.
U.S. Appl. No. 10/858,855, Office Action mailed Jun. 22, 2006.
U.S. Appl. No. 10/923,267, Office Action mailed Jul. 21, 2006.
U.S. Appl. No. 10/923,469, Office Action mailed Mar. 29, 2007.
U.S. Appl. No. 10/923,474, Office Action mailed Feb. 15, 2005.
U.S. Appl. No. 10/928,926, Office Action mailed Jan. 12, 2007.
U.S. Appl. No. 10/934,819, Office Action mailed Oct. 14, 2005.
U.S. Appl. No. 11/058,757, Office Action mailed May 3, 2005.

(56) References Cited

OTHER PUBLICATIONS

U.S. Appl. No. 11/058,757, Office Action mailed Aug. 24, 2005.
U.S. Appl. No. 11/244,678, Office Action mailed Apr. 18, 2007.
U.S. Appl. No. 11/245,524, Office Action mailed May 15, 2007.
U.S. Appl. No. 11/245,916, Office Action mailed Jan. 13, 2006.
U.S. Appl. No. 11/260,047, Office Action mailed Oct. 26, 2006.
U.S. Appl. No. 11/303,478, Office Action mailed Apr. 1, 2008.
U.S. Appl. No. 11/303,478, Office Action mailed Oct. 16, 2008.
U.S. Appl. No. 11/304,072, Office Action mailed Dec. 20, 2006.
U.S. Appl. No. 11/304,986, Office Action mailed Jan. 2, 2008.
U.S. Appl. No. 11/305,889, Office Action mailed May 4, 2007.
U.S. Appl. No. 11/305,889, Office Action mailed Jul. 25, 2008.
U.S. Appl. No. 11/305,899, Office Action mailed Apr. 4, 2008.
U.S. Appl. No. 11/342,353, Office Action mailed Mar. 26, 2008.
U.S. Appl. No. 11/342,353, Office Action mailed Jul. 9, 2008.
U.S. Appl. No. 11/454,772, Office Action mailed Feb. 27, 2007.
U.S. Appl. No. 11/516,724, Office Action mailed Jan. 27, 2009.
U.S. Appl. No. 11/520,438, Office Action mailed Apr. 2, 2009.
U.S. Appl. No. 11/707,639, Office Action mailed Apr. 3, 2009.
U.S. Appl. No. 11/842,085, Office Action mailed Apr. 14, 2009.
U.S. Appl. No. 11/842,113, Office Action mailed Dec. 17, 2009.
U.S. Appl. No. 11/842,116, Office Action mailed Mar. 31, 2010.
U.S. Appl. No. 11/842,120, Office Action mailed Apr. 14, 2009.
U.S. Appl. No. 12/106,206, Office Action mailed Feb. 5, 2010.
U.S. Appl. No. 12/253,929, Office Action mailed Jan. 25, 2010.
U.S. Appl. No. 12/297,636, Office Action mailed Jul. 20, 2011.
U.S. Appl. No. 12/297,636, Office Action mailed Oct. 28, 2011.
U.S. Appl. No. 12/328,740, Office Action mailed Oct. 9, 2009.
U.S. Appl. No. 12/608,869, Office Action mailed Jul. 5, 2011.
U.S. Appl. No. 13/123,898, Office Action mailed Nov. 15, 2011.
U.S. Appl. No. 09/201,430, Examiner Interview Summary mailed May 30, 2001.
U.S. Appl. No. 09/201,430, Office Action mailed Jan. 17, 2001.
U.S. Appl. No. 09/204,838, Office Action mailed Dec. 21, 2000.
U.S. Appl. No. 09/322,289, Examiner Interview Summary mailed Jun. 27, 2006.
U.S. Appl. No. 09/322,289, Examiner Interview Summary mailed Jan. 15, 2009.
U.S. Appl. No. 09/322,289, Office Action mailed Jun. 19, 2001.
U.S. Appl. No. 09/497,553, Office Action mailed Nov. 29, 2005.
U.S. Appl. No. 09/580,018, Office Action mailed May 20, 2003.
U.S. Appl. No. 09/723,384, Examiner Interview Summary mailed Mar. 28, 2003.
U.S. Appl. No. 09/723,384, Office Action mailed Oct. 9, 2002.
U.S. Appl. No. 09/723,544, Office Action mailed Aug. 11, 2003.
U.S. Appl. No. 09/723,713, Office Action mailed Mar. 26, 2002.
U.S. Appl. No. 09/723,760, Office Action mailed Dec. 19, 2002.
U.S. Appl. No. 09/723,762, Office Action mailed Oct. 2, 2001.
U.S. Appl. No. 09/723,765, Examiner Interview Summary mailed Mar. 18, 2003.
U.S. Appl. No. 09/723,765, Examiner Interview Summary mailed Jan. 25, 2006.
U.S. Appl. No. 09/723,765, Examiner Interview Summary mailed Oct. 8, 2008.
U.S. Appl. No. 09/723,765, Examiner Interview Summary mailed Jan. 16, 2009.
U.S. Appl. No. 09/723,765, Office Action mailed Dec. 3, 2002.
U.S. Appl. No. 09/723,766, Office Action mailed Nov. 1, 2002.
U.S. Appl. No. 09/724,102, Office Action mailed Oct. 3, 2001.
U.S. Appl. No. 09/724,273, Office Action mailed Apr. 21, 2003.
U.S. Appl. No. 09/724,288, Office Action mailed Dec. 11, 2002.
U.S. Appl. No. 09/724,319, Examiner Interview Summary mailed Jul. 19, 2004.
U.S. Appl. No. 09/724,319, Examiner Interview Summary mailed Apr. 9, 2008.
U.S. Appl. No. 09/724,319, Office Action mailed Apr. 26, 2004.
U.S. Appl. No. 09/724,477, Office Action mailed Oct. 2, 2001.
U.S. Appl. No. 09/724,489, Office Action mailed Oct. 2, 2002.
U.S. Appl. No. 09/724,495, Office Action mailed Jan. 16, 2004.
U.S. Appl. No. 09/724,551, Office Action mailed Jun. 3, 2003.
U.S. Appl. No. 09/724,552, Examiner Interview Summary mailed Dec. 3, 2003.
U.S. Appl. No. 09/724,552, Office Action mailed Jun. 3, 2003.
U.S. Appl. No. 09/724,567, Office Action mailed Nov. 15, 2002.
U.S. Appl. No. 09/724,575, Examiner Interview Summary mailed May 6, 2005.
U.S. Appl. No. 09/724,575, Office Action mailed Nov. 21, 2002.
U.S. Appl. No. 09/724,921, Office Action mailed Jan. 28, 2003.
U.S. Appl. No. 09/724,929, Office Action mailed Jul. 22, 2003.
U.S. Appl. No. 09/724,940, Office Action mailed Dec. 24, 2003.
U.S. Appl. No. 09/724,953, Office Action mailed Nov. 27, 2002.
U.S. Appl. No. 09/724,961, Examiner Interview Summary mailed Dec. 3, 2003.
U.S. Appl. No. 09/724,961, Office Action mailed May 16, 2003.
U.S. Appl. No. 09/979,701, Office Action mailed Jan. 10, 2006.
U.S. Appl. No. 09/979,952, Office Action mailed Dec. 30, 2003.
U.S. Appl. No. 09/980,568, Office Action mailed Feb. 23, 2004.
U.S. Appl. No. 10/010,942, Examiner Interview Summary mailed May 10, 2006.
U.S. Appl. No. 10/010,942, Examiner Interview Summary mailed May 11, 2006.
U.S. Appl. No. 10/010,942, Examiner Interview Summary mailed Nov. 18, 2004.
U.S. Appl. No. 10/010,942, Examiner Interview Summary mailed Feb. 22, 2006.
U.S. Appl. No. 10/010,942, Examiner Interview Summary mailed Jan. 19, 2005.
U.S. Appl. No. 10/010,942, Office Action mailed May 26, 2004.
U.S. Appl. No. 10/232,030, Examiner Interview Summary mailed Feb. 17, 2006.
U.S. Appl. No. 10/232,030, Office Action mailed Oct. 14, 2005.
U.S. Appl. No. 10/388,214, Examiner Interview Summary mailed Oct. 2, 2006.
U.S. Appl. No. 10/388,214, Examiner Interview Summary mailed Nov. 6, 2006.
U.S. Appl. No. 10/388,214, Office Action mailed Jan. 31, 2006.
U.S. Appl. No. 10/388,389, Examiner Interview Summary mailed May 31, 2006.
U.S. Appl. No. 10/388,389, Examiner Interview Summary mailed May 22, 2006.
U.S. Appl. No. 10/429,216, Examiner Interview Summary mailed Mar. 6, 2006.
U.S. Appl. No. 10/429,216, Office Action mailed Apr. 11, 2006.
U.S. Appl. No. 10/544,093, Office Action mailed Feb. 9, 2009.
U.S. Appl. No. 10/625,854, Examiner Interview Summary mailed Jun. 26, 2007.
U.S. Appl. No. 10/625,854, Office Action mailed Feb. 7, 2006.
U.S. Appl. No. 10/703,713, Examiner Interview Summary mailed Feb. 21, 2006.
U.S. Appl. No. 10/703,713, Examiner Interview Summary mailed Mar. 2, 2006.
U.S. Appl. No. 10/703,713, Office Action mailed Sep. 27, 2005.
U.S. Appl. No. 10/704,070, Office Action mailed Sep. 26, 2005.
U.S. Appl. No. 10/771,174, Office Action mailed Nov. 27, 2006.
U.S. Appl. No. 10/777,792, Office Action mailed Aug. 7, 2006.
U.S. Appl. No. 10/788,666, Office Action mailed Dec. 15, 2005.
U.S. Appl. No. 10/823,463, Office Action mailed Sep. 30, 2005.
U.S. Appl. No. 10/828,548, Office Action mailed Feb. 13, 2006.
U.S. Appl. No. 10/858,855, Office Action mailed Mar. 7, 2007.
U.S. Appl. No. 10/889,999, Office Action mailed Jan. 5, 2005.
U.S. Appl. No. 10/890,000, Office Action mailed Apr. 13, 2005.
U.S. Appl. No. 10/890,024, Office Action mailed Nov. 2, 2005.
U.S. Appl. No. 10/890,070, Office Action mailed Apr. 8, 2005.
U.S. Appl. No. 10/890,071, Office Action mailed Dec. 18, 2006.
U.S. Appl. No. 10/923,469, Examiner Interview Summary mailed Apr. 9, 2008.
U.S. Appl. No. 10/923,469, Office Action mailed Jul. 3, 2007.
U.S. Appl. No. 10/923,471, Examiner Interview Summary mailed Oct. 20, 2008.
U.S. Appl. No. 10/923,471, Office Action mailed Jan. 5, 2005.
U.S. Appl. No. 10/923,474, Office Action mailed Nov. 17, 2005.
U.S. Appl. No. 10/923,605, Office Action mailed Apr. 12, 2007.
U.S. Appl. No. 10/934,818, Office Action mailed Mar. 26, 2007.

(56) References Cited

OTHER PUBLICATIONS

U.S. Appl. No. 10/934,819, Office Action mailed Jan. 24, 2006.
U.S. Appl. No. 11/058,757, Office Action mailed Oct. 20, 2005.
U.S. Appl. No. 11/108,102, Office Action mailed Jan. 11, 2006.
U.S. Appl. No. 11/244,678, Office Action mailed Jul. 13, 2007.
U.S. Appl. No. 11/245,524, Office Action mailed Sep. 27, 2007.
U.S. Appl. No. 11/245,916, Office Action mailed May 19, 2006.
U.S. Appl. No. 11/260,047, Examiner Interview Summary mailed May 15, 2007.
U.S. Appl. No. 11/260,047, Office Action mailed May 15, 2007.
U.S. Appl. No. 11/274,493, Office Action mailed Apr. 23, 2007.
U.S. Appl. No. 11/303,478, Office Action mailed Mar. 18, 2009.
U.S. Appl. No. 11/304,986, Office Action mailed Dec. 31, 2008.
U.S. Appl. No. 11/305,889, Office Action mailed Aug. 14, 2007.
U.S. Appl. No. 11/305,899, Office Action mailed Dec. 10, 2008.
U.S. Appl. No. 11/342,353, Office Action mailed Nov. 14, 2008.
U.S. Appl. No. 11/454,772, Examiner Interview Summary mailed Apr. 13, 2007.
U.S. Appl. No. 11/454,772, Office Action mailed Jun. 27, 2007.
U.S. Appl. No. 11/520,438, Office Action mailed Aug. 6, 2009.
U.S. Appl. No. 11/842,023, Office Action mailed Nov. 13, 2008.
U.S. Appl. No. 11/842,042, Office Action mailed Jun. 24, 2009.
U.S. Appl. No. 11/842,056, Office Action mailed May 6, 2009.
U.S. Appl. No. 11/842,085, Office Action mailed Sep. 30, 2009.
U.S. Appl. No. 11/842,116, Office Action mailed Nov. 26, 2010.
U.S. Appl. No. 12/037,045, Office Action mailed Apr. 28, 2010.
U.S. Appl. No. 12/181,238, Examiner Interview Summary mailed Mar. 5, 2010.
U.S. Appl. No. 12/181,238, Office Action mailed May 28, 2009.
U.S. Appl. No. 12/253,929, Office Action mailed Apr. 28, 2010.
U.S. Appl. No. 12/336,340, Office Action mailed Mar. 4, 2010.
U.S. Appl. No. 12/608,869, Office Action mailed Oct. 25, 2011.
U.S. Appl. No. 09/201,430, Office Action mailed Oct. 1, 2002.
U.S. Appl. No. 09/204,838, Office Action mailed Apr. 18, 2003.
U.S. Appl. No. 09/322,289, Office Action mailed Feb. 7, 2008.
U.S. Appl. No. 09/322,289, Office Action mailed Feb. 24, 2005.
U.S. Appl. No. 09/322,289, Office Action mailed Nov. 4, 2008.
U.S. Appl. No. 09/322,289, Office Action mailed Nov. 17, 2006.
U.S. Appl. No. 09/723,713, Office Action mailed Apr. 19, 2005.
U.S. Appl. No. 09/723,713, Office Action mailed Oct. 24, 2003.
U.S. Appl. No. 09/723,725, Office Action mailed Dec. 9, 2002.
U.S. Appl. No. 09/723,760, Office Action mailed May 4, 2005.
U.S. Appl. No. 09/723,765, Office Action mailed May 22, 2008.
U.S. Appl. No. 09/723,765, Office Action mailed Aug. 10, 2004.
U.S. Appl. No. 09/723,765, Office Action mailed Dec. 20, 2004.
U.S. Appl. No. 09/724,273, Office Action mailed Jun. 8, 2006.
U.S. Appl. No. 09/724,273, Office Action mailed Jun. 22, 2004.
U.S. Appl. No. 09/724,273, Office Action mailed Dec. 22, 2006.
U.S. Appl. No. 09/724,288, Office Action mailed Mar. 18, 2008.
U.S. Appl. No. 09/724,288, Office Action mailed Apr. 23, 2007.
U.S. Appl. No. 09/724,288, Office Action mailed Jun. 21, 2006.
U.S. Appl. No. 09/724,288, Office Action mailed Oct. 3, 2007.
U.S. Appl. No. 09/724,288, Office Action mailed Dec. 14, 2004.
U.S. Appl. No. 09/724,319, Office Action mailed Jan. 11, 2008.
U.S. Appl. No. 09/724,319, Office Action mailed May 16, 2007.
U.S. Appl. No. 09/724,19, Office Action mailed Aug. 15, 2005.
U.S. Appl. No. 09/724,575, Office Action mailed Mar. 31, 2006.
U.S. Appl. No. 09/724,575, Office Action mailed May 6, 2005.
U.S. Appl. No. 09/724,575, Office Action mailed Oct. 17, 2005.
U.S. Appl. No. 09/980,568, Office Action mailed Nov. 2, 2004.
U.S. Appl. No. 10/010,942, Office Action mailed Jan. 19, 2005.
U.S. Appl. No. 10/010,942, Office Action mailed Mar. 10, 2005.
U.S. Appl. No. 10/232,030, Office Action mailed Jun. 15, 2007.
U.S. Appl. No. 10/429,216, Office Action mailed Jan. 28, 2008.
U.S. Appl. No. 10/429,216, Office Action mailed Mar. 12, 2010.
U.S. Appl. No. 10/429,216, Office Action mailed Sep. 15, 2010.
U.S. Appl. No. 10/544,093, Office Action mailed Jan. 22, 2010.
U.S. Appl. No. 10/625,854, Office Action mailed May 15, 2007.
U.S. Appl. No. 10/703,713, Office Action mailed Jun. 2, 2006.
U.S. Appl. No. 10/777,792, Office Action mailed Apr. 3, 2008.
U.S. Appl. No. 10/828,548, Office Action mailed Sep. 11, 2007.
U.S. Appl. No. 10/858,855, Office Action mailed Dec. 12, 2008.
U.S. Appl. No. 10/858,855, Office Action mailed Dec. 15, 2009.
U.S. Appl. No. 10/889,999, Office Action mailed Aug. 15, 2005.
U.S. Appl. No. 10/890,000, Office Action mailed Mar. 10, 2006.
U.S. Appl. No. 10/890,000, Office Action mailed Sep. 19, 2005.
U.S. Appl. No. 10/890,070, Office Action mailed Sep. 29, 2005.
U.S. Appl. No. 10/923,469, Office Action mailed Mar. 24, 2008.
U.S. Appl. No. 10/923,471, Office Action mailed Mar. 20, 2009.
U.S. Appl. No. 10/923,471, Office Action mailed May 15, 2006.
U.S. Appl. No. 10/923,471, Office Action mailed Jul. 31, 2007.
U.S. Appl. No. 10/923,471, Office Action mailed Aug. 24, 2005.
U.S. Appl. No. 10/923,474, Office Action mailed Jun. 26, 2007.
U.S. Appl. No. 11/244,678, Office Action mailed Sep. 23, 2008.
U.S. Appl. No. 11/245,524, Office Action mailed Apr. 17, 2009.
U.S. Appl. No. 11/245,524, Office Action mailed Jun. 4, 2008.
U.S. Appl. No. 11/245,524, Office Action mailed Dec. 10, 2010.
U.S. Appl. No. 11/245,916, Office Action mailed Jan. 28, 2008.
U.S. Appl. No. 11/245,916, Office Action mailed May 18, 2010.
U.S. Appl. No. 11/245,916, Office Action mailed Oct. 31, 2008.
U.S. Appl. No. 11/245,916, Office Action mailed Dec. 14, 2011.
U.S. Appl. No. 11/342,353, Office Action mailed Jul. 22, 2008.
U.S. Appl. No. 11/809,552, Office Action mailed Feb. 17, 2011.
U.S. Appl. No. 11/841,919, Office Action mailed Mar. 28, 2011.
U.S. Appl. No. 11/842,023, Office Action mailed Aug. 14, 2009.
U.S. Appl. No. 11/842,113, Office Action mailed Aug. 24, 2010.
U.S. Appl. No. 11/893,123, Office Action mailed May 11, 2011.
U.S. Appl. No. 12/106,206, Office Action mailed Jul. 9, 2010.
U.S. Appl. No. 09/201,430, Advisory Action mailed Jun. 18, 2002.
U.S. Appl. No. 09/201,430, Office Action mailed Nov. 26, 2001.
U.S. Appl. No. 09/204,838, Office Action mailed Sep. 27, 2001.
U.S. Appl. No. 09/322,289, Office Action mailed Jun. 4, 2009.
U.S. Appl. No. 09/322,289, Office Action mailed Jul. 17, 2007.
U.S. Appl. No. 09/322,289, Office Action mailed Oct. 16, 2005.
U.S. Appl. No. 09/322,289, Office Action mailed Nov. 29, 2005.
U.S. Appl. No. 09/723,713, Advisory Action mailed Dec. 20, 2004.
U.S. Appl. No. 09/723,713, Office Action mailed Jan. 11, 2006.
U.S. Appl. No. 09/723,713, Office Action mailed Feb. 12, 2002.
U.S. Appl. No. 09/723,713, Office Action mailed Jun. 3, 2004.
U.S. Appl. No. 09/723,760, Advisory Action mailed Dec. 16, 2004.
U.S. Appl. No. 09/723,760, Office Action mailed Feb. 23, 2004.
U.S. Appl. No. 09/723,760, Office Action mailed Dec. 29, 2005.
U.S. Appl. No. 09/723,765, Advisory Action mailed Feb. 9, 2004.
U.S. Appl. No. 09/723,765, Office Action mailed May 4, 2005.
U.S. Appl. No. 09/723,765, Office Action mailed Oct. 7, 2003.
U.S. Appl. No. 09/723,765, Office Action mailed Dec. 5, 2008.
U.S. Appl. No. 09/724,273, Advisory Action mailed Mar. 18, 2004.
U.S. Appl. No. 09/724,273, Advisory Action mailed Jun. 16, 2005.
U.S. Appl. No. 09/724,273, Office Action mailed Aug. 22, 2007.
U.S. Appl. No. 09/724,273, Office Action mailed Oct. 16, 2003.
U.S. Appl. No. 09/724,273, Office Action mailed Dec. 28, 2004.
U.S. Appl. No. 09/724,288, Advisory Action mailed Jan. 6, 2004.
U.S. Appl. No. 09/724,288, Advisory Action mailed Mar. 3, 2006.
U.S. Appl. No. 09/724,288, Office Action mailed Jul. 12, 2005.
U.S. Appl. No. 09/724,288, Office Action mailed Sep. 9, 2003.
U.S. Appl. No. 09/724,288, Office Action mailed Dec. 22, 2008.
U.S. Appl. No. 09/724,319, Advisory Action mailed Oct. 28, 2009.
U.S. Appl. No. 09/724,319, Office Action mailed Apr. 8, 2009.
U.S. Appl. No. 09/724,319, Office Action mailed May 2, 2006.
U.S. Appl. No. 09/724,319, Office Action mailed Dec. 21, 2010.
U.S. Appl. No. 09/724,495, Advisory Action mailed May 16, 2006.
U.S. Appl. No. 09/724,495, Office Action mailed Sep. 26, 2005.
U.S. Appl. No. 09/724,567, Office Action mailed Jul. 23, 2003.
U.S. Appl. No. 09/724,575, Advisory Action mailed Feb. 12, 2004.
U.S. Appl. No. 09/724,575, Office Action mailed Jul. 25, 2003.
U.S. Appl. No. 09/724,575, Office Action mailed Oct. 12, 2006.
U.S. Appl. No. 09/724,953, Office Action mailed Jul. 25, 2003.
U.S. Appl. No. 10/232,030, Advisory Action mailed Oct. 30, 2006.
U.S. Appl. No. 10/232,030, Office Action mailed Apr. 1, 2008.
U.S. Appl. No. 10/388,214, Office Action mailed Jul. 28, 2006.
U.S. Appl. No. 10/429,216, Office Action mailed Jan. 3, 2007.
U.S. Appl. No. 10/429,216, Office Action mailed Mar. 6, 2009.
U.S. Appl. No. 10/429,216, Office Action mailed Oct. 16, 2008.

(56) References Cited

OTHER PUBLICATIONS

U.S. Appl. No. 10/544,093, Office Action mailed Oct. 13, 2010.
U.S. Appl. No. 10/625,854, Advisory Action mailed Jan. 8, 2008.
U.S. Appl. No. 10/625,854, Office Action mailed Aug. 23, 2006.
U.S. Appl. No. 10/625,854, Office Action mailed Nov. 7, 2007.
U.S. Appl. No. 10/704,070, Office Action mailed Jun. 6, 2006.
U.S. Appl. No. 10/771,174, Office Action mailed Aug. 23, 2007.
U.S. Appl. No. 10/777,792, Advisory Action mailed Mar. 6, 2009.
U.S. Appl. No. 10/777,792, Office Action mailed May 8, 2007.
U.S. Appl. No. 10/777,792, Office Action mailed Nov. 18, 2008.
U.S. Appl. No. 10/828,548, Advisory Action mailed Jun. 8, 2007.
U.S. Appl. No. 10/828,548, Office Action mailed Jun. 4, 2008.
U.S. Appl. No. 10/828,548, Office Action mailed Oct. 24, 2006.
U.S. Appl. No. 10/858,855, Advisory Action mailed Apr. 7, 2008.
U.S. Appl. No. 10/858,855, Office Action mailed Nov. 23, 2007.
U.S. Appl. No. 10/889,999, Office Action mailed Mar. 14, 2006.
U.S. Appl. No. 10/890,000, Advisory Action mailed Jan. 14, 2008.
U.S. Appl. No. 10/890,000, Office Action mailed Nov. 24, 2006.
U.S. Appl. No. 10/890,024, Office Action mailed Jun. 1, 2006.
U.S. Appl. No. 10/890,070, Office Action mailed Jun. 1, 2006.
U.S. Appl. No. 10/923,469, Advisory Action mailed Apr. 16, 2009.
U.S. Appl. No. 10/923,469, Office Action mailed Dec. 29, 2008.
U.S. Appl. No. 10/923,471, Office Action mailed Apr. 24, 2008.
U.S. Appl. No. 10/923,471, Office Action mailed Dec. 24, 2009.
U.S. Appl. No. 10/923,471, Office Action mailed Dec. 29, 2006.
U.S. Appl. No. 10/923,474, Advisory Action mailed Feb. 22, 2007.
U.S. Appl. No. 10/923,474, Office Action mailed Aug. 4, 2006.
U.S. Appl. No. 11/058,757, Advisory Action mailed Mar. 5, 2007.
U.S. Appl. No. 11/058,757, Office Action mailed Aug. 11, 2006.
U.S. Appl. No. 11/108,102, Office Action mailed Sep. 6, 2006.
U.S. Appl. No. 11/244,678, Office Action mailed Mar. 24, 2008.
U.S. Appl. No. 11/245,524, Office Action mailed Nov. 20, 2009.
U.S. Appl. No. 11/245,916, Advisory Action mailed May 15, 2007.
U.S. Appl. No. 11/245,916, Advisory Action mailed Jun. 10, 2009.
U.S. Appl. No. 11/245,916, Advisory Action mailed Oct. 18, 2007.
U.S. Appl. No. 11/245,916, Office Action mailed Jan. 12, 2007.
U.S. Appl. No. 11/274,493, Office Action mailed Nov. 2, 2007.
U.S. Appl. No. 11/305,889, Office Action mailed May 23, 2008.
U.S. Appl. No. 11/454,772, Office Action mailed Dec. 21, 2007.
U.S. Appl. No. 11/664,865, Office Action mailed Feb. 11, 2011.
U.S. Appl. No. 11/842,042, Office Action mailed Mar. 30, 2010.
U.S. Appl. No. 12/037,045 , Office Action mailed Nov. 4, 2011.
U.S. Appl. No. 09/723,765, BPAI Decision on Request for Re-Hearing mailed Oct. 16, 2007.
U.S. Appl. No. 09/723,765, BPAI Order Returning Appeal to Examiner mailed Jun. 27, 2006.
U.S. Appl. No. 09/723,765, Examiner's Answer mailed Jan. 25, 2006.
U.S. Appl. No. 09/723,765, Reply Brief Noted mailed Jun. 16, 2006.
U.S. Appl. No. 10/777,792, BPAI Decision mailed Aug. 30, 2010.
U.S. Appl. No. 10/777,792, BPAI Decision on Request for Reconsideration mailed Nov. 30, 2010.
U.S. Appl. No. 10/777,792, Examiner's Answer mailed Oct. 27, 2009.
U.S. Appl. No. 10/777,792, Reply Brief Noted mailed Jan. 11, 2010.
U.S. Appl. No. 10/923,469, BPAI Decision mailed Feb. 22, 2011.
U.S. Appl. No. 10/923,469, Reply Brief Noted mailed Mar. 9, 2010.
Abcam, "Anti-beta Amyloid antibody 6F/3D", *Nucleic Acids Res.* 38:D142-D148 (2010).
Aihara, et al., "Immunocytochemical Localization of Immunoglobulins in the Rat Brain: Relationship to the Blood-Brain Barrier", *J of Comparative Neurology* 342:481-496 (1994).
Alzheimer Research Forum, "Drugs in Clinical Trials" Oct. 18, 2010.
Applicants' submission in EP 07012421.9 dated Jun. 16, 2009.
Assignment executed Dec. 8, 2000 in respect of U.S. Appl. No. 60/067,740.
Assignment executed Dec. 8, 2000 in respect of U.S. Appl. No. 60/080,970.

Birmingham et al., "Set back to Alzheimer vaccine studies" Nature Medicine 8(3):199-200 (2002).
Bruggermann, et al. "The Immunogenicity of Chimeric Antibodies" *J. Exp Med.*, 170(2):153-2157 (1989).
Communication in EP 07012421.9 pursuant to Art. 94(3) EPC dated Nov. 5, 2010.
Decision of Opposition Division in EP 1 160 256 dated Feb. 17, 2011.
Declaration of Shyra J. Gardai dated Mar. 2, 2009.
Druckexemplar in EP 1 160 256 dated Jan. 25, 2010.
Extract from EPO patent register of EP 1 160 256 retrieved on Sep. 7, 2011.
Extract from EPO patent register of EP 1 842 859 retrieved on Sep. 7, 2011.
Gambetti, et al., "Human brain amyloidosis," *Nephrology Dialysis Transplantation*, 13(Suppl. 7):33-40, (1998).
Hampel et al., "Measurement of Phosphorylated Tau epitopes in the Differential Diagnosis of Alzheimer Disease", Arch Gen Psychiatry (2004) 61(1):95-102.
Hyman, et al. "Kunitz Protease Inhibitor-Containing Amyloid β Protein Precursor Immunoreactivity in Alzheimer's Disease", *J. of Neuropathology*, 51(1):76-83 (1992).
Invitrogen Data Sheet, "Mouse anti-β-Amyloid Peptide", Catalog No. 13-0100Z (Rev 10/08) DCC-08-1089.
Jagust et al., "Brain Imaging Evidence of preclinical Alzheimer's disease in normal aging" Ann Neurol, (2006) 59:67-681: abstract p. 676, table 1.
Janeway, et al., *Immunobiology: The Immune System in Health and Disease* 3rd Edition; cover pages and pp. 3.22-3.27 (1997).
Jefferis, "Antibody therapeutic: isotype and glycoform selection", *Expert Opin. Biol. Ther.* 7(9):1401-1413 (2007).
Klafki et al., "Therapeutic approaches to Alzheimer's disease" *Brain* 129:2840-2825 (2006).
Kuby, *Immunology*, 2nd Ed., Freeman pp. 126 and 168-171 (1994).
Marx et al., "Immune recognition of the Alzheimer amyloid β protein" Poster presentation; Autoreactive T. cells P.5.18.03 Jun. 25, 1997.
Moretto, et al., "Conformation-sensitive Antibodies against Alzheimer Amyloid-β by Immunization with a Thioredoxin-constrained B-cell Epitope Peptide", *J of Biological Chemistry*, 282(14):11436-11445 (2007).
Patentee's Grounds of Appeal in EP Patent No. 1 033 996 dated Jul. 18, 2011.
PCT/US2011/026365 International Written Opinion and Search Report mailed Jul. 13, 2011.
PCT/US2011/033649 International Written Opinion and Search Report mailed Aug. 26, 2011.
Ray. "Wyeth Study Finds Alzheimer's Drug Works in ApoE4 Non-Carriers". Poster 2008, [retrieved from the internet Jun. 16, 2011: <URL: elan2006.blogspot.com/2008/07/elan-wyeth-studfindalzheimerdrug.html>].
Robert et al., Engineered antibody intervention strategies for Alzheimer's disease and related dementias by targeting amyloid and toxic oligomers:, Protein Eng Des Sel. (2009) 22:(2):199-208.
Stern, et al. "Monoclonal Antibodies to a Synthetic Peptide Homologous with the First 28 Amino Acids of Alzheimer's Disease β-Protein Recognize Amyloid and Diverse Glial and Neuronal Cell Types in the Central Nervous System" *Am J of Pathology*, 134(5):973-978 (1989).
Takahashi, et al. "Monoclonal antibody to β peptide, recognizing amyloid deposits, neuronal cells and lipofuscin pigments in systemic organs", *Acta Neuropathol*, 85:159-166 (1993).
Van Dam et al., "Symptomatic effect of donepezil, rivastigmine, galantamine and memantine on cognitive deficits in the APP23 model" *Psychopharmacology* 180:177-190 (2005).
Van Noort, Multiple sclerosis: an altered immune response or an altered stress response?, *J Mol Med* 74:285-296 (1996).
Wiessler, et al "The Second-Generation Active Aβ Immunotherapy CAD106 Reduces Amyloid Accumulation in APP Transgenic Mice While Minimizing Potential Side Effects", *J. Neurosci.* 31(25):9323-9331 (2011).
Wikipedia entry for "Monoclonal antibody therapy" accessed on Sep. 22, 2011.

(56) References Cited

OTHER PUBLICATIONS

Wu et al., "Saponin Adjuvant Enhancement of Antigen-Specific Immune Responses to an Experimental HIV-1 Vaccine" J of Immunology 149:1519-1525 (1992).
Zhao et al., "Macrophage-Mediated Degradation of β-Amyloid via an Apolipoprotein E Isoform-Dependent Mechanism", Neurobiology of disease (Mar. 18, 2009) 29(11):3603-3612.
Zotova et al., "Inflammation in Azheimer's disease: relevance to pathogenesis and therapy" Alzheimer's Research & Therapy 2:1 p. 2-9 (2010).
U.S. Appl. No. 60/999,423, filed Oct. 17, 2007, Black.
U.S. Appl. No. 11/894,789, filed Aug. 20, 2007, Basi.
U.S. Appl. No. 11/894,754, filed Aug. 20, 2007, Basi.
U.S. Appl. No. 11/894,714, filed Aug. 20, 2007, Basi.
U.S. Appl. No. 11/894,665, filed Aug. 20, 2007, Schenk.
U.S. Appl. No. 11/893,123, filed Aug. 20, 2007, Basi et al.
U.S. Appl. No. 11/893,110, filed Aug. 20, 2007, Basi et al.
U.S. Appl. No. 11/893,103, filed Aug. 20, 2007, Basi et al.
U.S. Appl. No. 11/893,094, filed Aug. 20, 2007, Basi et al.
U.S. Appl. No. 11/842,101, filed Aug. 20, 2007, Schenk.
U.S. Appl. No. 11/841,950, filed Aug. 20, 2007, Arumugham.
U.S. Appl. No. 11/841,897, filed Aug. 20, 2007, Arumugham.
U.S. Appl. No. 11/841,882, filed Aug. 20, 2007, Arumugham.
U.S. Appl. No. 11/841,857, filed Aug. 20, 2007, Warne et al.
U.S. Appl. No. 11/841,849, filed Aug. 20, 2007, Arumugham.
U.S. Appl. No. 11/841,794, filed Aug. 20, 2007, Warne et al.
U.S. Appl. No. 11/841,832, filed Aug. 20, 2007, Warne et al.
U.S. Appl. No. 60/925,228, filed Apr. 18, 2007, Schroeter et al.
U.S. Appl. No. 60/793,014, filed Apr. 18, 2006, not named.
U.S. Appl. No. 11/396,417, filed Mar. 30, 2006, Schenk.
U.S. Appl. No. 11/396,391, filed Mar. 30, 2006, Schenk.
U.S. Appl. No. 11/358,951, filed Feb. 22, 2006, Solomon et al.
U.S. Appl. No. 60/736,119, filed Nov. 10, 2005, Jacobson.
U.S. Appl. No. 60/736,045, filed Nov. 10, 2005, Johnson-Wood.
U.S. Appl. No. 60/735,687, filed Nov. 10, 2005, Jacobson.
U.S. Appl. No. 60/691,821, filed Jun. 17, 2005, Godavarti.
U.S. Appl. No. 09/980,568, filed Mar. 12, 2005, Hirtzer.
U.S. Appl. No. 60/648,639, filed Jan. 28, 2005, Luisi et al.
U.S. Appl. No. 60/648,631, filed Jan. 28, 2005, Luisi et al.
U.S. Appl. No. 60/637,253, filed Dec. 16, 2004, Jacobson.
U.S. Appl. No. 60/637,138, filed Dec. 16, 2004, Jacobson.
U.S. Appl. No. 60/636,842, filed Dec. 15, 2004, Jacobson.
U.S. Appl. No. 60/636,810, filed Dec. 15, 2004, Jacobson.
U.S. Appl. No. 60/636,776, filed Dec. 15, 2004, Basi.
U.S. Appl. No. 60/636,687, filed Dec. 15, 2004, Johnson-Wood.
U.S. Appl. No. 60/636,684, filed Dec. 15, 2004, Basi.
U.S. Appl. No. 60/622,525, filed Oct. 26, 2004, Pavliakova.
U.S. Appl. No. 60/616,474, filed Oct. 5, 2004, Sinacore.
U.S. Appl. No. 60/530,481, filed Dec. 17, 2003, Arumugham.
U.S. Appl. No. 60/530,480, filed Dec. 17, 2003, Arumugham.
U.S. Appl. No. 60/474,654, filed May 30, 2003, Basi.
U.S. Appl. No. 60/444,150, filed Feb. 1, 2003, Yednock.
U.S. Appl. No. 09/979,701, filed Mar. 13, 2002, Schenk.
U.S. Appl. No. 60/363,751, filed Mar. 12, 2002, Basi.
U.S. Appl. No. 60/254,465, filed Dec. 8, 2000, Holtzman et al.
U.S. Appl. No. 60/254,498, filed Dec. 8, 2000, Holtzman et al.
U.S. Appl. No. 60/251,892, filed Dec. 6, 2000, Basi et al.
U.S. Appl. No. 09/724,842, filed Nov. 28, 2000, Chalifour et al.
U.S. Appl. No. 09/724,929, filed Nov. 28, 2000, Weiner.
U.S. Appl. No. 09/724,921, filed Nov. 28, 2000, Weiner.
U.S. Appl. No. 09/724,575, filed Nov. 28, 2000, Schenk.
U.S. Appl. No. 09/724,291, filed Nov. 28, 2000, Schenk.
U.S. Appl. No. 09/724,273, filed Nov. 28, 2000, Schenk.
U.S. Appl. No. 09/723,544, filed Nov. 28, 2000, Schenk.
U.S. Appl. No. 09/724,495, filed Nov. 27, 2000, Schenk.
U.S. Appl. No. 09/724,319, filed Nov. 27, 2000, Schenk.
U.S. Appl. No. 09/723,766, filed Nov. 27, 2000, Hirtzer.
U.S. Appl. No. 09/723,760, filed Nov. 27, 2000, Schenk.
U.S. Appl. No. 09/723,725, filed Nov. 27, 2000, Hirtzer.
U.S. Appl. No. 09/723,713, filed Nov. 27, 2000, Schenk.
U.S. Appl. No. 09/585,656, filed Jun. 1, 2000, Hirtzer et al.
U.S. Appl. No. 09/580,019, filed May 26, 2000, Schenk.
U.S. Appl. No. 09/580,015, filed May 26, 2000, Schenk.
U.S. Appl. No. 09/579,690, filed May 26, 2000, Brayden.
U.S. Appl. No. 60/186,295, filed Mar. 1, 2000, Rasmussen et al.
U.S. Appl. No. 60/184,601, filed Feb. 24, 2000, Holtzman et al.
U.S. Appl. No. 09/497,553, filed Feb. 3, 2000, Schenk.
U.S. Appl. No. 60/169,687, filed Dec. 8, 1999, Chain.
U.S. Appl. No. 60/168,594, filed Nov. 29, 1999, Chalifour et al.
U.S. Appl. No. 09/441,140, filed Nov. 16, 1999, Solomon et al.
U.S. Appl. No. 60/139,408, filed Jun. 16, 1999, Raso.
U.S. Appl. No. 60/137,047, filed Jun. 1, 1999, Hirtzer.
U.S. Appl. No. 60/137,010, filed Jun. 1, 1999, Schenk.
U.S. Appl. No. 60/136,655, filed May 28, 1999, Brayden.
U.S. Appl. No. 09/322,289, filed May 28, 1999, Schenk.
U.S. Appl. No. 60/080,970, filed Jan. 11, 1999, Schenk.
U.S. Appl. No. 09/204,838, filed Dec. 3, 1998, Weiner.
U.S. Appl. No. 60/079,697, filed Mar. 27, 1998, Weiner et al.
U.S. Appl. No. 60/067,219, filed Dec. 3, 1997, Weiner et al.
U.S. Appl. No. 60/067,740, filed Dec. 2, 1997, Schenk.
"AAB-001 in Patients with Mild to Moderate Alzheimer's Disease" ClinicalTrials.gov last updated Sep. 22, 2009 3 pages.
"Researchers Develop Blood Test to Diagnose Alzheimer's-Type Changes in Mice," downloaded from www.businesswire.com on Dec. 15, 2004.
Agadjanyan et al., "Prototype Alzheimer's Disease Vaccine Using the Immunodominant B Cell Epitope From {beta}-Amyloid and Promiscuous T Cell Epitope Pan HLA DR-Binding Peptide," *J. Immunol.*, 174:1580-1586 (2005).
Aguzzi et al., "Prion research: the next frontiers," *Nature*, 389:795-798 (1997).
Aisen, P., "Inflammation and Alzheimer's Disease: Mechanisms and Therapeutic Strategies," *Gerontology*, 43:143-149 (1997).
Akiyama et al., "Occurrence of the Diffuse Amyloid β-Protein (Aβ) Deposits With Numerous Aβ-Containing Glial Cells in the Cerebral Cortex of Patients With Alzheimer's Disease," *Glia*, 25:324-331 (1999).
Akiyama et al., "The amino-terminally truncated forms of amyloid β-protein in brain macrophages in the ischemic lesions of Alzheimer's disease patients," *Neuroscience Letters*, 219:115-118 (1996).
Akiyama et al., "Inflammation and Alzheimer's disease," *Neurobiology of Aging*, 21:383-421 (2000).
Alberts et al., eds. *Molecular Biology of the Cell, Third Edition*, chapter 23, pp. 1208-1209 (1994).
Alberts et al., eds. *Molecular Biology of the Cell, Third Edition*, chapter 23, pp. 1216-1218 (1994).
Alberts et al., *Molecular Biology of the Cell, 2nd Edition*, pp. 266-267, Garland Publishing Inc., New York (1989).
Allen et al, "Reversible posterior leukoencephalopathy syndrome after bevacizumab/FOLFIRI Regimen for Metastatic Colon Caner," Arch. Neurol., 63(10): 1475-1478 (2006), abstract only.
American Type Culture Collection (ATCC) Search Results for "1KTR, IETZ, 1JRH", www.atcc.org/, pp. 1-3, Feb. 22, 2007.
Amit et al., "Three-Dimensional Structure of an Antigen-Antibody Complex at 2.8 Å Resolution," *Science*, 233:747-753 (1986).
Andersen et al., "Do nonsteroidal anti-inflammatory drugs decrease the risk for Alzheimer's disease?", *Neurology*, 45:1441-1445 (1995).
Anderson, J. P., "Exact cleavage site of Alzheimer amyloid precursor in neuronal PC-12 cells," *Neuroscience Letters*, 128(1):126-128 (1991).
Anderson, M. W., "Amending the amyloid hypothesis," *The Scientist*, 18(20):28-29 (2004).
Andrew et al., *Current Protocols in Immunology*, 2.7.1-2.9.8, John Wiley & Sons, Inc. (1997).
Ankarcrona et al., "Biomarkers for apoptosis in Alzheimer's disease," *Int. J. Geriatric Psychiatry*, 20:101-105 (2005).
Aquila Press Release, PR Newswire. May 6, 1997.
Ard et al., "Scavenging of Alzheimer's Amyloid β-Protein by Microglia in Culture," *J. Neuroscience Research*, 43:190-202 (1996).

(56) References Cited

OTHER PUBLICATIONS

Arendiash et al., "Behavioral assessment of Alzheimer's transgenic mice following long-term Aβ vaccination: Task specificity and correlations between Aβ deposition and spatial memory," *DNA and Cell Biology*, 20(11):737-744 (2001).

Armour et al., "Recombinant human IgG molecules lacking Fcγ receptor I binding and monocyte triggering activites," *J. Immunol*, 29:2613-2624 (1999).

Askelof et al., "Protective immunogenicity of two synthetic peptides selected from the amino acid sequence of *Bordetella pertussis* toxin subunit S1," *PNAS*, 87:1347-1351 (1990).

Associated Press, "Immune cells may promote Alzheimer's, a study finds," *The Boston Globe* (Apr. 13, 1995).

Auclair et al., "Effect of Active Immunization Against Oestriadiol in Developing Ram Lambs on Plasma Gonadotrophin and Testosterone Concentrations, Time of Onset of Puberty and Testicular Blood Flow," *Journal of Reproduction and Fertility*, 104:7-16 (1995).

Auld et al., "Alzheimer's disease and the basal forebrain cholinergic system: relations to β-amyloid peptides, cognition, and treatment strategies," *Progress in Neurobiol.*, 68:209-245 (2002).

Avis, "Perenteral Preparations," *Remington's Pharmaceutical Sciences*, 17:1518-1519 (1985).

Aylward et al., "Cerebellar Volume in Adults With Down Syndrome," *Arch Neurol.*, 4(2):209-212 (1997). Abstract only.

Bach et al., "Vaccination with AB-Displaying Virus-Like Particles Reduces Soluble and Insoluble Cerebral AB and Lowers Plaque Burden in APP Transgenic Mice," J. Immunol., 2009, 182 7613-7624.

Bacskai et al., "Imaging of amyloid-β deposits in brains of living mice permits direct observation of clearance of plaques with immunotherapy," *Nature Medicine*, 7(3):369-372 (2001).

Bacskai et al., "Non-Fc-mediated mechanisms are involved in clearance of amyloid-β in vivo by immunotherapy," *J. Neurosci.*, 22(18):7873-7878 (2002).

Balbach et al., "Amyloid fibril formation by $A\beta_{16-22}$, a seven-residue fragment of the Alzheimer's β-amyloid peptide, and structural characterization by solid state NMR," *Biochemistry*, 39:13748-13759 (2000).

Bales et al., "Administration of an Anti-Aβ Fab Fragment to $APP^{V717F}$ Transgenic Mice Reduces Neuritic Plaque," Abstract P4-396, presented at Poster Session P4: Therapeutics and Therapeutic Strategies-Therapeutic Strategies, Amyloid-Based, *Neurogiology of Aging*, 25:S587 (2004).

Bales et al., "Cholinergic dysfunction in a mouse model of Alzheimer disease is reversed by an anti-Aβ antibody," *J. Clin. Invest.*, 116(3):825-832 (2006).

Bandlow et al., "Untersuchungen Zum Mechanismus Der Immunologischen Adjvanswirung des Vacciniavirus[1]," *Archiv für due gesamte Virusfoschung*, 38:192-204 (1972). German article.

Bard et al., "Epitope and isotype specificities of antibodies to β-amyloid peptide for protection against Alzheimer's disease-like neuropathology," *PNAS*, 100(4):2023-2028 (2003).

Bard et al., "Peripherally administered antibodies against amyloid β-peptide enter the central nervous system and reduce pathology in a mouse model of Alzheimer disease," *Nature Medicine*, 6(8):916-919 (2000).

Barelli et al., "Characterization of New Polyclonal Antibodies Specific for 40 and 42 Amino Acid-Long Amyloid β Peptides: Their Use to Examine the Cell Biology of Presenilins and the Immunohistochemistry of Sporadic Alzheimer's Disease and Cerebral Amyloid Angiopathy Cases," *Molecular Medicine*, 3(10):695-707 (1997).

Barrow et al., "Solution Conformations and aggregational Properties of Synthetic Amyloid Beta-Peptides of Alzheimer's Disease. Analysis of Circular Dichroism Spectra," *J. Mol. Biol.*, 225(4):1075-1093 (1992).

Bauer et al., "Interleukin-6 and α-2-macroglobulin indicate an acute-phase state in Alzheimer's disease cortices," *FEBS Letters*, 285(1):111-114 (1991).

Beasley, "Alzheimer's traced to proteins caused by aging," Reuters, Apr. 20, 2001 7:56 PM ET.

Begley, "Delivery of Therapeutic Agents to the Central Nervouse System: The Problems and the Possibilities," *Pharmacol. Therapy*, 104(1): 29-45 (Oct. 2004).

Bellotti et al., "Application of Monoclonal Anti-idiotypes in the Study of AL Amyloidosi: Therapeutic Implications," *Renal Failure*, 15(3):365-371 (1993). Abstract.

Bendig, "Humanization of Rodent Monoclonal Antibodies by CDR Grafting," *A Companion to Methods in Enzymology*, 8:83-93 (1995).

Benjamini et al., from *Immunology A Short Course*, Second Edition, Chapter 4, Antibody Structure, pp. 49-65, 1991, published by Wiley-Liss, Inc., New York, New York.

Benjamini et al., from *Immunology A Short Course*, Second Edition, pp. 136-138, 143, 73-74, 372-373, and 400-401, 1991, published by Wiley-Liss, Inc., New York, New York.

Benkirane, et al, "Antigenicity and Immunogenicity of Modified Synthetic Peptides Containing D-Amino Acid Residues," *J. Biol. Chem.*, 268(23):26279-26285 (1993).

Ben-Yedidia et al., "Design of peptide and polypeptide vaccines," *Current Opinion in Biotechnology*, 8:442-448 (1997).

Bercovici et al., "Chronic Intravenous Injections of Antigen Induce and Maintain Tolerance in T Cell Receptor-Transgenic Mice," *Eur. J. Immunol.*, 29:345-354 (1999).

Bickel et al., "Development and in Vitro Characterization of a Cationized Monoclonal Antibody against βA4 Protein: A Potential Probe for Alzheimer's Disease," *Bioconiugate Chem.*, 5:119-125 (1994).

Bickel et al., "Site Protected, Cationized Monoclonal Antibody Against Beta Amyloid as a Potential Diagnostic Imaging Technique for Alzheimer's Diseases," *Soc. for Neuroscience Abstracts*, 18:764 (1992).

Biewenga et al., "Cleavage of Protein A-binding IgA1 with IgA1 Protease From *Streptococcus sanguls*," *Immunol Commun.*, 12(5):491-500 (1983), abstract only.

Black et al., "A Single Ascending Dose Study of Bainezumab, a Humanized Monoclonal Antibody to Aβ, in AD," *9th International Geneva/Springfield Symposium on Advances in Alzheimer Therapy*, 1 page (Apr. 20, 2006). Abstract only.

Blasberg et al., "Regional Localization of Glioma-assoicated Antigen Defined by Monoclonal Antibody 81C6 in Vivo: Kinetics and Implications for Diagnosis and Therapy," *Cancer Research*, 47:4432-4443 (1987).

Blass, "Immunologic Treatment of Alzheimer's Disease," *New England J. Medicine*, 341(22):1694 (1999).

Bodmer et al., "Transforming Growth Factor-Beta Bound to Soluble Derivatives of the Beta Amyloid Precursor Protein of Alzheimer's Disease," *Biochem. Biophys. Res. Comm.*, 171(2):890-897 (1990).

Boraschi et al., "Interleukin-1 and Interleukin-1 Fragments a Vaccine Adjuvants", Methods, 1999, 19, pp. 108-113.

Borchelt et al., "Accelerated Amyloid Deposition in the Brains of Transgenic Mice Coexpressing Mutant Presenilin 1 and Amyloid Precursor Proteins," *Neuron*, 19:939-945 (1997).

Borenstein, S., "New Alzheimer's vaccine to be tested on people soon, Early experiments on mice halted condition; considered safe for humans," *Free Press*, Jul. 23, 2001.

Boris-Lawrie et al., "Recent advances in retrovirus vector technology," *Cur. Opin. Genetic Develop.*, 3:102-109 (1993).

Bork et al., "Go hunting in sequence databases but watch out for the traps," *Trends in Genetics*, 12(10):425-427 (1996).

Bork, P., "Powers and Pitfalls in Sequence Analysis: The 70% Hurdle," *Genome Research*, 10:398-400 (2000).

Borras-Cuesta et al., "Engineering of Immunogenic Peptides by Co-Linear Synthesis of Determinants Recognized by B and T Cells," Eur. J. Immunol., 17:1213-1215 (1987).

Brazil et al., "Effects of Incorporation of Immunoglobulin G and Complement Component C1q on Uptake and Degradation of Alzheimer's Disease Amyloid Fibrils by Microglia," *J. Biol. Chem.*, 275(22):16941-16947 (2000).

Brenner, S. E., "Errors in genome annotation," *Trends in Genetics*, 15(4):132-133 (1999).

(56) References Cited

OTHER PUBLICATIONS

Brice et al., "Absence of the amyloid precursor protein gene mutation (APP717 : Val->lle) in 85 cases of early onset Alzheimer's disease," *J. Neurology, Neurosurg. Psychiatry*, 56:112-115 (1993).
Brinkman, "Splice Variants as Cancer Biomarkers," *Clinical Biochemisrty*, 37(7):584-594 (2004).
Britt et al., "Formulation of an immunogenic human cytomegalovirus vaccine: responses in mice," *J. Infect. Dis.*, 171:18-25 Abstract (1995).
Broadwell et al., "Serum proteins bypass the blood-brain fluid barriers for extracellular entry to the central nervous system," *Exp. Neurol.*, 120(2):245-263 (1993).
Brookmeyer et al., "Projections of Alzheimer's Disease in the United States and the Public Health Impact of Delaying Disease Onset," *Am. J. Public Health*, 88:1337-1342 (1998).
Burbach et al. "Vessel ultrastructure in APP23 transgenic mice after passive anti-Aβ immunotherapy and subsequent intracerebral hemorrhage" Neurobiology of Aging 28:202-212 (2007).
Burdick et al., "Assembly and aggregartion properties of synthetic Alzheimer's A4/β amyloid peptide antigens," *J. Biol. Chem.*, 267:546-555 (1992).
Bussiere et al., "Morphological Characterization of Thioflavin-S-Positive Amyloid Plaques in Transgenic Alzheimer Mice and Effect of Passive Aβ Immunotherapy on Their Clearance," *Am. J. Pathology*, 165(3):987-995 (2004).
Buttini et al., "β-Amyloid Immunotherapy Prevents Synaptic Degeneration in a Mouse Model of Alzheimer's Disease," *The Journal of Neuroscience*, 25(40):9096-9101 (2005).
Cameron, "Recent Advances in Transgenic Technology," *Molecular Biotechnology*, 7:253-265 (1997).
Caputo et al., "Therapeutic approaches targeted at the amyloid proteins in Alzheimer's disease," *Clin. Neuropharm.*, 15:414A-414B (1992).
Casadesus et al., "The Estrogen Myth: Potential Use of Gonadotropin-Releasing Hormone Agonists for the Treatment of Alzheimer's Disease," *Drugs R D*, 7(3):187-193 (2006).
Casey, S.O., "Posterior Reversible Encephalopathy Syndrome: Utility of Fluid-attenuated Inversion Recovery MR Imaging in the Detection of Cortical and Subcortical Lesions," *Amer J Neuroradiol*, 21:1199-1206 (2000).
Cassell et al., "Demography and Epidemiology of Age-Associated Neuronal Impairment," chapter 4, pp. 31-50 from *Funcitional Neurobiology of Aging*, Hof et al., eds., Academic Press (2001).
Casset et al., "A Peptide Mimetic of an Anti-CD4 Monoclonal Antibody by Rational Design," *Biochemical and Biophysical Research Commiunications*, 307:198-205 (2003).
Castillo et al., "Amylin / Islet Amyloid Polypeptide: Biochemistry, Physiology, Patho-Physiology," *Diabete & Metabolisme (Paris)*, 21:3-25 (1995).
Center for Biologics Evaluation and Research, U.S. Food and Drug Administration, Thimerosal in Vaccines (Mercury in Plasma-Derived Products), web site contents found at : www.fda.gov/cber/vaccine/thimerosal.htm, last updated May 16, 2002.
Chakrabarti et al., "Vaccinia Virus Expression Vector: Coexpression of B-Galactosidas Provides Visual Screening of Recombinant Virus Plaques," *Molecular and Cellular Biology*, 5(12):3403-3409 (1985).
Chang et al., "Adjuvant activity of incomplete Freund's adjuvant," *Advanced Drug Delivery Reviews*, 32:173-186 (1998).
Chao et al., "Transforming Growth Factor-β Protects human Neurons Against β-Amyloid-Induced Injury," *Soc. Neurosci. Abstracts*, 19:513-7 (1993).
Chapman, "Model behavior," *Nature*, 408:915-916 (2000).
Chauhan et al. "Intracerebroventricular Passive Immunization With Anti-Aβ Antibody in Tg2576" J of Neuroscience 74:142-147 (2003).
Check, "Battle of the Mind," *Nature*, 422:370-372 (2003).
Check, "Nerve Inflamtion Halts Trail for Alzheimer's Drugs," Nature, 415:462 (2002).
Chemical Abstract database, Abstract of "Injection of Newborn Mice with Seven Chemical Adjuvants to Help Determine Their Safety in Use in Biologicals," Chemical Abstract database, 75:242 (1971).
Chen et al., "Neurodegenerative Alzheimer-like pathology in PDAPP 717V→F transgenic mice," *Progress in Brain Research*, 117:327-337 (1998).
Chen et al., "A learning deficit related to age and beta-amyloid plaques in a mouse model of Alzheimer's disease," *Nature*, 408(6815):975-979 (2000).
Chen et al., "An Antibody to β Amyloid Precursor Protein Inhibits Cell-substratum Adhesion in Many Mammalian Cell Types," *Neuroscience Letters*, 125:223-226 (1991).
Chen et al., "Selection and Analysis of an Optimized Anti-VEGF Antibody: Crystal Structure of an Affinity-matured Fab in Complex with Antigen," *J. Mol. Biol.*, 293:865-881 (1999).
Chimicon International, "Mouse Anti-Amyloid Beta Protein Monoclonal Antibody," Catalog # MAB1561 (2003-2005).
Chishti et al., "Early-onset Amyloid Deposition and Cognitive Deficits in Transgenic Mice Expressing a Double Mutant Form of Amyloid Precursor Protein 695," *J. Biol.Chem.*, 276(24):21562-70 (2001).
Choi et al., "A Generic Intron Increases Gene Expression in Transgenic Mice," Molecular and Cellular Biology, 11(6):3070-3074 (1991).
Chothia et al., "Domain Association in Immunoglobulin Molecules," *J. Mol. Biol.*, 186:651-663 (1985).
Chromy et al., "Self-assembly of Aβ(1-42) into globular neurotoxins," *Biodhemistry*, 42(44):12749-12760 (2003).
Chung et al., "Uptake, Degradation, and Release of Fibrillar and Soluble Forms of Alzheimer's Amyloid β-Peptide by Microglial Cells," *J. Biol. Chem.*, 274(45):32301-32308 (1999).
Cirrito et al., "Amyloid β and Alzheimer disease therapeutics: the devil may be in the details," *J. Clin. Invest.*, 112:321-323 (2000).
Citron et al., "Evidence that the 42- and 40-amino acid forms of amyloid-β protein are generated from the β-amyloid precursor protein by different protease activities," *PNAS*, 93(23):13170-13175 (1996).
Citron, M., "Alzheimer's disease: treatments in discovery and development," *Nat. Neurosci.*, 5:1055-1057 (2002).
Clark et al., *Chemical Immunology Antibody Engineering IgG Effector Mechanisms*, 65:88-110 (1997).
Claudio, "Ultrastructural features of the blood-brain barrier in biopsy tissue for Alzheimer's disease patients." *Acta Neuropathol.* 91:6-14 (1996).
Clayton et al., "Synudeins in Synaptic Plasticity and Neurodegenerative Disorders," *J. Neurosci. Res.*, 58:120-129 (1999).
Co et al., "Chimeric and humanized antibodies with specificity for the CD33 antigen," *J. Immunol,*, 148:1149-1154 (1992).
Coico et al., *Immunology A Short Course, Fifth Edition*, pp. 18-24 (2003).
Colman, "Effects of Amino Acid Sequence Changes on Antibody-Antigen Interactions," *Research in Immunology*, 145:33-36 (1994).
Coloma et al., "Transport Across the Primate Blood-Brain Barrier of a Genetically Engineered Chimeric Monoclonal Antibody to the Human Insulin Receptor," *Pharm. Res.*, 17:266-274 (2000).
Colombian Patent Application No. 98071271, Technical Opinion of Jean Paul Vernot submitted on Jun. 22, 2005 as evidence with the brief amending the nullity action (with English translation) (drafted Nov. 2004).
Comery et al., "Passive Immunization Against β-Amyloid Leads to Acute Cognition Improvement," *Society for Neuroscience*, abstract, Washington DC, Nov. 12-16, 2005.
Constantino, Expert opinion Sep. 17, 2010.
Conway et al., "Acceleration of oligomerization, not fibrillization, is a shared property of both α-synuclein mutations linked to early-onset Parkinson's disease: Implications for pathogenesis and therapy," *PNAS*, 97(2):571-576 (2000).
Corcoran et al., "Overexpression of hAPPswe Impaires Rewarded Alternation and Contextual Fear Conditioning in a Transgenic Mouse Model of Alzheimer's Disease," Learn Mem. 9(5):243-252:2000.

(56) References Cited

OTHER PUBLICATIONS

Cordell, B., "β-Amyloid formation as a potential therapeutic target for Alzheimer's disease," *Ann. Rev. Pharmacol. Toxicol.*, 34:69-89 (1994).
Corey-Bloom et al., "Clinical features distinguishing large cohorts with possible AD, probable AD, and mixed dementia," *J. Am. Geriatr. Soc.*, 41(1):31-37 Abstract (1993).
Costa et al., "Immunoassay for transthyretin variants associated with amyloid neuropathy," *Scand. J. Immunol.*, 38:177-182 (1993).
Cox et al., "Adjuvants—a classification and review of their modes of action," *Vaccine*, 15(3):248-256 (1997).
Cribbs et al, "All-D-Erantiomers of Beta-Amyloid Exhibit Similar Biological Properties to All-L-Beta-Amyloids," *J. Biol. Chem.*, 272:7431-7436 (1997).
Cribbs et al., "Adjuvant-dependant modulation of th1 and th2 responses to immunization with B-amyloid", International Immunology, 2003, vol. 15, No. 4, pp. 505-514.
Daly, et al., "Detection of the membrane-retained carboxy-terminal tail containing polypeptides of the amyloid precursor protein in tissue from Alzheimer's Disease brain," *Life Sci.*, 63:2121-2131 (1998).
Das et al., "Amyloid-β Immunization Effectively Reduces Amyloid Deposition in FcRγ Knock-Out-Mice," *J. Neuroscience*, 23(24):8532-8538 (2003).
Das et al., "Reduced effectiveness of Aβ-42 immunization in APP transgenic mice with significant amyloid deposition," *Neurobiology of Aging*, 22:721-727 (2001).
Database Geneseq, "Nucleotide Sequence of a Variable Heavy Chain of IgG4," EBI Accession No. GSN:ADZ51216 (2005).
Davis, S. S., "Nasal Vaccines," *Advanced Drug Delivery Reviews*, 51:21-42 (2001).
De Felice et al., "β-Amyloid production, aggregation, and clearance as targets for therapy in Alzheimer's disease," *Cell Mol. Neurobiol.*, 22(5/6):545-563 (2002).
De La Cruz et al, "Immumogenicity [sic] and Epitope Mapping of Foreign Sequences via Genetically Engineered Filamentous Phage," *J Biol Chem*, 263(9):4318-4322 (1988).
De Lustig et al., "Peripheral Markers and Diagnostic Criteria in Alzheimer's Disease: Critical Evaluations," *Rev. In Neurosciences*, 5:213-225 (1994).
Declaration of Dr. Mattias Staufenbiel Ph D. Jul. 15, 2011.
Demattos et al., "Brain to plasma amyloid-β efflux: a measure of brain amyoid burden in a mouse model of Alzheimer's disease," *Science*, 295(5563):2264-2267 (2002).
Demattos et al., "Peripheral anti-Aβ antibody alters CNS and plasma clearance and decreases Aβ burden in a mouse model of Alzheimer's disease," *PNAS*, 98(15):8850-8855 (2001).
Demattos et al., "Plaque-associated disruption of CSF and plasma amyloid-β (Aβ) equilibrium in a mouse model of Alzheimer's disease," *J. Neurochem.*, 81:229-236.
Demattos et al., "Peripheral Anti Aβ Antibody Alters CNS and Plasma Aβ Clearance and Decreases Brain Aβ Burden in a Mouse Model of Alzheimer's Disease," published online before print Jul. 3, 2001 at 10.1073/pnas.151261398; *PNAS*, 98(15):8850-8855 (2001).
Dewitt et al., "Astrocytes regulate microglial phagocytosis of senile plaque cores of Alzheimer's disease," *Experimental Netirology*, 149:329-340 (1998).
Di Martino et al., "Production and Characterization of Antibodies to Mouse Scrapie-Amyloid Protein Elicited by Non-carrier Linked Synthetic Peptide Immunogens," *J. Molecular Recognition*, 4(2-3):85-91 (1991).
Dialog/Derwent, Abstract of WPI Acc No. 1995-261292/199534: Novel monoclonal antibody against human high-affinity IgE receptor—and DNA fragment encoding the MAb, for the specific identification of human Fc-epsilon RI, Derwent WPI database (1995).
Dialog/Derwent, Abstract of WPI Acc No. 1997-054436/199706: Stable vaccine compsns.—comprise a macrocyclic lactone, a milbemycin, an avermectin, an antigen, a dispersing agent, an adjuvant, a water sol. organic solvent and saline or water, Derwent File 351: Derwent WPI database (1997).
Dickey et al., "Duration and specificity of humoral immune responses in mice vaccinated with the Alzheimer's disease-associated β-amyloid 1-42 peptide," *DNA and Cell Biology*, 20(11):723-729 (2001).
Dickson et al., "Neuroimmunology of Alzheimer's disease: a conference report," *Neurobiology of Aging*, 13(6):793-798 (1992), abstract only.
Dictionary.com definition of "prophylactic", pp. 1-3 downloaded from internet Oct. 12, 2005.
Diomede et al., "Activation effects of a prion protein fragment [PrP-(106-126)] on human leucocytes," *Biochem. J.*, 320:563-570 (1996).
Disis et al., "Granulocyte-macrophage colony-stimulating factor: An effective adjuvant for protein and peptide-based vaccines," *Blood*, 88(1):202-210 (1996).
Do et al., "Reprogramming Somatic Gene Activity by Fusion With Pluripotent Cells" *Stem Cell Reviews.*, 2:257-264 (2006).
Dodart et al., "Immunization reverses memory deficits without reducing brain Aβ burden in Alzheimer's disease model," *Nat. Neurosci.*, 5(5):452-457 (2002).
Dodart, "Immunotherapy for Alzheimer's disease: will vaccination work?," *Trends in Molecular Medicine*, 9(3):85-87 (2003).
Dodel et al., "Immunotherapy for Alzheimer's disease," *Lancet Neurol.*, 2(4):215-220 (2003).
Doerks et al., "Protein annotation: detective work for function prediction," *Trends in Genetics*, 14(6):248-250 (1998).
Donnelly, "New Developments in Adjuvants," *Mechanism of Ageing and Development*, 93:171-177 (1997).
Dovey et al., "Functional gamma-secretase inhibitors reduce beta-amyloid peptide levels in brain," *J. Neurochem.*, 76(1):173-181 (2001).
Drew et al., "Vaccination by cholera toxin conjugated to a herpes simplex virus type 2 glycoprotein D peptide," *Journal of General Virology*, 73:2357-2366 (1992).
Du et al., "$\alpha_2$-Macroglobulin as a β-Amyloid Peptide-Binding Plasma Protein," *J. Neurochemistry*, 69(1):299-305 (1997).
Du et al., "Reduced levels of amyloid beta-peptide antibody in Alzheimer disease," *Neurology*, 57(5):801-5 (2001).
Duff et al., "Increased amyloid-β42(43) in brains of mice expressing mutant presenilin 1," *Nature*, 383(6602):710-713 (1996).
Duff et al., "Mouse model made," *Nature*, 373:476-477 (1995).
Dumery et al., "β-Amyloid protein aggregation: its implication in the physiopathology of Alzheimer's disease," *Pathol. Biol.*, 49:72-85 (2001).
Eck et al., *Goodman and Gilman's The pharmacological basis of therapeutics*, Chapter 5, pp. 77-101 (1996).
Ecuador Patent Application No. SP 98/2764, English translation of Expert Report submitted Apr. 19, 2007 in support of the Appeal filed on Jul. 29, 2005.
Ecuadorian Search Report of Jul. 2, 2009 for Ecuador Patent Application No. SP 03-4685.
El-Agnaf et al., "The influence of the central region containing residues 19-25 on the aggregation properties and secondary structure of Alzheimer's beta-amyloid peptide," *Eur. J. Biochem.*, 256(3):560-569 (1998).
Elan Reports First Quarter 2006 Financial Results. Business Wire (May 4, 2006) XP002620724.
Elan Reports First Quarter 2006 Financial Results. Business Wire (May 4, 2006) XP002620725.
Elan, "Elan and AHP Provide an Update on the Phase 2A Clinical Trial of AN-1792," Press Release. (Jan. 18, 2002).
Elan, "Elan and Wyeth Provide Update on Status of Alzheimer's Collaboration," Press Release (Mar. 1, 2002).
Elizan et al., "Antineurofilament antibodies in a postencephalitic and idiopathic Parkinson's disease," *J. Neurol. Sciences*, 59:341-347 (1983).
Eriksen et al., "NSAIDs and enantiomers of flurbiprofen target γ-secretase and lower AB42 in vivo," *J. Clin. Invest.*, 112(3):440-449 (2003).
Esiri, "Is an effective immune intervention for Alzheimer's disease in prospect?", *Trends in Pharm, Sci.*, 22:2-3 (2001).

(56) References Cited

OTHER PUBLICATIONS

Esler et al., "Point substitution in the central hydrophobic cluster of a human β-amyloid congener disrupts peptide folding and abolishes plaque competence," *Biochemistry*, 35:13914-13921 (1996).
European Examination Report as part of Dec. 8, 2008 communication for European Application 04720353.4.
European Examination Report of Mar. 9, 2007 for European Application 01995364.5-1222.
European Examination Report of Sep. 23, 2008 for European Application 04776252.1-2405.
European Examination Report of Sep. 26, 2007 for European Application 04720353.4-1222.
European Examination Report of Oct. 8, 2007 for European Application 01995364.5-1222.
European Examination Report of Nov. 20, 2008 for European Application 08011409.3.
European Search Report of Feb. 7, 2011 for European Application EP 08 74 6362.6.
European Search Report of Jan. 16, 2007 for European Application 04776252.1-2405.
European Search Report of May 22, 2006 for European Application 06075479.3-2107.
European Search Report of May 22, 2006 for European Application 06075704.4-2107.
Extended European Search Report of Dec. 18, 2008 for European Application 05812436.6-1212.
Family and legal status of EP0613007, Inpadoc Search (2009).
Felsenstein et al., "Processing of the β-amyloid precursor protein carrying the familial, Dutch-type, and a novel recombinant C-terminal mutation," *Neuroscience Letters*, 152:185-189 (1993).
Felsenstein et al., "Transgenic Rat and In-Vitro Studies of B-Amyloid Precursor Protein Processing;" *Alzheimer's and Parkinson's Diseases*, Hanin et al. Ed., pp. 401-409, Plenum Press, New York, (1995).
Finch et al., "Evolutionary Perspectives on Amyloid and Inflammatory Features of Alzheimer Disease," *Neurobiology of Aging*, 17(5):809-815 (1996).
Findeis et al, "Modified peptide inhibitors of amyloid B-peptide polymerization," *Biochemistry*, 38:6791-6800 (1999).
Findeis, M. A., "Approaches to discovery and characterization of inhibitors of amyloid β-peptide polymerization," *Biochem. Biophys. Acta*, 1502(1):76-84 (2000).
Fisher et al., "Expression of the amyloid precursor protein gene in mouse oocytes and embryos," *PNAS*, 88:1779-1782 (1991).
Flanders et al., "Altered expression of transforming growth factor-β in Alzheimer's disease," *Neurology*, 45:1561-1569 (1995).
Flood et al., "An amyloid β-Protein fragment, A β [12-28J, equipotently impairs post-training memory processing when injected into different limbic system structures," *Brain Res*, 663(2):271-276 (1994).
Flood, et al, "Topography of a binding site for small amnestic peptides deduced from structure-activity studies: Relation to amnestic effect of amyloid B protein," *PNAS*, 91:380-384 (1994).
Fonseca et al., "The Presence of Isoaspartic Acid in β-Amyloid Plaques Indicates Plaque Age," *Experimental Neurology*, 157(2):277-288 (1999).
Foote et al., "Antibody Framework Residues Affecting the Conformation of the Hypervariable Loops," *J. Mol. Biol.*, 224:487-499 (1992).
Fox et al., "Presymptomatic cognitive deficits in individuals at risk of familial Alzheimer's disease," *Brain*, 121:1631-1639 (1998).
Frangione et al., Familial cerebral amyloid angiopathy related to stroke and dementia. *Amyloid*, 8(Suppl 1):36-42 (2001), abstract only.
Frautschy et al., "Effects of injected Alzheimer β-amyloid cores in rat brain," *PNAS*, 88:8362-8366 (1991).
Frazer et al., "Immunoglobulins: Structure and Function," chapter 3, pp. 37-74 from *Fundamental Immunology, fourth edition*, W.E. Paul, eds., Lippincott-Raven publishers, Philadelphia (1999).

Frenkel et al., "Generation of auto-antibodies towards Alzheimer's disease vaccination," *Vaccine*, 19:2615-2619 (2001).
Frenkel et al., "High affinity binding of monoclonal antibodies to the sequential epitope EFRH of β-amyloid peptide is essential for modulation of fibrillar aggregation," *J. of Neuroimmunology*, 95:136-142 (1999).
Frenkel et al., "Immunization against Alzheimer's β-amyloid plaques via EFRH phage administration," *PNAS*, 97:11455-11459 (2000).
Frenkel et al., "N-terminal EFRH sequence of Alzheimer's β-amyloid peptide represents the epitope of its anti-aggregating antibodies," *J. of Neuroimmunology*, 88:85-90 (1998).
Frenkel et al., "Reduction of β-amyloid plaques in brain of transgenic mouse model of Alzheimer's disease by EFRH-phage immunization," *Vaccine*, 21(11-12):1060-1065 (2003).
Frenkel et al., "Towards Alzheimer's β-amyloid vaccination," *Biologicals*, 29(3-4):243-247 (2001).
Frenkel, et al., "Modulation of Alzheimer's β-amyloid neurotoxicity by site-directed single chain antibody," *J. of Neuroimmunology*, 106:23-31 (2000).
Friedland et al., "Development of an anti-Aβ monoclonal antibody for in vivo imaging of amyloid angiopathy in Alzheimer's disease," *Mol. Neurology*, 9:107-113 (1994).
Friedland, et al., "Neuroimaging of Vessel Amyloid in Alzheimer's Disease," in *Cerebrovascular Pathology in Alzheimer's Disease*, eds. de la Torre and Hachinski, New York Academy of Sciences, New York, New York, 826:242-247 (1997).
Fukutani et al., "Cerebeller pathology in sporadic and familial Alzheimer's disease including APP 717 (Val->lle) mutation cases: A morphometric investigation," *J. Neurologic Sci.*, 149:177-184 (1997).
Furlan et al., "Vaccination with amyloid-β peptide induces autoimmune encephalomyelitis in C57/BL6 mice," *Brain*, 126:285-291 (2003).
Games et al., "Alzheimer-type neuropathology in transgenic mice overexpressing V717F β-amyloid precursor protein," *Nature*, 373(6514):523-527 (1995).
Games et al., "Prevention and Reduction of AD-type Pathology in PDAPP Mice Immunized with $A\beta_{1-42}$," *Annals of the New York Academy of Science*, 920:274-284 (2000).
Gandy et al., "Amyloidogenesis in Alzheimer's disease: some possible therapeutic opportunities," *TiPS*, 13:108-113 (1992).
Gardella et al., "Intact Alzheimer amyloid precursor protein (APP) is present in platelet membranes and is encoded by platelet mRNA," *Biochem. Biophys. Res. Comm.*, 173:1292-1298 (1990).
Gaskin et al., "Human antibodies reactive with beta-amyloid protein in Alzheimer's disease," *J. Exp. Med.*, 177:1181-1186 (1993).
Gauthier et al., "Alzheimer's Disease: Current Knowledge, Management and Research," *Can. Med. Assoc. J.*, 157:1047-1052 (Oct. 15, 1997).
Geddes, "N-terminus truncated β-amyloid peptides and C-terminus truncated secreted forms of amyloid precursor protein: distinct roles in the pathogenesis of Alzheimer's disease," *Neurobiology of Aging*, 20:75-79 (1999).
Gelinas et al., "Immunotherapy for Alzheimer's disease," *PNAS*, 101(suppl. 2):14657-14662 (2004).
Genbank Accession No. AAD00856.1, "Igm Heavy Chain Variable Region [*Homo sapiens*]," Jul. 31, 2001.
Genbank Accession No. AAA69734, Schroeder et al., "Immunoglobulin heavy chain [*Homo sapiens*], Anti-DNA immunoglobulin light chain IgG [*Mus musculus*]," Jul. 11, 1995.
Genbank Accession No. AAB35009.1, Wang et al., "Antiidiotypic Ig 1F7 Light Chain Variable Region [Human, 1F7 Hybridoma Cells, Peptide Partial, 120aa]," Oct. 28, 1995.
Genbank Accession No. AAB48800, "Anti-DNA immunoglobulin light chain IgG [*Mus musculus*]," Sep. 14, 2001.
Genbank Accession No. AAD26773, "Immunoglobulin heavy chain VH3609-JH3 region [*Mus musculus*]," Apr. 22, 1999.
Genbank Accession No. BAC01733, Akahori et al., "Immunoglobulin kappa light chain VLJ region [*Homo sapiens*]", Jul. 2, 2002.
Genbank Accession No. CAA46659, "IgE antibody light chain(VJ)," Jun. 15, 1993.

(56) References Cited

OTHER PUBLICATIONS

Genbank Accession No. X65775.1, "M.musculus DNA for IgE antibody light chain (VJ)," Jun. 15, 1993.
Geylis et al., "Immunotherapy of Alzheimer's disease 9AD): From murine models to anti-amyloid beta 9Ab) human monoclonal antibodies," *Autoimmunity Rev.*, 5:33-39 (2000).
Ghersi-Egea et al., "Fate of Cerebrospinal Fluid-Borne Amyloid β-Peptide: Rapid Clearance into Blood and Appreciable Accumulation by Cerebral Arteries," *Journal of Neurochemistry*. vol. 67 No. 2:880-883 (1996).
Ghetie et al., "CD4 Peptide-Protein Conjugates, But Not Recombinant Human CD4, Bind to Recombinant gp120 From the Human Immunodeficiency Virus in the Presence of Serum From AIDS Patients.," Proc. Natl. Acad. Sci., 88:5690-5693 (1991).
Ghiso et al., "Epitope map of two polyclonal antibodies that recognize amyloid lesions in patients with Alzheimer's disease," *Biochem. J.*, 282 (Pt 2):517-522 (1992).
Ghochikyan, "Rationale for Peptide and DNA Based Epitope Vaccine for Alzheimer's Disease Immunotherapy", CNS Neurol Disord Drug Targets, 2009: 8(2): 128 1-18.
Gibson et al., "Abnormalities in Alzheimer's Disease Fibroblasts Bearing the APP670/671 Mutation," *Neurobiology of Aging*, 18(6):573-580 (1997).
Gilman, S. et al., "Clinical Effects of Aβ Immunization (AN1792) in Patients with AD in an Interrupted Trial," *Neurology*, 64(9):1553-1562 (2005).
Giulian et al., "Specific domains of β-amyloid from Alzheimer plaque elicit neuron killing in human microglia," *J Neurosci.*, 16 (19):6021-6037 (1996).
Giulian, et al., "The HHQK Domain of b-Amyloid Provides a Structural Basis for the Immunopathology of Alzheimer's Disease," *J. Biol. Chem..*, 273:29719-29726 (1998).
Glenn et al., "Skin immunization made possible by cholera toxin," *Nature*, 391:851 (1998).
Glenner et al., "Alzheimer's Disease and Downs Syndrome: Sharing of a Unique Cerebrovascular Amyloid Fibril Protein," *Biochem. Biophys. Res. Comm.*, 122(3): 1131-1135 (1984).
Glenner et al., "Alzheimer's Disease: Initial Report of the Purification and Characterization of a Novel Cerebrovascular Amyloid Protein," *Biochem. Biophys. Res. Comm.*, 120(3): 885-890 (1994).
Goate et al., "Segregation of a missense mutation in the amyloid precursor protein gene with familial Alzheimer's disease," Nature, 349:704-706 (1991).
Goldfarb et al., "The Transmissible Spongiform Encephalopathies," *Ann. Rev. Med.*, 46:57-65 (1995).
Golding et al., "Vaccine Strategies: Targeting Helper T Cell Responses," *Annals New York Academy of Sciences*, 31:126-137 (1995).
Goldsby et al., "Vaccines," Chapter 18 from *Immunology, 4th Edition*, W.H. Freeman and Company, New York, pp. 449-465 (2000).
Goldsteins et al., "Exposure of cryptic epitopes on transthyretin only in amypoid and in amyloidogenic mutants," *PNAS*, 96:3108-3113 (1999).
Gong et al., "Alzheimer's disease-affected brain: presence of oligomeric Aβ ligands (ADDLs) suggests a molecular basis for reversible memory loss," *PNAS*, 100(18):10417-10422 (2003).
Gonzales-Fernandez et al., "Low antigen dose favors selection of somatic mutants with hallmarks of antibody affinity maturation," *Immunology*, 93:149-153 (1998).
Gorevic et al., "Ten to Fourteen Residue Peptides of Alzheimer's Disease Protein are Sufficient for Amyloid Fibril Formation and Its Characteristic X Ray Diffraction Pattern" *Biochem. and Biophy. Res. Commun.*, 147(2):854-862 (1987).
Gortner, *Outlines of Biochemistry*, pp. 322-323, John Wiley & Sons, Inc., New York (1949).
Gozes et al., "Neuroprotective strategy for Alzheimer disease: Intranasal administration of a fatty neuropeptide," *PNAS*, 93:427-432 (1996).

Gravina et al., "Amyloid β Protein (Aβ) in Alzheimer's Disease," *J. Biol. Chem.*, 270(13):7013-7016 (1995).
Greenberg et al. "Amyloid Angiopathy-Related Vascular Congnitive Impairment" Stoke., 35:2616-2619 (2004).
Greenberg et al., "Alzheimer disease's double-edged vaccine," *Nat. Med.*, 9(4):389-390 (2003).
Greisman et al., "A General Strategy for Selecting High-Affinity Zinc finger Proteins for Diverse DNA Target Sites" Science vol. 275:657-661 (1997).
Gross et al., "Microvascular specializations promoting rapid interstitial solute dispersion in nucleus tractus solitarius," *Am J Physiol Regul Integr Comp Physiol*, 259:R1131-R1138 (1990).
Grubeck-Loebenstein, et al., "Immunization with β-amyloid: could T-cell activation have a harmful effect?", *TINS*, 23:114 (2000).
Gupta et al., "Differences in the immunogenicity of native and formalinized cross reacting material ($CRM_{197}$) of diptheria toxin in mice and guinea pigs and their implications on the development and control of diphtheria vaccine based on CRMs," *Vaccine*, 15(12/13): 1341-1343 (1997).
Gupta et al., "Adjuvants for human vaccines—current status, problems, and future prospects," *Vaccine*, 13(14):1263-1275 (1995).
Gustavsson et al., "Mechanisms of Transthyretin Amyloidogenesis Antigenic Mapping of Transthyretin Pruified from Plasma and Amyloid Fibrils and within in Situ Tissue Localizations" American Journal of Pathology 44(6):1301-1311 (1994).
Haass et al. "Amyloid beta-peptide is produced by cultured cells during normal metabolism," *Nature*, 359(6393):322-325 (1992).
Haass et al., "Protofibrils, the unifying toxic molecule of neurodegenerative disorders?," *Nature Neuroscience*, 4(9):859-860 (2001).
Haass, C., "New hope for Alzheimer disease vaccine," *Nat Med.*, 8(11):1195-1196 (2002).
Haga et al., "Synthetic Alzheimer amyloid β/A4 peptides enhance production of complement C3 component by cultured microglial cells," *Brain Research*, 601:88-94 (1993).
Hamilton, "Molecular Engineering: Applications to the Clinical Laboratory," Clin. Chem. 39(9):1988-1997 (1993).
Hanan and Solomon, "Inhibitory effect of monoclonal antibodies on Alzheimer's β-amyloid peptide aggregation," *Int. J. Exp Clin. Invest.*, 3:130-133 (1996).
Hanes et al., "New advances in microsphere-based single-dose vaccines," *Advanced Drug Delivery Reviews*, 28: 97-119 (1997).
Hara et al., "Development of a safe oral Aβ vaccine using recombinant adeno-associated virus vector for Alzheimer's disease," *J. Alzheimer's Disease*, 6:483-488 (2004).
Hardy, "Amyloid, the presenilins and Alzheimer's disease," *TINS*, 20(4): 154-159 (1997).
Hardy, John, "New Insights into the Genetics of Alzheimer's Disease," *Annals of Med.*, 28:255-258 (1996).
Harigaya, et al., "Modified amyloid β protein ending at 42 or 40 with different solubility accumulates in the brain of Alzheimer's disease," *Biochem. Biophys. Res. Comm.*, 211:1015-1022 (1995).
Harlow et al., eds., *Antibodies: A Laboratory Manual*, p. 98 (1988).
Harlow et al., eds., *Antibodies: A Laboratory Manual*, pp. 139-195 (1988).
Harlow et al., eds., *Antibodies: A Laboratory Manual*, pp. 71-82 (1988).
Harrington et al., "Characterization of an epitope specific to the neuron-specific isoform of human enolase recognized by a monoclonal antibody raised against a synthetic peptide corresponding to the C-terminus of β / A4-protein," *Biochimica Biophysica Acta*, 1158:120-128 (1993).
Hartwig, "Immune ageing and Alzheimer's disease," *NeuroReport* 6:1274-1276 (1995).
Hazama, et al., "Intranasal Immunization Against Herpes Simplex Virus Infection by Using a Recombinant Glycoprotein D Fused With Immunomodulating Proteins, the B Subunit of *Escherichia coli* Heat-Labile Enterotoxin and Interleukin-2," *Immunology*, 78:643-649 (1993).
He et al., "Humanization and pharmacokinetics of a monoclonal antibody with specificity for both E- and P- selectin," *J. Immunol*, 160:1029-1035 (1998).

(56) References Cited

OTHER PUBLICATIONS

Hellman et al., "Allergy Vaccines—A Review of Developments," *Clin. Immunother.*, 6(2): 130-142 (Aug. 1996).
Helmuth, "Further Progress on a β-Amyloid Vaccine," *Science*, 289:375 (2000).
Herlyn et al., "Monoclonal antibodies in cell-mediated cytotoxicity against human melanoma and colorectal carcinoma*," *Eur. J. Immunol.*, 9:657-659 (1979).
Hermanson et al., "Amino Acids as Spacers," *Immobilized Affinity Ligand Techniques*, section 3.1.1.5:150-152 (1992).
Hezareh et al., "Effector Function Activities of a Panel of Mutants of a Broadly Neutralizing Antibody against Human Immunodeficiency Virus Type 1," *Journal of Virology*, 24(75):12161-12168 (2001).
Hilbich et al., "Aggregation and secondary structure of synthetic amyloid βA4 peptides of Alzheimer's disease," *J. Mol. Biol.*, 218:149-163 (1991).
Hilbich et al., "Human and rodent sequence analogs of Alzheimer's amyloid βA4 share similar properties and can be solubilized in buffers of pH 7.4," Eur. J. Biochem., 201:61-69 (1991).
Hilbich et al., "Substitutions of hydrophobic amino acid reduce the amyloidogenicity of Alzheimer's disease βA4 peptides" *J. Mol. Biol.*, 228:460-473 (1992).
Hillen-Maske et al., "Konichalcit", *Rompp Chemie Lexilkon*, 9th edition, p. 2322 (1990).
Hirschfield et al., "Amylodiosis: new strategies for treatment," *Int. J. Biochem. & Cell Biol.*, 35:1608-1613 (2003).
Hock et al., "Antibodies against β-Amyloid Slow Cognitive Decline in Alzheimer's Disease," *Neuron*, 38:542-554 (2003).
Hock et al., "Generation of antibodies specific for β-amyloid by vaccination of patients with Alzheimer disease," *Nat. Med.*, 8(11):1270-1275 (2002).
Hogarth, Fc Receptors Are Major Mediators of Antibody Based Inflammation in Autoimmunity, *Current Opinion in Immunology*, 14:798-802 (2002).
Holm et al., "Functional Mapping and Single Chain Construction of the Anti-Cytokeratin 8 Monoclonal Antibody TS1," *Mol. Immunol.* 44(6):1075-1084 (Feb. 2007).
Holmes et al., "Long-term Effects of Aβ$_{42}$ Immunisation in Alzheimer's Disease: Follow-up of a Randomised, Placebo-controlled Phase I Trial, " *Lancet*, 372: 216-223 (2008).
Holtzman et al., "Aβ immunization and anti-Aβ antibodies: potential therapies for the prevention and treatment of Alzheimer's disease," *Advanced Drug Delivery Reviews*, 54:1603-1613 (2002).
Hopp et al., "Prediction of protein antigenic determiniants from amino acid sequences," *Proc. Natl. Acad. Sci. USA* 78:3824-3828 (1981).
Hsiao et al., "Correlative Memory Deficits, Aβ Elevation, and Amyloid Plaques in Transgenic Mice," *Science*, 274: 99-102 (1996).
Huang et al., "Amyloid β-Peptide Possesses a Transforming Growth Factor-β-Activity," *The Journal of Biological Chemistry*, 273(42):27640-27644 (Oct. 16, 1998).
Huberman et al., "Correlation of cytokine secretion by mononuclear cells of Alzheimer's patients and their disease stage," *J. Neuroimmunology*, 52:147-152 (1994).
Hudson et al., "Antibody as a Probe," *Practical Immunology*, Chapter 2, pp. 34-85 (1989).
Hussain et al., "Selective Increases in Antibody Isotopes and Immunoglobulin G Subclass Responses to Secreted Antigens in Tuberculosis Patients and Healthy Household Contacts of the Patients," *Clinical and Diagnostic Laboratory Immunology*, 2(6): 726-732 (1995).
Hyman et al., "Molecular Epidemiology of Alzheimer's Disease," *N. E. J. Medicine*, 333(19):1283-1284 (1995).
Hyslop et al., "Will Anti-amyloid Therapies Work for Alzheimer's Disease?," *Lancet*, 372:180-182 (2008).
Ida et al., "Analysis of Heterogeneous βA4 Peptides in Juman Cerebrospinal Fluid and Blood by a Newly Developed Sensitive Western Blot Assay " *J. Biol. Chem.*, 271(37):22908-22914 (1996).

Idusogie et al., "Mapping of the C1q Binding Site on Rituxan, a Chimeric Antibody with a Human IgG1 Fc," *J. Immunology*, 164:4178-4184 (2000).
Ikeda, et al., "Immunogold labeling of cerebrovascular and neuritic plaque amyloid fibrils in Alzheimer's disease with an anti-β protein monoclonal antibody," Lab. Invest., 57:446-449 (1987).
Irizarry et al., "Alzheimer disease therapeutics," *J. Neuropathol. Exp. Neurol.*, 60(10):923-928 (2001).
Irizarry et al., "Aβ Deposition Is Associated with Neuropil Changes, but not with Overt Neuronal Loss in the Human Amyloid Precursor Protein V717F (PDAPP) Transgenic Mouse," *J. Neuroscience*, 17(18):7053-7059 (1997).
Itagaki et al., "Relationship of microglia and astrocytes to amyloid deposits of Alzheimer's disease," *J. Neuroimmunology*, 24:173-182 (1989).
Iwatsubo et al., "Visualization of Aβ42(43) and Aβ40 in Senile Plaques with End-Specific Aβ Monoclonals: Evidence That an Initially Deposited Species Is Aβ 42(43)," *Neuron*, 13:45-53 (1994).
Jahrling et al., "Opsonization of Alphaviruses in Hamsters," *J. Medical Virology*, 12:1-16 (1983).
Jakes et al., "Characterisation of an Antibody Relevant to the Neuropathology of Alzheimer Disease," *Alzheimer Disease and Associated Disorders*, 9(1):47-51 (1995).
Janeway et al., *Immunobiology*, 3rd edition, pp. 2:7, 2:9, 2:12, 8:16-8:17, 12:43 (1997).
Janeway et al., *Immunobiology*, 3rd edition, pp. 8:18-8:19 (1997).
Jansen et al., "Immunotoxins: Hybrid Molecules Combining High Specificity and Potent Cytotoxicity," *Immun. Rev.*, 62: 185-216 (1982).
Jansen et al., "Use of Highly Encapsulated *Streptococcus pneumoniae* Strains in a Flow-Cytometric Assay for Assessment of the Phagocytic Capacity of Serotype-Specified Antibodies," *Clinical & Diagnostic Lab. Immunol.*, 5(5):703-710 (1998).
Janus et al., "A beta peptide immunization reduces behavioural impairment and plaques in a model of Alzheimer's disease," *Nature*, 408(6815):979-982 (2000).
Janus et al., "Transgenic mouse models of Alzheimer's Disease," *Physiol. Behav.*, 73(5):873-886 (2001).
Jarrett et al., "The Carboxy Terminus of the β Amyloid Protein is Critical for the Seeding of Amyloid Formation: Implications for the Pathogenesis of Alzheimer's Disease," *Biochemistry*, 32:4693-4697 (Nov. 5, 1993).
Jen, et al., "Preparation and purification of antisera against different regions or isoforms of b-amyloid precursor protein," *Brain Research Protocols*, 2:23-30 (1997).
Jennings, "Review of Selected Adjuvants Used in Antibody Production," *ILAR Journal*, 37(3) (1995).
Joachim et al., "Antibodies to Non-beta Regions of the Beta-amyloid Precursor Protein Detect a Subset of Senile Plaques," *Am. J. of Pathology*, 138:373-384 (1991).
Jobling et al., "Analysis of structure and function of the B subunit of cholera toxin by the use of site-directed mutagenesis," *Molecular Microbiology*, 5(7):1755-1767 (1991).
Johnson-Wood et al., "Amyloid precursor protein processing and Aβ42 deposition in a transgenic mouse model of Alzheimer disease," *PNAS*, 94: 1550-1555 (1997).
Johnson-Wood et al., "Amyloid precursor protein processing and Aβ$_{42}$ deposition in a transgenic mouse model of Alzheimer disease," *PNAS*, 94(4):1550-1555 (Feb. 18, 1997).
Johnstone et al., Nuclear and Cytoplasmic Localization of the β-Amyloid Peptide (1-43) in Transfected 293 Cells, *Biochem. Biophys. Res. Comm.*, 220:710-718 (1996).
Jorbeck et al., "Artificial *Salmonella* Vaccines: *Salmonella typhimurium* O-antigen-Specific Oligosaccharide-Protein Conjugates Elicit Opsonizing Antibodies that Enhance Phagocytosis," *Infection and Immunity*, 32(2):497-502 (1981).
Jung et al., "Alzheimer's Beta-amyloid Precursor Protein Is Expressed on the Surface of Immediately Ex Vivo Brain Cells: a Flow Cytometric Study," *J. Neurosci. Res.*, 46(3):336-348 (1996).
Kajkowski et al., "β-Amyloid Peptide-induced Apoptosis Regulated by a Novel Protein Containing a G Protein Activation Module," *J. Biol. Chem.*, 276(22):18748-18756 (2001).

(56) References Cited

OTHER PUBLICATIONS

Kalaria, R. N., "Serum amyloid P and related molecules associated with the acute-phase phase response in Alzheimer's disease," *Res. Immunology*, 143:637-641 (1992).
Kalback et al., "APP Transgenic Mice Tg2576 Accumulate Aβ Peptides That Are Distinct from the Chemically Modified and Insoluble Peptides Deposited in Alzheimer's Disease Senile Plaques," *Biochemistry*, 41:922-928 (2002).
Kallberg et al., "Prediction of Amyloid Fibril-Forming Proteins," *The Journal of Biological Chemistry*, 276(16):12945-12950 (Apr. 20, 2001).
Kardana et al., "Serum HCG β-Core Fragment is Masked by Associated Macromolecules," *Journal of Clinical Endocrinology and Metabolism*, 71(5):1393-1395.
Kascsak et al., "Mouse Polyclonal and Monoclonal Antibody to Scrapie-Associated Fibril Proteins," *J. Virology*, 61(12):3688-3693 (1987).
Katzav-Gozansky et al., "Effect of monoclonal antibodies in preventing carboxypeptidase A aggregation," *Biotechnol. Appl. Biochem.*, 23:227-230 (1996).
Kawabata et al., "Amyloid plaques, neurofibrillary tangles and neuronal loss in brains of transgenic mice overexpressing a C-terminal fragment of human amyloid precursor protein," *Nature*, 354:476-478 (1991).
Kayed et al., "Conformational Transitions of Islet Amyloid Polypeptide (IAPP) in Amyloid Formation In Vitro," *J. Mol. Biol.*, 287:781-796 (1999).
Kelly, J. W., "Alternative conformations of amyloidogenic proteins govern their behavior," *Current Opinion in Structural Biology*, 6:11-17 (1996).
Kettleborough et al., "Humanization of a mouse monoclonal antibody by CDR-grafting: the importance of framework residues on loop conformation," *Protein Engineering*, 4(7):773-783 (1991).
Khan et al., "Immunopotentiation and Delivery Systems for Antigens for Single-Step Immunization: Recent Trends and Progress," *Pharmaceutical Research*, 11(1):2-11 (1994).
Khatoon et al., "Levels of normal and abnormally phosphorylated tau in different cellular and regional compartments of Alzheimer's disease and control brains," *FEBS Letters*, 351:80-84 (1994).
Kida, et al., "Early amyloid-β deposits show different immunoreactivity to the amino- and carboxy-terminal regions of β-peptide in Alzheimer's disease and Down's syndrome brain," *Neuroscience Letters*, 193:105-108 (1995).
Kim et al., "In Vivo Engineering of a Cellular Immune Response by Coadministration of IL-12 Expression Vector with a DNA Immunogen," *J. Immunol.*, 158:816-826 (1997).
Kimchi et al., "Analysis of cerebral amyloid angiopathy in a transgenic mouse model of Alzheimer disease using in vivo multiphoton microscopy," *J. Neuropath Exp. Neurol.*, 60(3):274-279 (2001).
Kinnecom et al., "Course of Cerebral Amyloid Angiopathy? Related Inflation," *Neurology*, 68(17):1411-1416 (2007).
Klein et al., "Targeting small Aβ oligomers: the solution to an Alzheimer's disease conundrum?," *Trends in Neurosciences*, 24(4):219-224 (2001).
Klyubin et al., "Anti-Aβ Antibodies Prevent Block of Long-Term Potentiation in the CA1 Area of Rat Hippocampus InVivo by naturally Produced Aβ Oligomers," *Neurobiology of Aging*, 25:S224-S225, abstract P2-004, pp. S224-S225 (2004).
Kofke et al., "Remifentanil-Induced Cerebral Blood Flow Effects in Normal Humans: Dose and ApoE genotype," *Neurosurg Anesthes Neurosci.*, 105(1):167-175 (2007).
Kofler et al., "Immunoglobulin $_k$ Light Chain Variable Region Gene Complex Organization and Immunoglobulin Genes Encoding Anti-DNA Autoantibodies in Lupus Mice," *J. Clin. Invest.*, 82:852-860 (1988).
Kofler et al., "Mechanism of Allergic Cross-Reactions—III. cDNA Cloning and Variable-Region Sequence Analysis of Two IgE Antibodies Specific for Trinitrophenyl," *Mol. Immunology*, 29(2):161-166 (1992).

Koller et al., "Active Immunization of Mice with a Aβ-Hsp70 Vaccine," *Neurodegenerative Disases*, 1:20-28 (2004).
Konig et al., "Development and Characterization of a Monoclonal Antibody 369.2B Specific for the Carboxyl-Terminus of the βA4 Peptide," *Annals of NY Acad. Sci.*, 777:344-355 (1996).
Kotilinek et al., "Reversible memory loss in a mouse transgenic model of Alzheimer's disease," *J. Neurosci.*, 22(15):6331-6335 (2002).
Koudinov et al., "The soluble form of Alzheimer's amyloid beta protein is complexed to high density lipoprotein 3 and very high density lipoprotein in normal human plasma," *Biochem. & Biophys. Res. Comm*, 205:1164-1171 (1994).
Kovács et al., "Mutations of the Prion Protein Gene Phenotypic Spectrum," *J. Neurol.*, 249:1567-1582 (2002).
Krishnan et al., "Correlation Between the Amino Acid Position of Arginine in VH-CDR3 and Specificity for Native DNA Among Autoimmune Antibodies[1,2]," *J. Immunol.*, 157(6):2430-2439 (1996).
Kuby, J., eds., p. 123 from *Immunology, Third Edition*, W.H. Freeman & co., (1997).
Kuby, J., eds., pp. 108-109, 131-132 from *Immunology, Third Edition*, W.H. Freeman & co., (1997).
Kuo et al., "Comparative Analysis of Amyloid-β Chemical Structure and Amyloid Plaque Morphology of Transgenic Mouse and Alzheimer's Disease Brains," *J. Biol. Chem.*, 276(16):12991-12998 (2001).
Kuo et al., "High levels of circulating Abeta42 are sequestered by plasma proteins in Alzheimer's disease," *Biochem. Biophys. Res. Comm.*, 257(3):787-791 (1999).
Kuo et al., "Water-soluble Aβ (N-40, N-42) Oligomers in Normal and Alzheimer Disease Brains," *J. Biol. Chem.*, 271(8):4077-4081 (1996).
Kurashima et al., "Production of Monoclonal Antibody against Amyloid Fibril Protein and Its Immunohistochemical Application," *Appl. Pathol.*, 3(1-2):39-54 (1985).
LaDu et al., "Isoform-specific Binding of Apolipoprotein E to β-Amyloid," *J. Biol. Chem.*, 269(38):23403-23406 (1994).
Lambert et al., "Diffusible, nonfibrillar ligands derived from Aβ1-42 are potent central nervous system neurotoxins," *PNAS*, 95:6448-6453 (1998).
Lambert et al., "Vaccination with soluble Aβ oligomers generates toxicity-neutralizing antibodies," *J. Neurochem.*, 79:595-605 (2001).
Lampert-Etchells et al., "Regional Localization of Cells Containing Complement C1q and C4 mRNAs in the Frontal Cortex During Alzheimer's Disease," *Neurodegeneration*, 2:111-121 (1993).
Landolfi et al., "The Integrity of the Ball-and Socket Joint Between V and C Domains Is Essential for Complete Activity of a Humanized Antibody," *J. Immunology*, 166(3):1748-1754 (2001).
Langer, "New Methods of Drug Delivery," *Science*, 249:1527-1532 (1990).
Lannfelt et al., "Alzheimer's disease: molecular genetics and transgenic animal models," *Behavioural Brain Res.*, 57:207-213 (1993).
Lansbury, Peter T., "Inhibition of amyloid formation: a strategy to delay the onset of Alzheimer's disease," *Curr. Ops. in Chemical Biology*, 1:260-267 (1997).
Lavie et al., "EFRH-Phage Immunization of Alzheimer's Disease Animal Model Improves Behavioral Performance in Morris Water Maze Trials," *J. Molecular Neuroscience*, 24:105-113 (2004).
Lee et al., "Aβ immunization: Moving Aβ peptide from brain to blood," *PNAS*, 98(16):8931-8932 (2001).
Lemere et al., "Intranasal immunotherapy for the treatment of Alzheimer's disease: *Escherichia coli* LT and LT(R192G) as mucosal adjuvants," *Neurobiology of Aging*, 23(6):991-1000 (2002).
Lemere et al., "Mucosal Administration of Aβ Peptide Decreases Cerebral Amyloid Burden in Pd-App Transgenic Mice," *Society for Neuroscience Abstracts*, 25(part )I, Abstract 519.6, 29th Annual Meeting, (Oct. 23-28, 1999).
Lemere, "Developing novel immunogens for a safe and effective Alzheimer's disease vaccine" Prog Brain Res. 2009; 175: 83 1-13.

(56) References Cited

OTHER PUBLICATIONS

Lemere, et al., "Nasal Aβ treatment induces anti-Aβ antibody production and decreases cerebral amyloid burden in PD-APP mice," Annals of the NY Acad. Sci., 920:328-331 (2000).
Leverone et al., "Aβ1-15 is less immunogenic than Aβ1-40/42 for intranasal immunization of wild-type mice but may be effective for 'boosting'," Vaccine, 21:2197-2206 (2003).
Levey, A. I., "Immunization for Alzheimer's disease: A shot in the arm or a whiff?," Ann. Neurology, 48(4):553-555 (2000).
Levitt, M., "Molecular dynamics of native protein," J. Mol. Biol., 168:595-620 (1983).
Li et al., "Thermal Stabilization of Carboxypeptidase A as a Function of PH and Ionic Milieu," Biochem. Mol. Biol. Int., 43(3):601-611 (1997).
Licastro et al., "Is immunotherapy an effective treatment for Alzheimer's disease?," Immunity & Aging, 1:1-2 (2004).
Linke, "Monoclonal antibodies against amyloid fibril protein AA. Production, specificity, and use for immunohistochemical localization and classification of AA-type amyloidosis," J. Histochemistry and Cytochemistry, 32(3):322-328 (1982).
Liu et al., "Amyloid β peptide alters intracellular vesicle trafficking and cholesterol homeostasis," Proc. Natl. Acad. Sci., 95:13266-13271 (1998).
Livingston et al., "The Hepatitis B Virus-Specific CTL Responses Induced in Humans by Lipopeptide Vaccination Are Comparable to Those Elicited by Acute Viral Infection," J. Immunol., 159:1383-1392 (1997).
Lo et al., "High level expression and secretion of Fc-X fusion proteins in mammalian cells," Protein Engineering, 11(6):495-500 (1998).
Lopez et al., "Serum auto-antibodies in Alzheimer's disease," Acta. Neurol. Scand., 84:441-444 (1991).
Lue et al., "Soluble β-amyloid Peptide Concentration as a Predictor of Synaptic Change in Alzheimer's Disease," Am. J. Pathol., 155:853-562 (1999).
MacCallum et al., Antibody-antigen Interactions: Contact Analysis and Binding Site Topography, 262:732-745 (1996).
Maggio et al., "Brain Amyloid—A Physicochemical Perspective," Brain Pathology, 6:147-162 (1996).
Majocha et al., "Development of a Monoclonal Antibody Specific for β/A4 Amyloid in Alzheimer's Disease Brain for Application to In Vitro Imaging of Amyloid Angiopathy," The J. of Nuclear Med., 33:2184-2189 (1992).
Mak, et al., "Polyclonals to b-amyloid (1-42) identify most plaque and vascular deposits in Alzheimer cortex, but not striatum," Brain Research, 667:138-142 (1994).
Mamikonyan et al., "Anti-Aβ$_{1-11}$ Antibody Binds to Different β-Amyloid Species, Inhibits Fibril Formation, and Disaggregates Preformed Fibrils but Not the Most Toxic Oligomers," J Biol Chem, 282(31) 22376-22386 (2007).
Mandel et al., "Clinical trials in neurological disorders using AAV vectors: promises and challenges," Curr. Opin. Mol. Ther., 6(5):482-490 (2004).
Mann et al., "Atypical Amyloid (Abeta) Deposition in the cerebellum in Alzheimer's Disease: An immunohistochemical Study Using End-Specific Abeta Monoclonal Antibodies," ACTA Neuropathologica, 91:647-653 (1996).
Mann et al., "Predominant Deposition of Amyloid-B$_{42(43)}$ in Plaques in Cases of Alzheimer's Disease and Hereditary Cerebral Hemorrhage Associated with Mutations in the Amyloid Precursor Protein Gene," The American Journal of Pathology APR, 4(148): 1257-1266 (1996).
Mann, et al., "The extent of amyloid deposition in brain in patients with Down's syndrome does not depend upon the apolipoprotein E genotype," Neuroscience Letters, 196:105-108 (1995).
Mann, et al., "Amyloid β protein (Aβ) deposition in chromosome 14-linked Alzheimer's disease: Predominance of Aβ$_{42(43)}$," Annals of Neurology, 40:149-156 (1996).
Manning et al., "Genetic Immunization with Adeno-Associated Virus Vectors Expressing Herpes Simplex Virus Type 2 Glycoproteins B and D," Journal of Virology, 71(10):7960-7962 (1997).
Manoj et al., "Approaches to Enhance the Efficacy of DNA Vaccines," Critical Rev. Clin. Lab. Sci., 41(1):1-39 (2004).
Marhaug et al., "Monoclonal hybridoma antibodies to human amyloid related protein SAA," Clin. Exp. Immunol., 50(2):390-396 (1982).
Marotta et al., "Overexpression of amyloid precursor protein A4 (β-amyloid) immunoreactivity in genetically transformed cells: Implications for a cellular model of Alzheimer amyloidosis," PNAS, 86:337-341 (1989).
Marshall, E., "Gene Therapy's Growing Pains," Science, 269:1050-1055 (1995).
Masliah et al., "Amyloid Protien Precursor Stimulates Excitatory Amino Acid Transport," The Journal of Biological Chemisrty, 273(20):12548-12554 (1998).
Masliah et al., "Comparison of Neurodegenerative Pathology in Transgenic Mice Overexpressing V717F β-Amyloid Precursor Protein and Alzheimer's Disease," J. Neuroscience, 16(18):5795-5811 (1996).
Masliah et al., "β-Amyloid peptides enhance α-synuclein accumulation and neuronal deficits in a transgenic mouse model linking Alzheimer's disease and Parkinson's disease," PNAS, 98(21):12245-12250 (2001).
Masters et al., "Amyloid Plaque core protein in Alzheimer Disease and Down Syndrome," PNAS, 82:4245-4249 (1985).
Mattson et al., "Good and bad amyloid antibodies," Science, 301(5641):1845-1849 (2003).
Mattson, "Cellular actions of beta-amyloid precursor protein and its soluble and fibrillogenic derivatives," Physiol Rev., 77(4):1081-132 (1997).
Maury et al., "Immunohistochemical Localization of Amyloid in Finnish Hereditary Amyloidosis with Antibodies to Gelsolin Peptides," Laboratory Investigation, 64(3):400-404 (1991).
Mavragani et al., "A Case of Reversible Posterior Leucoencephalopathy Syndrome After Rityximab Infusion," Rheumatology, 43(11) 1450-1451 (2006).
McGee et al., "The encapsulation of a model protein in poly (D, L lactide-co-glycolide) microparticles of various sizes: an evaluation of process reproducibility," J. Micro. Encap., 14(2):197-210 (1997).
McGeer, et al., "Immunohistochemical localization of beta-amyloid precursor protein sequences in Alzheimer and normal brain tissue by light and electron microscopy," J. of Neuroscience Res., 31:428-442 (1992).
McLaurin et al., "Therapeutically effective antibodies against amyloid-β peptide target amyloid-β residues and 4-10 and inhibit cytotoxicity and fibrillogenesis," Nat Med., 8(11):1263-1269 (2002).
McLean et al., "Soluble pool of Ab amyloid as a determinant of severity of neurodegeneration in Alzheimer's disease," Amer. Neurological Assoc, 46:860-866 (1999).
McNeal et al., "Stimulation of local immunity and protection in mice by intramuscular immunization with triple- or double-layered rotavirus particles and QS-21," Virology, 243:158-166 (1998).
Meda et al., "Activation of microglial cells by β-amyloid protein and interferon-γ," Nature, 374:647-650 (1995).
Mena, et al., "Monitoring pathological assembly of tau and β-amyloid proteins in Alzheimer's disease," Acta Neuropathol., 89:50-56 (1995).
Merluzzi, et al., "Humanized antibodies as potential drugs for therapeutic use," Adv Clin Path., 4(2):77-85 (2000).
Merriam-Webster online medical dictionary, entry for "cure", accessed Sep. 5, 2006.
Miller et al., "Antigen-driven Bystander Suppression after Oral Administration of Antigens," J. Exp. Med., 174:791-798 (1991).
Misra et al., "Drug Delivery to the Central Nervous System: A review," J. Pharm Pharm Sci., 6(2):252-273 (May 2003). Abstract.
Mitchell et al, "Prevention of Intracerebral Hemorrhage," Current Drug Targets, 8(7):832-838 (2007).

(56) References Cited

OTHER PUBLICATIONS

Monsonego et al., "Immune hyporesponsiveness to amyloid β-peptide in amyloid precursor protein transgenic mice: Implications for the pathogenesis and treatment of Alzheimer's disease," *PNAS*, 98(18):10273-10278 (2001).
Monsonego et al., "Increased T cell reactivity to amyloid β protein in older humans and patients with Alzheimer's disease," *J. Clin. Invest.*, 112(3):415-422 (2003).
Monsonego et al., "Immunotherapeutic approaches to Alzheimer's disease," *Science*, 302(5646):834-838 (2003).
Morgan et al., "The N-terminal end of the $C_H2$ domain of chimeric human IgG1 anti-HLA-DR is necessary for C1q, FcγRII and FcγRII binding," *Immunology*, 86:319-324.
Morgan, et al., "A beta peptide vaccination prevents memory loss in an animal model of Alzheimer's disease," *Nature*, 408(6815):982-985 (2000).
Mori et al., "Mass Spectrometry of Purified Amyloid β Protein in Alzheimer's Disease," *J. Biol. Chem.*, 267(24):17082-17088 (1992).
Morris, et al., "The Consortium to Establish a registry for Alzheimer's Disease (CERAD)," *Neurology*, 39:1159-1165 (1989).
Mount et al. "Alzheimer disease: progress or profit?" Market Analysis Nature Medicine 12(7) 780-784 (Jul. 2006).
Movsesyan et al., "Reducing AD-Lide Pathology in 3xTg-AD Mouse Model by DNA epitope Vaccine—A Novel Immunotherapeutic Strategy", PloS ONE, 2008, vol. 3, issue 5, e2124 1-13.
Munch et al., "Potentional neurotoxic inflammatory response to Aβ vaccination in humans," *J. Neural Transm.*, 109:1081-1087 (2002).
Munson eds., *Principals of Pharmacology: Basic Concepts & Clinical Applications*, pp. 47-48, Chapman & Hall, New York, New York (1995).
Murphy et al., "Development of a Monoclonal Antibody Specific for the COOH-Terminal of β-Amyloid 1-42 and Its Immunohistochemical Reactivity in Alzheimer's Disease and Related Disorders," *Am. J. Pathology*, 144(5):1082-1088 (1994).
Mutschler et al., *Drug Actions: Basic Principles and Therapeutic Aspects* pp. 7, 11-12, Medpharm Scientific Publishers, Stuttgart, Germany (1995).
Mutschler et al., "*Arzneimittel-Wirkungen, Lehrbuch der Pharmakologie und Taxiklogie*," Wissenschftliche Verlagsgesellschaft mbH Stuttgart, 6th edition, pp. 651-656 (1991), (German Article).
Myers et. al., "Targeting Immune Effector Molecules to Human Tumor Cells Through Genetic Delivery of 5T4-Specific SCFV Fusion Protiens," Cancer Gene Therapy, 9(11):884-896 (2002).
Nakamura et al., "Histopathological studies on senile plaques and cerebral Amyloid angiopathy in aged cynomologus monkeys," *Exp. Anim.*, 43:711-718 (1995).
Nakamura, et al., "Carboxyl end-specific monoclonal antibodies to myloid β protein (Aβ) subtypes (Aβ40 and Aβ42(43) differentiate Ab in senile plaques and myloid angiopathy in brains of aged cynomolgus monkeys," *Neuroscience Letters*, 201:151-154 (1995).
Nakayama et al., "Histopathological studies of senile plaques and cerebral amyloidosis in cynomolgus monkeys," *J. of Med. Primatology*, 27:244-252 (1998).
Nalbantoglu, J., "Beta-amyloid protein in Alzheimer's disease," *Can. J. Neurol. Sci.*, 18(3 suppl.):424-427 (1991), abstract only.
Nashar et al., "Current progress in the development of the B subunits of cholera toxin and *Escherichia coli* heat-labile enterotoxin as carries for the oral delivery of herterologous antigens and epitopes," *Vaccine*, 11(2):235-40 (1993), abstract only.
Naslund et al., "Correlation between elevated levels of amyloid b peptide in the brain and cognitive decline," *J. Am. Med. Assoc.*, 283:1571 (2000).
Nathanson et al., "Bovine Spongiform Encephalopathy (BSE): Causes and Consequences of a Common Source Epidemic," *Am. J. Epidemiol.*, 145(11):959-969 (1997).
New York Times National, "Anti-Inflammatory Drugs May Impede Alzheimer's," (Feb. 20, 1994).

Newcombe et al., "Solubility characteristics of isolated amyloid fibrils," Biochim. Biophys. Acta, 104:480-486 (1965).
Ngo et al., "Computational Complexity, Protein Structure Prediction, and the Levinthal Paradox," pp. 492-495 from Chapter 14 of *The Protein Folding Problem and Tertiary Structure Prediction*, Merz et al., eds., Birkhauser Boston (1994).
Nicoll et al., "Neuropathology of human Alzheimer's disease after immunization with amyloid-β peptide: a case report," *Nature Medicine*, 9(4):448-452 (2003).
Niemann, "Transgenic farm animals get off the ground;" *Transgenic Research*, 7:73-75 (1998).
Novartis, "Novartis MF59™—Adjuvanted Influenza Vaccine (Fluad®) Significantly Reduces Hospitalization in Elderly," Novartis Press Release, Oct. 19, 2007.
Novotny et al., "Structural invariants of antigen binding: Comparison of immunoglobulin $V_L$-$V_H$ and $V_L$-$V_L$ domain dimmers," *PNAS*, 82:4592-4596 (1985).
Okie, S., "Promising Vaccine Targets Ravager of Minds," *Washington Post*, p. A01, May 8, 2001.
Okura et al., "Nonviral Aβ DNA vaccine therapy against Alzheimer's disease: Long-term effect and safety," *PNAS*, 103(25):9619-9624 (2006).
Orkin et al., *Report and Recommendations of the Panel to Assess the NIH Investment in Research on Gene Therapy*, Dec. 7, 1995.
Orlandi et al., "Cloning immunoglobulin variable domains for expression by the polymerase chain reaction," *PNAS*, 86:3833-3837 (1989).
Padlan et al., Structure of an Antibody-Antigen Complex: Crystal Structure of the HyHEL-10 Fab-lysozyme Complex, Immunology, 86:5938-5942 (1989).
Paganetti et al., "Amyloid precursor protein truncated at any of the γ-secretase sites is not cleaved to β-amyloid," *J. Neurosci. Res.*, 46(3):283-293 (1996).
Palha et al., "Antibody recognition of amyloidogenic transthyretin variants in serum of patients with familial amyloidiotic polyneuropathy," *J. Mol. Med.*, 78:703-707 (2001).
Pallitto et al., "Recognition sequence design for peptidyl modulators of β-amyloid aggregation and toxicity," *Biochemistry*, 38(12):3570-3578 (1999).
Pan et al., "Antibodies to β-Amyloid Decrease the Blood-to-Brain Transfer of β-Amyloid Peptide," *Exp. Biol. Med.*, 227(8):609-615 (2002).
Pangalos et al., "Disease Modifiying Strategies for the Treatment of Alzheimer's Disease Targeted at Modulating Levels of β-amyloid Peptide," Biochemical Socity Transactions, 33(4):553-558 (2005).
Panka et al., "Variable region framework differences result in decreased or increased affinity of variant anti-digoxin antibodies," *PNAS*, 85:3080-3084 (1998).
Pardridge et al., "Chimeric peptides as a vehicle for peptide pharmaceutical delivery through the blood-brain barrier," *Biochem. Biophys. Res. Comm.*, 146:307-313 (1987).
Pardridge et al., "The Blood-Brain Barrier: Bottleneck in Brain Drug Development," *J. Am. Soc. Exp. Neurotherapeutics*, 2:3-14 (2005).
Paresce et al., "Microglial cells influence aggregates of the Alzheimer's disease amyloid β-protein via a scavenger receptor," Neuron, 17:553-565 (Sep. 1996).
Parnetti et al., "Cognitive Enhancement Therapy for Alzheimer's Disease, The Way Forward," *Drugs*, 53(5):752-768 (1997).
Pascalis et al., "Grafting of "Abbreviated" Complementarity-Determining Containing Specifictiy-Determining Residues Essential for Ligand Contact to Engineer a Less Immunogenic Humanized Monoclonal Antibody," *The Journanal Immunology*, 169:3076-3084 (2002).
Paul et al., "Transdermal immunization with large proteins by means of ultradeformable drug carriers," *Eur. J. Immunol.*, 25: 3521-3524 (1995).
Paul, W. E., eds., *Fundamental Immunology*, Third Edition, pp. 292-295, Raven Press, New York (1993).
PCT International Preliminary Examination Report of Feb. 9, 2004 for application PCT/US01/46587.

(56) References Cited

OTHER PUBLICATIONS

PCT International Preliminary Report on Patentability (Chapter I) of Sep. 16, 2005 with Written Opinion of May 9, 2005 for application PCT/US04/007503.
PCT International Preliminary Report on Patentability (Chapter I) of Jul. 31, 2007 with Written Opinion for application PCT/US2006/004741.
PCT International Preliminary Report on Patentability (Chapter I) of Oct. 20, 2009 with Written Opinion of Oct. 3, 2008 for application PCT/US2008/060926.
PCT International Preliminary Report on Patentability (Chapter I) of Feb. 2, 2010 for application PCT/US07/09499.
PCT International Preliminary Report on Patentability (Chapter I) and Written Opinion Completed Dec. 22, 2008 for PCT/US2008/080370.
PCT International Preliminary Report on Patentability (Chapter II) of Apr. 27, 2006 for application PCT/US04/007503.
PCT International Preliminary Report on Patentability (Chapter II) of Dec. 21, 2006 for application PCT/US2006/002837.
PCT Search Report of Jan. 22, 2009 for application PCT/US2008/80370.
PCT Search Report of Mar. 25, 2009 for application PCT/US2008/80382.
PCT Search Report of Oct. 1, 2007 and Written Opinion of Oct. 1, 2007 for application PCT/US07/09499.
PCT Search Report of Oct. 9, 2008 for application PCT/US2008/060926.
PCT Search Report of Apr. 6, 2006 and Written Opinion of Apr. 8, 2006 for application PCT/US04/44093.
PCT Search Report of Aug. 11, 2006 for application PCT/US2006/002837.
PCT Search Report of Aug. 8, 2006 for application PCT/US2005/045515.
PCT Written Opinion of Mar. 8, 2009 for application PCT/US2008/80382.
PCT Written Opinion of Dec. 14, 2004 for application PCT/US04/02856.
PCT Written Opinion of Dec. 22, 2008 for application PCT/US2008/80370.
PCT Written Opinion of Aug. 11, 2006 for application PCT/US2006/002837.
Peeters et al., "Comparison of four bifunctional reagents for coupling peptides to proteins and the effect of the three moieties on the immunogenicity of the conjugates," *J. Immunological Methods*, 120:133-143 (1989).
Perez et al., "The β-Amyloid Precursor Protein of Alzheimer's Disease Enhances Neuron Viability and Modulates Neuronal Polarity," *J. Neurosci.*, 17(24):9407-9414 (1997).
Persson et al., "IgG subclass-associated affinity differences of specific antibodies in humans," *J. Immunology*, 140(11):3875-3879 (1988), abstract only.
Perutz et al., "Amyloid fibers are water-filed nanotubes," *PNAS*, 99(8):5591-5595 (2002).
Peterson, et al., "Recombinant Antibodies: Alternative Strategies for Developing and Manipulating Murine-Derived Monoclonal Antibodies," *Laboratory Animal Science*, 46(1):8-14 (1996).
Pfeifer et al., "Cerebral hemorrhage after passive anti-Aβ immunotherapy," *Science*, 298(5597):1379 (2002).
Phelps et al., "Development and Characterization of Monoclonal Antibodies Specific for Amylin," *Hybridoma*, 15(5):379-386 (1996).
Philippe, et al. "Generation of a monoclonal antibody to the carboxy-terminal domain of tau by immunization with the amino-terminal domain of the amyloid precursor protein," J. of Neuroscience Res., 46:709-719 (1996).
Piera et al., "Cytokines as adjuvants: effects on the immunogenicity of NeuAc alpha 2-GalNAc alpha-O-Ser/Thr (sialyl-Tn)," *Int. J. Cancer*, 55(1):148-152 (1993).

Plant et al., "The Production of Amyloid β Peptide Is a Critical Requirement for the Viability of Central Neurons," *The Journal of Neuroscience*, 23(13):5531-5535, (2003).
Pluckthun, A., "Mono- and Bivalent Antibody Fragments Produced in *Escherichia coli*: Engineering, Folding and Antigen Binding," *Immunological Reviews*, 130:151-188 (1992).
PNAS Information for Authors (revised Jan. 1997), Retrieved Apr. 21, 2008 from http://web.archive.org/web/19970610092808/www.pnas.org/iforc.shtml.
Poduslo et al., "Macromolecular permeability across the blood-nerve and blood-brain barriers." *Proc. Natl. Acad. Sci USA*. vol. 91 pp. 5705-5709 (1994).
Poduslo et al., "Permeability of proteins at the blood-brain barrier in the normal adult mouse and double transgenic mouse model of Alzheimer's disease," *Neurobiol. Dis.*, 8(4):555-567 (2001).
Prada et al., "Antibody-Mediated Clearance of Amyloid-β Peptide From Cerebral Amyloid Angiopathy Revealed by quantitative in Vivo Imaging," Journal of Neuroscience, 27(8):1973-1980 (2007).
Press Release, "Alzheimer's vaccine developer awarded Potamkin Prize," American Academy of Neurology, May 7, 2001.
Prieels et al., "Synergistic adjuvants for vaccines," *Chemical Abstracts*, 120(8):652, col. 1, abstract 86406t (1994).
Probert et al., "Spontaneous inflammatory demyelinating disease in transgenic mice showing central nervous system-specific expression of tunmor necrosis factor α," *PNAS*, 92:11294-11298 (1995).
Prusiner et al., "Ablation of the prion protein (PrP) gene in mice prevents scrapie and facilitates production of anti-PrP antibodies," *PNAS*, 90:10608-10612 (1993).
Putative CDR determination for SEQ Id Nos. 2 and 4 (pp. 1-2), Jun. 10, 2004.
Qu et al., "Aβ42 gene vaccination reduces brain amyloid plaque burden in transgenic mice," *J. Neurological Sciences*, 244:151-158 (2006).
Qu et al., "$A\beta_{42}$ gene Vaccine Prevents $A\beta_{42}$ deposition in brain of Double Trangenic Mice," *J. Neurological Sciences*, 260:204-213 (2007).
Queen et al., "A humanized antibody that binds to the interleukin 2 receptor," *PNAS*, 86:10029-10033 (1989).
Quon et al., "Formation of β-Amyloid protein deposits in brains of transgenic mice," *Nature*, 352:239-241 (1991).
Racke et al., "Exacerbation of Cerebral Amyloid Angiopathy-Assoiciated Microhemorrhage in Amyloid Precursor Protein Trasngenic Mice by Immunotherapy Is Dependent on Antibody Recognition of Deposited Forms of Amyloid β," *J. Neurosci.*, 25(3):629-636 (2005).
Ragusi et al., "Redistribution of Imipramine from Regions of the Brain Under the Influence of Circulating Specific Antibodies," *J. Neurochem.*, 70(5):2099-2105 (1998).
Rammensee, H.G., "Chemistry of peptides associated with MHC class I and class II molecules," *Current Opinion in Immunology*, 7:85-96 (1995).
Ramshaw et al., "DNA vaccines for the treatment of autoimmune disease," *Immunology and Cell Biology*, 75:409-413 (1997).
Raso, "Immunotherapy of Alzheimer's Disease," *Immunotherapy Weekly*, Abstract (Apr. 2, 1998).
Research Corporation Technology News, "THP and SangStat Partner to Develop Humanized Polyclonal Antibody Drugs," Nov. 11, 2002.
Riechmann et al., "Reshaping Human Antibodies for Therapy," Nature, 332:323-327 (1988).
Robbins et al., "The Intronic Region of an Imcompletely Spliced gp100 Gene Transcript Encodes an Epitope Recognized by Melanoma-Reactive Tumor-Infiltrarting Lymphocytes," Journal of Immunology, 159(1):303-308 (1997).
Rodriguez et al., "Enfermedad de Azlheimer. Situacion Actual y Estrategias Terapeuticas" (Alzheimer Disease: present situation and therapeutic strategies), *Rev Cubana Med* [online], 38(2):134-142 (1999).
Rogers et al., "Complement activation by β-amyloid in Alzheimer Disease," *PNAS*, 89:1-5 (1992).
Rolph et al., "Recombinant viruses as vaccines and immunological tools," *Immunity to Infection*, 9:517-521 (1997).

(56) References Cited

OTHER PUBLICATIONS

Roses, A.D., "Apoplipoprotein E alleles as risk factors in Alzheimer's disease," *Annu. Rev. Med.*, 47:387-400 (1996).
Rossor et al., "Alzheimer's Disease Families with Amyloid Precursor Protein Mutations," *Annals of New York Academy of Sciences*, 695:198-202 (1993).
Rudikoff et al., "Single amino acid substitution altering antigen-binding specificity," *PNAS*, 79:1979-1983 (1982).
Rudinger, "Characteristics of the Amino Acids as Components of a Peptide Hormone Sequence," in *Peptide Hormones*, J.A. Parson, ed. University Park Press, Baltimore, pp. 1-7 (1976).
Saido et al., "Amino-and-Carboxyl-Terminal Heterogeneity of β-Amyloid Peptides Deposited in Human Brain," Neuroscience Letters, 215:173-176 (Aug. 8, 1996).
Saido et al., "Autolytic Transition of μ-Calpain Upon Activation as Resolved by Antibodies Distinguishing Between the Pre- and Post-Autolysis Forms," J. Biochem., 111:81-86 (1992).
Saido et al., "Spatial Resolution of Fodrin Proteolysis in Postischemic Brain," *J. Biol. Chem.*, 268(33):25239-25243 (1993).
Saido et al., "Spatial Resolution of the Primary β-Amyloidogenic Process Induced in Postischemic Hippocampus," *J. Biol. Chem.*, 269(21):15253-15257 (1994).
Saito et al., "Vector-mediated delivery of 125I-labeled β-amyloid peptide Ab1-40 through the blood-brain barrier and binding to Alzheimer disease amyloid of the Aβ1-40 vector complex," *PNAS*, 92:10227-10231 (1995).
Saitoh, N. et al., "Immunological analysis of Alzheimer's disease using anti-β-protein monoclonal antibodies," *Sapporo Med. J.*, 60:309-320 (1991).
Saldanha et al., "A single backmutation in the human kIV framework of a previously unsuccessfully humanized antibody restores the binding activity and increases the secretion in cos cells," *Molecular Immunology*, 36:709-719 (1999).
Sasaki et al., "Human choroid plexus is an uniquely involved area of the brain in amyloidosis: a histochemical, immunohistochemical and ultrastructural study," *Brain Res.*, 755:193-201 (1997).
Schenk et al., "Immunization with amyloid-β attenuates Alzheimer-disease-like pathology in the PDAPP mouse," *Nature*, 400:173-177 (1999).
Schenk et al., "Current progress in beta-amyloid immunotherapy," *Curr. Opin. Immunology*, 16(5):599-606 (2004).
Schenk et al., "Immunotherapy with beta-amyloid for Alzheimer's disease: a new frontier," *DNA Cell Biol.*, 20(11):679-81 (2001).
Schenk et al., "Therapeutic Approaches Related to Amyloid-β Peptide and Alzheimer's Disease," *J. Med. Chem.*, 38(21):4141-4154 (1995).
Schenk et al., "β-peptide immunization," *Arch. Neurol.*, 57:934-936 (2000).
Schenk, D., "Amyloid-β immunotherapy for Alzheimer's disease: the end of the beginning," *Nature Reviews*, 3:824-828 (2002).
Schmid, R. E., "Study suggest Alzheimer vaccine fix," from www.msnbc.com/news, pp. 1-5 (2002).
Schmidt et al., "Monoclonal Antibodies to a 100-kd protein reveal abundant A beta-negative plaques throughout gray matter of Alzheimer's disease brains," *The American Journal of Pathology*, 1(151):69-80 (1997).
Schmitt et al., "Interactions of the alzheimer β amyloid fragment(25-35) with peripheral blood dendritic cells," *Mechanisms of Ageing and Development*, 94:223-232 (1997).
Schroeder et al., "Preferential Utilization of Conserved Immunoglobulin Heavy Chain Variable Gene Segments During Human Fetal Life," *Immunology*, 87:6146-6150 (1990).
Schwarzman et al., "Transthyretin sequesters amyloid b protein and prevents amyloid formation," *PNAS*, 91:8368-8372 (1994).
Seabrook et al., "Species-specific Immune response to Immunization with Human Versus rodent Abeta Peptide," Neuobiology of Aging, 25(9) 1141-1151 (2004).
Seidl et al., "Predominant $V_H$ genes expressed in innate antibodies are associated with distinctive antigen-binding sites," *PNAS*, 96:2262-2267 (1999).

Sela et al, "Different roles of D-amino acids in immune phenomena," *FASEB J*, 11(6):449-456 (1999).
Selkoe, "Alzheimer's Disease: A Central Role for Amyloid," *J. Neuropathol. Exp. Neurol.*, 53(5): 438-447 (1994).
Selkoe, "Physiological production of the β-amyloid protein and the mechanism of Alzheimer's disease," *Trends in Neurosciences*, 16(10): 403-409 (1993).
Selkoe, "The cell biology of beta-amyloid precursor protein and presenilin in Alzheimer's disease," *Trends Cell Biol.*, 8(11):447-53 (1998).
Selkoe, D. J., "Alzheimer's disease is a synaptic failure," *Science*, 298(5594):789-791 (2002).
Selkoe, D.J., "Imaging Alzheimer's Amyloid," *Nat. Biotech.*, 18:823-824 (2000).
Selkoe, Dennis J., "Alzheimer's Disease: Genotypes, Phenotype, and Treatments," *Science*, 275:630-631 (1997).
Selkoe, Dennis J., "Amyloid Protein and Alzheimer's Disease . . . ," *Scientific American*, pp. 68-78 (1991).
Selkoe, Dennis J., "In the Beginning . . . ," *Nature*, 354:432-433 (1991).
Selkoe, Dennis J., "The Molecular pathology of Alzheimer's Disease," *Neuron*, 6:487-498 (1991).
Sergeant et al., "Truncated beta-amyloid peptide species in pre-clinical Alzheimer's disease as new targets for the vaccination approach," *J. Neurochem.*, 85(6):1581-1591 (2003).
Seubert et al., "Antibody Capture of Soluble Aβ does not Reduce Cortical Aβ Amyloidosis in the PDAPP Mouse," *Neurodegenerative Diseases*, 5:65-71 (2008).
Seubert et al., "Isolation and quantification of soluble Alzheimer's β-peptide from biological fluids," *Nature*, 359: 325-327 (1992).
Sheehan et al., "The Utilization of Individual $V_H$ Exons in the Primary Repertoire of Adult BALB/c Mice[1]," The Journal of Immunology, 151(10):5364-5375 (Nov. 15, 1993).
Shepherd et al., "The design of the humanized antibody," Monocolonal Antibodies: A Pratical Approcach 58-66 (2000).
Shinkai et al., "Amyloid β-Proteins 1-40 and 1-42(43) in the Soluble Fraction of Extra- and Intracranial Blood Vessels," *Ann. Neurol.*, 38:421-428 (1995).
Shiosaka, S., "Attempts to make models for Alzheimer's disease," *Neuroscience Res.*, 13:237-255 (1992).
Sidhu, "Page display in pharmaceutical biotechnology," *Current Opinoin in Biotechnology*, 11:610-616 (2000).
Sigmund, "Viewpoint: Are Studies in Genetically Altered Mice Out of Control," *Arterioscler Thromb Vasc Biol.*, 20:1425-1429 (2000).
Signet Laboratories, Inc., Product data sheet for mouse monoclonal clone 6E10, revised Jul. 13, 2005.
Sigurdsson et al., "A safer vaccine for Alzheimer's disease?," *Neurobiology of Aging*, 23:1001-1008 (2002).
Sigurdsson et al., "Anti-prion antibodies for prophylaxis following prion exposure in mice," *Neurosciences Letters*, 336:185-187 (2003).
Sigurdsson et al., "Immunization Delays the Onset of Prion Disease in Mice," *American Journal of Pathology*, 161:13-17 (2002).
Sigurdsson et al., "Immunization with a Nontoxic/Nonfibrillar Amyloid-β Homologous Peptide Reduces Alzheimer's Disease-Associated Pathology in Trasngenic Mice," *Am. J. Pathology*, 159(2):439-447 (2001).
Sigurdsson, et al., "In vivo reversal of amyloid-β lesions in rat brain," *J Neuropathol Exp Neurol.*, 59(1):11-17 (2000).
Simmons, L., "Secondary Structure of Amyloid β Peptide Correlates with Neurotoxic Activity In Vitro," *Molecular Pharmacology*, 45:373-379 (1994).
Singh, K. S., "Neuroautoimmunity: Pathogenic Implications for Alzheimer's Disease," *Gerontology*, 43:79-94 (1997).
Singh, V. K., "Studies of neuroimmune markers in Alzheimer's disease," *Mol. Neurobiology*, 9(1-3):73-81 (1994), abstract only.
Sinha, et al., "Recent advances in the understanding of the processing of APP to beta amyloid peptide," *Ann N Y Acad Sci.*, 920:206-8 (2000).
Sipe, "Amyloidosis," *Annu. Rev. Biochem.*, 61:947-975 (1992).
Skolnick and Fetrow, "From genes to protein structure and function: novel applications of computational approaches in the genomic era," *Trends in Biotech*, 18(1):34-39 (2000).

(56) References Cited

OTHER PUBLICATIONS

Small et al., "Alzheimer's disease and Abeta toxicity: from top to bottom," *Nat Rev Neurosci.*, 2(8):595-598 (2001).
Small et al., "Cerebral metabolic and cognitive decline in persons at genetic risk for Alzheimer's disease," *PNAS*, 97(11):6037-6042 (2000).
Small, "The Role of the Amyloid Protien Precursors (APP) in Alzheimer's Disease: Does the Normal Function of APP Explain the Topography of Neurodegeneration?," *Neurochemical Research*, 23(5):795-806, (1998).
Smith et al., "Phage Display," *Chemical Reviews, American Chemical Society*, 97(2):391-410 (1997).
Smith et al., "The challenges of genome sequence annotation or 'The devil is in the details,'" *Nature Biotechnology*, 15:1222-1223 (1997).
Smits et al., "Prion Protein and Scrapie Susceptibility," *Vet. Quart.*, 19(3):101-105 (1997).
Solomon and et al., "Modulation of the Catalytic Pathway of Carboxypeptidase A by Conjugation with Polyvinyl Alcohols," *Adv. Mol. Cell Biology*, 15A:33-45 (1996).
Solomon et al., "Activity of monoclonal antibodies in prevention of in vitro aggregation of their antigens," *Immunotechnology*, 2(4):305 (1996).
Solomon et al., "Disaggregation of Alzheimer β-amyloid by site-directed mAb," *PNAS*, 94:4109-4112 (1997).
Solomon et al., "Fast induction of anti-β-amyloid peptide immune response," *Research and Practice in Alzheimer's Disease*, 6:260-264 (2002).
Solomon et al., "Monoclonal antibodies inhibit in vitro fibrillar aggregation of the Alzheimer β-amyloid peptide," *PNAS*, 93:452-455 (1996).
Solomon et al., "The Amino Terminus of the β-Amyloid Peptide Contains an Essential Epitope for Maintaining Its Solubility," from *Progress in Alzheimer's and Parkinson's Diseases*, edited by Fisher et al., Plenum Press, New York, pp. 205-211 (1995).
Solomon, B., "Generation and brain delivery of anti-aggregating antibodies against β-amyloid plaques using phage display technology," *J. Neural Transm. Suppl.*, 62:321-325 (2002).
Solomon, B., "Immunological approaches as therapy for Alzheimer's disease," *Expert Opin. Biol. Ther.*, 2(8):907-917 (2002).
Solomon, B., "Immunotherapeutic strategies for prevention and treatment of Alzheimer's disease," *DNA and Cell Biology*, 20(11):697-703 (2001).
Sood et al., "Synthetic Peptides: A Modern Approach to Vaccination," *Indian Journal of Experimental Biology*, 34:849-861 (1998).
Soto et al., "The α-helical to β-strand transition in the amino-terminal fragment of the amyloid β-peptide modulates amyloid formation," *J. Biol. Chem*, 270(7):3063-3067 (1995).
Soto et al., "The conformation of Alzheimer's beta peptide determines the rate of amyloid formation and its resistance to proteolysis," *Biochem. J.*, 314:701-707 (1996).
Soto et al., "Beta sheet breaker peptides inhibit fibrillogenesis in a rat brain model of amyloidosis: implications for Alzheimer's therapy," *Nature Medicine.*, 4(7):822-826 (1998).
Souder et al., "Overview of Alzheimer's disease," *Nurs. Clin. N. Am.*, 39:545-559 (2004).
Southwick et al., "Assessment of Amyloid β protein in Cerebrospinal fluid as an Aid in the Diagnosis of Alzheimer's Disease," *J. Neurochemistry*, 66:259-265 (1996).
Spellerberg et al., "DNA Vaccines Against Lymphoma," Journal of Immunology, 159:1885-1892 (1997).
Spooner et al., "The generation and characterization of potentially therapeutic Aβ antibodies in mice: differences according to strain and immunization protocol," *Vaccine*, 21:290-297 (2002).
St. George-Hyslop et al., "Antibody clears senile plaques," *Nature*, 40:116-117 (1999).
Staunton et al., "Primary structures of ICAM-1 demonstrates interaction between members of the immunoglobulin and intergrin supergene families," *Cell* 52(6):925-33 (1988), abstract only.

*Stedman's Medical Dictionary*, 27th Edition, "Vaccine," p. 1922, lines 1-3 (2000).
Stein et al., "Lack of Neurodegeneration in Transgenic Mice Overexpressing Mutant Amyloid Precursor Protein is Associated with Increased Levels of Transthyretin and Activation of Cell Survival Pathways," *The Journal of Neuroscience*, 22(17):7380-7388 (2002).
Stern et al., "Antibodies to the β-amyloid peptide cross-react with conformational epitopes in human fibrinogen subunits from peripheral blood," *FEBS Letters*, 264(1):43-47 (1990).
Stoute et al., "A Preliminary Evaluation of a Recombinant Circumsporozoite Protein Vaccine Against *Plasmodium falciparum* malaria", *N. Engl. J. Med.*, 336(2):86-91 (1997).
Strbak et al., "Passive Immunization and Hypothalamic Peptide Secretion", *Neuroendocrinology*, 58:210-217 (1993).
Studnicka et al., "Human-engineered monocilnal antibodies retain full specific binding activity by preserving non-CDR complemenataryl-modullating resudes," Protien Eng., 7(6):805-814 (1994), Abstract only.
Sturchler-Pierrat et al., "Two amyloid precursor protein transgenic mouse models with Alzheimer disease-like pathology," PNAS, 94: 13287-13292 (1997).
Su et al., "Intravascular infusions of soluble β-amyloid compromise the blood-brain barrier, activate CNS Glial cells and induce peripheral hemorrhage," *Brain Research*, 818:105-107 (1999).
Suo et al., "Soluble Alzhelmers β-amyloid constricts the cerebral vasculature in vivo" *Neuroscience Letters*, 257:77-80 (1998).
Supplementary Partial European Search Report of Apr. 10, 2007 for European Application 04720353.4-1222.
Szendrei, et al., "The effects of aspartic acid-bond isomerization on in vitro properties of the amyloid β-peptide as modeled with N-terminal decapeptide fragments," Int. J. Peptide Protein Res., 47:289-296 (1996).
Tabaton et al., "Soluble amyloid b-protein is a marker of Alzheimer amyloid in brain but not in cerebrospinal fluid," *Biochem. and Biophys. Res. Comm.*, 200(3):1598-1603 (1994).
Tahtinen et al., "Minimal Size of HIV-1 NEF Antigenic Epitopes Reconzied by Human Sera," Int. Conf. AIDS Jun. 16-21, 1991, Published Jun. 1991, abstract No. W.A. 1334.
Tal et al., "Complete Freund's Adjuvant Immunization Prolongs Survival in Experimental Prion Disease in Mice," *Journal of Neuroscience Research*, 71:286-290 (2003).
Tam, "Synthetic peptide vaccine design: synthesis and properties of a high-density multiple antigenic peptide system", Proc. Natl. Acad. Sci., 1988, vol. 85, pp. 5409-5413.
Tamaokaet al., "Antibodies to amyloid β protein (A β) crossreact with glyceraldehyde-3-phosphate dehydrogenase (GAPDH)," *Neurobiology of Aging*, 3(17):405-414 (1996).
Tan et al., "Amyloidosis," *Histopathology*, 25:403-414 (1994).
Tanaka et al., "NC-1900, an active fragment analog of arginine vasopressin, improves learning and memory deficits induced by beta-amyloid protein in rats," *European J. Pharmacology*, 352:135-142 (1998).
Tang et al., "Genetic immunization is a siple method for eliciting an immune response," *Nature*, 356:152-154 (1992).
Teller et al., "Presence of soluble amyloid b-peptide precedes amyloid plaque formation in Down's syndrome" *Nature Medicine*, 2(1):93-95 (1996).
Tennent et al., "Serum amyloid P component prevents proteolysis of the amyloid fibrils of Alzheimer's disease and systemic amyloidosis," *PNAS*, 92:4299-4303 (1995).
Thorsett, E.D. et al., "Therapeutic approaches to Alzheimer's disease," *Curr. Op. in Chem. Biology*, 4:377-382 (2000).
Tjernberg et al., "A molecular model for Alzheimer amyloid b-peptide fibril formation," *J. Biol. Chem.*, 274(18):12619-12625 (1999).
Tjernberg et al., "Arrest of β-amyloid fibril formation by a pentapeptide ligand," *J. Biol. Chem.*, 271:8545-8548 (1996).
Tjernberg, et al, "Controlling amyloid β-peptide fibril formation with protease-stable ligands," *J. Biol Chem.*, 272(19):12601-12605 (1997).

(56) References Cited

OTHER PUBLICATIONS

Town et al., "Characterization of murine immunoglobulin G antibodies against human amyloid-b1-42" *Neurosci. Lett*, 307:101-104 (2001).
Trang et al., "Pharmacokinetics of a Mouse/Human Chimeric Monoclonal Antibody (C-17-1A) in Metastatic Adencarcinoma Patients," *Pharmacutical Research* 7(6):587-592 (1990).
Travis, J., "A Vaccine for Alzheimer's Disease?®," *Science News Online*, 156(2) pp. 1-3 downloaded from internet (1999).
Travis, J., "Saving the Mind Faces High Hurdles," *Science*, 309:731-734 (2005).
Trieb et al., "Is Alzheimer beta amyloid precursor protein (APP) an autoantigen? Peptides corresponding to parts of the APP sequence stimulate T lymphocytes in normals, but not in patients with Alzheimer's disease," Immunobiology, 191(2-3):114-115 Abstract C.37, (1994).
Trieb et al., "APP Peptides Stimulate Lymphocyte Proliferation in Normals, But Not in Patients With Alzheimer's Disease," *Neurobiology of Aging*, 17(4):541-547 (1996).
Tsuzuki et al., "Amyloid β protein in rat soleus in choroquine-induced myopthy using end-specific antibodies for Aβ40 and Aβ42: immunohistochemical evidence for amyloid β protein," *Neuroscience Letters*, 2002:77-80 (1995).
U.S. Appl. No. 09/316,387, Declaration of Solomon, Hrncic, and Wall under 37 C.F.R. § 1.131 filed Mar. 6, 2006.
U.S. Appl. No. 09/316,387, Office Action mailed Jun. 20, 2005.
U.S. Appl. No. 09/316,387, Office Action mailed Sep. 10, 2007.
U.S. Appl. No. 09/316,387, Response to Jun. 20, 2005 Office Action filed Dec. 20, 2005.
Ulvestad et al., "Fc Receptors for IgG on Cultured Human Microglia Mediate Cytotoxicity and Phagocytosis of Antibody-coated Targets," *Journal of Neuropathology and Experimental Neurology*, 53(1):27-36 (1994).
UniProtKB/Swiss-Prot entry P18525, pp. 1-3 downloaded from www.expasy.org/cgi-bin/niceprot.pl/printable?ac=P18525 on Feb. 8, 1997, "HV54_Mouse" (Nov. 1, 1990).
Urmoneit et al., "Cerebrovascular Smooth Muscle Cells Internalize Alzheimer Amyloid Beta Protein via a Lipoprotein Pathway: Implications for Cerebral Amyloid Angiopathy," *Laboratory Investigation*, 77(2):157-166 (1997).
Vajdos et al., "Comprehensive Functional Maps of the Antigen-binging site of an Anti_ErbB2 Antibody Obtained with Shotgun Scanning Mutagenesis," *J. Mol. Biol.*, 320:415-428 (2002).
Valleix et al., "Hereditary renal amyloidosis caused by a new variant lysozyme W64R in a French family," *Kidney International*, 61:907-912 (2002).
Van Den Dobbelsteen et al., "Characteristics of Immune Responses to Native and Protein Conjugated Pneumococcal Polysaccharide Type 14," *Scand. J. Immunol.*, 41:273-280 (1995).
Van Gool et al., "Concentrations of amyloid-β protein in cerebrospinal fluid increase with age in patients free from neurodegenerative disease," Neuroscience Letters, 172:122-124 (1994).
Van Leuven, F., "Single and multiple transgenic mice as models for Alzheimer's disease," *Progress in Neurobiology*, 61:305-312 (2000).
Van Regenmortel et al, "D-peptides as immunogens and diagnostic reagents," *Curr. Opin. Biotechnol.*, 9(4):377-382 (1998).
Vanderstichele et al., "Standardization of Measurement of B-amyloid(1-42) in Cerebrospinal Fluid and Plasma:," *Int. J. Exp. Clin. Invest.*, 7(4):245-258 (2000).
Vastag, "Monoclonals expand into neural disorders" Nature 24:6 p. 595-596 (Jun. 2006).
Vehmas et al., "Beta-Amyloid peptide vaccination results in marked changes in serum and brain Abeta levels in APPswe/PS1 DeltaE9 mice, as detected by SELDI-TOF-based ProteinChip® technology," *DNA Cell Biol.*, (11):713-721 (2001).
Velazquez et al., "Aspartate residue 7 in Amyloid β-protein is critical for classical complement pathway activation: Implications for Alzheimer's disease pathogenesis," *Nature Medicine*, 3(1):77-79 (1997).
Verbeek et al., "Accumulation of Intercellular Adhesion Molecule-1 in Senile Plaques in Brain Tissue of patients with Alzheimer's Disease," *Amer. Journ. Pathology*, 144(1):104-116 (1994).
Verma et al., "Gene therapy—promises, problems and prospects," *Nature*, 389:239-242 (1997).
Vershigora A. E. Obshchaya Immynologiya, pp. 35, 229-231 and 152-153 (1990).
Vickers, J. C., "A Vaccine Against Alzheimer's Disease," *Drugs Aging*, 19(7):487-494 (2002).
Vidanovic et al., "Effects of nonionic surfactants on the physical stability of immunoglobulin G in aqueous solution during mechanical agitation," *Die Pharmazie*, 58(6):399-404 (2003).
Viswanathan et al., "Cerebral Microhemorrhage", *Stroke.*, 37:550-555 (2006).
Walker et al., "Labeling of Cerebral Amyloid In Vivo with a Monoclonal Antibody," *J. Neuropath. Exp. Neurology*, 53(4):377-383 (1994).
Walsh et al., "Naturally secreted oligomers of amyloid β protein potently inhibit hippocampal long-term potentiation in vivo," *Nature*, 416(6880):535-539 (2002).
Wang et al, "Site-specific UBITh amyloid-β vaccine for immunotherapy of Alzheimer's disease" *Vaccine* 25 (2007) 3041-3052.
Wang et al., "Soluble oligomers of b amyloid (1-42) inhibit long-term potentiation but not long-term depression in rate dentate gyrus," *Brain Research*, 924:133-140 (2002).
Wang et al., "The levels of soluble versus insoluble brain Aβ distinguish Alzheimer's disease from normal and pathologic aging," *Experimental Neurology*, 158:328-337 (1999).
Wang, W., "Instability, stabilization, and formulation of liquid protein pharmaceuticals," *Int. J. Pharmaceutics*, 185(2):129-188 (1999).
Ward et al., "Spontaneous Deletions in IG Heavy Chain Genes Flaking Seuences Influence Splice Site Selection Nucleic Acids Research," 19(23): 6475-6480 (1991).
Washington University in St. Louis School of Medicine, "Study gives Clues to Working of Anti-Alzheimer Antibody," downloaded from www.medicine.wustl.edu/~wumpa/news on Dec. 15, 2004.
*Webster's New World Dictionary of American English*, Third College Edition, p. 1078 (1988).
*Webster's New World Dictionary*, p. 1387, therapeutic (1988).
Wehner, Declaration May 21, 2007.
Weiner et al., "Nasal administration of amyloid-β peptide decreases cerebral amyloid burden in a mouse model of Alzheimer's disease," *Ann. Neurol.*, 48:567-579 (2000).
Weiner et al., "Oral Tolerance: Immunologic Mechanisms and Treatment of Animal and Human Organ-Specific Autoimmune Diseases by Oral Administration of Autoantigens," *Annu. Rev. Immunol.*, 12:809-837 (1994).
Weiner, H. L., "Oral tolerance: immune mechanisms and treatment of autoimmune diseases," *Immunology Today*, 18:335-343 (1997).
Weinreb et al., "NACP, a Protein Implicated in Alzheimer's Disease and Learning, Is Natively Unfolded," *Biochemistry*, 35(43):13709-13715 (1996).
Weissmann et al., "Bovine spongiform encephalopathy and early onset variant Creutzfeldt-Jakob disease," *Curr. Opin. Neurobiol.*, 7:695-700 (1997).
Weldon et al., "Neurotoxicity of Aβ Peptide: Confocal Imaging of Cellular Changes Induced by —Amyloid in Rat CNS In Vivo," *Society for Neuroscicence Abstracts*, 22(Part 1) (1996).
Welling et al., "Choice of Peptide and Peptide Length for the Generation of Antibodies Reactive With the Intact Protein," *FEBS Letters*, 182(1):81-84 (Mar. 1985).
Wells, J. A., "Additivity of Mutational Effects in Proteins," *Biochemistry*, 29(37):8509-8517 (1990).
Wen, G.Y., "Alzheimer's Disease and Risk Factors," *J. Food Drug Analysis*, 6(2):465-476 (1998).
Wengenack et al., "Targeting Alzheimer amyloid plaques in vivo," *Nature Biotech.*, 18:868-872 (2000).
Whitcomb et al., "Characterization of saturable binding sites for circulating pancreatic polypeptide in rat brain," *Am J Pysiol Gastrointest Liver Physiol*, 259:G687-G691 (1990).

(56) References Cited

OTHER PUBLICATIONS

White et al., "Immunotherapy as a therapeutic treatment for neurodegenerative disorders," *J. Neurochem.*, 87(4):801-808 (2003).
Wikipedia definition of "antigen" printed from internet on Apr. 26, 2006.
Wikipedia definition of "epitope" printed from internet on Apr. 26, 2006.
Wikipedia definition of "route of administration including parenteral" printed from internet on Apr. 26, 2006.
Wikipedia entry for Antibody, retrieved Apr. 27, 2009 from en.wikipedia.org/wiki/Antibody.
Wilcock, et al. "Deglycosylated anti-Amyloid-β Antibodies Eliminate Cognitive Deficits and Reduce Parenchymal Amyloid with Minimal Vascular Consequences in Aged Amyloid Precursor Protein Transgenic Mice" Neurobiology of Disease 26(20:5340-5346 (May 17, 2006).
Wilson et al., "Phage display: applications, innovations, and issues in phage and host biology," *Can. J. Microbiol*, 44:313-329 (1998).
Winblad et al., "Hints of a therapeutic Vaccine for Alzheimer's?" *Neuron*, 38:517-519 (2003).
Winter et al., "Humanized antibodies" *Immunology Today*, 14(6):243-246 (1996).
Wisconsin Alumni Research Foundation, "Injection of Newborn Mice with Seven Chemical Adjuvants to Help Determine Their Safety in Use in Biologicals", U.S. Govt. Res. Develop. Rep., 70(24), 56 (1969).
Wisniewski et al., "Alzheimer's disease and soluble A beta," *Neurobiol. Aging*, 15(2):143-52 (1994).
Wisniewski et al., "Therapeutics in Alzheimer's and Prion Diseases," *Biochemical Society Transactions*, 30(4):574-587 (2002).
Wong et al., "Neuritic Plaques and Cerebrovascular Amyloid in Alzheimer Disease are Antigenically Related," *PNAS*, 82:8729-8732 (1985).
Wood et al., "Prolines and amyloidogenicily in fragments of the Alzheimer's peptide β/A4" *Biochemistry*, 34:724-730 (1995).
Wu et al., "An Analysis of the Sequences of the Variable Regions of Bence Jones Proteins and Myeloma Light Chains and their Implications for Antibody Complementarity," *J. Exp. Med.*, 132:211-250 (1970).
Wu et al., "Expression of immunogenic epitopes of hepatitis B surface antigen with hybrid flagellin proteins by a vaccine strain of *Salmonella*," *PNAS*, 86:4726-4730 (1989).
Wu et al., "Humanization of a Murine Monoclonal Antibody by Simultaneous Optimization of Framework and CDR Residues," *J. Mol. Biol.*, 294:151-162 (1999).
Wu, et al., "Drug targeting of a peptide radiopharmaceutical through the primate blood-brain barrier in vivo with a monoclonal antibody to the human insulin receptor," *J. Clin. Invest.*, 100:1804-1812 (1997).
Wyeth, Annual Review 2005: Creating Value . . . Advancing Health (Feb. 27, 2006).
Xiang et al., "Manipulation of the immune response to a plasmid-encoded viral antigen by coinoculation with plasmids expressing cytokines," *Immunity*, 2(2):129-135 Abstract (1995).
Xu et al., "Increased incidence of anti-β-amyloid autoantibodies secreted by Epstein-Barr virus transformed B cell lines from patients with Alzheimer's disease," *Mechanisms of Ageing and Development*, 94:213-222 (1997).
Yamada et al., "Generation and Characterization of Rat Monoclonal Antibodies Against Human Serum Amyloid A," *Scand. J. Immunol.*, 46(2):175-179 (1997).
Yamaguchi et al., Diffuse plaques associated with astroglial amyloid β protein, possibly showing a disappearing stage of senile plaques, *Acta Neuropathol.*, 95:217-222 (1998).
Yanagisawa K et al., "Amyloid BETA-protein (Alpha-Beta) associated with lipid molecules: immunoreactivity distinct from that of soluble Alpha-Beta," *FEBS Letters*, 1(420): 43-46 (1997).

Yang et al., "Effects of Racemization on the Aggregational Properties of the Amyloid β-Peptide in Alzheimer's Disease," abstract # 255 from American Chemical Society 214th National Meeting (1997).
Yang et al., "Monoclonal Antibody to the C-terminus of Beta-Amyloid," Neuroreport, 16(5):2117-2120 (1994).
Yankner et al., "Neurotrophic and Neurotoxic effects of Amyloid β Protein: Reversal by Tachykinin Neuropeptides," *Science*, 250:279-282 (1990).
Younkin, "Amyloid β vaccination: reduced plaques and improved cognition," *Nature Medicine*, 7:18-19 (2001).
Zameer et al., "Single Chain Fv Antibodies against 25-35 Peptide Fragment of Amyloid-β: Potential Therapeutic for Alzheimer's Disease," Abstract P4-420, p. S593, presented at Poster Session P4:Therapeutics and Therapeutic Strategies—Therapeutic Strategies, Amyloid-Based, also *Neurobiology of Aging*, 25(Suppl. 2): p. S593 (Jul. 2004).
Zhang et al., "A novel recombinant adeno-associated virus vaccine reduces behavioral impairment and β-amyloid plaques in a mouse model of Alzheimer's disease," *Neurobiology of Disease*, 14:365-379 (2003).
Zhang et al., "Specialized Applications, Purification of Recombinant Proteins and Study of Protein Interaction by Epitope Tagging," *Current Protocols in Mol. Biol.*, Supp 41, pp. 10.15.1 through 10.15.9 (1998).
Zlokovic et al., "Blood-Brain Barrier Transport of Circulating Alzheimer's Amyloid β" *Biochemical and Biophysical Research Communications*. vol. 197, No. 3, pp. 1034-1040 (1993).
Zlokovic et al., "Clearance of amyloid β-peptide from brain: transport or metabolism?," *Nature Medicine*, 6(7):718-719 (2000).
Zlokovic et al., "Glycoprotein 330/megalin: probable role in receptor-mediated transport of apolipoprotein J alone and in a complex with Alzheimer disease amyloid beta at the blood-brain and blood-cerebrospinal fluid barriers," *PNAS*, 93(9):4229-4334 (1996) abstract only.
U.S. Appl. No. 09/201,430, Notice of Allowance mailed Mar. 26, 2003.
U.S. Appl. No. 09/201,430, Notice of Allowance mailed Sep. 23, 2003.
U.S. Appl. No. 09/322,289, Notice of Allowance mailed Nov. 15, 2010.
U.S. Appl. No. 09/580,018, Notice of Allowance mailed Dec. 3, 2003.
U.S. Appl. No. 09/723,384, Notice of Allowance mailed Mar. 31, 2003.
U.S. Appl. No. 09/723,762, Notice of Allowance mailed May 1, 2003.
U.S. Appl. No. 09/723,927, Notice of Allowance mailed Sep. 23, 2003.
U.S. Appl. No. 09/724,102, Notice of Allowance mailed Aug. 22, 2003.
U.S. Appl. No. 09/724,288, Notice of Allowance mailed Mar. 23, 2009.
U.S. Appl. No. 09/724,477, Notice of Allowance mailed Apr. 30, 2003.
U.S. Appl. No. 09/724,477, Notice of Allowance mailed Sep. 23, 2003.
U.S. Appl. No. 09/724,489, Notice of Allowance mailed Mar. 25, 2003.
U.S. Appl. No. 09/724,489, Notice of Allowance mailed Sep. 22, 2003.
U.S. Appl. No. 09/724,551, Notice of Allowance mailed Dec. 4, 2003.
U.S. Appl. No. 09/724,552, Notice of Allowance mailed Dec. 3, 2003.
U.S. Appl. No. 09/724,567, Notice of Allowance mailed Mar. 3, 2004.
U.S. Appl. No. 09/724,940, Notice of Allowance mailed Oct. 4, 2004.
U.S. Appl. No. 09/724,953, Notice of Allowance mailed Mar. 11, 2004.
U.S. Appl. No. 09/724,961, Notice of Allowance mailed Dec. 3, 2003.

(56) References Cited

OTHER PUBLICATIONS

U.S. Appl. No. 09/979,952, Notice of Allowance mailed Nov. 12, 2004.
U.S. Appl. No. 10/010,942, Notice of Allowance mailed May 11, 2006.
U.S. Appl. No. 10/232,030, Notice of Allowance mailed Sep. 4, 2008.
U.S. Appl. No. 10/388,214, Notice of Allowance mailed Mar. 1, 2007.
U.S. Appl. No. 10/388,389, Notice of Allowance mailed May 31, 2006.
U.S. Appl. No. 10/815,353, Notice of Allowance mailed Jul. 1, 2004.
U.S. Appl. No. 10/815,391, Notice of Allowance mailed Jul. 1, 2004.
U.S. Appl. No. 10/815,404, Notice of Allowance mailed Oct. 15, 2004.
U.S. Appl. No. 10/816,022, Notice of Allowance mailed Jul. 1, 2004.
U.S. Appl. No. 10/816,380, Notice of Allowance mailed Dec. 22, 2004.
U.S. Appl. No. 10/816,529, Notice of Allowance mailed Jul. 1, 2004.
U.S. Appl. No. 10/858,855, Notice of Allowance mailed Jul. 12, 2010.
U.S. Appl. No. 10/884,892, Notice of Allowance mailed Mar. 28, 2005.
U.S. Appl. No. 10/923,469, Notice of Allowance mailed Jun. 1, 2011.
U.S. Appl. No. 10/933,559, Notice of Allowance mailed Aug. 17, 2005.
U.S. Appl. No. 10/933,559, Notice of Allowance mailed Sep. 7, 2005.
U.S. Appl. No. 10/933,559, Notice of Allowance mailed Dec. 22, 2004.
U.S. Appl. No. 10/934,609, Notice of Allowance mailed Aug. 17, 2005.
U.S. Appl. No. 10/934,609, Notice of Allowance mailed Dec. 22, 2004.
U.S. Appl. No. 11/304,986, Notice of Allowance mailed Jul. 10, 2009.
U.S. Appl. No. 11/707,639, Notice of Allowance mailed Aug. 20, 2009.
U.S. Appl. No. 11/842,023, Notice of Allowance mailed Oct. 6, 2010.
U.S. Appl. No. 11/893,123, Notice of Allowance mailed Nov. 2, 2011.
U.S. Appl. No. 12/181,238, Notice of Allowance mailed Mar. 5, 2010.
U.S. Appl. No. 12/181,238, Notice of Allowance mailed Mar. 11, 2011.
U.S. Appl. No. 10/429,216, Office Action mailed May 24, 2011.
Andrews, et al., "Amino acid sequence of the variable regions of heavy chains from two idiotypically cross-reactive human IgM anti-gamma-globulins of the Wa group", *Biochemistry*, Sep. 29, 1981;20(20):5822-5830.
Andrews, et al., "Complete amino acid sequence of variable domains from two monoclonal human anti-gamma globulins of the Wa cross-idiotypic group: Suggestion that the J segments are involved in the structural correlate of the idiotype", *Proc. Natl. Acad. Sci. USA*, vol. 78, No. 6, pp. 3799-3803, Jun. 1981.
Capra, et al., "Structure of Antibodies with Shared Idiotypy: The Complete Sequence of the Heavy Chain Variable Regions of Two Immunoglobulin M Anti-Gamma Globulins", *Proc. Nat. Acad. Sci. USA*, vol. 71, No. 10, pp. 4032-4036, Oct. 1974.
Chalmers et al., "APOE epsilon 4 influences the pathological phenotype of Alzhemier's disease by favouring cerebrovascular over parechyma accumulation of A beta protein", Neuropathology and Applied Neurobiology, vol. 29, No. 3 pp. 231-238 (2003).

European Extended Search Report of Mar. 1, 2012 for European Application 08839961.
European Extended Search Report of Mar. 15, 2012 for European Application 09075267.6.
GenBank, Accession No. AAA38630.1, "Immunoglobulin gamma-1 chain [*Mus musculus*]"May 5, 1994.
Greaves, et al., "Posterior reversible encephalopathy syndrome following anti-lymphocyte globulin treatment for severe aplastic anaemia" *British Journal of Heamatology*, Aug. 2006: 13493):251.
PCT/US2011/026365 International Preliminary Report on Patentability mailed Mar. 5, 2012.
Raber, et al., "ApoE genotype accounts for the vast majority of AD risk and AD pathology" *Neurobiology of Aging*, 25:641-650 (2004).
Vanengelen, et al "Immunoglobulin treatment in human and experimental epilepsy" *J of Neuro* (1994); 57 (supplement):72-75.
U.S. Appl. No. 12/977,013, Office Action mailed Jan. 6, 2012.
U.S. Appl. No. 12/297,636, Office Action mailed Oct. 15, 2012.
U.S. Appl. No. 13/076,379, Office Action mailed Nov. 28, 2012.
U.S. Appl. No. 13/123,898, Office Action mailed Jul. 20, 2012.
Castillo, "Poor results halt production, studies on promising Alzheimer's drug bapineuzumab" *CBS Interactive Inc.*, Nov. 7, 2012 pp. 1/1.
Centers for Disease Control and Prevention, "Vaccine Safety" Retrieved from www.cdc.gov/vaccinesafety/concerns/adjuants.html (Oct. 18, 2012) p. 1-2.
Dohi et al., "Reactivity of a Mouse/Human Chimeric Anti-GM2 Antibody KM966 with Brain Tumors" *Anticancer Research*, 14:2577-2582 (1994).
Eli Lilly, "Eli Lilly and Company Announces Top-Line Results on Solanezumab Phase 3 Clinical Trials in Patients with Alzheimer's Disease" Press Release, Aug. 24, 2012.
Geeraedts et al., "Superior Immunogenicity of Inactivated Whole Virus H5N1 Influenza Vaccine is Primarily Controlled by Toll-like Receptors Signalling", *PLoS Pathogens*, 2008, 4:1-8.
Gluck et al., "Immunopotentiating Reconstituted Influenza Virus Virosome Vaccine Delivery System for Immunization against Hepatitis A", *J. Clin. Invest.*,(1992) vol.90:2491-2495.
Gluck, "Immunopotentiating reconstituted influenza virosomes (IRIVs) and other adjuvants for improved presentation of small antigens", *Vaccine*, vol. 10, Issue 13 (1992) 915-919.
Hagen, Declaration Oct. 31, 2011.
Johnson & Johnson, "Johnson & Johnson Announces Discontinuation of Phase 3 Development of Bapineuzumab Intravenous (IV) in Mild-to-Moderate Alzheimer's Disease", Press Release, Aug. 6, 2012.
Kerchner, et al., "Bapineuzumab", NIH Public Access, Expert Opin Biol Ther., 10(7) 1121-1130 Jul. 2010.
Lee et al., "Aspects of Immunobiology and Immunotherapy and Uses of Monoclonal Antibodies and Biologic Immune Modifiers in Human Gliomas" *Neurologic Clinics*, vol. 3, No. 4, Nov. 1985, 901-917.
Lemere et al., "Amyloid-Beta Immunotherapy for the Prevention and Treatment of Alzheimer Disease: Lessons from Mice, Monkeys, and Humans", Rejuvenation Reasearch 9(1):77-84 (2006).
Marx et al., "The Possible Role of the Immune System in Alzheimer's Disease" *Exp Gerontology*, vol. 33, Nos. 7/8 pp. 871-881, 1998.
Miller et al., "Comparative efficacy of two immunocontraceptive vaccines" *Vaccine*, (1997) 15(17-18):1858-1862 (abstract only).
Oh, et al., "Reversible leukoencephalopathy associated with cerebral amyloid angiopathy", *Neurology*, 62 (Feb. 2004) 494-497.
Pfizer Announces Co-Primary Clinical Endpoints Not Met in Second Phase 3 Bapineuzumab Study in Mild-to-Moderate Alzheimer's Disease Patients Who Do Not Carry the Apoe4 Genotype, Press Release, Aug. 6, 2012.
Pfizer, "Pfizer Announces Topline Results of First of Four Studies in Bapineuzumab Phase 3 Program", Press Release, Jul. 23, 2012.
Remes et al., "Hereditary dementia with intracerevbral hemorrhages and cerebral amyloid angiopathy". *Neurology* 63(2):234-240 (2004).
Rivero et al., "Suppression of experimental autoimmune encephalomyelitis (EAE) by intraperitoneal administration of soluble myelin antigens in Wistar rats" *J. Neuroimmunology*, (1997) 72, 3-10.

(56) References Cited

OTHER PUBLICATIONS

Solomon, "Alzheimer's Disease and Immunotherapy", *Current Alzheimer Research*, 2004, 1, 149-163.
Solomon, "Beta-Amyloid-Based Immunotherapy as a Treatment of Alzheimer's Disease", *Drugs of Today*, 2007, 43(5):333-342.
Spack, "Antigen-specific therapies for the treatment of multiple sclerosis: a clinical trial update", *Exp. Opin. Invest. Drugs*, (1997) 6(11):1715-1727.
Sperling, et al., "Amyloid-related imaging abnormalities in amyloid-modifying therapeutic trials: Recommendations from the Alzheimer's Association Research Roundtable Workgroup" *Alzheimer's & Dementia*, 7 (2011) 397-385.
Triozzi et al., "Effects of a beta-human chorionic gonadotropin subunit immunogen administered in aqueous solution with a novel nonionic block copolymer adjuvant in patients with advanced cancer", *Clin. Cancer Res.*, (1997) 3(12 pt 1):2355-2362 (abstract only).
Wick et al., "The Aging Immune System: Primary and Secondary Alterations of Immune Reactivity in the Elderly" *Exp. Geronology*, vol. 32, Nos. 4/5, pp. 401-413, 1997.
U.S. Appl. No. 12/608,869, Office Action mailed Aug. 23, 2012.
U.S. Appl. No. 12/977,013, Office Action mailed Sep. 14, 2012.
Abbott, et al., "Transporting therapeutics across the blood-brain barrier" *Molecular Medicine Today*, pp. 106-113, Mar. 1996.
Annual Report of Johnson and Johnson p. 1-6 (2012).
Arriagada, et al., "Neurofibrillary tangles but not senile plaques parallel duration and severity of Alzheimer's disease", *Neurology*, 42:631-639 (1992).
Barbour, et al., Presentation of "Efficacy and Neuropathology of Passively Administered N-Terminal and Midregion Anti-Abeta Antibodies Alone and in Combination in the PDAPP Mouse" Elan Report pp. 1-99 May 2007.
Check, "Nerve inflammation halts trial for Alzheimer's drug", *Nature*, vol. 415:462 Jan. 2002.
Curriculum Vitae Professor Nancy Joan Abbott, Mar. 2013.
Deane, et al. "IgG-Assisted Age-Dependent Clearance of Alzheimer's Amyloid β Peptide by the Blood-Brain Barrier Neonatal Fc Receptor" *The Journal of Neuroscience*, Dec. 14, 2005 25(50):11495-11503.
Declaration by Dr. Dale Schenk dated Nov. 21, 2011.
Declaration of Dr. Michael John Owen with CV and list of publications May 10, 2013.
Declaration of Georg Friedrich Melchers with CV and list of publications Apr. 6, 2013.
Declaration of Professor Nancy Joan Abbott, Apr. 8, 2013.
Dodel, et al., "Intravenous immunoglobulins containing antibodies against beta-amyloid for the treatment of Alzheimer's disease", *J. Neurol. Neurosurg. Psychiatry*, 75:1472-1474 (2004).
Eli Lilly and Company vs Janssen Alzheimer Immunotherapy, Approved Judgment, Case No. HC11C03400, Royal Courts of Justice, London, Jun. 25, 2013.
EP 1 994 937 Minutes of Oral Proceedings from EP Opposition Division, Jun. 24, 2013.
EP 1160256 B2 Response to Notice of Opposition Jan. 19, 2009.
Extract from EPO patent register of EP1842859 Communication under Rule 71(3) Mar. 28, 2013.
Extract from EPO patent register of EP1842859 Decision to Grant Mar. 28, 2012.
Farlow, et al., "Safety and biomarker effects of solanezumab in patients with Alzheimer's disease" *Alzheimer's & Dementia*, 8:261-271 (2012).
Gerald, et al., "Alzheimer's disease market: hope deferred", *Nature*, vol. 12:19-20 Jan. 2013.
Hyslop et al., " Antibody Clears Senile Plaques" *Nature*, vol. 400, Jul. 8, 1999, p. 116-117.
Jacobsen, et al., "Reversal of CM Deficits: A) 2nd Generation of mAbs to central AB epitopes B) PSAPP (18 mo) by 12A11 fly. 1.0 & m266", *Wyeth Presentation* Apr. 27, 2004.
Janeway et al., Immunobiology, 3rd edition, pp. 8:32-8:36 (1997).

Janeway, et al., *Basic Concepts in Immunology*; pp. 1:21-1:13and 8:1-8:2 (1997).
Janssen Alzheimer Immunotherapy Research & Development, LLC, "AAB-001 in Patients With Mild to Moderate Alzheimer's Disease", *Clinical Trials. Gov, NIH*, 2005, [retrieved on Jun. 19, 2012] Retrieved from the Internet: clinicaltrials.gov/ct2/show/NCT00112073?term=aab-001&rant=3>.
Karran, "Current status of vaccination therapies in Alzheimer's disease" *Journal of Neurochemistry*, 123:647-651 (2012).
Laino, "Cerebral Edema Common, but Found to Be Manageable, With Bapineuzumab", *Neurology Today*, Aug. 19, 2011.
Lu, "In Vitro Binding Analysis of LY2062430: Surface Plasmon Resonance and FACS Analysis" Report: bTDR185 Eli Lilly and Company Apr. 2012.
Muhs, et al., "Liposomal vaccines with conformation-specific amyloid peptide antigens define immune response and efficacy in AAP transgenic mice", *PNAS*, Jun. 5, 2007, vol.104:23 pp. 9810-9815.
Orgogozo, et al., "Subacute meningoencephalitis in a subset of patients with AD after Aβ42 immunization" *Neurology*, 61:46-54 (2003 ).
Pfizer Halts Development of AB Antibody, Alzheimer Research Forum, Nov. 2, 2011.
Rieber, et al., "The Effect of Freund's Adjuvants on Blood-Cerebrospinal Fluid Barrier Permeability" *Journal of the Neurological Sciences*, 63:55-61 (1984).
Roitt, Extracts from Roitt's Essential Immunology, Ninth Edition, (1997).
Servillo, et al., "Posterior reversible encphalopathy syndrome in intensive care medicine" *Intensive Care Med*, (2007) 33:230-236.
Smith, et al., "Use of structural inaging to study the progression of Alzheimer's disease", *Brit. Med. Bull.*, 52(3):575-586, (1996).
Sperling, et al., Presentation and Transcript of "Bapineuzumab Phase 3 trials in mild to moderate Alzheimer's disease dementia in apolipoprotein E ϵ4 carriers (Study 302) and non-carriers (Study 301)", *American Neurological Association*, Oct. 8, 2012.
Staykov, et al., "Posterior Reversible Encephalopathy Syndrome", *Journal of Intensive Care Medicine*, originally published online Jan. 21, 2011 at: jic.sagepub.com/content/27/1/11.
Thompson, et al., "Laboratory investigation of cerebrospinal fluid proteins" *Ann Clin Biochem*, 27:425-435 (1990).
Triguero, et al., "Blood-brain barrier transport of cationized immunoglobulin G: Enhanced delivery compared to native protein" *Proc. Natl. Acad. Sci. USA*, vol. 86:4761-4765 Jun. 1989.
Trojano, et al., "Serum IgG to brain microvascular endothelial cells in multiple sclerosis" *Journal of the Neurological Sciences*, 143:107-113 (1996).
Tuomanen, et al., "Reversible opening of the blood-brain barrier by anti-bacterial antibodies" *Proc. Natl. Acad. Sci. USA*, vol. 90:7824-7828 (Aug. 1993).
Walls, et al., "Autoantibody responses in the cerebrospinal fluid of guinea pigs with chronic relapsing experimental allergic encephalomyelitis", *Acta Neruol. Scan.*, 78:422-428 (1988).
Weyer, et al., "A controlled study of 2 doses of idebenone in the treatment of Alzheimer's disease", *Neuropsychobiology*, 36(2):73-82, Abstract only (Jan. 1997).
Wilcock, et al. "Passive Amyloid Immunotherapy Clears Amyloid and Transiently Activates Microglia in a Transgenic Mouse Model of Amyloid Deposition" *The Journal of Neuroscience*, Jul. 7, 2004 24(27):6144-6151.
Wilcock, et al., "Number of AB Inoculations in APP+PSI Transgenic Mice Influences Antibody Titers, Microglial Activation, and Congophilic Plaque Levels" *DNA and Celll Biology*, vol. 20 No. 11: 731-736 (2001).
U.S. Appl. No. 13/271,081, Office Action mailed Mar. 1, 2013.
U.S. Appl. No. 13/270,015, Office Action mailed Jun. 19, 2013.
U.S. Appl. No. 10/923,471, Notice of Allowance mailed May 21, 2013.
U.S. Appl. No. 12/297,636, Notice of Allowance mailed May 28, 2013.
U.S. Appl. No. 10/923,471, Office Action mailed Apr. 23, 2013.
U.S. Appl. No. 13/123,898, Office Action mailed Apr. 17, 2013.

(56) References Cited

OTHER PUBLICATIONS

U.S. Appl. No. 11/842,116, Notice of Allowance mailed Sep. 24, 2013.
U.S. Appl. No. 13/123,898, Notice of Allowance mailed Jan. 17, 2014.
U.S. Appl. No. 11/303,478, Office Action mailed Jan. 31, 2014.
U.S. Appl. No. 11/842,042, Office Action mailed May 22, 2014.
U.S. Appl. No. 12/608,869, Office Action mailed Nov. 4, 2014.
U.S. Appl. No. 12/738,396, Office Action mailed Nov. 17, 2014.
U.S. Appl. No. 12/977,013, Office Action mailed Jul. 1, 2013.
U.S. Appl. No. 10/010,942, filed Dec. 6, 2001; issued as U.S. Pat. No. 7,189,819 on Mar. 13, 2007.
U.S. Appl. No. 10/232,030, filed Aug. 30, 2002; issued as U.S. Pat. No. 7,582,733 on Sep. 1, 2009.
U.S. Appl. No. 10/388,214, filed Mar. 12, 2003; issued as U.S. Pat. No. 7,256,273 on Aug. 14, 2007.
U.S. Appl. No. 10/388,389, filed Mar. 12, 2003; issued as U.S. Pat. No. 7,179,892 on Feb. 20, 2007.
U.S. Appl. No. 10/583,503, filed Jun. 16, 2006; issued as U.S. Pat. No. 8,227,403 on Jul. 24, 2012.
U.S. Appl. No. 10/858,855, filed Jun. 1, 2004; issued as U.S. Pat. No. 7,871,615 on Jan. 18, 2011.
U.S. Appl. No. 11/244,678, filed Oct. 5, 2005; issued as U.S. Pat. No. 7,807,804 on Oct. 5, 2010.
U.S. Appl. No. 11/303,478, filed Dec. 15, 2005; issued as U.S. Pat. No. 8,916,165 on Dec. 24, 2014.
U.S. Appl. No. 11/304,986, filed Dec. 15, 2005; issued as U.S. Pat. No. 7,825,223 on Dec. 1, 2009.
U.S. Appl. No. 11/342,353, filed Jan. 27, 2006; issued as U.S. Pat. No. 7,635,473 on Dec. 22, 2009.
U.S. Appl. No. 11/454,772, filed Jun. 16, 2006; issued as U.S. Pat. No. 7,825,223 on Nov. 2, 2010.
U.S. Appl. No. 11/455,203, filed Jun. 16, 2006; issued as U.S. Pat. No. 7,820,799 on Oct. 26, 2010.
U.S. Appl. No. 11/707,639, filed Feb. 16, 2007; issued as U.S. Pat. No. 7,700,751 on Apr. 20, 2010.
U.S. Appl. No. 11/841,919, filed Aug. 20, 2007.
U.S. Appl. No. 12/181,238, filed Jul. 28, 2008; issued as U.S. Pat. No. 8,003,097 on Aug. 23, 2011.
U.S. Appl. No. 12/297,636, filed May 10, 2010 (US National Stage of PCT/US07/009499 filed Apr. 18, 2007 (contested)); issued as U.S. Pat. No. 8,613,920 on Dec. 24, 2013.
U.S. Appl. No. 12/608,869, filed Oct. 29, 2009.
U.S. Appl. No. 12/637,508, filed Dec. 14, 2009; issued as U.S. Pat. No. 8,318,164 on Nov. 27, 2012.
U.S. Appl. No. 12/738,396, filed Jun. 24, 2010 (US National Stage of PCT/US08/080382 filed Oct. 17, 2008).
U.S. Appl. No. 12/903,053, filed Oct. 12, 2010; issued as U.S. Pat. No. 8,440,799 on May 15, 2013.
U.S. Appl. No. 13/123,898, filed Apr. 13, 2011; issued as U.S. Pat. No. 8,784,810 on Jul. 22, 2014.
U.S. Appl. No. 13/178,428, filed Jul. 7, 2011.
U.S. Appl. No. 13/231,903, filed Sep. 13, 2011.
U.S. Appl. No. 13/396,543, filed Feb. 14, 2012.
U.S. Appl. No. 13/580,866, filed Aug. 23, 2012.
U.S. Appl. No. 13/642,845, filed Oct. 22, 2012.
U.S. Appl. No. 14/017,177, filed Sep. 3, 2013.
U.S. Appl. No. 09/201,430, filed Nov. 30, 1998; issued as U.S. Pat. No. 6,787,523 on Sep. 7, 2004.
U.S. Appl. No. 09/322,289, filed May 28, 1999; issued as U.S. Pat. No. 7,964,020 on Jun. 21, 2011.
U.S. Appl. No. 09/580,018, filed May 26, 2000; issued as U.S. Pat. No. 6,761,888 on Jul. 13, 2004.
U.S. Appl. No. 09/723,384, filed Nov. 27, 2000; issued as U.S. Pat. No. 6,710,226 on Mar. 23, 2004.
U.S. Appl. No. 09/723,762, filed Nov. 28, 2000; issued as U.S. Pat. No. 6,787,144 on Sep. 7, 2004.
U.S. Appl. No. 09/723,765, filed Nov. 28, 2000; issued as U.S. Pat. No. 7,588,766 on Sep. 15, 2009.
U.S. Appl. No. 09/723,927, filed Nov. 28, 2000; issued as U.S. Pat. No. 6,787,138 on Sep. 7, 2004.
U.S. Appl. No. 09/724,102, filed Nov. 28, 2000; issued as U.S. Pat. No. 6,787,139 on Sep. 7, 2004.
U.S. Appl. No. 09/724,288, filed Nov. 28, 2000; issued as U.S. Pat. No. 7,575,880 on Aug. 18, 2009.
U.S. Appl. No. 09/724,477, filed Nov. 28, 2000; issued as U.S. Pat. No. 6,787,143 on Sep. 7, 2004.
U.S. Appl. No. 09/724,489, filed Nov. 28, 2000; issued as U.S. Pat. No. 6,787,140 on Sep. 7, 2004.
U.S. Appl. No. 09/724,551, filed Nov. 28, 2000; issued as U.S. Pat. No. 6,787,637 on Sep. 7, 2004.
U.S. Appl. No. 09/724,552, filed Nov. 28, 2000; issued as U.S. Pat. No. 6,750,324 on Jun. 15, 2004.
U.S. Appl. No. 09/724,567, filed Nov. 28, 2000; issued as U.S. Pat. No. 6,890,535 on May 10, 2005.
U.S. Appl. No. 09/724,570, filed Nov. 28, 2000; issued as U.S. Pat. No. 6,936,246 on Aug. 30, 2005.
U.S. Appl. No. 09/724,940, filed Nov. 28, 2000; issued as U.S. Pat. No. 6,905,686 on Jun. 14, 2005.
U.S. Appl. No. 09/724,953, filed Nov. 28, 2000; issued as U.S. Pat. No. 6,875,434 on Apr. 5, 2005.
U.S. Appl. No. 09/724,961, filed Nov. 28, 2000; issued as U.S. Pat. No. 6,743,427 on Jun. 1, 2004.
U.S. Appl. No. 09/979,952, filed Apr. 9, 2002 (US National Stage of PCT/US00/15239 filed Jun. 1, 2000); issued as U.S. Pat. No. 6,913,745 on Jul. 5, 2005.
U.S. Appl. No. 10/699,517, filed Oct. 31, 2003; issued as U.S. Pat. No. 7,727,957 on Jun. 1, 2010.
U.S. Appl. No. 10/815,353, filed Mar. 31, 2004; issued as U.S. Pat. No. 6,808,712 on Oct. 26, 2004.
U.S. Appl. No. 10/815,391, filed Mar. 31, 2004; issued as U.S. Pat. No. 6,866,849 on Mar. 15, 2005.
U.S. Appl. No. 10/815,404, filed Mar. 31, 2004; issued as U.S. Pat. No. 6,982,084 on Jan. 3, 2006.
U.S. Appl. No. 10/816,022, filed Mar. 31, 2004; issued as U.S. Pat. No. 6,866,850 on Mar. 15, 2005.
U.S. Appl. No. 10/816,380, filed Mar. 31, 2004; issued as U.S. Pat. No. 7,014,855 on Mar. 21, 2006.
U.S. Appl. No. 10/816,529, filed Mar. 31, 2004; issued as U.S. Pat. No. 6,818,218 on Nov. 16, 2004.
U.S. Appl. No. 10/884,892, filed Jul. 1, 2004; issued as U.S. Pat. No. 6,962,707 on Nov. 8, 2005.
U.S. Appl. No. 10/923,469, filed Aug. 20, 2004; issued as U.S. Pat. No. 8,034,339 on Oct. 11, 2011.
U.S. Appl. No. 10/923,471, filed Aug. 20, 2004; issued as U.S. Pat. No. 8,535,673 on Sep. 17, 2013.
U.S. Appl. No. 10/933,559, filed Sep. 2, 2004; issued as U.S. Pat. No. 6,972,127 on Dec. 6, 2005.
U.S. Appl. No. 10/934,609, filed Sep. 2, 2004; issued as U.S. Pat. No. 6,946,135 on Sep. 20, 2005.
U.S. Appl. No. 11/520,438, filed Sep. 12, 2006; issued as U.S. Pat. No. 7,790,856 on Sep. 7, 2010.
U.S. Appl. No. 11/809,552, filed Jun. 1, 2007; issued as U.S. Pat. No. 8,357,781 on Jan. 22, 2013.
U.S. Appl. No. 11/842,023, filed Aug. 20, 2007; issued as U.S. Pat. No. 7,893,214 on Feb. 22, 2010.
U.S. Appl. No. 11/842,042, filed Aug. 20, 2007.
U.S. Appl. No. 11/842,113, filed Aug. 20, 2007; issued as U.S. Pat. No. 8,034,348 on Oct. 11, 2011.
U.S. Appl. No. 11/842,116, filed Aug. 20, 2007; issued as U.S. Pat. No. 8,642,044 on Feb. 4, 2014.
U.S. Appl. No. 13/270,015, filed Oct. 10, 2011.
U.S. Appl. No. 10/703,713, filed Nov. 7, 2003.
U.S. Appl. No. 10/704,070, filed Nov. 7, 2003.
U.S. Appl. No. 10/771,174, filed Feb. 4, 2004.
U.S. Appl. No. 10/789,273, filed Feb. 27, 2004.
U.S. Appl. No. 11/260,047, filed Oct. 26, 2005.
U.S. Appl. No. 11/304,072, filed Dec. 15, 2005.
U.S. Appl. No. 11/305,889, filed Dec. 15, 2005.
U.S. Appl. No. 11/305,899, filed Dec. 15, 2005.
U.S. Appl. No. 11/342,252, filed Jan. 27, 2006.
U.S. Appl. No. 11/396,417, filed Mar. 30, 2006.

(56) References Cited

OTHER PUBLICATIONS

U.S. Appl. No. 11/413,638, filed Apr. 28, 2006.
U.S. Appl. No. 11/516,724, filed Sep. 5, 2006.
U.S. Appl. No. 11/841,794, filed Aug. 20, 2007.
U.S. Appl. No. 11/841,832, filed Aug. 20, 2007.
U.S. Appl. No. 11/841,849, filed Aug. 20, 2007.
U.S. Appl. No. 11/841,857, filed Aug. 20, 2007.
U.S. Appl. No. 11/841,882, filed Aug. 20, 2007.
U.S. Appl. No. 11/841,897, filed Aug. 20, 2007.
U.S. Appl. No. 11/841,950, filed Aug. 20, 2007.
U.S. Appl. No. 11/842,056, filed Aug. 20, 2007.
U.S. Appl. No. 11/893,094, filed Aug. 13, 2007.
U.S. Appl. No. 11/893,103, filed Aug. 13, 2007.
U.S. Appl. No. 11/893,110, filed Aug. 13, 2007.
U.S. Appl. No. 11/893,123, filed Aug. 13, 2007.
U.S. Appl. No. 11/894,714, filed Aug. 20, 2007.
U.S. Appl. No. 11/894,754, filed Aug. 20, 2007.
U.S. Appl. No. 11/894,789, filed Aug. 20, 2007.
U.S. Appl. No. 12/106,206, filed Apr. 18, 2008.
U.S. Appl. No. 12/253,929, filed Oct. 17, 2008.
U.S. Appl. No. 60/251,892, filed Dec. 6, 2000.
U.S. Appl. No. 60/363,751, filed Mar. 12, 2002.
U.S. Appl. No. 60/444,150, filed Feb. 1, 2003.
U.S. Appl. No. 60/474,654, filed May 30, 2003.
U.S. Appl. No. 60/530,480, filed Dec. 17, 2003.
U.S. Appl. No. 60/530,481, filed Dec. 17, 2003.
U.S. Appl. No. 60/616,474, filed Oct. 5, 2004.
U.S. Appl. No. 60/622,525, filed Oct. 26, 2004.
U.S. Appl. No. 60/636,684, filed Dec. 15, 2004.
U.S. Appl. No. 60/636,687, filed Dec. 15, 2004.
U.S. Appl. No. 60/636,776, filed Dec. 15, 2004.
U.S. Appl. No. 60/636,810, filed Dec. 15, 2004.
U.S. Appl. No. 60/636,842, filed Dec. 15, 2004.
U.S. Appl. No. 60/637,138, filed Dec. 16, 2004.
U.S. Appl. No. 60/637,253, filed Dec. 16, 2004.
U.S. Appl. No. 60/648,631, filed Jan. 28, 2005.
U.S. Appl. No. 60/648,639, filed Jan. 28, 2005.
U.S. Appl. No. 60/691,821, filed Jun. 17, 2005.
U.S. Appl. No. 60/735,687, filed Nov. 10, 2005.
U.S. Appl. No. 60/736,045, filed Nov. 10, 2005.
U.S. Appl. No. 60/736,119, filed Nov. 10, 2005.
U.S. Appl. No. 60/793,014, filed Apr. 18, 2006.
U.S. Appl. No. 60/925,228, filed Oct. 17, 2007.
U.S. Appl. No. 60/999,423, filed Oct. 17, 2007.
U.S. Appl. No. 61/083,827, filed Jul. 25, 2008.
U.S. Appl. No. 61/110,538, filed Oct. 31, 2008.
U.S. Appl. No. 61/197,878, filed Oct. 30, 2008.
U.S. Appl. No. 61/308,253, filed Feb. 25, 2010.
U.S. Appl. No. 61/327,062, filed Apr. 22, 2010.
U.S. Appl. No. 61/450,619, filed Mar. 8, 2011.
U.S. Appl. No. 13/004,014, filed Jan. 10, 2011.
U.S. Appl. No. 13/076,379, filed Mar. 20, 2011.
U.S. Appl. No. 10/583,464, filed Jan. 16, 2007 (US National Stage of PCT/US04/042701 filed Dec. 17, 2004).
U.S. Appl. No. 12/037,045, filed Feb. 25, 2008.
U.S. Appl. No. 10/544,093, filed Aug. 1, 2005 (US National Stage of PCT/US04/002856 filed Jan. 31, 2004).
U.S. Appl. No. 11/664,865, filed Jan. 15, 2009.
U.S. Appl. No. 11/841,993, filed Aug. 20, 2007.
U.S. Appl. No. 09/204,838, filed Dec. 3, 1998.
U.S. Appl. No. 09/497,553, filed Feb. 3, 2000.
U.S. Appl. No. 09/579,690, filed May 26, 2000.
U.S. Appl. No. 09/580,015, filed May 26, 2000.
U.S. Appl. No. 09/580,019, filed May 26, 2000.
U.S. Appl. No. 09/585,656, filed Jun. 1, 2000.
U.S. Appl. No. 09/723,544, filed Nov. 28, 2000.
U.S. Appl. No. 09/723,713, filed Nov. 27, 2000.
U.S. Appl. No. 09/723,725, filed Nov. 27, 2000.
U.S. Appl. No. 09/723,760, filed Nov. 27, 2000.
U.S. Appl. No. 09/723,766, filed Nov. 27, 2000.
U.S. Appl. No. 09/724,273, filed Nov. 28, 2000.
U.S. Appl. No. 09/724,291, filed Nov. 28, 2000.
U.S. Appl. No. 09/724,495, filed Nov. 27, 2000.
U.S. Appl. No. 09/724,575, filed Nov. 28, 2000.
U.S. Appl. No. 09/724,921, filed Nov. 28, 2000.
U.S. Appl. No. 09/724,929, filed Nov. 28, 2000.
U.S. Appl. No. 09/979,701, filed Mar. 13, 2001 (US National Stage of PCT/US00/14810 filed May 26, 2000).
U.S. Appl. No. 09/980,568, filed Mar. 12, 2002 (US National Stage of PCT/US00/15302 filed Jun. 1, 2000).
U.S. Appl. No. 10/777,792, filed Feb. 11, 2004.
U.S. Appl. No. 10/788,666, filed Feb. 27, 2004.
U.S. Appl. No. 10/822,968, filed Apr. 12, 2004.
U.S. Appl. No. 10/823,463, filed Apr. 12, 2004.
U.S. Appl. No. 10/828,548, filed Apr. 19, 2004.
U.S. Appl. No. 10/889,999, filed Apr. 12, 2004.
U.S. Appl. No. 10/890,000, filed Jul. 12, 2004.
U.S. Appl. No. 10/890,024, filed Apr. 12, 2004.
U.S. Appl. No. 10/890,070, filed Jul. 12, 2004.
U.S. Appl. No. 10/890,071, filed Jul. 12, 2004.
U.S. Appl. No. 10/923,267, filed Aug. 20, 2004.
U.S. Appl. No. 10/923,474, filed Aug. 20, 2004.
U.S. Appl. No. 10/923,605, filed Aug. 20, 2004.
U.S. Appl. No. 10/928,926, filed Aug. 27, 2004.
U.S. Appl. No. 10/934,818, filed Sep. 2, 2004.
U.S. Appl. No. 10/934,819, filed Sep. 2, 2004.
U.S. Appl. No. 11/058,757, filed Feb. 14, 2005.
U.S. Appl. No. 11/108,102, filed Apr. 15, 2005.
U.S. Appl. No. 11/245,524, filed Oct. 7, 2005.
U.S. Appl. No. 11/245,916, filed Oct. 7, 2005.
U.S. Appl. No. 11/396,391, filed Mar. 30, 2006.
U.S. Appl. No. 11/842,085, filed Aug. 20, 2007.
U.S. Appl. No. 11/842,101, filed Aug. 20, 2007.
U.S. Appl. No. 11/842,120, filed Aug. 20, 2007.
U.S. Appl. No. 11/894,665, filed Aug. 20, 2007.
U.S. Appl. No. 12/328,740, filed Dec. 4, 2008.
U.S. Appl. No. 60/067,219, filed Dec. 3, 1997.
U.S. Appl. No. 60/067,740, filed Dec. 2, 1997.
U.S. Appl. No. 60/079,697, filed Mar. 27, 1998.
U.S. Appl. No. 60/080,970 filed Apr. 7, 1998.
U.S. Appl. No. 60/136,655, filed May, 28, 1999.
U.S. Appl. No. 60/137,010, filed Jun. 1, 1999.
U.S. Appl. No. 60/137,047, filed Jun. 1, 1999.
U.S. Appl. No. 60/810,245, filed Jun. 1, 2006.
U.S. Appl. No. 09/724,319, filed Nov. 27, 2000.
U.S. Appl. No. 10/429,216, filed May 30, 2003.
U.S. Appl. No. 12/729,902, filed Mar. 23, 2010.
U.S. Appl. No. 12/977,013, filed Dec. 22, 2010.
U.S. Appl. No. 13/271,081, filed Oct. 11, 2011.
U.S. Appl. No. 10/544,093, Office Action mailed Mar. 13, 2014.
U.S. Appl. No. 12/608,869, Advisory Action mailed Mar. 13, 2013.
U.S. Appl. No. 12/738,396, Office Action mailed Apr. 16, 2013.
U.S. Appl. No. 13/270,015, Office Action mailed Nov. 14, 2013.
U.S. Appl. No. 13/231,903, Office Action mailed Oct. 24, 2014.
U.S. Appl. No. 13/231,903, Office Action mailed Mar. 18, 2014.
"Madrid: News from the Vaccine Front," Aug. 1, 2008 (Aug. 1, 2008) pp. 1-7.
The web page retrieved from >www.elan.com/company/about_us as archived by web.archive.org on Sep. 7, 2013 (downloaded from web.archive.org on Feb. 6, 2014).
Alzheimer's Forum report on Ponezumab, retrieved on Apr. 7, 2014 at www.alzforum.org/therapeutics/ponezumab<.
Arai, et al., "Safety, Tolerability and Immunogenicity of an lmmunotherapeutic Vaccine (Vanutide Cridificar (ACC-001)) and the QS-21Adjuvant in Japanese Individuals with Mild-to-Moderate Alzheimer's Disease: A Phase IIA, Multicenter, Randomized Adjuvant and Placebo Clinical Trial," *Alzheimer's and Dementia*, 9(4) supplemental p. P282 (2013).
Baxter Press Release, "Baxter Announces Topline Results of Phase III Study of Immunoglobulin for Alzheimer's Disease," retrieved at www.baxter.com/press_room/press_releases/2013/05_07_13_gat_study.html<.

(56) References Cited

OTHER PUBLICATIONS

Board of Appeal of the European Patent Office Appeal Decision in Case No. T219/01 on Dec. 15, 2004.
Chan, et al., "Therapeutic antibodies for autoimmunity and inflammation," *Nature Reviews Immunology*, 10:301-316 (2010).
Chao, et al., "Cerebral amyloid Angiopathy: CT and MR Imaging Findings," *Radiographics*, 26(5):1517-1531 (2006).
Cleland, et al., "Emerging protein delivery methods," *Current Op Biotech*, 12(2):212-219 (2001).
Communication from European Patent Office that no opposition was filed in EP1842859 dated Nov. 13, 2013.
Consolidated list of documents of opposition proceedings against EP 1 994 937 (annexed to decision to revoke EP 1 994 937) dated Jul. 24, 2013.
Decision from European Patent Office to maintain the patent EP1160256 in amended form dated Oct. 13, 2011.
Doody, et al., "Phase 3 Trials of Solanezumab for Mild-to Moderate Alzheimer's Disease," *New England J Med*, 370;4, 311 321 (2014).
EP 1 994 937 Decision of Oral Proceedings from EPO Opposition Division dated Jul. 24, 2013.
EP1160256 Druckexemplar in European Opposition Proceedings (2011).
European Search Report of Oct. 25, 2013 for European Application 08746362.6.
Extract from the online Oxford Dictionary retrieved on Apr. 3, 2014 from >www.oxforddictionaries.com/definition/english/intact?a-intact<.
Kambhampaty, "Roche's gantenerumab could face similar fate as failed drug bapineuzumab in Alzheimer's, experts say," Retrieved from the Internet sussexdrugdiscovery.wordpress.com/tag/bapineuzumab, (retrieved on Sep. 27, 2013) Jul. 5, 2013.
Kirschner, et al., "Synthetic peptide homologous to beta protein from Alzheimer disease forms amyloid-like fibrils in vitro", *Proc. Natl. Acad. Sci. USA*, 84:6953-6957 (1987).
Opposition by Biogen Idec, Inc. filed Sep. 29, 2011 against EP 1 994 937 B1.
Opposition by Eli Lilly filed Sep. 27, 2011 against EP 1 994 937 B1.
Opposition by F. Hoffman-La Roche AG filed Sep. 27, 2011 against EP 1 994 937 B1.
Pfizer Pipeline Report Aug. 11, 2011.
Pfizer Pipeline Report Aug. 9, 2013.
Preliminary Opinion by European Opposition Division in EP 1 994 937 dated Nov. 12, 2012.
Reilly, et al., "Oral Delivery of Antibodies," *Clin. Pharmacokinet*, 32(4):313-323 (1997).
Salloway, et al., "Two Phase 3 Trials of Bapineuzumab in Mild-to-Moderate Alzheimer's Disease," *New England J Med*, 370;4, 322 333 (2014).
Seubert, et al., "Comparison of Immunization with AN1792 and AB1-7MAP and Passive Immunization of 3D6 and 266," *Elan Pharmaceuticals Final Report*, Study 150-006-98-040, Jul. 22, 2003.
Submission, dated Apr. 10, 2013, filed by Opponent 2 (Eli Lilly) during Opposition proceedings against EP 1 994 937 B1.
Submission, dated Apr. 9, 2013, filed by Opponent 1 (F. Hoffman-La Roche AG) during Opposition proceedings against EP 1 994 937 B1.
Submission, dated Apr. 9, 2013, filed by Opponent 3 (Biogen Idec, Inc.) during Opposition proceedings against EP 1 994 937 B1.
Sussex Drug Discovery, "Bexarontene in Alzheimer's Disease: A case of lack of replication, lace of replication, lack of replication," Retrieved from the Internet sussexdrugdiscover.wordpress.com/tag/bapineuzumab, pp. 1-4 (retrieved on Sep. 27, 2013) Jun. 20, 2013.
Wikipedia "Bapineuzumab", printed on Feb. 24, 2014.
Wilcock, et al. Anti-AB immunotherapy in Alzheimer's disease; relevance of transgenic mouse studies to clinical trials, *J. Alzheimers Dis.*, 15(4):555-569 (2008).
Wisniewski, et al., "Spectrum of morphological appearance of amyloid deposits in Alzheimer's disease," *Acta Neuropathol*, 78:337-347 (1989).
"Biogen Notes Progress With Alzheimer's Drug," *The Wall Street Journal*, retrieved www.wsj.com/articles/biogen-shares-rise-on-results-of-early-sta . . . www.wsj.com/articles/biogen-shares-rise-on-results-of-early-stages> (Dec. 2, 2014).
Alzheimer's Research UK, "Southhampton researchers tackle Alzheimer's clinical trials failure," retrieved from <www.alzheimersresearchuk.org/news-detail/11217/Southampton-researchers-ta> (Jan. 14, 2015).
Clark et al., "Variability in Annual Mini-Mental State Examination Score in Patients With Probable Alzheimer Disease," *Arch Neurol*, vol. 56:857-862 (Jul. 1999).
EP 1679080 Interlocutory decision in Oposition Proceedings Jun. 5, 2012.
EP 1690547 Interlocutory decision in Oposition Proceedings Jun. 28, 2012.
Jacobs, et al., "PET-based molecular imaging in neuroscience," *Eur J. Nucl Med Mol*, 30:1051-1065 (2003).
Janssen Alzheimer Immunotherapy Research & Development, LLC, "AAB-001 in Patients With Mild to Moderate Alzheimer's Disease",retrived from https://clinicalTrials.gov/ct2/show/results/NCT01284387 (Jun. 20, 2015).
Lannfelt, et al., "Amyloid-B-directed immunotherapy for Alzheimer's Disease," *Journal of Internal Medicine*, 275:284-295 (2014).
Lilly France, et al vs Janssen Sciences Ireland UC summons before the Paris High Court filed Jul. 23, 2015.
Nordberg, "Amyloid plaque imaging in vivo: current achievement and future prospects," *Eur J. Nucl Med Mol Imaging*, 35 (Suppl 1):S46-S50 (2008).
Novartis, "Novartis announces collaboration with Banner Alzheimer's Institute on pioneering prevention study for Alzheimer's Disease," *Media Release*, retrieved from http://www.novartis.com (Jul. 15, 2014).
Paquet, et al., "Effect of active AB immunotherapy on neurons in human Alzheimer's disease," *Journal of Pathology*, Published online in Wiley Online Library (wileyonlinelibrary.com) DOI: 10.1002/path.4491 (2015).
Pardridge, "Alzheimer's disease drug development and the problem of the blood-brain barrier," *Alzheimers Dement.*, (5):427-432 (2009).
Rabchevsky, et al., "Peripheral injections of Freund's adjuvant in mice provoke leakage of serum proteins through the blood-brain barrier without inducing reactive gliosis," *Brain Research*, 832:84-96 (1999).
Solomon, "Clinical immunologic approaches for the treatment of Alzheimer's disease," *Expert Opin. Invest. Drugs*, 16:(6) p. 819-828 (2007).
Spencer, et al., "Immunotherapy for Alzheimer's disease: past, present and future," *Frontiers in Aging Neuroscience*, vol. 6 Art. 114 pp. 1-7 (Jun. 2014).
Wang, et al., "Clearance of amyloid-beta in Alzheimer's disease: progress, problems and perspectives," *Drug Discovery Today*, vol. 11:19/20 pp. 931-938 (2006).
Wilcock, et al., "Microglial activation facilitates AB plaque removal following intractranial anti-AB antibody administration," *Neurobiology of Disease*, 15:11-20 (2004).
Wilcock, et al., "Passive immunotherapy against AB in aged APP-transgenic mice reverses cognitive deficits and depletes parenchymal amyloid deposits in spite of increased vascular amyloid and microhemorrhage," *Journal of Neuroinflammation*, 1:24 pp. 1-11 (2004).
Winblad, et al., "Active immunotherapy options for Alzheimer's disease," *Alzheimer's Research & Therapy*, 6:7 (2014).
Winnington, "Tracing a Future for Diagnostic Imaging in AD," *DementiaInsights*, pp. 47-48 (2009).
U.S. Appl. No. 13/580,866, Office Action mailed Feb. 26, 2015.
U.S. Appl. No. 14/017,177, Office Action mailed May 5, 2015.
U.S. Appl. No. 14/146,700, Office Action mailed May 7, 2015.
U.S. Appl. No. 13/231,903, Office Action mailed Jun. 25, 2015.
U.S. Appl. No. 13/580,866, Office Action mailed Jul. 23, 2015.
Dorpe, et al., "Prominent Cerebral Amyloid Angiopathy in Transgenic Mice Overexpressing the London Mutant of Human AP in Neurons," *American Journal of Pathology*, vol. 157, No. 4, Oct. 2000.

(56) References Cited

OTHER PUBLICATIONS

EP 11748201 Supplemental European Search Report completed Jan. 13, 2016.
EP 15161872 Extended Search Report completed Oct. 13, 2015.
Lilly, "Lilly Announces Change to Primary Endpoint of EXPEDITION3 Study", Mar. 15, 2016 /PRNewswire/ retrieved at <http://www.prnewswire.com/news-releases/lilly-announces-change-to-primary-endpoint-of-expedition3-study-300235846.html>.
Mathis, et al., "Impact of amyloid imaging on drug development in Alzheimer's disease," *Nuclear Medicine & Biology*, 34:809-922, (2007).
Norbert, "Pet imaging of amyloid in Alzheimer's disease," *The Lancet Neurology*, vol.3, pp. 519-527, Sep. 2004.
Selkoe, et al., "The amyloid hypothesis of Alzheimer's disease at 25 years", *EMBO Molecular Medicine*, published online: Mar. 29, 2016.
Wines, et al., "The IgG Fc Contains Distinct Fc Receptor (FcR) Binding Sites: The Leukocyte Receptors FcγRI and FcγRIIa Bind to a Region in the Fc Distinct from That Recognized by Neonatal FcR and Protein A", *The Journal of Immunology*, 164:5313-5318, 2000.

\* cited by examiner

SEQUENCE LISTING

```
<160> NUMBER OF SEQ ID NOS: 99

<210> SEQ ID NO 1
<211> LENGTH: 42
<212> TYPE: PRT
<213> ORGANISM: Homo sapiens

<400> SEQUENCE: 1

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 2
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Asp Val Val Met Thr Gln Ser Pro Leu Ser Leu Pro Val Thr Pro Gly
1               5                   10                  15

Glu Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Lys Pro Gly Gln Ser
        35                  40                  45
```

```
Pro Gln Arg Leu Ile Tyr Leu Val Ser Lys Leu Asp Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Trp Gln Gly
                 85                  90                  95

Thr His Phe Pro Arg Thr Phe Gly Gln Gly Thr Lys Val Glu Ile Lys
                100                 105                 110
```

<210> SEQ ID NO 3
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

```
Glu Val Gln Leu Leu Glu Ser Gly Gly Gly Leu Val Gln Pro Gly Gly
 1                5                  10                  15

Ser Leu Arg Leu Ser Cys Ala Ala Ser Gly Phe Thr Phe Ser Asn Tyr
                 20                  25                  30

Gly Met Ser Trp Val Arg Gln Ala Pro Gly Lys Gly Leu Glu Trp Val
             35                  40                  45

Ala Ser Ile Arg Ser Gly Gly Gly Arg Thr Tyr Tyr Ser Asp Asn Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Val Arg Tyr Asp His Tyr Ser Gly Ser Ser Asp Tyr Trp Gly Gln Gly
                100                 105                 110

Thr Leu Val Thr Val Ser Ser
        115
```

<210> SEQ ID NO 4
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

```
Tyr Val Val Met Thr Gln Ser Pro Leu Ser Leu Pro Val Thr Pro Gly
 1                5                  10                  15

Glu Pro Ala Ser Ile Ser Cys Lys Ser Ser Gln Ser Leu Leu Asp Ser
                 20                  25                  30

Asp Gly Lys Thr Tyr Leu Asn Trp Leu Leu Gln Lys Pro Gly Gln Ser
             35                  40                  45

Pro Gln Arg Leu Ile Tyr Leu Val Ser Lys Leu Asp Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Trp Gln Gly
                 85                  90                  95

Thr His Phe Pro Arg Thr Phe Gly Gln Gly Thr Lys Val Glu Ile Lys
                100                 105                 110
```

-continued

```
<210> SEQ ID NO 5
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ala Ser Ile Arg Ser Gly Gly Arg Thr Tyr Tyr Ser Asp Asn Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Arg Tyr Asp His Tyr Ser Gly Ser Ser Asp Tyr Trp Gly Gln Gly
            100                 105                 110

Thr Leu Val Thr Val Ser Ser
        115

<210> SEQ ID NO 6
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Asp Val Val Met Thr Gln Ser Pro Leu Ser Leu Pro Val Thr Leu Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Gln Gln Arg Pro Gly Gln Ser
        35                  40                  45

Pro Arg Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Arg Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175
```

```
Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
            210                 215

<210> SEQ ID NO 7
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Gly Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ala Ser Ile Arg Ser Gly Gly Gly Arg Thr Tyr Tyr Ser Asp Asn Val
    50                  55                  60

Lys Gly Arg Phe Thr Ile Ser Arg Glu Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Val Arg Tyr Asp His Tyr Ser Gly Ser Ser Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320
```

-continued

```
Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 8
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Asn Ile Ile His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Lys Lys Val Glu Ala Glu Asp Leu Gly Ile Tyr Tyr Cys Phe Gln Gly
                85                  90                  95

Ser His Val Pro Leu Thr Phe Gly Ala Gly Thr Lys Leu Glu Leu Glu
            100                 105                 110

<210> SEQ ID NO 9
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Gln Ala Thr Leu Lys Glu Ser Gly Pro Gly Ile Leu Gln Ser Ser Gln
1               5                   10                  15

Thr Leu Ser Leu Thr Cys Ser Phe Ser Gly Phe Ser Leu Ser Thr Ser
            20                  25                  30

Gly Met Gly Val Ser Trp Ile Arg Gln Pro Ser Gly Lys Gly Leu Glu
        35                  40                  45
```

```
Trp Leu Ala His Ile Tyr Trp Asp Asp Asp Lys Arg Tyr Asn Pro Ser
    50                  55                  60

Leu Lys Ser Arg Leu Thr Ile Ser Lys Asp Thr Ser Arg Lys Gln Val
65                  70                  75                  80

Phe Leu Lys Ile Thr Ser Val Asp Pro Ala Asp Thr Ala Thr Tyr Tyr
                85                  90                  95

Cys Val Arg Arg Pro Ile Thr Pro Val Leu Val Asp Ala Met Asp Tyr
                100                 105                 110

Trp Gly Gln Gly Thr Ser Val Thr Val Ser Ser
            115                 120

<210> SEQ ID NO 10
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Ile Val His Ser
                20                  25                  30

Asn Gly Asn Thr Tyr Leu Glu Trp Tyr Leu Gln Lys Pro Gly Gln Ser
            35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Ser
                85                  90                  95

Ser His Val Pro Leu Thr Phe Gly Gln Gly Thr Lys Leu Glu Ile Lys
                100                 105                 110

<210> SEQ ID NO 11
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Gln Val Gln Leu Val Glu Ser Gly Gly Gly Val Val Gln Pro Gly Arg
1               5                   10                  15

Ser Leu Arg Leu Ser Cys Ala Phe Ser Gly Phe Ser Leu Ser Thr Ser
                20                  25                  30

Gly Met Ser Val Gly Trp Ile Arg Gln Ala Pro Gly Lys Gly Leu Glu
            35                  40                  45

Trp Leu Ala His Ile Trp Trp Asp Asp Asp Lys Tyr Tyr Asn Pro Ser
    50                  55                  60

Leu Lys Ser Arg Leu Thr Ile Ser Lys Asp Thr Ser Lys Asn Thr Val
65                  70                  75                  80

Tyr Leu Gln Met Asn Ser Leu Arg Ala Glu Asp Thr Ala Val Tyr Tyr
                85                  90                  95

Cys Ala Arg Arg Thr Thr Ala Asp Tyr Phe Ala Tyr Trp Gly Gln
                100                 105                 110
```

```
Gly Thr Thr Val Thr Val Ser Ser
        115                 120
```

<210> SEQ ID NO 12
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

```
Gln Val Gln Leu Val Glu Ser Gly Gly Gly Val Val Gln Pro Gly Arg
1               5                   10                  15

Ser Leu Arg Leu Ser Cys Ala Phe Ser Gly Phe Thr Leu Ser Thr Ser
            20                  25                  30

Gly Met Ser Val Gly Trp Ile Arg Gln Ala Pro Gly Lys Gly Leu Glu
        35                  40                  45

Trp Val Ala His Ile Trp Trp Asp Asp Lys Tyr Tyr Asn Pro Ser
    50                  55                  60

Leu Lys Ser Arg Phe Thr Ile Ser Lys Asp Thr Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Arg Thr Thr Thr Ala Asp Tyr Phe Ala Tyr Trp Gly Gln
            100                 105                 110

Gly Thr Thr Val Thr Val Ser Ser
        115                 120
```

<210> SEQ ID NO 13
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

```
Gln Val Gln Leu Val Glu Ser Gly Gly Gly Val Val Gln Pro Gly Arg
1               5                   10                  15

Ser Leu Arg Leu Ser Cys Ala Phe Ser Gly Phe Thr Leu Ser Thr Ser
            20                  25                  30

Gly Met Ser Val Gly Trp Ile Arg Gln Ala Pro Gly Lys Gly Leu Glu
        35                  40                  45

Trp Val Ala His Ile Trp Trp Asp Asp Lys Tyr Tyr Asn Pro Ser
    50                  55                  60

Leu Lys Ser Arg Phe Thr Ile Ser Lys Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Arg Thr Thr Thr Ala Asp Tyr Phe Ala Tyr Trp Gly Gln
            100                 105                 110

Gly Thr Thr Val Thr Val Ser Ser
        115                 120
```

<210> SEQ ID NO 14
<211> LENGTH: 120
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 14

Gln Val Gln Leu Val Glu Ser Gly Gly Gly Val Val Gln Pro Gly Arg
1               5                   10                  15

Ser Leu Arg Leu Ser Cys Ala Phe Ser Gly Phe Thr Leu Ser Thr Ser
            20                  25                  30

Gly Met Ser Val Gly Trp Ile Arg Gln Ala Pro Gly Lys Gly Leu Glu
        35                  40                  45

Trp Val Ala His Ile Trp Trp Asp Asp Lys Tyr Tyr Asn Pro Ser
    50                  55                  60

Leu Lys Ser Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Arg Thr Thr Thr Ala Asp Tyr Phe Ala Tyr Trp Gly Gln
            100                 105                 110

Gly Thr Thr Val Thr Val Ser Ser
        115                 120

<210> SEQ ID NO 15
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Gln Val Gln Leu Val Glu Ser Gly Gly Gly Val Val Gln Pro Gly Arg
1               5                   10                  15

Ser Leu Arg Leu Ser Cys Ala Phe Ser Gly Phe Thr Leu Ser Thr Ser
            20                  25                  30

Gly Met Ser Val Gly Trp Ile Arg Gln Ala Pro Gly Lys Gly Leu Glu
        35                  40                  45

Trp Leu Ala His Ile Trp Trp Asp Asp Lys Tyr Tyr Asn Pro Ser
    50                  55                  60

Leu Lys Ser Arg Leu Thr Ile Ser Lys Asp Thr Ser Lys Asn Thr Val
65                  70                  75                  80

Tyr Leu Gln Met Asn Ser Leu Arg Ala Glu Asp Thr Ala Val Tyr Tyr
                85                  90                  95

Cys Ala Arg Arg Thr Thr Thr Ala Asp Tyr Phe Ala Tyr Trp Gly Gln
            100                 105                 110

Gly Thr Thr Val Thr Val Ser Ser
        115                 120

<210> SEQ ID NO 16
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Gln Val Gln Leu Val Glu Ser Gly Gly Gly Val Val Gln Pro Gly Arg
1               5                   10                  15

Ser Leu Arg Leu Ser Cys Ala Phe Ser Gly Phe Ser Leu Ser Thr Ser

```
            20                  25                  30

Gly Met Ser Val Gly Trp Ile Arg Gln Ala Pro Gly Lys Gly Leu Glu
        35                  40                  45

Trp Val Ala His Ile Trp Trp Asp Asp Lys Tyr Tyr Asn Pro Ser
    50                  55                  60

Leu Lys Ser Arg Leu Thr Ile Ser Lys Asp Thr Ser Lys Asn Thr Val
65                  70                  75                  80

Tyr Leu Gln Met Asn Ser Leu Arg Ala Glu Asp Thr Ala Val Tyr Tyr
                85                  90                  95

Cys Ala Arg Arg Thr Thr Thr Ala Asp Tyr Phe Ala Tyr Trp Gly Gln
                100                 105                 110

Gly Thr Thr Val Thr Val Ser Ser
            115                 120

<210> SEQ ID NO 17
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Gln Val Gln Leu Val Glu Ser Gly Gly Gly Val Val Gln Pro Gly Arg
1               5                   10                  15

Ser Leu Arg Leu Ser Cys Ala Phe Ser Gly Phe Ser Leu Ser Thr Ser
            20                  25                  30

Gly Met Ser Val Gly Trp Ile Arg Gln Ala Pro Gly Lys Gly Leu Glu
        35                  40                  45

Trp Leu Ala His Ile Trp Trp Asp Asp Lys Tyr Tyr Asn Pro Ser
    50                  55                  60

Leu Lys Ser Arg Phe Thr Ile Ser Lys Asp Thr Ser Lys Asn Thr Val
65                  70                  75                  80

Tyr Leu Gln Met Asn Ser Leu Arg Ala Glu Asp Thr Ala Val Tyr Tyr
                85                  90                  95

Cys Ala Arg Arg Thr Thr Thr Ala Asp Tyr Phe Ala Tyr Trp Gly Gln
                100                 105                 110

Gly Thr Thr Val Thr Val Ser Ser
            115                 120

<210> SEQ ID NO 18
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Gln Val Gln Leu Val Glu Ser Gly Gly Gly Val Val Gln Pro Gly Arg
1               5                   10                  15

Ser Leu Arg Leu Ser Cys Ala Phe Ser Gly Phe Ser Leu Ser Thr Ser
            20                  25                  30

Gly Met Ser Val Gly Trp Ile Arg Gln Ala Pro Gly Lys Gly Leu Glu
        35                  40                  45

Trp Leu Ala His Ile Trp Trp Asp Asp Lys Tyr Tyr Asn Pro Ser
    50                  55                  60

Leu Lys Ser Arg Leu Thr Ile Ser Lys Asp Thr Ser Lys Asn Thr Leu
```

```
              65                  70                  75                  80
Tyr Leu Gln Met Asn Ser Leu Arg Ala Glu Asp Thr Ala Val Tyr Tyr
                85                  90                  95

Cys Ala Arg Arg Thr Thr Thr Ala Asp Tyr Phe Ala Tyr Trp Gly Gln
            100                 105                 110

Gly Thr Thr Val Thr Val Ser Ser
            115                 120

<210> SEQ ID NO 19
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Gln Val Gln Leu Val Glu Ser Gly Gly Gly Val Val Gln Pro Gly Arg
1               5                   10                  15

Ser Leu Arg Leu Ser Cys Ala Phe Ser Gly Phe Thr Leu Ser Thr Ser
            20                  25                  30

Gly Met Ser Val Gly Trp Ile Arg Gln Ala Pro Gly Lys Gly Leu Glu
        35                  40                  45

Trp Val Ala His Ile Trp Trp Asp Asp Lys Tyr Tyr Asn Pro Ser
    50                  55                  60

Leu Lys Ser Arg Leu Thr Ile Ser Lys Asp Thr Ser Lys Asn Thr Val
65                  70                  75                  80

Tyr Leu Gln Met Asn Ser Leu Arg Ala Glu Asp Thr Ala Val Tyr Tyr
                85                  90                  95

Cys Ala Arg Arg Thr Thr Thr Ala Asp Tyr Phe Ala Tyr Trp Gly Gln
            100                 105                 110

Gly Thr Thr Val Thr Val Ser Ser
            115                 120

<210> SEQ ID NO 20
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Gln Val Gln Leu Val Glu Ser Gly Gly Gly Val Val Gln Pro Gly Arg
1               5                   10                  15

Ser Leu Arg Leu Ser Cys Ala Phe Ser Gly Phe Thr Leu Ser Thr Ser
            20                  25                  30

Gly Met Ser Val Gly Trp Ile Arg Gln Ala Pro Gly Lys Gly Leu Glu
        35                  40                  45

Trp Leu Ala His Ile Trp Trp Asp Asp Lys Tyr Tyr Asn Pro Ser
    50                  55                  60

Leu Lys Ser Arg Phe Thr Ile Ser Lys Asp Thr Ser Lys Asn Thr Val
65                  70                  75                  80

Tyr Leu Gln Met Asn Ser Leu Arg Ala Glu Asp Thr Ala Val Tyr Tyr
                85                  90                  95

Cys Ala Arg Arg Thr Thr Thr Ala Asp Tyr Phe Ala Tyr Trp Gly Gln
            100                 105                 110

Gly Thr Thr Val Thr Val Ser Ser
```

-continued

```
                115                 120

<210> SEQ ID NO 21
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Gln Val Gln Leu Val Glu Ser Gly Gly Gly Val Val Gln Pro Gly Arg
1               5                   10                  15

Ser Leu Arg Leu Ser Cys Ala Phe Ser Gly Phe Thr Leu Ser Thr Ser
            20                  25                  30

Gly Met Ser Val Gly Trp Ile Arg Gln Ala Pro Gly Lys Gly Leu Glu
        35                  40                  45

Trp Leu Ala His Ile Trp Trp Asp Asp Lys Tyr Tyr Asn Pro Ser
    50                  55                  60

Leu Lys Ser Arg Leu Thr Ile Ser Lys Asp Thr Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Arg Thr Thr Thr Ala Asp Tyr Phe Ala Tyr Trp Gly Gln
            100                 105                 110

Gly Thr Thr Val Thr Val Ser Ser Val
        115                 120

<210> SEQ ID NO 22
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Gln Val Gln Leu Val Glu Ser Gly Gly Gly Val Val Gln Pro Gly Arg
1               5                   10                  15

Ser Leu Arg Leu Ser Cys Ala Phe Ser Gly Phe Ser Leu Ser Thr Ser
            20                  25                  30

Gly Met Ser Val Gly Trp Ile Arg Gln Ala Pro Gly Lys Gly Leu Glu
        35                  40                  45

Trp Val Ala His Ile Trp Trp Asp Asp Lys Tyr Tyr Asn Pro Ser
    50                  55                  60

Leu Lys Ser Arg Phe Thr Ile Ser Lys Asp Thr Ser Lys Asn Thr Val
65                  70                  75                  80

Tyr Leu Gln Met Asn Ser Leu Arg Ala Glu Asp Thr Ala Val Tyr Tyr
                85                  90                  95

Cys Ala Arg Arg Thr Thr Thr Ala Asp Tyr Phe Ala Tyr Trp Gly Gln
            100                 105                 110

Gly Thr Thr Val Thr Val Ser Ser Val
        115                 120

<210> SEQ ID NO 23
<211> LENGTH: 120
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 23

Gln Val Gln Leu Val Glu Ser Gly Gly Gly Val Val Gln Pro Gly Arg
1               5                   10                  15

Ser Leu Arg Leu Ser Cys Ala Phe Ser Gly Phe Ser Leu Ser Thr Ser
            20                  25                  30

Gly Met Ser Val Gly Trp Ile Arg Gln Ala Pro Gly Lys Gly Leu Glu
        35                  40                  45

Trp Val Ala His Ile Trp Trp Asp Asp Asp Lys Tyr Tyr Asn Pro Ser
    50                  55                  60

Leu Lys Ser Arg Leu Thr Ile Ser Lys Asp Thr Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Arg Thr Thr Thr Ala Asp Tyr Phe Ala Tyr Trp Gly Gln
            100                 105                 110

Gly Thr Thr Val Thr Val Ser Ser
        115                 120

<210> SEQ ID NO 24
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Gln Val Gln Leu Val Glu Ser Gly Gly Gly Val Val Gln Pro Gly Arg
1               5                   10                  15

Ser Leu Arg Leu Ser Cys Ala Phe Ser Gly Phe Ser Leu Ser Thr Ser
            20                  25                  30

Gly Met Ser Val Gly Trp Ile Arg Gln Ala Pro Gly Lys Gly Leu Glu
        35                  40                  45

Trp Leu Ala His Ile Trp Trp Asp Asp Asp Lys Tyr Tyr Asn Pro Ser
    50                  55                  60

Leu Lys Ser Arg Phe Thr Ile Ser Lys Asp Thr Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Arg Thr Thr Thr Ala Asp Tyr Phe Ala Tyr Trp Gly Gln
            100                 105                 110

Gly Thr Thr Val Thr Val Ser Ser
        115                 120

<210> SEQ ID NO 25
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Gln Val Gln Leu Val Glu Ser Gly Gly Gly Val Val Gln Pro Gly Arg
1               5                   10                  15

Ser Leu Arg Leu Ser Cys Ala Phe Ser Gly Phe Thr Leu Ser Thr Ser
            20                  25                  30

Gly Met Ser Val Gly Trp Ile Arg Gln Ala Pro Gly Lys Gly Leu Glu
            35                  40                  45

Trp Val Ala His Ile Trp Trp Asp Asp Lys Tyr Tyr Asn Pro Ser
    50                  55                  60

Leu Lys Ser Arg Phe Thr Ile Ser Lys Asp Thr Ser Lys Asn Thr Val
65                  70                  75                  80

Tyr Leu Gln Met Asn Ser Leu Arg Ala Glu Asp Thr Ala Val Tyr Tyr
                85                  90                  95

Cys Ala Arg Arg Thr Thr Thr Ala Asp Tyr Phe Ala Tyr Trp Gly Gln
                100                 105                 110

Gly Thr Thr Val Thr Val Ser Ser
            115                 120

<210> SEQ ID NO 26
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Gln Val Gln Leu Val Glu Ser Gly Gly Gly Val Val Gln Pro Gly Arg
1               5                   10                  15

Ser Leu Arg Leu Ser Cys Ala Phe Ser Gly Phe Thr Leu Ser Thr Ser
                20                  25                  30

Gly Met Ser Val Gly Trp Ile Arg Gln Ala Pro Gly Lys Gly Leu Glu
            35                  40                  45

Trp Val Ala His Ile Trp Trp Asp Asp Lys Tyr Tyr Asn Pro Ser
    50                  55                  60

Leu Lys Ser Arg Leu Thr Ile Ser Lys Asp Thr Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Arg Thr Thr Thr Ala Asp Tyr Phe Ala Tyr Trp Gly Gln
                100                 105                 110

Gly Thr Thr Val Thr Val Ser Ser
            115                 120

<210> SEQ ID NO 27
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Gln Val Gln Leu Val Glu Ser Gly Gly Gly Val Val Gln Pro Gly Arg
1               5                   10                  15

Ser Leu Arg Leu Ser Cys Ala Phe Ser Gly Phe Thr Leu Ser Thr Ser
                20                  25                  30

Gly Met Ser Val Gly Trp Ile Arg Gln Ala Pro Gly Lys Gly Leu Glu
            35                  40                  45

Trp Leu Ala His Ile Trp Trp Asp Asp Lys Tyr Tyr Asn Pro Ser
    50                  55                  60

Leu Lys Ser Arg Phe Thr Ile Ser Lys Asp Thr Ser Lys Asn Thr Leu
65                  70                  75                  80

Tyr Leu Gln Met Asn Ser Leu Arg Ala Glu Asp Thr Ala Val Tyr Tyr
             85                  90                  95

Cys Ala Arg Arg Thr Thr Thr Ala Asp Tyr Phe Ala Tyr Trp Gly Gln
            100                 105                 110

Gly Thr Thr Val Thr Val Ser Ser
        115                 120

<210> SEQ ID NO 28
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Gln Val Gln Leu Val Glu Ser Gly Gly Gly Val Val Gln Pro Gly Arg
1               5                   10                  15

Ser Leu Arg Leu Ser Cys Ala Phe Ser Gly Phe Ser Leu Ser Thr Ser
            20                  25                  30

Gly Met Ser Val Gly Trp Ile Arg Gln Ala Pro Gly Lys Gly Leu Glu
        35                  40                  45

Trp Val Ala His Ile Trp Trp Asp Asp Lys Tyr Tyr Asn Pro Ser
    50                  55                  60

Leu Lys Ser Arg Phe Thr Ile Ser Lys Asp Thr Ser Lys Asn Thr Leu
65                  70                  75                  80

Tyr Leu Gln Met Asn Ser Leu Arg Ala Glu Asp Thr Ala Val Tyr Tyr
             85                  90                  95

Cys Ala Arg Arg Thr Thr Thr Ala Asp Tyr Phe Ala Tyr Trp Gly Gln
            100                 105                 110

Gly Thr Thr Val Thr Val Ser Ser
        115                 120

<210> SEQ ID NO 29
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Gln Val Gln Leu Val Glu Ser Gly Gly Gly Val Val Gln Pro Gly Arg
1               5                   10                  15

Ser Leu Arg Leu Ser Cys Ala Phe Ser Gly Phe Thr Leu Ser Thr Ser
            20                  25                  30

Gly Met Ser Val Gly Trp Val Arg Gln Ala Pro Gly Lys Gly Leu Glu
        35                  40                  45

Trp Leu Ala His Ile Trp Trp Asp Asp Lys Tyr Tyr Asn Pro Ser
    50                  55                  60

Leu Lys Ser Arg Leu Thr Ile Ser Lys Asp Thr Ser Lys Asn Thr Val
65                  70                  75                  80

Tyr Leu Gln Met Asn Ser Leu Arg Ala Glu Asp Thr Ala Val Tyr Tyr
             85                  90                  95

Cys Ala Arg Arg Thr Thr Thr Ala Asp Tyr Phe Ala Tyr Trp Gly Gln
            100                 105                 110

Gly Thr Thr Val Thr Val Ser Ser
        115                 120

<210> SEQ ID NO 30
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Gln Val Gln Leu Val Glu Ser Gly Gly Gly Val Val Gln Pro Gly Arg
1               5                   10                  15

Ser Leu Arg Leu Ser Cys Ala Phe Ser Gly Phe Ser Leu Ser Thr Ser
            20                  25                  30

Gly Met Ser Val Gly Trp Ile Arg Gln Ala Pro Gly Lys Gly Leu Glu
        35                  40                  45

Trp Leu Ala His Ile Trp Trp Asp Asp Lys Tyr Tyr Asn Pro Ser
    50                  55                  60

Leu Lys Ser Arg Leu Thr Ile Ser Lys Asp Asn Ser Lys Asn Thr Val
65                  70                  75                  80

Tyr Leu Gln Met Asn Ser Leu Arg Ala Glu Asp Thr Ala Val Tyr Tyr
                85                  90                  95

Cys Ala Arg Arg Thr Thr Thr Ala Asp Tyr Phe Ala Tyr Trp Gly Gln
            100                 105                 110

Gly Thr Thr Val Thr Val Ser Ser
        115                 120

<210> SEQ ID NO 31
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Asn Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Leu Thr Phe Gly Ala Gly Thr Lys Leu Glu Leu Lys
            100                 105                 110

<210> SEQ ID NO 32
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

```
Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Asn
            20                  25                  30

Gly Met Gly Val Ser Trp Ile Arg Gln Pro Ser Gly Lys Gly Leu Glu
        35                  40                  45

Trp Leu Ala His Ile Tyr Trp Asp Glu Asp Lys Arg Tyr Asn Pro Ser
    50                  55                  60

Leu Lys Ser Arg Leu Thr Ile Ser Lys Asp Thr Ser Asn Asn Gln Val
65                  70                  75                  80

Phe Leu Lys Ile Thr Asn Val Asp Thr Ala Asp Thr Ala Thr Tyr Tyr
                85                  90                  95

Cys Ala Arg Arg Arg Ile Ile Tyr Asp Val Glu Asp Tyr Phe Asp Tyr
            100                 105                 110

Trp Gly Gln Gly Thr Thr Leu Thr Val Ser Ser
            115                 120
```

<210> SEQ ID NO 33
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Val or Ile
<220> FEATURE:
<221> NAME/KEY: MOD_RES
<222> LOCATION: (7)..(7)
<223> OTHER INFORMATION: Ser or Thr
<220> FEATURE:
<221> NAME/KEY: MOD_RES
<222> LOCATION: (14)..(14)
<223> OTHER INFORMATION: Thr or Ser
<220> FEATURE:
<221> NAME/KEY: MOD_RES
<222> LOCATION: (15)..(15)
<223> OTHER INFORMATION: Leu or Pro
<220> FEATURE:
<221> NAME/KEY: MOD_RES
<222> LOCATION: (30)..(30)
<223> OTHER INFORMATION: Ile or Val
<220> FEATURE:
<221> NAME/KEY: MOD_RES
<222> LOCATION: (50)..(50)
<223> OTHER INFORMATION: Arg, Gln or Lys
<220> FEATURE:
<221> NAME/KEY: MOD_RES
<222> LOCATION: (88)..(88)
<223> OTHER INFORMATION: Val or Leu
<220> FEATURE:
<221> NAME/KEY: MOD_RES
<222> LOCATION: (105)..(105)
<223> OTHER INFORMATION: Gln or Gly
<220> FEATURE:
<221> NAME/KEY: MOD_RES
<222> LOCATION: (108)..(108)
<223> OTHER INFORMATION: Lys or Arg
<220> FEATURE:
<221> NAME/KEY: MOD_RES
<222> LOCATION: (109)..(109)
<223> OTHER INFORMATION: Val or Leu

<400> SEQUENCE: 33

```
Asp Xaa Val Met Thr Gln Xaa Pro Leu Ser Leu Pro Val Xaa Xaa Gly
1               5                   10                  15

Gln Pro Ala Ser Ile Ser Cys Arg Ser Ser Gln Ser Leu Xaa Tyr Ser
```

-continued

```
                 20                  25                  30
Asp Gly Asn Ala Tyr Leu His Trp Phe Leu Gln Lys Pro Gly Gln Ser
             35                  40                  45

Pro Xaa Leu Leu Ile Tyr Lys Val Ser Asn Arg Phe Ser Gly Val Pro
         50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Xaa Gly Val Tyr Tyr Cys Ser Gln Ser
                 85                  90                  95

Thr His Val Pro Trp Thr Phe Gly Xaa Gly Thr Xaa Xaa Glu Ile Lys
            100                 105                 110

Arg

<210> SEQ ID NO 34
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Glu or Gln
<220> FEATURE:
<221> NAME/KEY: MOD_RES
<222> LOCATION: (7)..(7)
<223> OTHER INFORMATION: Ser or Leu
<220> FEATURE:
<221> NAME/KEY: MOD_RES
<222> LOCATION: (46)..(46)
<223> OTHER INFORMATION: Glu, Val, Asp or Ser
<220> FEATURE:
<221> NAME/KEY: MOD_RES
<222> LOCATION: (63)..(63)
<223> OTHER INFORMATION: Thr or Ser
<220> FEATURE:
<221> NAME/KEY: MOD_RES
<222> LOCATION: (75)..(75)
<223> OTHER INFORMATION: Ala, Ser, Val or Thr
<220> FEATURE:
<221> NAME/KEY: MOD_RES
<222> LOCATION: (76)..(76)
<223> OTHER INFORMATION: Lys or Arg
<220> FEATURE:
<221> NAME/KEY: MOD_RES
<222> LOCATION: (89)..(89)
<223> OTHER INFORMATION: Glu or Asp
<220> FEATURE:
<221> NAME/KEY: MOD_RES
<222> LOCATION: (107)..(107)
<223> OTHER INFORMATION: Leu or Thr

<400> SEQUENCE: 34

Xaa Val Gln Leu Val Glu Xaa Gly Gly Gly Leu Val Gln Pro Gly Gly
 1               5                  10                  15

Ser Leu Arg Leu Ser Cys Ala Ala Ser Gly Phe Thr Phe Ser Arg Tyr
             20                  25                  30

Ser Met Ser Trp Val Arg Gln Ala Pro Gly Lys Gly Leu Xaa Leu Val
         35                  40                  45

Ala Gln Ile Asn Ser Val Gly Asn Ser Thr Tyr Tyr Pro Asp Xaa Val
     50                  55                  60

Lys Gly Arg Phe Thr Ile Ser Arg Asp Asn Xaa Xaa Asn Thr Leu Tyr
 65                  70                  75                  80

Leu Gln Met Asn Ser Leu Arg Ala Xaa Asp Thr Ala Val Tyr Tyr Cys
             85                  90                  95
```

```
Ala Ser Gly Asp Tyr Trp Gly Gln Gly Thr Xaa Val Thr Val Ser Ser
            100                 105                 110
```

<210> SEQ ID NO 35
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

```
Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Ile Tyr Ser
            20                  25                  30

Asp Gly Asn Ala Tyr Leu His Trp Phe Leu Gln Lys Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Trp Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 36
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Ser Met Ser Trp Val Ala Arg Tyr Gln Ala Pro Gly Lys Gly Leu Glu
        35                  40                  45

Leu Val Ala Gln Ile Asn Ser Val Gly Asn Ser Thr Tyr Tyr Pro Asp
    50                  55                  60
```

Thr Val Lys Gly Arg Phe Thr Ile Ser Arg Asp Asn Ala Lys Asn Thr
65                  70                  75                  80

Leu Tyr Leu Gln Met Asn Ser Leu Arg Ala Glu Asp Thr Ala Val Tyr
            85                  90                  95

Tyr Cys Ala Ser Gly Asp Tyr Trp Gly Gln Gly Thr Leu Val Thr Val
        100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Ala Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 37
<211> LENGTH: 112
<212> TYPE: PRT
<213> ORGANISM: Artificial Sequence
<220> FEATURE:

<223> OTHER INFORMATION: Description of Artificial Sequence: Synthetic
    polypeptide

<400> SEQUENCE: 37

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Ile Leu His Ser
            20                  25                  30

Asn Gly Asn Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser Leu Val Pro Leu Thr Phe Gly Gln Gly Thr Lys Leu Glu Ile Lys
            100                 105                 110

<210> SEQ ID NO 38
<211> LENGTH: 123
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 38

Gln Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Gly Val Gly Trp Ile Arg Gln Pro Pro Gly Lys Ala Leu Glu
        35                  40                  45

Trp Leu Ala His Ile Trp Trp Asp Asp Lys Ser Tyr Asn Pro Ser
    50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Arg Gln Leu Gly Leu Arg Ser Ile Asp Ala Met Asp Tyr
            100                 105                 110

Trp Gly Gln Gly Thr Thr Val Thr Val Ser Ser
        115                 120

<210> SEQ ID NO 39
<211> LENGTH: 122
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 39

Gln Val Thr Leu Lys Glu Ser Gly Pro Ala Leu Val Lys Pro Thr Gln
1               5                   10                  15

Thr Leu Thr Leu Thr Cys Thr Leu Ser Gly Phe Ser Leu Ser Thr Ser
            20                  25                  30

Gly Met Gly Val Gly Trp Ile Arg Gln Pro Pro Gly Lys Ala Leu Glu

```
                35                  40                  45
Trp Leu Ala His Ile Trp Trp Asp Asp Asp Lys Ser Tyr Asn Pro Ser
        50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Arg Gln Leu Gly Leu Arg Ser Ile Asp Ala Met Asp Tyr
            100                 105                 110

Trp Gly Gln Gly Thr Thr Val Thr Val Ser
        115                 120

<210> SEQ ID NO 40
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Met Lys Leu Pro Val Arg Leu Leu Val Leu Met Phe Trp Ile Pro Gly
1               5                   10                  15

Ser Ser Ser Asp Val Met Met Thr Gln Thr Pro Leu Ser Leu Pro Val
            20                  25                  30

Ser Leu Gly Asp Gln Ala Ser Ile Ser Cys Arg Ser Ser Gln Ser Leu
        35                  40                  45

Val His Ser Asn Gly Asn Thr Tyr Leu Glu Trp Tyr Met Gln Lys Pro
    50                  55                  60

Gly Gln Ser Pro Met Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Ser Val Glu Ala Glu Asp Leu Gly Val Phe Tyr Cys
            100                 105                 110

Phe Gln Gly Ser Arg Val Pro Leu Thr Phe Gly Ala Gly Thr Lys Leu
        115                 120                 125

Glu Leu Lys Arg
    130

<210> SEQ ID NO 41
<211> LENGTH: 142
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Met Asp Arg Leu Thr Ser Ser Phe Leu Leu Leu Ile Val Pro Ala Tyr
1               5                   10                  15

Val Leu Ser Gln Val Thr Leu Lys Glu Ser Gly Pro Gly Ile Leu Gln
            20                  25                  30

Pro Ser Gln Thr Leu Ser Leu Thr Cys Ser Phe Ser Gly Phe Ser Leu
        35                  40                  45

Ser Thr Ser Gly Met Gly Val Ser Trp Ile Arg Gln Pro Ser Gly Lys
    50                  55                  60

Gly Leu Glu Trp Leu Ala His Ile Tyr Trp Asp Asp Asp Lys Arg Tyr
```

```
            65                  70                  75                  80
Asn Pro Ser Leu Lys Ser Arg Leu Thr Ile Ser Lys Asp Thr Ser Arg
                    85                  90                  95
Asn Gln Val Phe Leu Lys Ile Thr Ser Val Asp Thr Asp Thr Ala
                    100                 105                 110
Thr Tyr Tyr Cys Thr Arg Ser Ser Gly Ser Ile Val Ile Ala Thr Gly
                    115                 120                 125
Phe Ala Tyr Trp Gly Gln Gly Thr Leu Val Thr Val Ser Ala
                    130                 135                 140
```

<210> SEQ ID NO 42
<211> LENGTH: 128
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 42

```
Met Asp Phe Gln Val Gln Ile Phe Ser Phe Leu Leu Ile Ser Ala Ser
1               5                   10                  15
Val Ile Ile Ser Arg Gly Gln Ile Val Leu Thr Gln Ser Pro Ala Ile
                20                  25                  30
Met Ser Ala Ser Pro Gly Glu Lys Val Thr Met Thr Cys Ser Ala Ser
                35                  40                  45
Ser Ser Val Ser Tyr Met His Trp Tyr Gln Gln Lys Ser Gly Thr Ser
            50                  55                  60
Pro Lys Arg Trp Ile Tyr Asp Ser Ser Arg Leu Ala Ser Gly Val Pro
65                  70                  75                  80
Ser Arg Phe Ser Gly Gly Gly Ser Gly Thr Ser Tyr Ser Pro Thr Ile
                    85                  90                  95
Ser Asn Met Glu Ala Glu Asp Ala Ala Thr Tyr Phe Cys Gln Asn Trp
                    100                 105                 110
Arg Ser Ser Pro Thr Phe Gly Ala Gly Thr Lys Leu Glu Leu Lys Arg
                    115                 120                 125
```

<210> SEQ ID NO 43
<211> LENGTH: 138
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 43

```
Met Glu Trp Thr Trp Val Phe Leu Phe Leu Leu Ser Val Thr Ala Gly
1               5                   10                  15
Val His Ser Gln Val Gln Leu Gln Gln Ser Gly Pro Glu Leu Met Lys
                20                  25                  30
Pro Gly Ala Ser Val Lys Ile Ser Cys Lys Ala Thr Gly Tyr Thr Phe
                35                  40                  45
Ser Thr Ser Trp Ile Glu Trp Ile Lys Gln Arg Pro Gly His Gly Leu
            50                  55                  60
Glu Trp Ile Gly Glu Val Leu Pro Gly Ser Gly Lys Ser Asn His Asn
65                  70                  75                  80
Ala Asn Phe Lys Gly Arg Ala Thr Phe Thr Ala Asp Thr Ala Ser Asn
                    85                  90                  95
Thr Ala Tyr Met Gln Leu Ser Ser Leu Thr Ser Glu Asp Ser Ala Val
```

```
                      100                 105                 110

Tyr Tyr Cys Ala Arg Glu Gly Ser Asn Asn Ala Leu Ala Tyr Trp
            115                 120                 125

Gly Gln Gly Thr Leu Val Thr Val Ser Ala
        130                 135

<210> SEQ ID NO 44
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Gly Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Ser Leu His Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Arg Lys Leu Pro Tyr
                85                  90                  95

Thr Phe Gly Gly Gly Thr Lys Val Glu Ile Lys Arg
            100                 105

<210> SEQ ID NO 45
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asp Phe Ser Arg Tyr
            20                  25                  30

Trp Met Asn Trp Val Arg Gln Ala Pro Gly Lys Gly Leu Glu Trp Val
        35                  40                  45

Ser Glu Ile Asn Pro Asp Ser Ser Thr Ile Asn Tyr Thr Pro Ser Leu
    50                  55                  60

Lys Asp Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gln Met Gly Tyr Trp Gly Gln Gly Thr Thr Leu Thr Val Ser
            100                 105                 110

Ser

<210> SEQ ID NO 46
<211> LENGTH: 113
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 46

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Asp Phe Ser Arg Tyr
            20                  25                  30

Trp Met Asn Trp Ile Arg Gln Pro Pro Gly Lys Gly Leu Glu Trp Ile
        35                  40                  45

Gly Glu Ile Asn Pro Asp Ser Ser Thr Ile Asn Tyr Thr Pro Ser Leu
    50                  55                  60

Lys Asp Arg Val Thr Ile Ser Lys Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gln Met Gly Tyr Trp Gly Gln Gly Thr Leu Val Thr Val Ser
            100                 105                 110

Ser

<210> SEQ ID NO 47
<211> LENGTH: 241
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Met Asp Met Arg Val Pro Ala Gln Leu Leu Gly Leu Leu Met Leu Trp
1               5                   10                  15

Val Ser Gly Ser Ser Gly Asp Val Val Met Thr Gln Ser Pro Leu Ser
            20                  25                  30

Leu Pro Val Thr Pro Gly Glu Pro Ala Ser Ile Ser Cys Lys Ser Ser
        35                  40                  45

Gln Ser Leu Leu Asp Ser Asp Gly Lys Thr Tyr Leu Asn Trp Leu Leu
    50                  55                  60

Gln Lys Pro Gly Gln Ser Pro Gln Arg Leu Ile Tyr Leu Val Ser Lys
65                  70                  75                  80

Leu Asp Ser Gly Val Pro Asp Arg Phe Ser Gly Ser Gly Ser Gly Thr
                85                  90                  95

Asp Phe Thr Leu Lys Ile Ser Arg Val Glu Ala Glu Asp Val Gly Val
            100                 105                 110

Tyr Tyr Cys Trp Gln Gly Thr His Phe Pro Arg Thr Phe Gly Gln Gly
        115                 120                 125

Thr Lys Val Glu Ile Lys Arg Thr Val Ala Ala Pro Ser Val Phe Ile
    130                 135                 140

Phe Pro Pro Ser Asp Glu Gln Leu Lys Ser Gly Thr Ala Ser Val Val
145                 150                 155                 160

Cys Leu Leu Asn Asn Phe Tyr Pro Arg Glu Ala Lys Val Gln Trp Lys
                165                 170                 175

Val Asp Asn Ala Leu Gln Ser Gly Asn Ser Gln Glu Ser Val Thr Glu
            180                 185                 190

Gln Asp Ser Lys Asp Ser Thr Tyr Ser Leu Ser Ser Thr Leu Thr Leu
        195                 200                 205
```

```
Ser Lys Ala Asp Tyr Glu Lys His Lys Val Tyr Ala Cys Glu Val Thr
    210                 215                 220

His Gln Gly Leu Ser Ser Pro Val Thr Lys Ser Phe Asn Arg Gly Glu
225                 230                 235                 240

Cys

<210> SEQ ID NO 48
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Asp Val Val Met Thr Gln Ser Pro Leu Ser Leu Pro Val Thr Pro Gly
1               5                   10                  15

Glu Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Lys Pro Gly Gln Ser
        35                  40                  45

Pro Gln Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Arg Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 49
<211> LENGTH: 726
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 49
atggacatgc gcgtgcccgc ccagctgctg ggcctgctga tgctgtgggt gtccggctcc      60
tccggcgacg tggtgatgac ccagtccccc ctgtccctgc ccgtgacccc cggcgagccc     120
gcctccatct cctgcaagtc ctcccagtcc ctgctggact ccgacggcaa gacctacctg     180
aactggctgc tgcagaagcc cggccagtcc cccagcgcc tgatctacct ggtgtccaag     240
```

```
ctggactccg gcgtgcccga ccgcttctcc ggctccggct ccggcaccga cttcaccctg    300
aagatctccc gcgtggaggc cgaggacgtg ggcgtgtact actgctggca gggcacccac    360
ttcccccgca ccttcggcca gggcaccaag gtggagatca gcgtactgt ggctgcacca    420 tctgtcttca tcttcccgcc atctgatgag cagttgaaat ctggaactgc ctctgttgtg    480
tgcctgctga ataacttcta tcccagagag gccaaagtac agtggaaggt ggataacgcc    540
ctccaatcgg gtaactccca ggagagtgtc acagagcagg acagcaagga cagcacctac    600
agcctcagca gcaccctgac gctgagcaaa gcagactacg agaaacacaa agtctacgcc    660
tgcgaagtca cccatcaggg cctgagctcg cccgtcacaa agagcttcaa caggggagag    720
tgttag                                                                726
```

<210> SEQ ID NO 50
<211> LENGTH: 330
<212> TYPE: PRT
<213> ORGANISM: Homo sapiens

<400> SEQUENCE: 50

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Leu Gly Ala Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
```

```
                    275                 280                 285
Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 51
<211> LENGTH: 329
<212> TYPE: PRT
<213> ORGANISM: Homo sapiens

<400> SEQUENCE: 51

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Leu Gly Ala Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320
```

-continued

Gln Lys Ser Leu Ser Leu Ser Pro Gly
            325

<210> SEQ ID NO 52
<211> LENGTH: 468
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Met Glu Phe Gly Leu Ser Trp Leu Phe Leu Val Ala Ile Leu Lys Gly
1               5                   10                  15

Val Gln Cys Glu Val Gln Leu Leu Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Asn Tyr Gly Met Ser Trp Val Arg Gln Ala Pro Gly Lys Gly Leu
    50                  55                  60

Glu Trp Val Ala Ser Ile Arg Ser Gly Gly Gly Arg Thr Tyr Tyr Ser
65                  70                  75                  80

Asp Asn Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Val Arg Tyr Asp His Tyr Ser Gly Ser Ser Asp Tyr Trp
        115                 120                 125

Gly Gln Gly Thr Leu Val Thr Val Ser Ser Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
    210                 215                 220

His Lys Pro Ser Asn Thr Lys Val Asp Lys Lys Val Glu Pro Lys Ser
225                 230                 235                 240

Cys Asp Lys Thr His Thr Cys Pro Pro Cys Pro Ala Pro Glu Ala Leu
                245                 250                 255

Gly Ala Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu
    290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

```
Ile Glu Lys Thr Ile Ser Lys Ala Lys Gly Gln Pro Arg Glu Pro Gln
        355                 360                 365

Val Tyr Thr Leu Pro Pro Ser Arg Glu Glu Met Thr Lys Asn Gln Val
    370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
                420                 425                 430

Val Asp Lys Ser Arg Trp Gln Gln Gly Asn Val Phe Ser Cys Ser Val
                435                 440                 445

Met His Glu Ala Leu His Asn His Tyr Thr Gln Lys Ser Leu Ser Leu
    450                 455                 460

Ser Pro Gly Lys
465

<210> SEQ ID NO 53
<211> LENGTH: 467
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Met Glu Phe Gly Leu Ser Trp Leu Phe Leu Val Ala Ile Leu Lys Gly
1               5                   10                  15

Val Gln Cys Glu Val Gln Leu Leu Glu Ser Gly Gly Gly Leu Val Gln
                20                  25                  30

Pro Gly Gly Ser Leu Arg Leu Ser Cys Ala Ala Ser Gly Phe Thr Phe
            35                  40                  45

Ser Asn Tyr Gly Met Ser Trp Val Arg Gln Ala Pro Gly Lys Gly Leu
    50                  55                  60

Glu Trp Val Ala Ser Ile Arg Ser Gly Gly Gly Arg Thr Tyr Tyr Ser
65                  70                  75                  80

Asp Asn Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Val Arg Tyr Asp His Tyr Ser Gly Ser Ser Asp Tyr Trp
        115                 120                 125

Gly Gln Gly Thr Leu Val Thr Val Ser Ser Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
    210                 215                 220

His Lys Pro Ser Asn Thr Lys Val Asp Lys Lys Val Glu Pro Lys Ser
```

```
            225                 230                 235                 240

Cys Asp Lys Thr His Thr Cys Pro Pro Cys Pro Ala Pro Glu Ala Leu
            245                 250                 255

Gly Ala Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
            275                 280                 285

His Glu Asp Pro Glu Val Lys Phe Asn Trp Tyr Val Asp Gly Val Glu
            290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
            325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
            355                 360                 365

Val Tyr Thr Leu Pro Pro Ser Arg Glu Glu Met Thr Lys Asn Gln Val
            370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
            405                 410                 415

Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
            435                 440                 445

Met His Glu Ala Leu His Asn His Tyr Thr Gln Lys Ser Leu Ser Leu
            450                 455                 460

Ser Pro Gly
465

<210> SEQ ID NO 54
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ala Ser Ile Arg Ser Gly Gly Gly Arg Thr Tyr Tyr Ser Asp Asn Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Arg Tyr Asp His Tyr Ser Gly Ser Ser Asp Tyr Trp Gly Gln Gly
            100                 105                 110
```

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Ala Leu Gly Ala Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 55
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ala Ser Ile Arg Ser Gly Gly Gly Arg Thr Tyr Tyr Ser Asp Asn Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Val Arg Tyr Asp His Tyr Ser Gly Ser Ser Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Ala Leu Gly Ala Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly

<210> SEQ ID NO 56
<211> LENGTH: 327
<212> TYPE: PRT
<213> ORGANISM: Homo sapiens

<400> SEQUENCE: 56

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 57
<211> LENGTH: 326
<212> TYPE: PRT
<213> ORGANISM: Homo sapiens

<400> SEQUENCE: 57

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly
                325

<210> SEQ ID NO 58
<211> LENGTH: 465
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Met Glu Phe Gly Leu Ser Trp Leu Phe Leu Val Ala Ile Leu Lys Gly
1               5                   10                  15

-continued

```
Val Gln Cys Glu Val Gln Leu Leu Glu Ser Gly Gly Gly Leu Val Gln
             20                  25                  30
Pro Gly Gly Ser Leu Arg Leu Ser Cys Ala Ala Ser Gly Phe Thr Phe
         35                  40                  45
Ser Asn Tyr Gly Met Ser Trp Val Arg Gln Ala Pro Gly Lys Gly Leu
     50                  55                  60
Glu Trp Val Ala Ser Ile Arg Ser Gly Gly Gly Arg Thr Tyr Tyr Ser
 65                  70                  75                  80
Asp Asn Val Lys Gly Arg Phe Thr Ile Ser Arg Asp Asn Ser Lys Asn
                 85                  90                  95
Thr Leu Tyr Leu Gln Met Asn Ser Leu Arg Ala Glu Asp Thr Ala Val
            100                 105                 110
Tyr Tyr Cys Val Arg Tyr Asp His Tyr Ser Gly Ser Ser Asp Tyr Trp
        115                 120                 125
Gly Gln Gly Thr Leu Val Thr Val Ser Ser Ala Ser Thr Lys Gly Pro
    130                 135                 140
Ser Val Phe Pro Leu Ala Pro Cys Ser Arg Ser Thr Ser Glu Ser Thr
145                 150                 155                 160
Ala Ala Leu Gly Cys Leu Val Lys Asp Tyr Phe Pro Glu Pro Val Thr
                165                 170                 175
Val Ser Trp Asn Ser Gly Ala Leu Thr Ser Gly Val His Thr Phe Pro
            180                 185                 190
Ala Val Leu Gln Ser Ser Gly Leu Tyr Ser Leu Ser Ser Val Val Thr
        195                 200                 205
Val Pro Ser Ser Ser Leu Gly Thr Lys Thr Tyr Thr Cys Asn Val Asp
    210                 215                 220
His Lys Pro Ser Asn Thr Lys Val Asp Lys Arg Val Glu Ser Lys Tyr
225                 230                 235                 240
Gly Pro Pro Cys Pro Pro Cys Pro Ala Pro Glu Phe Leu Gly Gly Pro
                245                 250                 255
Ser Val Phe Leu Phe Pro Pro Lys Pro Lys Asp Thr Leu Met Ile Ser
            260                 265                 270
Arg Thr Pro Glu Val Thr Cys Val Val Val Asp Val Ser Gln Glu Asp
        275                 280                 285
Pro Glu Val Gln Phe Asn Trp Tyr Val Asp Gly Val Glu Val His Asn
    290                 295                 300
Ala Lys Thr Lys Pro Arg Glu Glu Gln Phe Asn Ser Thr Tyr Arg Val
305                 310                 315                 320
Val Ser Val Leu Thr Val Leu His Gln Asp Trp Leu Asn Gly Lys Glu
                325                 330                 335
Tyr Lys Cys Lys Val Ser Asn Lys Gly Leu Pro Ser Ser Ile Glu Lys
            340                 345                 350
Thr Ile Ser Lys Ala Lys Gly Gln Pro Arg Glu Pro Gln Val Tyr Thr
        355                 360                 365
Leu Pro Pro Ser Gln Glu Glu Met Thr Lys Asn Gln Val Ser Leu Thr
    370                 375                 380
Cys Leu Val Lys Gly Phe Tyr Pro Ser Asp Ile Ala Val Glu Trp Glu
385                 390                 395                 400
Ser Asn Gly Gln Pro Glu Asn Asn Tyr Lys Thr Thr Pro Pro Val Leu
                405                 410                 415
Asp Ser Asp Gly Ser Phe Phe Leu Tyr Ser Arg Leu Thr Val Asp Lys
            420                 425                 430
Ser Arg Trp Gln Glu Gly Asn Val Phe Ser Cys Ser Val Met His Glu
```

```
                  435                 440                 445
Ala Leu His Asn His Tyr Thr Gln Lys Ser Leu Ser Leu Ser Leu Gly
    450                 455                 460

Lys
465

<210> SEQ ID NO 59
<211> LENGTH: 464
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Met Glu Phe Gly Leu Ser Trp Leu Phe Leu Val Ala Ile Leu Lys Gly
1               5                   10                  15

Val Gln Cys Glu Val Gln Leu Leu Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Asn Tyr Gly Met Ser Trp Val Arg Gln Ala Pro Gly Lys Gly Leu
    50                  55                  60

Glu Trp Val Ala Ser Ile Arg Ser Gly Gly Gly Arg Thr Tyr Tyr Ser
65                  70                  75                  80

Asp Asn Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Val Arg Tyr Asp His Tyr Ser Gly Ser Ser Asp Tyr Trp
        115                 120                 125

Gly Gln Gly Thr Leu Val Thr Val Ser Ser Ala Ser Thr Lys Gly Pro
    130                 135                 140

Ser Val Phe Pro Leu Ala Pro Cys Ser Arg Ser Thr Ser Glu Ser Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Lys Thr Tyr Thr Cys Asn Val Asp
    210                 215                 220

His Lys Pro Ser Asn Thr Lys Val Asp Lys Arg Val Glu Ser Lys Tyr
225                 230                 235                 240

Gly Pro Pro Cys Pro Pro Cys Pro Ala Pro Glu Phe Leu Gly Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser Gln Glu Asp
        275                 280                 285

Pro Glu Val Gln Phe Asn Trp Tyr Val Asp Gly Val Glu Val His Asn
    290                 295                 300

Ala Lys Thr Lys Pro Arg Glu Glu Gln Phe Asn Ser Thr Tyr Arg Val
305                 310                 315                 320
```

-continued

Val Ser Val Leu Thr Val Leu His Gln Asp Trp Leu Asn Gly Lys Glu
            325                 330                 335

Tyr Lys Cys Lys Val Ser Asn Lys Gly Leu Pro Ser Ser Ile Glu Lys
        340                 345                 350

Thr Ile Ser Lys Ala Lys Gly Gln Pro Arg Glu Pro Gln Val Tyr Thr
    355                 360                 365

Leu Pro Pro Ser Gln Glu Glu Met Thr Lys Asn Gln Val Ser Leu Thr
370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
            405                 410                 415

Asp Ser Asp Gly Ser Phe Phe Leu Tyr Ser Arg Leu Thr Val Asp Lys
        420                 425                 430

Ser Arg Trp Gln Glu Gly Asn Val Phe Ser Cys Ser Val Met His Glu
    435                 440                 445

Ala Leu His Asn His Tyr Thr Gln Lys Ser Leu Ser Leu Ser Leu Gly
450                 455                 460

<210> SEQ ID NO 60
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ala Ser Ile Arg Ser Gly Gly Gly Arg Thr Tyr Tyr Ser Asp Asn Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Arg Tyr Asp His Tyr Ser Gly Ser Ser Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

```
Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
            245                 250                 255

Glu Val Thr Cys Val Val Val Asp Val Ser Gln Glu Asp Pro Glu Val
        260                 265                 270

Gln Phe Asn Trp Tyr Val Asp Gly Val Glu Val His Asn Ala Lys Thr
    275                 280                 285

Lys Pro Arg Glu Glu Gln Phe Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys
        435                 440                 445

<210> SEQ ID NO 61
<211> LENGTH: 445
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ala Ser Ile Arg Ser Gly Gly Gly Arg Thr Tyr Tyr Ser Asp Asn Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Arg Tyr Asp His Tyr Ser Gly Ser Ser Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
```

```
            130                 135                 140
Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly
        435                 440                 445

<210> SEQ ID NO 62
<211> LENGTH: 330
<212> TYPE: PRT
<213> ORGANISM: Homo sapiens

<400> SEQUENCE: 62

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60
```

```
Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Ala Ala Gly Ala Pro Ser Val Phe Leu Phe Pro Pro
            115                 120                 125

Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 63
<211> LENGTH: 329
<212> TYPE: PRT
<213> ORGANISM: Homo sapiens

<400> SEQUENCE: 63

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
         50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110
```

```
Pro Ala Pro Glu Ala Ala Gly Ala Pro Ser Val Phe Leu Phe Pro Pro
        115                 120                 125
Lys Pro Lys Asp Thr Leu Met Ile Ser Arg Thr Pro Glu Val Thr Cys
130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Ala Pro Ile Glu Lys Thr Ile Ser Lys Ala Lys Gly
    210                 215                 220
Gln Pro Arg Glu Pro Gln Val Tyr Thr Leu Pro Pro Ser Arg Glu Glu
225                 230                 235                 240
Met Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
    290                 295                 300
Val Phe Ser Cys Ser Val Met His Glu Ala Leu His Asn His Tyr Thr
305                 310                 315                 320
Gln Lys Ser Leu Ser Leu Ser Pro Gly
                325

<210> SEQ ID NO 64
<211> LENGTH: 468
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Met Glu Phe Gly Leu Ser Trp Leu Phe Leu Val Ala Ile Leu Lys Gly
1               5                   10                  15
Val Gln Cys Glu Val Gln Leu Leu Glu Ser Gly Gly Gly Leu Val Gln
            20                  25                  30
Pro Gly Gly Ser Leu Arg Leu Ser Cys Ala Ala Ser Gly Phe Thr Phe
        35                  40                  45
Ser Asn Tyr Gly Met Ser Trp Val Arg Gln Ala Pro Gly Lys Gly Leu
    50                  55                  60
Glu Trp Val Ala Ser Ile Arg Ser Gly Gly Arg Thr Tyr Tyr Ser
65                  70                  75                  80
Asp Asn Val Lys Gly Arg Phe Thr Ile Ser Arg Asp Asn Ser Lys Asn
                85                  90                  95
Thr Leu Tyr Leu Gln Met Asn Ser Leu Arg Ala Glu Asp Thr Ala Val
            100                 105                 110
Tyr Tyr Cys Val Arg Tyr Asp His Tyr Ser Gly Ser Ser Asp Tyr Trp
        115                 120                 125
Gly Gln Gly Thr Leu Val Thr Val Ser Ser Ala Ser Thr Lys Gly Pro
```

```
            130                 135                 140
Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
            195                 200                 205

Val Pro Ser Ser Ser Leu Gly Thr Gln Thr Tyr Ile Cys Asn Val Asn
        210                 215                 220

His Lys Pro Ser Asn Thr Lys Val Asp Lys Lys Val Glu Pro Lys Ser
225                 230                 235                 240

Cys Asp Lys Thr His Thr Cys Pro Pro Cys Pro Ala Pro Glu Ala Ala
                245                 250                 255

Gly Ala Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
            275                 280                 285

His Glu Asp Pro Glu Val Lys Phe Asn Trp Tyr Val Asp Gly Val Glu
        290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
            355                 360                 365

Val Tyr Thr Leu Pro Pro Ser Arg Glu Glu Met Thr Lys Asn Gln Val
        370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
            435                 440                 445

Met His Glu Ala Leu His Asn His Tyr Thr Gln Lys Ser Leu Ser Leu
        450                 455                 460

Ser Pro Gly Lys
465

<210> SEQ ID NO 65
<211> LENGTH: 467
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Met Glu Phe Gly Leu Ser Trp Leu Phe Leu Val Ala Ile Leu Lys Gly
1               5                   10                  15
```

-continued

```
Val Gln Cys Glu Val Gln Leu Leu Glu Ser Gly Gly Gly Leu Val Gln
             20                  25                  30
Pro Gly Gly Ser Leu Arg Leu Ser Cys Ala Ala Ser Gly Phe Thr Phe
         35                  40                  45
Ser Asn Tyr Gly Met Ser Trp Val Arg Gln Ala Pro Gly Lys Gly Leu
     50                  55                  60
Glu Trp Val Ala Ser Ile Arg Ser Gly Gly Gly Arg Thr Tyr Tyr Ser
 65                  70                  75                  80
Asp Asn Val Lys Gly Arg Phe Thr Ile Ser Arg Asp Asn Ser Lys Asn
                 85                  90                  95
Thr Leu Tyr Leu Gln Met Asn Ser Leu Arg Ala Glu Asp Thr Ala Val
            100                 105                 110
Tyr Tyr Cys Val Arg Tyr Asp His Tyr Ser Gly Ser Ser Asp Tyr Trp
        115                 120                 125
Gly Gln Gly Thr Leu Val Thr Val Ser Ser Ala Ser Thr Lys Gly Pro
    130                 135                 140
Ser Val Phe Pro Leu Ala Pro Ser Ser Lys Ser Thr Ser Gly Gly Thr
145                 150                 155                 160
Ala Ala Leu Gly Cys Leu Val Lys Asp Tyr Phe Pro Glu Pro Val Thr
                165                 170                 175
Val Ser Trp Asn Ser Gly Ala Leu Thr Ser Gly Val His Thr Phe Pro
            180                 185                 190
Ala Val Leu Gln Ser Ser Gly Leu Tyr Ser Leu Ser Ser Val Val Thr
        195                 200                 205
Val Pro Ser Ser Ser Leu Gly Thr Gln Thr Tyr Ile Cys Asn Val Asn
    210                 215                 220
His Lys Pro Ser Asn Thr Lys Val Asp Lys Lys Val Glu Pro Lys Ser
225                 230                 235                 240
Cys Asp Lys Thr His Thr Cys Pro Pro Cys Pro Ala Pro Glu Ala Ala
                245                 250                 255
Gly Ala Pro Ser Val Phe Leu Phe Pro Pro Lys Pro Lys Asp Thr Leu
            260                 265                 270
Met Ile Ser Arg Thr Pro Glu Val Thr Cys Val Val Val Asp Val Ser
        275                 280                 285
His Glu Asp Pro Glu Val Lys Phe Asn Trp Tyr Val Asp Gly Val Glu
    290                 295                 300
Val His Asn Ala Lys Thr Lys Pro Arg Glu Glu Gln Tyr Asn Ser Thr
305                 310                 315                 320
Tyr Arg Val Val Ser Val Leu Thr Val Leu His Gln Asp Trp Leu Asn
                325                 330                 335
Gly Lys Glu Tyr Lys Cys Lys Val Ser Asn Lys Ala Leu Pro Ala Pro
            340                 345                 350
Ile Glu Lys Thr Ile Ser Lys Ala Lys Gly Gln Pro Arg Glu Pro Gln
        355                 360                 365
Val Tyr Thr Leu Pro Pro Ser Arg Glu Glu Met Thr Lys Asn Gln Val
    370                 375                 380
Ser Leu Thr Cys Leu Val Lys Gly Phe Tyr Pro Ser Asp Ile Ala Val
385                 390                 395                 400
Glu Trp Glu Ser Asn Gly Gln Pro Glu Asn Asn Tyr Lys Thr Thr Pro
                405                 410                 415
Pro Val Leu Asp Ser Asp Gly Ser Phe Phe Leu Tyr Ser Lys Leu Thr
            420                 425                 430
Val Asp Lys Ser Arg Trp Gln Gln Gly Asn Val Phe Ser Cys Ser Val
```

```
                435                 440                 445
Met His Glu Ala Leu His Asn His Tyr Thr Gln Lys Ser Leu Ser Leu
        450                 455                 460

Ser Pro Gly
465

<210> SEQ ID NO 66
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ala Ser Ile Arg Ser Gly Gly Arg Thr Tyr Tyr Ser Asp Asn Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Arg Tyr Asp His Tyr Ser Gly Ser Ser Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Ala Ala Gly Ala Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320
```

```
Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 67
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ala Ser Ile Arg Ser Gly Gly Gly Arg Thr Tyr Tyr Ser Asp Asn Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Arg Tyr Asp His Tyr Ser Gly Ser Ser Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220
```

```
Thr His Thr Cys Pro Pro Cys Pro Ala Pro Glu Ala Ala Gly Ala Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
        260                 265                 270

Pro Glu Val Lys Phe Asn Trp Tyr Val Asp Gly Val Glu Val His Asn
    275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
        340                 345                 350

Leu Pro Pro Ser Arg Glu Glu Met Thr Lys Asn Gln Val Ser Leu Thr
    355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
        420                 425                 430

Ala Leu His Asn His Tyr Thr Gln Lys Ser Leu Ser Leu Ser Pro Gly
    435                 440                 445

<210> SEQ ID NO 68
<211> LENGTH: 1407
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 68
atggagtttg ggctgagctg gcttttctt gtggctattt taaaaggtgt ccagtgtgag      60
gtgcagctgc tggagtccgg cggcggcctg gtgcagcccg gcggctccct gcgcctgtcc     120
tgcgccgcct ccggcttcac cttctccaac tacggcatgt cctgggtgcg ccaggccccc     180
ggcaagggcc tggagtgggt ggcctccatc cgctccggcg gcggccgcac ctactactcc     240
gacaacgtga agggccgctt caccatctcc cgcgacaact ccaagaacac cctgtacctg     300
cagatgaact ccctgcgcgc cgaggacacc gccgtgtact actgcgtgcg ctacgaccac     360
tactccggct cctccgacta ctggggccag ggcaccctgg tgaccgtgtc ctccgcgtcg     420
accaagggcc catcggtctt ccccctggca ccctcctcca agagcacctc tgggggcaca     480
gcggccctgg gctgcctggt caaggactac ttccccgaac cggtgacggt gtcgtggaac     540
tcaggcgccc tgaccagcgg cgtgcacacc ttccggctg tcctacagtc ctcaggactc     600
tactccctca gcagcgtggt gaccgtgccc tccagcagct gggcacccca gacctacatc     660
tgcaacgtga atcacaagcc cagcaacacc aaggtggaca gaaagttgag cccaaatct      720 tgtgacaaaa ctcacacatg cccaccgtgc ccagcacctg aagccgctgg ggcaccgtca     780
```

```
gtcttcctct tcccccaaa acccaaggac accctcatga tctcccggac ccctgaggtc     840
acatgcgtgg tggtggacgt gagccacgaa gaccctgagg tcaagttcaa ctggtacgtg     900
gacggcgtgg aggtgcataa tgccaagaca aagccgcggg aggagcagta caacagcacg     960
taccgtgtgg tcagcgtcct caccgtcctg caccaggact ggctgaatgg caaggagtac    1020
aagtgcaagg tctccaacaa agccctccca gcccccatcg agaaaaccat ctccaaagcc    1080
aaagggcagc cccgagaacc acaggtgtac accctgcccc catcccggga ggagatgacc    1140
aagaaccagg tcagcctgac ctgcctggtc aaaggcttct atcccagcga catcgccgtg    1200
gagtgggaga gcaatgggca gccggagaac aactacaaga ccacgcctcc cgtgctggac    1260
tccgacggct ccttcttcct ctatagcaag ctcaccgtgg acaagagcag gtggcagcag    1320
gggaacgtct tctcatgctc cgtgatgcat gaggctctgc acaaccacta cacgcagaag    1380
agcctctccc tgtccccggg taaatga                                       1407
```

<210> SEQ ID NO 69
<211> LENGTH: 449
<212> TYPE: PRT
<213> ORGANISM: Homo sapiens

<400> SEQUENCE: 69

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ala Ser Ile Arg Ser Gly Gly Gly Arg Thr Tyr Tyr Ser Asp Asn Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Arg Tyr Asp His Tyr Ser Gly Ser Ser Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
```

```
                260                 265                 270
Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 70
<211> LENGTH: 448
<212> TYPE: PRT
<213> ORGANISM: Homo sapiens

<400> SEQUENCE: 70

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ala Ser Ile Arg Ser Gly Gly Gly Arg Thr Tyr Tyr Ser Asp Asn Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Arg Tyr Asp His Tyr Ser Gly Ser Ser Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
```

```
                    180                 185                 190

Ser Ser Leu Gly Thr Gln Thr Tyr Ile Cys Asn Val Asn His Lys Pro
                    195                 200                 205

Ser Asn Thr Lys Val Asp Lys Lys Val Glu Pro Lys Ser Cys Asp Lys
                    210                 215                 220

Thr His Thr Cys Pro Pro Cys Pro Ala Pro Glu Leu Leu Gly Gly Pro
        225                 230                 235                 240

Ser Val Phe Leu Phe Pro Pro Lys Pro Lys Asp Thr Leu Met Ile Ser
                            245                 250                 255

Arg Thr Pro Glu Val Thr Cys Val Val Val Asp Val Ser His Glu Asp
                        260                 265                 270

Pro Glu Val Lys Phe Asn Trp Tyr Val Asp Gly Val Glu Val His Asn
                    275                 280                 285

Ala Lys Thr Lys Pro Arg Glu Glu Gln Tyr Asn Ser Thr Tyr Arg Val
                    290                 295                 300

Val Ser Val Leu Thr Val Leu His Gln Asp Trp Leu Asn Gly Lys Glu
        305                 310                 315                 320

Tyr Lys Cys Lys Val Ser Asn Lys Ala Leu Pro Ala Pro Ile Glu Lys
                        325                 330                 335

Thr Ile Ser Lys Ala Lys Gly Gln Pro Arg Glu Pro Gln Val Tyr Thr
                        340                 345                 350

Leu Pro Pro Ser Arg Glu Glu Met Thr Lys Asn Gln Val Ser Leu Thr
                    355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
        385                 390                 395                 400

Asp Ser Asp Gly Ser Phe Phe Leu Tyr Ser Lys Leu Thr Val Asp Lys
                        405                 410                 415

Ser Arg Trp Gln Gln Gly Asn Val Phe Ser Cys Ser Val Met His Glu
                    420                 425                 430

Ala Leu His Asn His Tyr Thr Gln Lys Ser Leu Ser Leu Ser Pro Gly
                    435                 440                 445

<210> SEQ ID NO 71
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Asp Val Val Met Thr Gln Ser Pro Leu Ser Leu Pro Val Thr Leu Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Gln Gln Arg Pro Gly Gln Ser
        35                  40                  45

Pro Arg Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95
```

```
Thr His Phe Pro Arg Thr Phe Gly Gly Gly Thr Lys Val Glu Ile Lys
            100                 105                 110
Arg

<210> SEQ ID NO 72
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Glu Val Gln Leu Val Glu Ser Gly Gly Gly Leu Val Gln Pro Gly Gly
1               5                   10                  15

Ser Leu Arg Leu Ser Cys Ala Gly Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ala Ser Ile Arg Ser Gly Gly Gly Arg Thr Tyr Tyr Ser Asp Asn Val
    50                  55                  60

Lys Gly Arg Phe Thr Ile Ser Arg Glu Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Val Arg Tyr Asp His Tyr Ser Gly Ser Ser Asp Tyr Trp Gly Gln Gly
            100                 105                 110

Thr Leu Val Thr Val Ser Ser
        115

<210> SEQ ID NO 73
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Asn Ile Ile His Ser
            20                  25                  30

Asn Gly Asn Thr Tyr Leu Glu Trp Tyr Leu Gln Lys Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Leu Thr Phe Gly Gly Gly Thr Lys Val Glu Ile Lys
            100                 105                 110

Arg

<210> SEQ ID NO 74
<211> LENGTH: 123
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 74

Gln Val Thr Leu Lys Glu Ser Gly Pro Val Leu Val Lys Pro Thr Glu
1               5                   10                  15

Thr Leu Thr Leu Thr Cys Thr Phe Ser Gly Phe Ser Leu Ser Thr Ser
            20                  25                  30

Gly Met Gly Val Ser Trp Ile Arg Gln Pro Pro Gly Lys Ala Leu Glu
        35                  40                  45

Trp Leu Ala His Ile Tyr Trp Asp Asp Lys Arg Tyr Asn Pro Ser
50                  55                  60

Leu Lys Ser Arg Leu Thr Ile Ser Lys Asp Thr Ser Lys Ser Gln Val
65                  70                  75                  80

Val Leu Thr Met Thr Asn Met Asp Pro Val Asp Thr Ala Thr Tyr Tyr
                85                  90                  95

Cys Val Arg Arg Pro Ile Thr Pro Val Leu Val Asp Ala Met Asp Tyr
            100                 105                 110

Trp Gly Gln Gly Thr Leu Val Thr Val Ser Ser
        115                 120

<210> SEQ ID NO 75
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Asp Ile Val Met Thr Gln Ser Pro Leu Ser Leu Pro Val Thr Pro Gly
1               5                   10                  15

Glu Pro Ala Ser Ile Ser Cys Arg Val Ser Gln Ser Leu Leu His Ser
            20                  25                  30

Asn Gly Tyr Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Thr
                85                  90                  95

Arg His Val Pro Tyr Thr Phe Gly Gly Gly Thr Lys Val Glu Ile Lys
            100                 105                 110

<210> SEQ ID NO 76
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Asn
            20                  25                  30
```

```
Gly Met Ala Trp Val Arg Gln Ala Pro Gly Lys Gly Leu Glu Trp Val
            35                  40                  45

Ser Phe Ile Ser Asn Leu Ala Tyr Ser Ile Asp Tyr Ala Asp Thr Val
 50                  55                  60

Thr Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Val Ser Gly Thr Trp Phe Ala Tyr Trp Gly Gln Gly Thr Leu Val Thr
            100                 105                 110

Val Ser Ser
        115

<210> SEQ ID NO 77
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Glu Val Gln Leu Val Glu Ser Gly Gly Gly Leu Val Gln Pro Gly Gly
 1               5                  10                  15

Ser Leu Arg Leu Ser Cys Ala Val Ser Gly Phe Thr Phe Ser Asp Asn
             20                  25                  30

Gly Met Ala Trp Val Arg Gln Ala Pro Gly Lys Gly Leu Glu Trp Val
            35                  40                  45

Ser Phe Ile Ser Asn Leu Ala Tyr Ser Ile Asp Tyr Ala Asp Thr Val
 50                  55                  60

Thr Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Val Ser Gly Thr Trp Phe Ala Tyr Trp Gly Gln Gly Thr Leu Val Thr
            100                 105                 110

Val Ser Ser
        115

<210> SEQ ID NO 78
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Asp Asn
             20                  25                  30

Gly Met Ala Trp Val Arg Gln Ala Pro Gly Lys Gly Leu Glu Trp Ile
            35                  40                  45

Ser Phe Ile Ser Asn Leu Ala Tyr Ser Ile Asp Tyr Ala Asp Thr Val
 50                  55                  60

Thr Gly Arg Phe Thr Ile Ser Arg Asp Asn Ala Lys Asn Ser Leu Tyr
 65                  70                  75                  80
```

```
Leu Gln Met Asn Ser Leu Arg Ala Glu Asp Thr Ala Val Tyr Tyr Cys
                85                  90                  95

Val Ser Gly Thr Trp Phe Ala Tyr Trp Gly Gln Gly Thr Leu Val Thr
            100                 105                 110

Val Ser Ser
        115

<210> SEQ ID NO 79
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Tyr Thr Glu Ala Tyr
            20                  25                  30

Tyr Ile His Trp Val Arg Gln Ala Pro Gly Gln Gly Leu Glu Trp Met
        35                  40                  45

Gly Arg Ile Asp Pro Ala Thr Gly Asn Thr Lys Tyr Ala Pro Arg Leu
    50                  55                  60

Gln Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Ser Leu Tyr Ser Leu Pro Val Tyr Trp Gly Gln Gly Thr Thr Val
            100                 105                 110

Thr Val Ser Ser
        115

<210> SEQ ID NO 80
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Asp Val Met Thr Gln Ser Pro Leu Ser Leu Pro Val Thr Leu Gly
1               5                   10                  15

Gln Pro Ala Ser Ile Ser Cys Lys Ser Ser Gln Ser Leu Leu Tyr Ser
            20                  25                  30

Asp Ala Lys Thr Tyr Leu Asn Trp Phe Gln Gln Arg Pro Gly Gln Ser
        35                  40                  45

Pro Arg Arg Leu Ile Tyr Gln Ile Ser Arg Leu Asp Pro Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Leu Gln Gly
                85                  90                  95

Thr His Tyr Pro Val Leu Phe Gly Gln Gly Thr Arg Leu Glu Ile Lys
            100                 105                 110

Arg Thr
```

```
<210> SEQ ID NO 81
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
            20                  25                  30

Ala Ile His Trp Val Arg Gln Ala Pro Gly Gln Gly Leu Glu Trp Met
        35                  40                  45

Gly Phe Thr Ser Pro Tyr Ser Gly Val Ser Asn Tyr Asn Gln Lys Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Phe Asp Asn Tyr Asp Arg Gly Tyr Val Arg Asp Tyr Trp Gly
            100                 105                 110

Gln Gly Thr Leu Val
        115

<210> SEQ ID NO 82
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Asp Ile Val Met Thr Gln Ser Pro Asp Ser Leu Ala Val Ser Leu Gly
1               5                   10                  15

Glu Arg Ala Thr Ile Asn Cys Arg Ala Ser Glu Ser Val Asp Asn Asp
            20                  25                  30

Arg Ile Ser Phe Leu Asn Trp Tyr Gln Gln Lys Pro Gly Gln Pro Pro
        35                  40                  45

Lys Leu Leu Ile Tyr Ala Ala Thr Lys Gln Gly Thr Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Lys
                85                  90                  95

Glu Phe Pro Trp Ser Phe Gly Gly Gly Thr Lys Val Glu Ile Lys Arg
            100                 105                 110

Thr Val

<210> SEQ ID NO 83
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83
```

-continued

```
Gln Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Arg Thr Ser
                20                  25                  30

Gly Met Gly Val Gly Trp Ile Arg Gln Pro Pro Gly Lys Ala Leu Glu
            35                  40                  45

Trp Leu Ala His Ile Trp Trp Asp Asp Lys Ser Tyr Asn Pro Ser
    50                  55                  60

Leu Lys Ser Gln Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Arg Asn Tyr Tyr Tyr Asp Asp Tyr Phe Ala Tyr Trp Gly
                100                 105                 110

Gln Gly Thr Leu Val Thr Val Ser Ser
            115                 120
```

<210> SEQ ID NO 84
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

```
Asp Val Leu Met Thr Gln Ser Pro Leu Ser Leu Pro Val Thr Leu Gly
1               5                   10                  15

Gln Pro Ala Ser Ile Ser Cys Arg Ser Ser Gln Ser Ile Val His Ser
                20                  25                  30

Asn Gly Asn Thr Tyr Leu Glu Trp Tyr Leu Gln Arg Pro Gly Gln Ser
            35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Leu Thr Phe Gly Ala Gly Thr Lys Leu Glu Ile Lys
                100                 105                 110
```

<210> SEQ ID NO 85
<211> LENGTH: 9
<212> TYPE: PRT
<213> ORGANISM: Homo sapiens

<400> SEQUENCE: 85

```
Ala Glu Phe Arg His Asp Ser Gly Tyr
1               5
```

<210> SEQ ID NO 86
<211> LENGTH: 6
<212> TYPE: PRT
<213> ORGANISM: Homo sapiens

<400> SEQUENCE: 86

```
Ala Glu Phe Arg His Asp
1               5
```

```
<210> SEQ ID NO 87
<211> LENGTH: 7
<212> TYPE: PRT
<213> ORGANISM: Homo sapiens

<400> SEQUENCE: 87

Glu Phe Arg His Asp Ser Gly
1               5

<210> SEQ ID NO 88
<211> LENGTH: 5
<212> TYPE: PRT
<213> ORGANISM: Homo sapiens

<400> SEQUENCE: 88

Glu Phe Arg His Asp
1               5

<210> SEQ ID NO 89
<211> LENGTH: 16
<212> TYPE: PRT
<213> ORGANISM: Homo sapiens

<400> SEQUENCE: 89

Tyr Glu Val His His Gln Lys Leu Val Phe Phe Ala Glu Asp Val Gly
1               5                   10                  15

<210> SEQ ID NO 90
<211> LENGTH: 4
<212> TYPE: PRT
<213> ORGANISM: Homo sapiens

<400> SEQUENCE: 90

Val Phe Phe Ala
1

<210> SEQ ID NO 91
<211> LENGTH: 9
<212> TYPE: PRT
<213> ORGANISM: Homo sapiens

<400> SEQUENCE: 91

Gln Lys Leu Phe Phe Ala Glu Asp Val
1               5

<210> SEQ ID NO 92
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Lys Leu Val Phe Phe Ala Gly Asp Val
1               5

<210> SEQ ID NO 93
<211> LENGTH: 5
<212> TYPE: PRT
<213> ORGANISM: Artificial Sequence
<220> FEATURE:
<223> OTHER INFORMATION: Description of Artificial Sequence: Synthetic
      5xHis tag

<400> SEQUENCE: 93
```

His His His His His
1               5

<210> SEQ ID NO 94
<211> LENGTH: 5
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Asp Ala Glu Phe Arg
1               5

<210> SEQ ID NO 95
<211> LENGTH: 110
<212> TYPE: PRT
<213> ORGANISM: Homo sapiens

<400> SEQUENCE: 95

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110

<210> SEQ ID NO 96
<211> LENGTH: 109
<212> TYPE: PRT
<213> ORGANISM: Homo sapiens

<400> SEQUENCE: 96

Ala Pro Pro Val Ala Gly Pro Ser Val Phe Leu Phe Pro Pro Lys Pro
1               5                   10                  15

Lys Asp Thr Leu Met Ile Ser Arg Thr Pro Glu Val Cys Val Val
            20                  25                  30

Val Asp Val Ser His Glu Asp Pro Glu Val Gln Phe Asn Trp Tyr Val
        35                  40                  45

Asp Gly Val Glu Val His Asn Ala Lys Thr Lys Pro Arg Glu Glu Gln
    50                  55                  60

Phe Asn Ser Thr Phe Arg Val Val Ser Val Leu Thr Val His Gln
65                  70                  75                  80

Asp Trp Leu Asn Gly Lys Glu Tyr Lys Cys Lys Val Ser Asn Lys Gly
                85                  90                  95

Leu Pro Ala Pro Ile Glu Lys Thr Ile Ser Lys Thr Lys
            100                 105

<210> SEQ ID NO 97
<211> LENGTH: 110
<212> TYPE: PRT

<213> ORGANISM: Homo sapiens

<400> SEQUENCE: 97

Ala Pro Glu Phe Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser Gln Glu Asp Pro Glu Val Gln Phe Asn Trp Tyr
        35                  40                  45

Val Asp Gly Val Glu Val His Asn Ala Lys Thr Lys Pro Arg Glu Glu
    50                  55                  60

Gln Phe Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Gly Leu Pro Ser Ser Ile Glu Lys Thr Ile Ser Lys Ala Lys
            100                 105                 110

<210> SEQ ID NO 98
<211> LENGTH: 107
<212> TYPE: PRT
<213> ORGANISM: Mus sp.

<400> SEQUENCE: 98

Val Pro Glu Val Ser Ser Val Phe Ile Phe Pro Pro Lys Pro Lys Asp
1               5                   10                  15

Val Leu Thr Ile Thr Leu Thr Pro Lys Val Thr Cys Val Val Val Asp
            20                  25                  30

Ile Ser Lys Asp Asp Pro Glu Val Gln Phe Ser Trp Phe Val Asp Asp
        35                  40                  45

Val Glu Val His Thr Ala Gln Thr Gln Pro Arg Glu Glu Gln Phe Asn
    50                  55                  60

Ser Thr Phe Arg Ser Val Ser Glu Leu Pro Ile Met His Gln Asp Trp
65                  70                  75                  80

Leu Asn Gly Lys Glu Phe Lys Cys Arg Val Asn Ser Ala Ala Phe Pro
                85                  90                  95

Ala Pro Ile Glu Lys Thr Ile Ser Lys Thr Lys
            100                 105

<210> SEQ ID NO 99
<211> LENGTH: 110
<212> TYPE: PRT
<213> ORGANISM: Mus sp.

<400> SEQUENCE: 99

Ala Pro Asn Leu Leu Gly Gly Pro Ser Val Phe Ile Phe Pro Pro Lys
1               5                   10                  15

Ile Lys Asp Val Leu Met Ile Ser Leu Ser Pro Ile Val Thr Cys Val
            20                  25                  30

Val Val Asp Val Ser Glu Asp Asp Pro Asp Val Gln Ile Ser Trp Phe
        35                  40                  45

Val Asn Asn Val Glu Val His Thr Ala Gln Thr Gln Thr His Arg Glu
    50                  55                  60

Asp Tyr Asn Ser Thr Leu Arg Val Val Ser Ala Leu Pro Ile Gln His
65                  70                  75                  80

Gln Asp Trp Met Ser Gly Lys Glu Phe Lys Cys Lys Val Asn Asn Lys
                85                  90                  95

```
Asp Leu Pro Ala Pro Ile Glu Arg Thr Ile Ser Lys Pro Lys
            100             105             110
```

IMMUNOTHERAPY REGIMES DEPENDENT ON APOE STATUS

CROSS-REFERENCE TO RELATED APPLICATION

This application is a national stage filing of PCT/US2008/080382, which claims priority To provisional U.S. Application Nos. 60/999,423 and 61/083,827, filed Oct. 17, 2007 and Jul. 25, 2008, respectively, are incorporated by reference in their entirety for all purposes.

BACKGROUND OF THE INVENTION

General

Alzheimer's disease (AD) is a progressive disease resulting in senile dementia. See generally Selkoe, *TINS* 16:403 (1993); Hardy et al., WO 92/13069; Selkoe, *J. Neuropathol. Exp. Neurol.* 53:438 (1994); Duff et al., *Nature* 373:476 (1995); Games et al., *Nature* 373:523 (1995). Broadly speaking, the disease falls into two categories: late onset, which occurs in old age (65+years) and early onset, which develops well before the senile period, i.e., between 35 and 60 years. In both types of disease, the pathology is the same but the abnormalities tend to be more severe and widespread in cases beginning at an earlier age. The disease is characterized by at least two types of lesions in the brain, neurofibrillary tangles and senile plaques. Neurofibrillary tangles are intracellular deposits of microtubule associated tau protein consisting of two filaments twisted about each other in pairs. Senile plaques (i.e., amyloid plaques) are areas of disorganized neuropile up to 150 μm across with extracellular amyloid deposits at the center which are visible by microscopic analysis of sections of brain tissue. The accumulation of amyloid plaques within the brain is also associated with Down's syndrome and other cognitive disorders.

The principal constituent of the plaques is a peptide termed Aβ or β-amyloid peptide. Aβ peptide is a 4-kDa internal fragment of 39-43 amino acids of a larger transmembrane glycoprotein named amyloid precursor protein (APP). As a result of proteolytic processing of APP by different secretase enzymes, Aβ is primarily found in both a short form, 40 amino acids in length, and a long form, ranging from 42-43 amino acids in length. Part of the hydrophobic transmembrane domain of APP is found at the carboxy end of Aβ, and may account for the ability of Aβ to aggregate into plaques, particularly in the case of the long form. Accumulation of amyloid plaques in the brain eventually leads to neuronal cell death. The physical symptoms associated with this type of neural deterioration characterize Alzheimer's disease.

Several mutations within the APP protein have been correlated with the presence of Alzheimer's disease. See, e.g., Goate et al., *Nature* 349:704 (1991) (valine$^{717}$ isoleucine); Chartier Harlan et al., *Nature* 353:844 (1991)) (valine$^{717}$ to glycine); Murrell et al., *Science* 254:97 (1991) (valine$^{717}$ to phenylalanine); Mullan et al., *Nature Genet.* 1:345 (1992) (a double mutation changing lysine$^{595}$-methionine$^{596}$ to asparagine$^{595}$-leucine$^{596}$). Such mutations are thought to cause Alzheimer's disease by increased or altered processing of APP to Aβ, particularly processing of APP to increased amounts of the long form of Aβ (i.e., Aβ1-42 and Aβ1-43). Mutations in other genes, such as the presenilin genes, PS1 and PS2, are thought indirectly to affect processing of APP to generate increased amounts of long form Aβ (see Hardy, *TINS* 20: 154 (1997)).

Apolipoprotein E (ApoE) encodes a cholesterol-processing protein. The gene, which maps to 19q13.2, has three allelic variants: ApoE4, ApoE3, and ApoE2. The frequency of the apoE4 version of the gene in the general population varies, but is always less than 30% and frequently 8%-15%. ApoE3 is the most common form and ApoE2 is the least common. Persons with one E4 allele usually have about a two to three fold increased risk of developing Alzheimer's disease. Persons with two E4 alleles (usually around 1% of the population) have about a nine-fold increase in risk. Nonetheless, even persons with two E4 alleles do not always get Alzheimer's disease. At least one E4 allele is found in about 40% of patients with late-onset Alzheimer's disease. Genetic screening for E4 has not been routinely performed, because it has not been known how to use this information for a therapeutic regime.

SUMMARY OF THE CLAIMED INVENTION

The invention provides a method of treating Alzheimer's disease, comprising administering to a patient having zero ApoE4 alleles ("ApoE4 non-carrier patient") and Alzheimer's disease, an effective regime of an antibody that specifically binds to an N-terminal epitope of Aβ. Optionally, the antibody specifically binds to an epitope within residues 1-7 of Aβ, or an epitope within residues 1-5 of Aβ, or an epitope within residues 3-7 of Aβ. Optionally, the dosage of the antibody within a range of about 0.15 mg/kg to about 2 mg/kg is administered by intravenous infusion. Optionally, the dosage is administered every 4 to 16 weeks. Optionally, the dosage is administered every 10 to 14 weeks. Optionally, the dosage is administered every 13 weeks. Optionally, the dosage is about 0.5 mg/kg to about 1 mg/kg. Optionally, the dosage is about 0.5 mg/kg to 2 mg/kg. Optionally, the dosage is about 2 mg/kg. Optionally, the antibody is bapineuzumab. Optionally, the method also involves monitoring for vasogenic edema, and optionally administering a corticosteroid to the patient to treat vasogenic edema detected by the monitoring.

The invention also provides a method of reducing cognitive decline in a patient having zero ApoE4 alleles ("ApoE4 non-carrier patient"), comprising administering to the patient an antibody that specifically binds to an N-terminal epitope of Aβ in a regime effective to reduce the cognitive decline of the patient relative to a control patient to whom the antibody is not administered; wherein: the ApoE4 non-carrier patient and control patient have been diagnosed with mild to moderate Alzheimer's disease; and the cognitive decline is measured by ADAS-COG, NTB, MMSE or CDR-SB. Optionally, the antibody is administered by intravenous infusion at a dosage within a range of about 0.15 mg/kg to about 2 mg/kg. Optionally, the antibody is bapineuzumab. Optionally, the dosage is about 0.5 mg/kg and the cognitive decline is measured by ADAS-COG. Optionally, the dosage is about 2 mg/kg and the cognitive decline is measured by ADAS-COG. Optionally, the cognitive decline is measured by NTB. Optionally, the dosage is 0.5 mg/kg. Optionally, the dosage is about 0.5 mg/kg and the cognitive decline is measured by CDR. Optionally, the dosage is about 0.5 mg/kg and the cognitive decline is measured by MMSE. Optionally, the dosage is about 2 mg/kg and the cognitive decline is measured by MMSE.

The invention also provides a method of reducing brain volume decline in a patient having zero ApoE4 alleles ("ApoE4 non-carrier patient"), comprising administering to the ApoE4 non-carrier patient an antibody that specifically binds to an N-terminal epitope of Aβ in a regime effective to reduce the brain volume decline of the ApoE4 non-carrier patient relative to a control patient to whom the antibody is not administered; wherein the ApoE4 non-carrier patient and control patient have been diagnosed with mild to moderate Alzheimer's disease. Optionally, the antibody is administered by intravenous infusion at a dosage within a range of about 0.15 mg/kg to about 2 mg/kg. Optionally, the antibody is bapineuzumab. Optionally, the dosage is about 0.5 mg/kg. Optionally, the dosage is about 2 mg/kg. Optionally, the brain volume decline is measured by MRI.

The invention also provides a method of treating Alzheimer's disease, comprising administering to an ApoE4 non-carrier patient an antibody that specifically recognizes the N-terminal region of Aβ in a regime effective to maintain a mean serum concentration of the antibody in the range of about 0.1 µg/ml to about 60 µg/ml. Optionally, the range is about 0.4 µg/ml to about 20 µg/ml. Optionally, the range is about 1 µg/ml to about 5 µg/ml. Optionally, the maximum serum concentration of the antibody in the patient less than about 28 µg antibody/ml serum. Optionally, the maximum serum concentration is within a range of about 4-18 µg antibody/ml serum. Optionally, the antibody is bapineuzumab.

The invention also provides a method of treating Alzheimer's disease, comprising administering to an ApoE4 non-carrier patient an antibody that specifically recognizes the N-terminal region of Aβ in a regime effective to achieve a mean plasma Aβ concentration of at least 450 pg/ml. Optionally, the mean plasma Aβ concentration is in the range of about 600 pg/ml to about 3000 pg/ml. Optionally, the mean plasma Aβ concentration is in the range of about 700 pg/ml to about 2000 pg/ml. Optionally, the mean plasma Aβ concentration is in the range of about 700 pg/ml to about 2000 pg/ml. Optionally, the mean plasma Aβ concentration is in the range of about 800 pg/ml to about 1000 pg/ml.

The invention also provides a method of treating Alzheimer's disease, comprising subcutaneously administering to a patient having the disease and one or two copies of an ApoE4 allele an effective regime of an antibody that binds to an N-terminal epitope of Aβ. Optionally, the method further comprises monitoring for vasogenic edema. Optionally, the antibody is administered at a dose of 0.01-0.6 mg/kg and a frequency of between weekly and monthly. Optionally, the antibody is administered at a dose of 0.05-0.5 mg/kg. Optionally, the antibody is administered at a dose of 0.05-0.25 mg/kg. Optionally, the antibody is administered at a dose of 0.015-0.2 mg/kg weekly to biweekly. Optionally, the antibody is administered at a dose of 0.05-0.15 mg/kg weekly to biweekly. Optionally, the antibody is administered at a dose of 0.05-0.07 mg/kg weekly. Optionally, the antibody is administered at a dose of 0.06 mg/kg weekly. Optionally, the antibody is administered at a dose of 0.1 to 0.15 mg/kg biweekly. Optionally, the antibody is administered at a dose of 0.1 to 0.3 mg/kg monthly. Optionally, the antibody is administered at a dose of 0.2 mg/kg monthly. Optionally, the antibody is administered at a dose of 1-40 mg and a frequency of between weekly and monthly. Optionally, the antibody is administered at a dose of 5-25 mg. Optionally, the antibody is administered at a dose of 2.5-15 mg. Optionally, the antibody is administered at a dose of 1-12 mg weekly to biweekly. Optionally, the antibody is administered at a dose of 2.5-10 mg weekly to biweekly. Optionally, the antibody is administered at a dose of 2.5-5 mg weekly. Optionally, the antibody is administered at a dose of 4-5 mg weekly. Optionally, the antibody is administered at a dose of 7-10 mg biweekly. Optionally, the method further comprises monitoring for vasogenic edema.

The invention further comprises a method of treating Alzheimer's disease, comprising administering to a patient having the disease and one or two ApoE4 alleles an effective regime of an antibody that binds to an N-terminal epitope of Aβ; administering a corticosteroid to the patient to treat vasogenic edema arising from the administration of the antibody. Optionally, the method further comprises monitoring the patient for vasogenic edema. Optionally, the dose or frequency of administration of the antibody is reduced or eliminated during the vasogenic edema relative to the dose or frequency before the vasogenic edema. Optionally, the dose or frequency of administration of the antibody is increased after resolution of the vasogenic edema relative to the dose or frequency either before or during the vasogenic edema.

The invention further comprises a method of treating or effecting prophylaxis in a population of patients of an amyloidogenic disease characterized by amyloid deposits of Aβ in the brain, comprising: administering different regimes to different patients in the population depending on which allelic forms of ApoE are present in the patients; wherein at least one of the regimes comprises administering an agent that is an antibody to Aβ or an agent that induces an antibody to Aβ on administration to a patient. Optionally, the different regimes each comprise administering an agent that is an antibody to Aβ or an agent that induces an antibody to Aβ on administration to a patient; and the dose of the agent and/or the frequency of administration of the agent and/or the capacity of the agent to induce a clearing response to amyloid deposits and/or the mean serum concentration of the agent or antibodies induced by the agent and/or the maximum serum concentration of the agent or antibodies induced by the agent is reduced and/or the time of initiation of treatment relative to disease progression is earlier in (a) patients having two copies of an ApoE4 allele relative to patients having zero copies of an ApoE4 allele, and/or (b) patients having one copy of an ApoE4 allele relative to patients having zero copies of an ApoE4 allele, and/or (c) patients having two copies of an ApoE4 allele relative to patients having one copy of an ApoE4 allele.

Optionally, a first regime comprises administering an agent that is an antibody to Aβ or an agent that induces an antibody to Aβ on administration to a patient and a second regime lacks an antibody to Aβ or an agent that induces an antibody to Aβ and the first regime is administered to patients having zero copies of an ApoE4 allele and the second regime is administered to patients having one or two copies of an ApoE4 allele. Optionally, a first regime comprises administering a first antibody to Aβ and the second regime comprises administering a second antibody to Aβ and the second antibody has reduced binding to an Fcγ receptor or C1q relative to the first antibody, and the first antibody is administered to patients having zero copies of an ApoE4 allele and the second antibody is administered to patients having one or two copies of an ApoE4 allele. Optionally, the second antibody has one or more mutations in the constant region that reduce binding to the Fcγ receptor and/or C1q, the mutations not being present in the first antibody. Optionally, the one or more mutations is/are at position(s) in a heavy chain constant region selected from the group consisting of positions 234, 235, 236 and 237 (EU numbering). Optionally, the one or more mutations are mutations at positions 234, 235 and 237. Optionally, the one or more mutations are L234A, L235A and G237A. Optionally, the isotype of the constant region is human IgG1. Optionally, the isotype of the constant region is human IgG2 or IgG4. Optionally, the first antibody is bapineuzumab and the second antibody is an L234A, L235A, G237A variant of bapineuzumab. Optionally, a first regime comprises administering a first antibody to Aβ and a second regime comprises administering a second antibody to Aβ, the first antibody being of human IgG1 isotype and the second antibody of human IgG4 isotype, and the first antibody is administered to patients having zero copies of an ApoE4 allele and the second antibody is administered to patients having one or two copies of an ApoE4 allele.

In some methods, the disease is Alzheimer's disease. Some methods further comprise determining which alleles of ApoE are present in the patient.

Optionally, the different regimes differ in dose of the agent administered. Optionally, the different regimes differ in frequency of the agent administered. Optionally, the different regimes differ in the type of agent administered.

Optionally, the dose of the agent and/or the frequency of administration of the agent and/or the capacity of the agent to induce a clearing response to amyloid deposits is reduced in (a) patients having two ApoE4 alleles relative to patients having one ApoE4 allele; and/or (b) patients having one copy of an ApoE4 allele relative to patients having zero copies of an ApoE4 allele, and/or (c) patients having two copies of an ApoE4 allele relative to patients having one copy of an ApoE4 allele. Optionally, the dose of the agent and/or the frequency of administration of the agent and/or the capacity of the agent to induce a clearing response to amyloid deposits is reduced in patients having one or two ApoE4 alleles relative to patients having zero ApoE4 alleles of an ApoE4 allele. Optionally, patients in the population having one or two ApoE4 alleles are administered a dose of 0.15-1 mg/kg, and patients in the population having zero ApoE4 alleles are administered a dose of 0.5-2 mg/kg of an antibody specifically binding within residues 1-11 of Aβ. Optionally, the patients in the population having one or two ApoE4 alleles are administered a lower dosage of agent than patients having zero ApoE4 alleles until vasogenic edema has appeared and resolved, and the same dosage of agent thereafter.

Optionally, the patients in the population having one or two ApoE4 alleles are administered a lower frequency of the agent than the patients having zero ApoE4 alleles until vasogenic edema has appeared and resolved, and the same dosage of agent thereafter. Optionally, the patients in the population having one or two ApoE4 alleles are administered an antibody with reduced capacity to induce a clearing response to amyloid deposits relative to bapineuzumab.

Optionally, the method further comprises monitoring at least some of the patients in the population for vasogenic edema. Optionally, the monitoring is performed by MRI. Optionally, patients in the population with zero ApoE4 alleles are not monitored by MRI. Optionally, the agent is an antibody binding to an epitope within residues 1-11 of Aβ. Optionally, the antibody has human IgG1 isotype. Optionally, the antibody is bapineuzumab. Optionally, the agent is an antibody having reduced capacity to induce a clearing response to amyloid deposits relative to bapineuzumab. Optionally, the antibody is an L234A, L235A, G237A variant of bapineuzumab.

Optionally, wherein patients with one or two ApoE4 alleles are administered 1-3 doses of humanized 266 antibody following by subsequent doses of bapineuzumab and patients with zero ApoE4 alleles are administered the same total number of doses but all with bapineuzumab. In some methods, the antibody is a humanized 266 antibody. Optionally, patients with one or two ApoE4 alleles are administered humanized 266 and patients with zero ApoE4 alleles are administered bapineuzumab.

The invention further provides a method of monitoring a population of patients undergoing treatment or prophylaxis for a disease characterized by amyloid deposits of Aβ in the brain with an agent that is an antibody to Aβ or an agent that induces an antibody to Aβ, the method comprising: performing different monitoring regimes in different patients in the population for vasogenic edema, wherein the frequency of monitoring is greater for (a) patients having two copies of ApoE4 relative to patients having zero copies of ApoE4 and/or (b) patients having one copy of an ApoE4 allele relative to patients having zero copies of an ApoE4 allele, and/or (c) patients having two copies of an ApoE4 allele relative to patients having one copy of an ApoE4 allele. Optionally, the disease is Alzheimer's disease. Optionally, the method further comprises determining which allelic forms of ApoE are present in each patient in the population. Optionally, the monitoring is by brain imaging. Optionally, the monitoring is by MRI. Optionally, patients having one ApoE4 allele are monitored more frequently than patients having zero ApoE4 alleles. Optionally, patients having two ApoE4 alleles are monitored more frequently than patients having one ApoE4 allele. Optionally, patients having one ApoE4 allele are monitored more frequently than patients having zero ApoE4 alleles. Optionally, patients having zero ApoE4 alleles are not monitored by MRI for vasogenic edema.

The invention further provides a method of treating or effecting prophylaxis of a patient for a disease characterized by amyloid deposits of Aβ in the brain, comprising administering to a patient with at least one ApoE4 allele an agent that is an antibody to an epitope within residue 1-11 of Aβ or an agent that induces such an antibody to Aβ, and monitoring the patient for vasogenic edema by MRI. Optionally, the agent is bapineuzumab. Optionally, the agent is an L234A, L235A, G237A variant of bapineuzumab.

The invention further provides a method of treating or effecting prophylaxis of a disease characterized by amyloid deposits of Aβ in the brain in a patient having at least one ApoE4 allele, comprising administering a first regime to the patient before vasogenic edema appears, and a second regime after vasogenic edema has resolved; wherein the first and second regimes each comprise administering an agent that is an antibody to Aβ or an agent that induces an antibody to Aβ on administration to a patient; and the dose of the agent and/or the frequency of administration of the agent and/or the capacity of the agent to clear amyloid deposits is reduced in the first regime relative to the second regime. Optionally, the disease is Alzheimer's disease. Optionally, the patient has one or two ApoE4 alleles. Optionally, the first and second regimes each comprises administering an antibody that specifically binds to an epitope within residues 1-11 of Aβ to the patient, and the antibody is administered at a dose of 0.15-1 mg/kg before vasogenic edema appears and 0.5-2 mg/kg after vasogenic edema has resolved. Optionally, the antibody is bapineuzumab. Optionally, the antibody is a L234A, L235A, G237A variant of bapineuzumab.

The invention further provides a method of treating or effecting prophylaxis of Alzheimer's disease in a patient, comprising administering to the patient an antibody that specifically binds to an epitope within residues 1-11 of Aβ to a patient having one or two ApoE4 alleles, wherein the antibody is administered in a regime in which 0.15-1 mg/kg of antibody is administered quarterly by intravenous administration, or at a dose frequency and route of administration that generates an equivalent average serum concentration or area under the curve. Optionally, the antibody is bapineuzumab. Optionally the dose is 0.5 mg/kg.

The invention further provides a method of treating or effecting prophylaxis of Alzheimer's disease in a patient, comprising administering to the patient an antibody that specifically binds to an epitope within residues 1-11 of Aβ to a patient having zero ApoE4 alleles, wherein the dose of the antibody is 0.5-2 mg/kg administered quarterly by intravenous administration, or a dose frequency and route of administration that generates an equivalent serum concentration or area under the curve. Optionally, the antibody is an L234A, L235A, G237A variant of bapineuzumab.

The invention further provides a method of treating or effecting prophylaxis of Alzheimer's disease in a population of patients, comprising administering an antibody that specifically binds to an epitope within residues 1-11 of Aβ to the patients, wherein the antibody is administered at a dose of 0.15-1 mg/kg in patients of the population having one or two ApoE4 alleles and a dose of 0.5-2.5 mg/kg in patients of the population having zero ApoE4 alleles, and the mean dose is higher in the patients having zero ApoE4 alleles. Optionally, the antibody is bapineuzumab. Optionally, the antibody is an L234A, L235A, G237A variant of bapineuzumab. Optionally, the dose is 0.5 mg/kg in patients of the population having one or two ApoE4 alleles and 2 mg/kg in patients of the population having zero ApoE4 alleles.

The invention further provides a use of a measurement of ApoE4 copy number is selecting from different regimes for treatment or prophylaxis of a disease characterized by amyloid deposits in the brain in the patient wherein the different regimes each comprise administering an agent that is an antibody to Aβ or an agent that induces an antibody to Aβ on administration to a patient, and the dose of the agent and/or the frequency of administration of the agent and/or the capacity of the agent to induce a clearing response to amyloid deposits and/or the mean serum concentration of the agent or antibodies induced by the agent and/or the maximum serum concentration of the agent or antibodies induced by the agent is reduced and/or the time of initiation of treatment relative to disease progression is earlier in a regime administered to (a) patients having two copies of an ApoE4 allele relative to patients having zero copies of an ApoE4 allele, and/or (b) patients having one copy of an ApoE4 allele relative to patients having zero copies of an ApoE4 allele, and/or (c) patients having two copies of an ApoE4 allele relative to patients having one copy of an ApoE4.

The invention further provides a method of selecting a regime for treatment or prophylaxis of a disease characterized by amyloid deposits in the brain of a patient, the method comprising determining the number of ApoE4 alleles present in a patient; selecting from different regimes based on the number of ApoE4 alleles present, wherein the different regimes each comprise administering an agent that is an antibody to Aβ or an agent that induces an antibody to Aβ on administration to a patient, and the dose of the agent and/or the frequency of administration of the agent and/or the capacity of the agent to induce a clearing response to amyloid deposits and/or the mean serum concentration of the agent or antibodies induced by the agent and/or the maximum serum concentration of the agent or antibodies induced by the agent is reduced and/or the time of initiation of treatment relative to disease progression is earlier in (a) patients having two copies of an ApoE4 allele relative to patients having zero copies of an ApoE4 allele, and/or (b) patients having one copy of an ApoE4 allele relative to patients having zero copies of an ApoE4 allele, and/or (c) patients having two copies of an ApoE4 allele relative to patients having one copy of an ApoE4.

The invention further provides a use of a measurement of ApoE4 copy number in the manufacture of a medicament to treat Alzheimer's disease, wherein the medicament comprises an antibody to Aβ or an agent that induces an antibody to Aβ.

The invention further provides a use of at least one agent that is an antibody to Aβ or an agent that induces an antibody to Aβ on administration to a patient in the manufacture of a medicament for the treatment or prophylaxis of a disease characterized by amyloid deposits in the brain of a patient by different regimes depending on the number of ApoE4 alleles in the patient, wherein the different regimes comprise administering an agent to a patient and the dose of the agent and/or the frequency of administration of the agent and/or the capacity of the agent to induce a clearing response to amyloid deposits and/or the mean serum concentration of the agent or antibodies induced by the agent and/or the maximum serum concentration of the agent or antibodies induced by the agent is reduced and/or the time of initiation of treatment relative to disease progression is earlier in (a) patients having two copies of an ApoE4 allele relative to patients having zero copies of an ApoE4 allele, and/or (b) patients having one copy of an ApoE4 allele relative to patients having zero copies of an ApoE4 allele, and/or (c) patients having two copies of an ApoE4 allele relative to patients having one copy of an ApoE4.

The invention further provides a method of treating or effecting prophylaxis in a population of patients of an amyloidogenic disease characterized by amyloid deposits of Aβ in the brain, comprising: administering different regimes to different patients in the population depending on which allelic forms of ApoE are present in the patients; wherein the different regimes each comprise administering an agent that is an antibody to Aβ or an agent that induces an antibody to Aβ on administration to a patient; and the mean serum concentration of the agent or antibodies induced by the agent and/or the maximum concentration of the agent or antibodies induced by the agent is reduced in patients having two copies of an ApoE4 allele relative to patients having zero copies of an ApoE4 allele, and/or (b) patients having one copy of an ApoE4 allele relative to patients having zero copies of an ApoE4 allele, and/or (c) patients having two copies of an ApoE4 allele relative to patients having one copy of an ApoE4.

The invention further provides a method of treating or effecting prophylaxis in a population of patients of an amyloidogenic disease characterized by amyloid deposits of Aβ in the brain, comprising: determining the ApoE4 status of the patient; administering different regimes to different patients in the population depending on which allelic forms of ApoE are present in the patients; wherein the different regimes each comprise administering an agent that is an antibody to Aβ or an agent that induces an antibody to Aβ on administration to a patient; and the dose of the agent and/or the frequency of administration of the agent and/or the capacity of the agent to induce a clearing response to amyloid deposits and/or the mean serum concentration of the agent or antibodies induced by the agent and/or the maximum serum concentration of the agent or antibodies induced by the agent is reduced and/or the time of initiation of treatment relative to disease progression is earlier in (a) patients having two copies of an ApoE4 allele relative to patients having zero copies of an ApoE4 allele, and/or (b)

patients having one copy of an ApoE4 allele relative to patients having zero copies of an ApoE4 allele, and/or (c) patients having two copies of an ApoE4 allele relative to patients having one copy of an ApoE4.

The invention further provides a humanized form of a 10D5 antibody comprising a human heavy chain constant region with L234A, L235A and G237A mutations, wherein positions are numbered by the EU numbering system. Optionally, the isotype is human IgG1, IgG2 or IgG4, preferably IgG1. The 10D5 hybridoma was deposited with the ATCC on Apr. 8, 2003 and assigned accession number PTA-5129. The ATCC is located at 10801 University Blvd., Manassas, Va. 20110.

The invention further provides a humanized form of a 12A11 antibody comprising a humanized light chain variable region of SEQ ID NO: 10 and a humanized heavy chain variable region of SEQ ID NO: 11 and a human heavy chain constant region with L234A, L235A and G237A mutations, wherein positions are numbered by the EU numbering system. Optionally, the isotype is human IgG1, IgG2 or IgG4, preferably IgG1.

The invention further provides a humanized form of a 3D6 antibody comprising a human heavy chain constant region with L234A, L235A and G237A mutations, wherein positions are numbered by the EU numbering system. The 3D6 hybridoma was deposited with the ATCC on Apr. 8, 2003 and assigned accession number PTA-5130. The ATCC is located at 10801 University Blvd., Manassas, Va. 20110. Optionally, the isotype is human IgG1, IgG2 or IgG4, preferably IgG1. The 3D6 hybridoma was deposited with the ATCC on Apr. 8, 2003.

The invention further provides an isolated humanized antibody comprising a mature light chain variable region sequence of SEQ ID NO: 2 and a mature heavy chain variable region sequence of SEQ ID NO: 3, and a human heavy chain constant region of IgG isotype with L234A, L235A, and G237A mutations, wherein positions are numbered by the EU numbering system. Optionally, the isotype is human IgG1 isotype.

The invention further provides an isolated humanized form of a 12B4 antibody, wherein the 12B4 antibody is characterized by a mature light chain variable region sequence of SEQ ID NO: 31 and a mature heavy chain variable region sequence of SEQ ID NO: 32, and a human heavy chain constant region of IgG isotype with L234A, L235A, and G237A mutations, wherein positions are numbered by the EU numbering system. Optionally, the isotype is human IgG1 isotype.

The invention further provides a method of treating or effecting prophylaxis of a disease characterized by Aβ deposits in the brain of patient comprising administering an effective regime of a humanized antibody to the patient; wherein the humanized antibody comprises a mature light chain variable region sequence of SEQ ID NO: 2 and a mature heavy chain variable region sequence of SEQ ID NO: 3, and a human heavy chain constant of IgG1 isotype with L234A, L235A, and G237A mutations, wherein position are numbered by the EU numbering system. Optionally, the patient has at least one ApoE4 allele. Optionally the dose is 0.15-1 mg/kg. Optionally, the dose is 0.15-2 mg/kg. Optionally, the method further comprises monitoring the patient by MRI for vasogenic edema. Optionally, the method is for treating a population of the patients and the regime administered to different patients in the population does not depend on the number of ApoE4 alleles present in a patient.

The invention further provides a method of effecting prophylaxis of a disease characterized by deposits of Aβ deposits in the brain of a patient comprising administering an effective regime of an agent that is an antibody to Aβ or an agent that induces an antibody to Aβ on administration to a patient, wherein the patient has at least one ApoE4 allele. Optionally, the patient has two ApoE4 alleles. Optionally, the patient is asymptomatic. Optionally, the patient has a mini-mental test score of 27 or higher. Optionally, the patient has a mini-mental test score of 20-26. Optionally, the patient is at least sixty years of age. Optionally, the method further comprises determining the number of ApoE4 alleles in the patient.

The invention further provides a method of treating or effecting prophylaxis of a disease characterized by amyloid deposits of Aβ in the brain in a patient comprising administering a first regime comprise administering an agent that is an antibody to Aβ or an agent that induces an antibody to Aβ to the patient; monitoring the patient for vasogenic edema; maintaining the first regime if vasogenic edema does not appear; and administering a second regime to the patient if vasogenic edema does appear, wherein the second regime is a reduced dose of the agent and/or a reduced frequency of the agent, and/or a different agent with reduced capacity to bind an Fcγ receptor and/or C1q or is a lack of antibody to Aβ or an agent that induces an antibody to Aβ; wherein the second regime is maintained at least for the duration of the vasogenic edema. Optionally, the agent in the first regime is an antibody that specifically binds to an epitope within residues 1-11 of Aβ. Optionally, the first regime comprises administering a first antibody to A and the second regime comprises administering a second antibody to Aβ with reduced capacity to find to an Fcγ receptor and or C1q relative to the first antibody. Optionally, the first antibody is bapineuzumab and the second antibody is an L234A, L235A, G237A variant of bapineuzumab.

The invention further provides a method of treating or effecting prophylaxis of Alzheimer's disease in a patient population, comprising administering an antibody that specifically binds to an epitope within residues 1-11 of Aβ and has mutations in the constant region that reduce binding to an Fcγ receptor and or C1q to the patient, wherein the antibody is administered at the same dose and/or frequency to each patient regardless of the number of ApoE4 alleles in the patient. Optionally, the antibody is an L234A, L235A, and G237A variant of bapineuzumab. Optionally, the method further comprises a step of monitoring the patient for vasogenic edema.

The invention further provides a method of treating or effecting prophylaxis of Alzheimer's disease in a patient population, comprising administering an agent that is an antibody to Aβ or which induces an antibody to Aβ on administration to some of the patients in the population, wherein patients in the population having zero ApoE4 alleles receive the agent and patients in the population having two ApoE4 alleles do not receive the agent. Optionally, patients in the population having one ApoE4 allele do not receive the agent. Optionally, the antibody is administered by intravenous infusion at a dosage within a range of about 0.15 mg/kg to about 2 mg/kg. Optionally, the antibody is bapineuzumab. Optionally, the dosage is about 0.5 mg/kg. Optionally, the dosage is about 2 mg/kg. Optionally, the brain volume decline is measured by MRI.

The invention further provides a method of determining a regime for bapineuzumab administration, comprising providing instructions to a healthcare professional that assists the healthcare professional determine a regime of bapineuzumab to administer to a patient having zero copies of an ApoE4 allele. Optionally, the regime is characterized by administering bapineuzumab at a dose of 0.5-2 mg/kg. Optionally, the regime is characterized by administering 0.5-2 mg/kg of bapineuzumab quarterly by intravenous administration, or at a dose frequency and route of administration that generates an equivalent average serum concentration or area under the curve. Optionally, the regime further comprises monitoring the patient for vasogenic edema. Optionally, the monitoring regime is different than the monitoring regime for a patient having or two copies of an ApoE4 allele. Optionally, the method further comprises the step of determining the number of ApoE4 alleles present in a patient. Optionally, the method further comprises providing bapineuzumab to a healthcare professional. Optionally, the instructions and bapineuzumab are provided in combination. Optionally, the regime further comprises monitoring at the patient for vasogenic edema. Optionally, the monitoring is performed by MRI. Optionally, the monitoring is by brain imaging.

The invention further provides a method of determining a regime for bapineuzumab administration comprising providing instructions to a healthcare professional that assists the healthcare professional determine a regime of bapineuzumab to administer to a patient having one or two copies of an ApoE4 allele. Optionally, the regime is characterized by administering bapineuzumab at a dose of 0.15-1 mg/kg. Optionally, the regime is characterized by administering bapineuzumab at a dose of 0.15-1 mg/kg quarterly by intravenous administration, or at a dose frequency and route of administration that generates an equivalent average serum concentration or area under the curve. Optionally, the determined regime comprises a first and a second regime, wherein the first regime is administered to the patient before vasogenic edema appears, and the second regime after vasogenic edema has resolved; and wherein the first and second regimes each comprise administering bapineuzumab; wherein the first regime differs relative to the second regime in at least one of (i)-(ii) below: (i) the dose of the bapineuzumab is reduced; (ii) the frequency of administration of the bapineuzumab is reduced. Optionally, the regime further comprises monitoring the patient for vasogenic edema. Optionally, the monitoring regime is different than the monitoring regime for a patient having or two copies of an ApoE4 allele. Optionally, the method further comprises the step of determining the number of ApoE4 alleles present in a patient. Optionally, the method further comprises providing bapineuzumab to a healthcare professional. Optionally, the instructions and bapineuzumab are provided in combination. Optionally, the regime further comprises monitoring at the patient for vasogenic edema. Optionally, the monitoring is performed by MRI. Optionally, the monitoring is by brain imaging. Optionally, the monitoring regime is different than the monitoring regime for a patient having zero copies of an ApoE4 allele. Optionally, the frequency of monitoring is greater for: (a) patients having two copies of the ApoE4 allele relative to patients having zero copies of an ApoE4 allele; (b) patients having one copy of an ApoE4 allele relative to patients having zero copies of an ApoE4 allele; and/or (c) patients having two copies of an ApoE4 allele relative to patients having one copy of an ApoE4 allele.

The invention further provides a kit for determining a regime for bapineuzumab administration comprising instructions to a healthcare professional that assist the healthcare professional determine which regime of bapineuzumab to administer to a patient having zero copies of an ApoE4 allele. Optionally, the instructions specify a regime characterized by administering bapineuzumab at a dose of 0.5-2 mg/kg. Optionally, the instructions specify administering 0.5-2 mg/kg of bapineuzumab quarterly by intravenous administration, or at a dose frequency and route of administration that generates an equivalent average serum concentration or area under the curve. Optionally, the instructions specify monitoring the patient for vasogenic edema. Optionally, the instructions specify that the monitoring regime is different that the monitoring regime for a patient having one or two copies of an ApoE4 allele. Optionally, the instructions specify that the determined regime comprises a first and a second regime, wherein the first regime is administered to the patient before vasogenic edema appears, and the second regime after vasogenic edema has resolved; and wherein the first and second regimes each comprise administering bapineuzumab; wherein the first regime differs relative to the second regime in at least one of (i)-(ii) below: (i) the dose of the bapineuzumab is reduced; (ii) the frequency of administration of the bapineuzumab is reduced. Optionally, the instructions specify determining the number of ApoE4 alleles present in a patient. Optionally, the kit further comprises bapineuzumab. Optionally, the instructions specify monitoring at the patient for vasogenic edema. Optionally, the instructions specify the monitoring is performed by MRI. Optionally, the instructions specify the monitoring is by brain imaging.

The invention further provides a kit for determining a regime for bapineuzumab administration comprising instructions to a healthcare professional that assist the healthcare professional determine which regime of bapineuzumab to administer to a patient having one or two copies of an ApoE4 allele. Optionally, the instructions specify administering bapineuzumab at a dose of 0.15-1 mg/kg. Optionally, the instructions specify administering bapineuzumab at a dose of 0.15-1 mg/kg quarterly by intravenous administration, or at a dose frequency and route of administration that generates an equivalent average serum concentration or area under the curve. Optionally, the instructions specify that the determined regime comprises a first and a second regime, wherein the first regime is administered to the patient before vasogenic edema appears, and the second regime after vasogenic edema has resolved; and wherein the first and second regimes each comprise administering bapineuzumab; wherein the first regime differs relative to the second regime in at least one of (i)-(ii) below: (i) the dose of the bapineuzumab is reduced; (ii) the frequency of administration of the bapineuzumab is reduced. Optionally, the instructions specify determining the number of ApoE4 alleles present in a patient. Optionally, the kit further comprises bapineuzumab. Optionally, the instructions specify monitoring at the patient for vasogenic edema. Optionally, the instructions specify the monitoring is performed by MRI. Optionally, the instructions specify the monitoring is by brain imaging. Optionally, the instructions specify the monitoring regime is different that the monitoring regime for a patient having zero copies of an ApoE4 allele. Optionally, the instructions specify that the frequency of monitoring is greater for: (a) patients having two copies of the ApoE4 allele relative to patients having zero copies of an ApoE4 allele; (b) patients having one copy of an ApoE4 allele relative to patients having zero copies of an ApoE4 allele; and/or (c) patients having two copies of an ApoE4 allele relative to patients having one copy of an ApoE4 allele.

The invention further provides a method for improving the safety of bapineuzumab in patients having one or two ApoE4 alleles, comprising advising the physician to administer a lower dose of bapineuzumab to a patient having one or two ApoE alleles relative to that of a patient having zero ApoE alleles.

The invention further provides a method for improving the safety of bapineuzumab in patients having one or two ApoE4 alleles, comprising advising the physician to monitor the patient by MRI more frequently than a patient having one or two ApoE alleles relative to that of a patient having zero ApoE alleles.

The invention further provides an isolated antibody comprising a human heavy chain constant region of isotype IgG1, wherein amino acids at positions 234, 235, and 237 (EU numbering) are each alanine. Optionally, no other amino acid from positions 230-240 or 315-325 in the human heavy chain constant region is occupied by an amino acid not naturally found at that position in a human IgG1 constant region. Optionally, no amino acid in the human heavy chain constant region other than positions 234, 235 and 237 is occupied by an amino acid not naturally found at that position in a human IgG1 constant region. Optionally, the human heavy chain constant region comprise CH1, hinge, CH2 and C3 regions. Optionally, the human heavy chain constant region has an amino acid sequence comprising SEQ ID NO:66 or SEQ ID NO:67 or an allotype of either of these sequences. Optionally, the human heavy chain constant region has an amino acid sequence comprising SEQ ID NO:66 or SEQ ID NO:67. Optionally, the antibody is a fully human antibody. Optionally, the antibody is a humanized antibody. Optionally, the antibody is chimeric antibody.

DEFINITIONS

Figure 1:
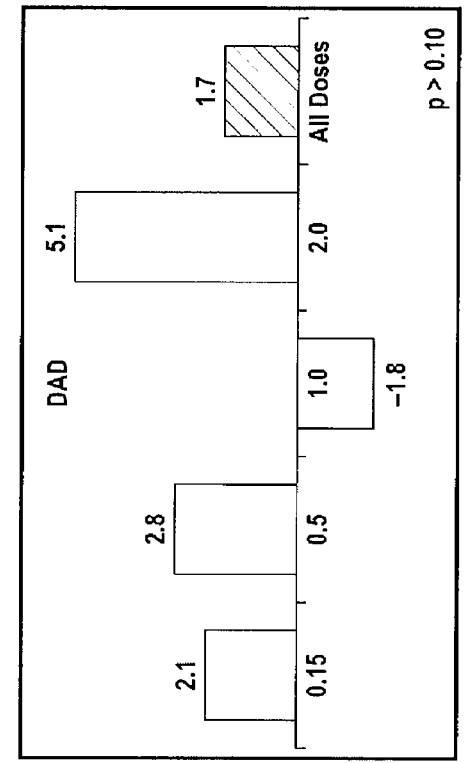
FIG. 1 shows changes in ADAS-Cog, DAD, NTB and CDR-SB in treated patients relative to placebo patients using a repeated measures statistical model without assumption of linearity. Bars above zero indicate improvement relative to placebo. MITT=modified intent to treat.
Figure 1:
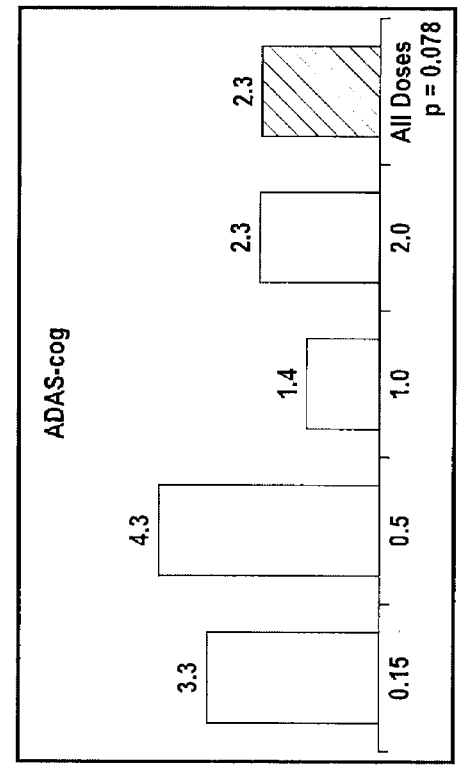
Figure 1:
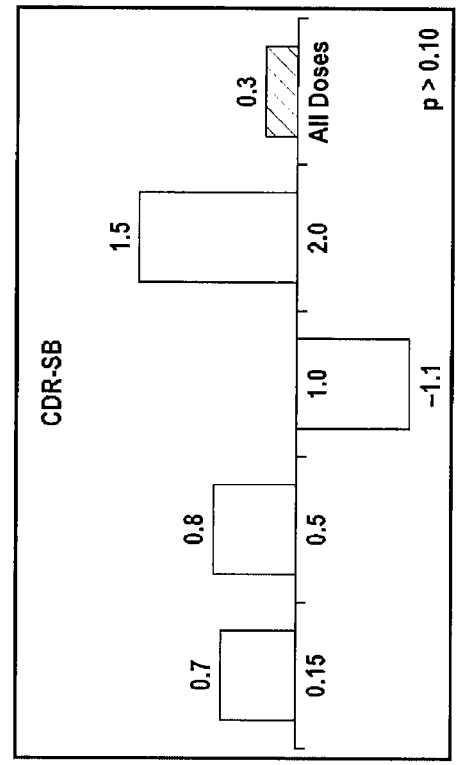
Figure 1:
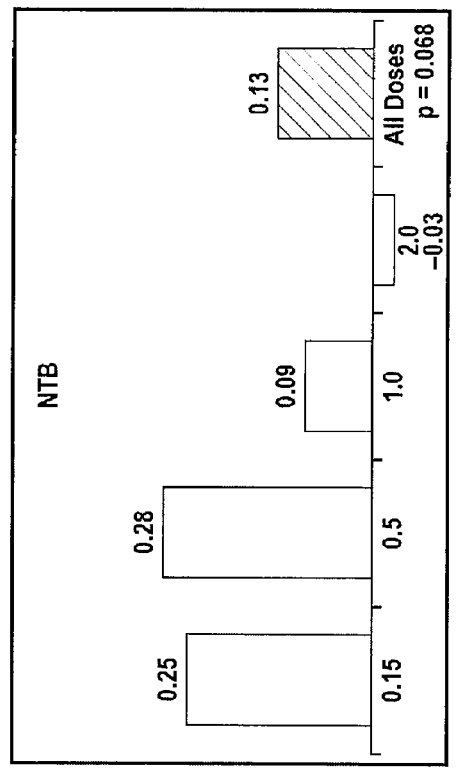

The term "immunoglobulin" or "antibody" (used interchangeably herein) refers to an antigen-binding protein having a basic four-polypeptide chain structure consisting of two heavy and two light chains, said chains being stabilized, for example, by interchain disulfide bonds, which has the ability to specifically bind antigen. Both heavy and light chains are folded into domains. The term "domain" refers to a globular region of a heavy or light chain polypeptide comprising peptide loops (e.g., comprising 3 to 4 peptide loops) stabilized, for example, by pleated sheet and/or intrachain disulfide bond. Domains are further referred to herein as "constant" or "variable", based on the relative lack of sequence variation within the domains of various class members in the case of a "constant" domain, or the significant variation within the domains of various class members in the case of a "variable" domain. "Constant" domains on the light chain are referred to interchangeably as "light chain constant regions", "light chain constant domains", "CL" regions or "CL" domains). "Constant" domains on the heavy chain are referred to interchangeably as "heavy chain constant regions", "heavy chain constant domains", "CH" regions or "CH" domains). A heavy chain constant region is also commonly understood to refer collectively to the domains present in a full length constant region, which are CH1, hinge, CH2, and CH3 domains in the case of antibodies of IgG isotype. "Variable" domains on the light chain are referred to interchangeably as "light chain variable regions", "light chain variable domains", "VL" regions or "VL" domains). "Variable" domains on the heavy chain are referred to interchangeably as "heavy chain constant regions," "heavy chain constant domains," "CH" regions or "CH" domains).

The term "region" refers to a part or portion of an antibody chain and includes constant or variable domains as defined herein, as well as more discrete parts or portions of said domains. For example, light chain variable domains or regions include "complementarity determining regions" or "CDRs" interspersed among "framework regions" or "FRs", as defined herein.

References to an antibody or immunoglobulin include intact antibodies and binding fragments thereof. Typically, fragments compete with the intact antibody from which they were derived for specific binding to an antigen. Fragments include separate heavy and light chains, Fab, Fab' F(ab')$_2$, Fabc, and Fv. Separate chains include NANOBODIES™ (i.e., the isolated VH fragment of the heavy chain of antibodies from camels or llamas, optionally humanized). Isolated VH fragments can also be obtained from other sources, such as human antibodies. Fragments are produced by recombinant DNA techniques, or by enzymatic or chemical separation of intact immunoglobulins. The term "antibody" also includes one or more immunoglobulin chains that are chemically conjugated to, or expressed as, fusion proteins with other proteins. The term "antibody" also includes bispecific antibody. A bispecific or bifunctional antibody is an artificial hybrid antibody having two different heavy/light chain pairs and two different binding sites. Bispecific antibodies can be produced by a variety of methods including fusion of hybridomas or linking of Fab' fragments. (See, e.g., Songsivilai & Lachmann, *Clin. Exp. Immunol.* 79:315-321 (1990); Kostelny et al., *J. Immunol.* 148, 1547-1553 (1992).)

"Specific binding" of an antibody means that the antibody exhibits appreciable affinity for antigen or a preferred epitope and, preferably, does not exhibit significant cross reactivity. Appreciable or preferred binding includes binding with an affinity of at least $10^6$, $10^7$, $10^8$, $10^9$ $M^{-1}$, or $10^{10}$ $M^{-1}$. Affinities greater than $10^7$ $M^{-1}$, preferably greater than $10^8$ $M^{-1}$ are more preferred. Values intermediate of those set forth herein are also intended to be within the scope of the present invention and a preferred binding affinity can be indicated as a range of affinities, for example, $10^6$ to $10^{10}$ $M^{-1}$, preferably $10^7$ to $10^{10}$ $M^{-1}$, more preferably $10^8$ to $10^{10}$ $M^{-1}$. An antibody that "does not exhibit significant cross reactivity" is one that will not appreciably bind to an undesirable entity (e.g., an undesirable proteinaceous entity). For example, an antibody that specifically binds to Aβ will appreciably bind Aβ but will not significantly react with non-Aβ proteins or peptides (e.g., non-Aβ proteins or peptides included in plaques). An antibody specific for a preferred epitope will, for example, not significantly cross react with remote epitopes on the same protein or peptide. Specific binding can be determined according to any art-recognized means for determining such binding. Preferably, specific binding is determined according to Scatchard analysis and/or competitive binding assays.

The term "humanized immunoglobulin" or "humanized antibody" refers to an immunoglobulin or antibody that includes at least one humanized immunoglobulin or antibody chain (i.e., at least one humanized light or heavy chain). The term "humanized immunoglobulin chain" or "humanized antibody chain" (i.e., a "humanized immunoglobulin light chain" or "humanized immunoglobulin heavy chain") refers to an immunoglobulin or antibody chain (i.e., a light or heavy chain, respectively) having a variable region that includes a variable framework region (also known as variable region framework) substantially from a human immunoglobulin or antibody and complementarity determining regions (CDRs) (e.g., at least one CDR, preferably two CDRs, more preferably three CDRs) substantially from a non-human immunoglobulin or antibody (e.g., rodent, and optionally, mouse), and further includes constant regions (e.g., at least one constant region or portion thereof, in the case of a light chain, and preferably three constant regions in the case of a heavy chain). The term "humanized variable region" (e.g., "humanized light chain variable region" or "humanized heavy chain variable region") refers to a variable region that includes a variable framework region (also known as a variable region framework) substantially from a human immunoglobulin or antibody and complementarity determining regions (CDRs) substantially from a non-human immunoglobulin or antibody.

The phrase "substantially from a human immunoglobulin or antibody" or "substantially human" means that, when aligned to a human immunoglobulin or antibody amino sequence for comparison purposes, the region shares at least 80-90% (e.g., at least 90%), preferably 90-95%, more preferably 95-99% identity (i.e., local sequence identity) with the human framework or constant region sequence, allowing, for example, for conservative substitutions, consensus sequence substitutions, germline substitutions, backmutations, and the like. The introduction of conservative substitutions, consensus sequence substitutions, germline substitutions, backmutations, and the like, is often referred to as "optimization" of a humanized antibody or chain. The phrase "substantially from a non-human immunoglobulin or antibody" or "substantially non-human" means having an immunoglobulin or antibody sequence at least 80-95%, preferably 90-95%, more preferably, 96%, 97%, 98%, or 99% identical to that of a non-human organism, e.g., a non-human mammal.

Accordingly, all regions or residues of a humanized immunoglobulin or antibody, or of a humanized immunoglobulin or antibody chain, except possibly the CDRs, are substantially identical to the corresponding regions or residues of one or more native human immunoglobulin sequences. The term "corresponding region" or "corresponding residue" refers to a region or residue on a second amino acid or nucleotide sequence which occupies the same (i.e., equivalent) position as a region or residue on a first amino acid or nucleotide sequence, when the first and second sequences are optimally aligned for comparison purposes.

The terms "humanized immunoglobulin" or "humanized antibody" are not intended to encompass chimeric immunoglobulins or antibodies, as defined infra. Although humanized immunoglobulins or antibodies are chimeric in their construction (i.e., comprise regions from more than one species of protein), they include additional features (i.e., variable regions comprising donor CDR residues and acceptor framework residues) not found in chimeric immunoglobulins or antibodies, as defined herein.

The term "chimeric immunoglobulin" or antibody refers to an immunoglobulin or antibody whose variable regions derive from a first species and whose constant regions derive from a second species. Chimeric immunoglobulins or antibodies can be constructed, for example by genetic engineering, from immunoglobulin gene segments belonging to different species.

An "antigen" is an entity (e.g., a proteinaceous entity or peptide) to which an antibody specifically binds.

The term "epitope" or "antigenic determinant" refers to a site on an antigen to which an immunoglobulin or antibody (or antigen binding fragment thereof) specifically binds. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, 4, 5, 6, 7, 8, 9, 10, 11, 12, 13, 14 or 15 amino acids in a unique spatial conformation. Methods of determining spatial conformation of epitopes include, for example, x-ray crystallography and 2-dimensional nuclear magnetic resonance. See, e.g., *Epitope Mapping Protocols in Methods in Molecular Biology*, Vol. 66, G. E. Morris, Ed. (1996).

Antibodies that recognize the same epitope can be identified in a simple immunoassay showing the ability of one antibody to block the binding of another antibody to a target antigen, i.e., a competitive binding assay. Competitive binding is determined in an assay in which the immunoglobulin under test inhibits specific binding of a reference antibody to a common antigen, such as Aβ. Numerous types of competitive binding assays are known, for example: solid phase direct or indirect radioimmunoassay (RIA), solid phase direct or indirect enzyme immunoassay (EIA), sandwich competition assay (see Stahli et al., *Methods in Enzymology* 9:242 (1983)); solid phase direct biotin-avidin EIA (see Kirkland et al., *J. Immunol.* 137:3614 (1986)); solid phase direct labelled assay, solid phase direct labelled sandwich assay (see Harlow and Lane, *Antibodies: A Laboratory Manual*, Cold Spring Harbor Press (1988)); solid phase direct label RIA using 1-125 label (see Morel et al., *Mol. Immunol.* 25(1):7 (1988)); solid phase direct biotin-avidin EIA (Cheung et al., *Virology* 176:546 (1990)); and direct labelled RIA (Moldenhauer et al., *Scand. J. Immunol.* 32:77 (1990). Typically, such an assay involves the use of purified antigen bound to a solid surface or cells bearing either of these, an unlabelled test immunoglobulin and a labelled reference immunoglobulin. Competitive inhibition is measured by determining the amount of label bound to the solid surface or cells in the presence of the test immunoglobulin. Usually the test immunoglobulin is present in excess. Usually, when a competing antibody is present in excess, it will inhibit specific binding of a reference antibody to a common antigen by at least 50-55%, 55-60%, 60-65%, 65-70% 70-75% or more.

An epitope is also recognized by immunologic cells, for example, B cells and/or T cells. Cellular recognition of an epitope can be determined by in vitro assays that measure antigen-dependent proliferation, as determined by $^3$H-thymidine incorporation, by cytokine secretion, by antibody secretion, or by antigen-dependent killing (cytotoxic T lymphocyte assay).

Exemplary epitopes or antigenic determinants can be found within the human amyloid precursor protein (APP), but are preferably found within the Aβ peptide of APP. Multiple isoforms of APP exist, for example APP$^{695}$, APP$^{751}$ and APP$^{770}$. Amino acids within APP are assigned numbers according to the sequence of the APP$^{770}$ isoform (see e.g., GenBank Accession No. P05067). The sequences of Aβ peptides and their relationship to the APP precursor are illustrated by FIG. 1 of Hardy et al., TINS 20, 155-158 (1997). For example, Aβ42 has the sequence:

```
                                          (SEQ ID NO: 1)
H2N-Asp-Ala-Glu-Phe-Arg-His-Asp-Ser-Gly-Tyr-Glu-

Val-His-His-Gln-Lys-Leu-Val-Phe-Phe-Ala-Glu-Asp-

Val-Gly-Ser-Asn-Lys-Gly-Ala-Ile-Ile-Gly-Leu-Met-

Val-Gly-Gly-Val-Val-Ile-Ala-OH.
```

Unless otherwise apparent from the context, reference to Aβ also includes natural allelic variations of the above sequence, particularly those associated with hereditary disease, such as the Arctic mutation, E693G, APP 770 numbering. Aβ41, Aβ40 and Aβ39 differ from Aβ42 by the omission of Ala, Ala-Ile, and Ala-Ile-Val respectively from the C-terminal end. Aβ43 differs from Aβ42 by the presence of a threonine residue at the C-terminus. Preferred epitopes or antigenic determinants, as described herein, are located within the N-terminus of the Aβ peptide and include residues within amino acids 1-11 of Aβ, preferably from residues 1-10, 1-3, 1-4, 1-5, 1-6, 1-7 or 3-7 of Aβ42. Additional preferred epitopes or antigenic determinants include residues 2-4, 5, 6, 7 or 8 of Aβ, residues 3-5, 6, 7, 8 or 9 of Aβ, or residues 4-7, 8, 9 or 10 of Aβ42. Other preferred epitopes occur within central or C-terminal regions as described below.

An N-terminal epitope of Aβ means an epitope with residues 1-11. An epitope within a C-terminal region means an epitope within residues 29-43, and an epitope within a central regions means an epitope with residues 12-28

"Soluble" or "dissociated" Aβ refers to non-aggregating or disaggregated Aβ polypeptide.

"Insoluble" Aβ refers to aggregating Aβ polypeptide, for example, Aβ held together by noncovalent bonds. Aβ (e.g., Aβ42) is believed to aggregate, at least in part, due to the presence of hydrophobic residues at the C-terminus of the peptide (part of the transmembrane domain of APP). One method to prepare soluble Aβ is to dissolve lyophilized peptide in neat DMSO with sonication. The resulting solution is centrifuged to remove any insoluble particulates.

The term "Fc region" refers to a C-terminal region of an IgG antibody, in particular, the C-terminal region of the heavy chain(s) of said IgG antibody. Although the boundaries of the Fc region of an IgG heavy chain can vary slightly, a Fc region is typically defined as spanning from about amino acid residue Cys226 to the carboxyl-terminus of an IgG heavy chain(s).

The term "effector function" refers to an activity that resides in the Fc region of an antibody (e.g., an IgG antibody) and includes, for example, the ability of the antibody to bind effector molecules such as complement and/or Fc receptors, which can control several immune functions of the antibody such as effector cell activity, lysis, complement-mediated activity, antibody clearance, and antibody half-life. Effector function can also be influenced by mutations in the hinge region.

The term "effector molecule" refers to a molecule that is capable of binding to the Fc region of an antibody (e.g., an IgG antibody) including a complement protein or a Fc receptor.

The term "effector cell" refers to a cell capable of binding to the Fc portion of an antibody (e.g., an IgG antibody) typically via an Fc receptor expressed on the surface of the effector cell including, but not limited to, lymphocytes, e.g., antigen presenting cells and T cells.

The term "Kabat numbering" unless otherwise stated, is defined as the numbering of the residues as in Kabat et al. (Sequences of Proteins of Immunological Interest, 5th Ed. Public Health Service, National Institutes of Health, Bethesda, Md. (1991)), incorporated herein by reference.

The term "Fc receptor" or "FcR" refers to a receptor that binds to the Fc region of an antibody. Typical Fc receptors which bind to an Fc region of an antibody (e.g., an IgG antibody) include, but are not limited to, receptors of the FcγRI, FcγRII, and FcγRIII subclasses, including allelic variants and alternatively spliced forms of these receptors. Fc receptors are reviewed in Ravetch and Kinet, Annu. Rev. Immunol 9:457-92 (1991); Capel et al., Immunomethods 4:25-34 (1994); and de Haas et al., J. Lab. Clin. Med. 126:330-41 (1995).

The term "adjuvant" refers to a compound that when administered in conjunction with an antigen augments and/or redirects the immune response to the antigen, but when administered alone does not generate an immune response to the antigen. Adjuvants can augment an immune response by several mechanisms including lymphocyte recruitment, stimulation of B and/or T cells, and stimulation of macrophages.

The area under the curve (AUC) is the area under the curve in a plot of concentration of drug in plasma against time. In an individual patient, the area under the curve represents the area under the curve based on that patient. In a population of patients, the area under the curve represents the mean area under the curve for a comparable time interval of different patients in the population.

The mean serum concentration in an individual patient represents the mean concentration of an antibody (or induced antibodies for an active agent) over a period of time. The mean serum concentration in a population of patients represents the mean of the mean serum concentrations of the individual patients over comparable periods of time.

The maximum serum concentration in an individual patient represents the maximum concentration of an antibody (or induced antibodies for an active agent) during a course of treatment. The maximum serum concentration in a population of individuals represents the mean of maximum concentrations of the antibody or induces antibodies between individuals in the population.

For brevity, the term "ApoE4 carrier" is sometimes used to refer to patients having one or two ApoE4 alleles and "ApoE4 noncarrier", ApoE4 non-carrier" or "non-ApoE4 carrier" to refer to patients having zero ApoE4 alleles.

DETAILED DESCRIPTION OF THE INVENTION

I. General

The invention provides methods of immunotherapy of Alzheimer's and similar diseases in which the regime administered to a patient depends on the ApoE genotype of the patient. The methods are based in part on (1) the observation that certain immunotherapy regimes lead to higher instances in the appearance of vasogenic edema (VE) in patients having an ApoE4 allele (E4) than in patients lacking an E4 allele, and more frequently still in patients having two E4 alleles, and/or (2) the initial observation of differential efficacy in ApoE4 carrier patients compared to ApoE4 non-carrier patients or patients receiving at least six doses compared to patients receiving less than six doses. The results also show that frequency of cases of vasogenic edema increases with dose frequency and amount.

Although practice of the invention is not dependent on an understanding of mechanism, it is hypothesized that the association of the vasogenic edema with an ApoE4 genotype may stem from a greater deposition of Aβ deposits and hence induction of a greater clearing response when antibodies bind to the deposits. Clearing of amyloid deposits may lead to vasogenic edema by any or all of several mechanisms. Removal of amyloid from blood vessel walls (vascular amyloid) may cause leakiness of blood vessels; more amyloid in perivascular space may cause slower drainage of interstitial fluid, and/or net increased flow of amyloid from intravascular compartment to brain parenchyma may lead to osmotic gradients. Although vasogenic edema effect is usually asymptomatic and reversible and does not preclude further treatment, it is desirable nevertheless to adjust the therapeutic regime to reduce the risk of vasogenic edema occurring.

The invention thus provides methods in which the immunotherapy regime is varied, for example to adjust the phagocytic response, depending on the ApoE status of the patient. Although the phagocytic response is useful in clearing amyloid deposits, the response, can optionally be controlled to avoid vasogenic edema. In general, patients having two E4 alleles, who are most susceptible to the vasogenic edema are administered either a lower dose or a lower frequency of the same agent as patients with zero E4 alleles, or are administered a different agent that is less prone to induce a phagocytic response or receive the agent through an alternate mode of administration, such as, for example, subcutaneous administration. Patients with one E4 allele can be treated the same as either patients with zero or two E4 alleles or a treatment can be customized for them in which the dose and/or frequency of administration is intermediate between that administered to patients with zero or two ApoE4 alleles.

II. APOE

Human ApoE has the UniProtKB/Swiss-Prot entry accession number P02649. The E2, E3, and E4 variants are described in *Genomics* 3:373-379 (1988), *J. Biol. Chem.* 259:5495-5499 (1984); and *Proc. Natl. Acad. Sci. U.S.A.* 82:3445-3449 (1985). Association of the E4 form with late onset Alzheimer's disease has been reported by e.g., Corder, *Science* 261, 921-3 (1993); Farrer, *JAMA*, 278, 1349-56 (1997); and Saunders, *Neurology* 43, 1467-72 (1993). The allelic forms present in any individual can be determined by many conventional techniques, such as direct sequencing, use of GeneChip® arrays or the like, allele-specific probes, single-base extension methods, allelic specific extension. Allelic forms can also be determined at the protein level by ELISA using antibodies specific for different allelic expression products. Kits for genetic and immunological analysis are commercially available (e.g., Innogenetics, Inc.; Graceful Earth, Inc.). Determination of allelic forms are usually made in vitro, that is, on samples removed and never returned to a patient.

III. Different Strategies for Treating or Monitoring Depending on ApoE

A. Different Treatment Regimes

Some immunotherapy regimes for immunotherapy of Alzheimer's and other diseases have been associated with vasogenic edema (VE) in the brain of some patients. Generally, the incidence of VE is greater in ApoE4 carriers than in ApoeE4 non-carriers and in patients receiving higher doses of certain agents in certain immunotherapy regimes. VE has been observed on magnetic resonance imaging (MRI) as high signal intensities on the fluid-attenuated inversion recovery (FLAIR) sequence involving cerebral abnormalities and gyral swelling. VE generally is observed after the first or second administration of the immunotherapeutic agent, although it has been observed after the third or fourth administration. Most patients with VE discovered on MRI are asymptomatic. VE is heterogeneous on presentation, and MRI findings in a particular patient may vary over time. The gyral swelling and to some extent, the larger magnetic resonance (MR) changes seen on FLAIR differentiate VE from the commonly observed white matter changes seen on FLAIR in both normal elderly and Alzheimer's disease patients (Hentschel et al., 2005; de Leeuw et al. 2001).

Vasogenic edema (VE) is characterized by an increase in extracellular fluid volume due to increased permeability of brain capillary endothelial cells to macromolecular serum proteins (e.g., albumin). VE may be the result of increased brain capillary permeability. Clinical symptoms observed in patients with VE, when existent, are varied and to date have been largely mild in nature. Of the cases of VE observed on regularly scheduled MRI, the majority of patients are asymptomatic. Clinical observations associated with the symptomatic cases of VE have included altered mental states (e.g., increased confusion, lethargy, disorientation, and hallucinations), vomiting, headache, gait difficulties, visual disturbances, fatigue, irritability, ataxia, decreased appetite, and diarrhea.

As summarized above, the invention provides different treatment regimes depending on whether a patient has zero, one or two E4 alleles. Thus, in a population of treated individuals, those having zero E4 alleles can be treated differently from those having two alleles. Those having one E4 allele can be treated differently (in an intermediate fashion) to those with either zero or two E4 alleles or can be grouped with individuals having zero or two the E4 allele in any of the regimes that follow. It follows that individuals having one E4 allele can be treated differently than individuals with zero alleles and/or that individual with two ApoE4 alleles can be treated differently than individuals with one ApoE4 allele. Ongoing experience with some immunotherapeutic agents suggests that VE is more likely to occur at doses greater than 5 mg/kg (see PCT/US07/09499).

In some methods, ApoE4 status is the only genetic marker determining different treatment regimes in different patients. In other methods, differential treatment regimes can be based on ApoE4 in combination with other genetic markers associated with Alzheimer's disease susceptibility or resistance.

A population of treated individuals optionally has sufficient total number of patients and sufficient numbers of subpopulations with different numbers of ApoE4 alleles that an association between different treatment regimes and different ApoE4 alleles can be seen relative to a random assignment of the different regimes with a statistical confidence of at least 95%. For example, the treated population can consist of at least 100, 500 or 1000 individuals of who 10-70% and more typically 30-50% have at least one an ApoE4 allele. A treated population can also (i.e., optionally) be recognized as the total population treated with a particular drug produced by a particular manufacturer.

In some methods, as discussed in greater detail below, individuals having zero ApoE4 alleles are administered an agent in a regime designed to achieve efficacy as assessed from one or more clinical endpoints, such as, for example, cognitive measures (e.g., ADAS-cog, NTB, DAD, MMSE, CDR-SB, NPI), biomarkers (e.g., CSF tau), and brain volume (e.g., BBSI, VBSI), as well as other parameters, such as, for example desirable safety, pharmacokinetics and pharmacodynamics. In some methods, one or two E4 alleles are administered a reduced dose and/or frequency of the same agent as individuals with zero E4 alleles. A goal of such method is to deliver a reduced mean serum concentration of the agent over a period of time (reduced area under curve) and/or to reduce the maximum peak concentration. This can be accomplished for example, by reducing the dose and administering at the same frequency, or reducing the frequency and administering at the same dose or administering at reduced dose and frequency. If the dose is reduced but the frequency kept constant, the dose is usually reduced between 10-90%, often about 30-75 or 40-60%. If the frequency is reduced, but the dose kept constant, then the frequency is typically reduced between two and five fold. Sometimes, the frequency is reduced by simply omitting an occasional dose or two consecutive doses from the regime administered to patients with zero ApoE4 alleles. Such doses can for example be omitted during the period a patient is experiencing vasogenic edema.

In other methods, individual having one or two E4 alleles are administered a reduce dose of the agent at an increased frequency relative to individuals having zero E4 alleles. For, example, the dose can be halved and the frequency doubled. In such methods, the total drug delivered to the two subpopulations over time (i.e., area under the curve) can be the same within experimental error, but the maximum plasma concentration is lower in individuals having two E4 alleles. For example, in patients having one or two E4 alleles the maximum serum concentration of antibody is preferably below 14 µg/ml and for patients having zero alleles, the maximum serum concentration of antibody is preferably below 28 µg/ml.

In other methods, treatment is administered at different stages relative to disease progression depending on ApoE4 status. In such methods, treatment is administered earlier in patients having two ApoE4 alleles relative to patients having zero ApoE4 alleles or in patients having one ApoE4 allele relative to patients having zero ApoE4 alleles and/or in patients having two ApoE4 alleles relative to patients having one ApoE4 allele. Disease progression can be measured by e.g., the MMSE scale on which a score of 27 to 20 is considered normal, and 20-26 considered mild Alzheimer's. Thus, for example, the mean MMSE score of non-ApoE4 carriers on commencement of treatment can be higher than that of ApoE4 carriers (patients with one or two ApoE4 alleles). Optionally, treatment of ApoE4 carriers can be begun prophylactically before clinical symptoms are evident. Such patients can be identified by screening populations for ApoE4 status. Treatment can be commenced on detecting such status or subsequently when the patient reaches a certain age (e.g., 55, 60 or 65 years) when there is a high risk of Alzheimer's developing. Although understanding of mechanism is not required for practice of such methods, it is believed that early treatment of ApoE4 carriers may be beneficial because the ApoE4 allele reduces capacity to repair neuronal damage, and/or because deposition of Aβ is greater in such patients.

In some methods, treatment is administered by a different route in patients having zero ApoE4 alleles and patients having one ApoE4 allele and/or patients having two ApoE4 alleles. For example, treatment can be administered intravenously in patients having zero ApoE4 alleles and subcutaneously in patients having one or two alleles. The dosage is typically greater and/or frequency of administration less in such non-ApoE4 carrier patients relative to ApoE4 carrier patients.

In some methods, a positive response to treatment (i.e., inhibition of cognitive decline or inhibition of decline in brain volume) takes longer to develop in ApoE4 carriers than non-carriers. The greater time may reflect reduced capacity for neuronal repair and/or greater amyloid burden in such patients; and/or use of a less potent treatment regime. In such methods, treatment can be administered for at least one year and optionally at least 2, 3 or 4 years before ceasing treatment for lack of effect. In some methods, treatment is administered for at least six quarterly administrations.

As noted, agents are sometimes provided with a label contraindicating use in ApoE4 carriers. Such agents can be used in methods of treatment in which only non-ApoE4 carriers receive an agent of the invention (i.e., an antibody that binds to Aβ or an agent that induces such an antibody). In such methods ApoE4 carriers do not receive an antibody that binds to Aβ or an agent that induces such an antibody but can receive other treatments such memantine.

Methods in which dose and/or frequency of administration are reduced depending on ApoE4 are most useful for agents that initiate a clearing response against amyloid deposits. In general, such agents are antibodies binding to an epitope within Aβ1-11, and which have an Fc region, or fragments of Aβ that induce such antibodies (i.e., contain an epitope within Aβ1-11). Antibodies binding to epitopes within central or C-terminal regions of Aβ usually bind predominantly to soluble forms of Aβ rather than amyloid deposits, and thus initiate little, if any clearing response against amyloid deposits, particularly dense or vascular deposits.

Examples of suitable dosages ranges and frequencies for administration are provided below. Different dosages and/or frequencies of administration for patients with different E4 status can be selected from within such ranges of dose and frequency. For example, patients with one or two E4 alleles can be administered a dose of 0.1 to 1 mg/kg antibody by intravenous infusion every thirteen weeks, and patients with zero E4 alleles can be administered a dose of 1 to 2 mg/kg every thirteen weeks. Optionally, patients with two E4 alleles are administered a dose of 0.15 to 0.5 mg/kg, patients with one E4 allele are administered a dose of 0.15 to 1 mg/kg (e.g., 0.5 to 1 mg/kg) and patients with zero E4 alleles are administered a dose of 0.15-2 mg/kg (e.g., 1-2 mg/kg) every thirteen weeks. In a preferred regime, patients with one or two E4 alleles are administered a dose of 0.5 mg/kg of an antibody binding to an epitope within residues 1-11 of Aβ (e.g., bapineuzumab) and patients with zero E4 alleles a dose of 2 mg/kg. The doses are administered intravenously at quarterly intervals until vasogenic edema appears (if it does). After vasogenic edema appears, the next dose is missed and thereafter, patients return to the quarterly dosing schedule at a lower dose of 0.15 mg/kg. If vasogenic edema appears again treatment can be terminated. Patients with zero E4 alleles are administered a dose of 0.5-2 mg/kg, with individually patients with zero E4 alleles optionally receiving doses of 0.5 mg/kg, 1.0 mg/kg, 1.5 mg/kg and 2.0 mg/kg.

As another example, patients with two E4 alleles are given a first dose of 0.5 mg/kg, and subsequent doses of 1 mg/kg. Alternatively, patients with two E4 alleles are given a first dose of 0.5 mg/kg, second and third doses of 1 mg/kg and subsequent doses of 2.0 mg/kg.

As another example, patients with zero E4 alleles can be administered a dose of 0.015-0.2 mg/kg antibody subcutaneously once per week and patients with two E4 alleles can be administered the same dose every two weeks. Equivalent regimes to any of the above can be devised by varying either the amount or frequency or route of administration to deliver the same area under the curve (i.e., mean dose integrated with time) of antibody to the serum.

In some methods, patients with one or two E4 alleles are administered agent to achieve a lower mean serum concentration of antibody over time than patients with zero E4 alleles. The lower mean serum concentration is maintained over a period of at least one or threes month, and usually three months to one year, or indefinitely. The mean serum concentration of all such patients is preferably within the range 2-7 μg antibody/ml serum with that for patients with one or two E4 alleles being lower than that for patients with zero E4 alleles. For example patients with zero E4 alleles can be administered to achieve a mean serum concentration of antibody within a range of 4.5-7 μg antibody/ml and patients with one or two E4 alleles can be administered agent to achieve a mean serum concentration in the range of 2-4.5 μg antibody/ml.

In such methods, individuals within any subpopulation defined by presence of two, one or zero E4 alleles are usually administered the same regime. However, the regime can also be customized for individuals within a subpopulation. In this case, the mean dose and/or frequency and/or average serum concentration and/or maximum concentration of agent or antibodies induced by the agent in a subpopulation of individuals with two E4 alleles is lower than that of individuals having zero E4 alleles.

In some methods, a different agent is administered to individuals with two E4 alleles than individuals with zero E4 alleles. The different agents usually differ in their capacity to induce a clearing response against amyloid deposits (i.e., preexisting deposits). Such a capacity can be tested, for example, in an ex vivo clearing assay as described by U.S. Pat. No. 6,750,324. In brief, an antibody and microglial cells are incubated with an amyloid deposit from a diseased Alzheimer's patient or transgenic mouse model, and the clearing reaction is monitored using a labelled antibody to Aβ. Clearing capacity of active agents can be similarly tested using sera induced by the active agent as a source of antibody for the assay. Clearing capacity of both passive and active agents can also be evaluated in a transgenic mouse model as also described U.S. Pat. No. 6,750,324 or in a human patient by MRI monitoring. Optionally, the clearing response is measured in an assay that distinguishes between compact and diffuse amyloid deposits. Differences in clearing capacity of some antibodies are more evident or only evident when the comparison is made with respect to clearing capacity of compact amyloid deposits. Optionally, the clearing response is evaluated from a reduction in clearing of vascular amyloid of a mutated antibody relative to an isotype matched otherwise-identical antibody. Vascular amyloid clearing can be assessed by a statistical significant difference between populations of animal models or human patients treated with a mutated antibody and an otherwise-identical isotype-matched antibody without the mutations.

Additionally or alternatively to assays measuring a clearing response, some antibodies suitable for use in the methods of the invention can be recognized by reduced binding to C1q and/or to Fcγ receptor(s). Capacity to bind C1q and/or an Fcγ receptor can be reduced by mutations near the hinge region of a heavy chain as discussed in more detail below. Reduced capacity can be determined, for example, by comparing a mutated antibody with an isotype matched otherwise identical antibody lacking the mutation(s) present in the mutated antibody (i.e., having residues from a wild type human constant region (e.g., bapineuzumab vs. AAB-003), or by comparing otherwise identical antibodies having different isotypes (e.g., human IgG1 versus human IgG4).

Some antibodies having reduced capacity to bind C1q and/or Fcγ receptor(s) reduce micro-hemorrhaging relative to isotype matched controls but retain at least some activity in inhibiting cognitive decline and/or clearing amyloid deposits. In some antibodies, reduced amyloid clearing capacity is mainly associated with reduced clearing capacity of vascular amyloid and/or compact amyloid deposits and not with diffuse amyloid deposits. Such antibodies offer a potentially improved efficacy:side-effects profile, particularly for use in ApoE4 carriers.

Antibodies having reduced binding to C1q and/or an Fcγ receptor can be used in differential methods of treatment as described above. For example, an antibody with reduced binding to C1q and/or and Fcγ receptor can be administered to patients having one or two ApoE4 alleles and an otherwise identical antibody without the mutation(s) to patients with zero ApoE4 alleles. Alternatively, an antibody with reduced binding to C1q and/or an Fcγ receptor can be administered to patients irrespective of the number of ApoE4 alleles.

Antibodies with constant regions mutated to reduce C1q and/or Fcγ receptor binding are sometimes administered at higher dosages than otherwise identical antibodies without the mutation. For some such antibodies, the dosage can be adjusted upward to achieve an equivalent therapeutic effect with reduced side effects.

Clearing capacity is affected both by the epitope specificity of an antibody (or antibodies induced by a fragment for active administration) and on the presence of, and type of effector function of the antibody, in particular by the capacity of the Fc region if present to bind to Fcγ receptors. Although clearing amyloid deposits is one useful mechanism of action, agents that lack the capacity to clear deposits can be useful by other mechanisms, such as binding to soluble Aβ and/or soluble oligomeric forms of Aβ. Such binding may reduce toxicity of such species and/or inhibit their aggregating to form deposits among other possible mechanisms.

Agents with a propensity to induce such a clearing response include antibodies binding to an epitope within residues 1-11 and particularly 1-7 of Aβ, particularly such antibodies having a human IgG1 isotype, which interacts most strongly with Fcγ receptors. Fragments of Aβ that contain epitopes within residues 1-11 and particularly 1-7 are similarly effective in inducing a clearing response. Optionally, agents which initiate a clearing response, can be provided with a label contraindicating use to patients with one or two ApoE4 alleles. Agents with less or no propensity to induce a clearing response include antibodies to Aβ that have isotypes other than human IgG1, antibodies that lack an Fc region (e.g., Fab fragments, Fv fragments, or Nanobodies), or antibodies with Fc regions mutated by genetic engineering to reduce interactions with Fcγ receptors. Such agents also include antibodies that specifically bind to an epitope within a region of Aβ other than residues 1-11, (i.e., to a mid-epitope or C-terminal epitope, as described above) and antibodies that specifically bind to soluble or oligomeric forms of Aβ without binding to amyloid deposits. Such agents also include fragments of Aβ that lack epitopes within residues 1-11 of Aβ. In such methods, individuals having two E4 alleles are administered an agent with a lower tendency to induce a phagocytic clearing response than individuals having zero alleles. For example, individuals having zero E4 alleles can be administered an antibody binding to an epitope within residues 1-11 of Aβ and having human IgG1 isotype and individuals having two E4 alleles can be administered the same antibody except that the antibody is a Fab fragment or has an isotype other than human IgG1 or has an engineered Fc region to reduce binding to Fcγ receptors. The agent administered to individuals having two E4 alleles can also be an antibody to a mid or C-terminal epitope of Aβ or a fragment of Aβ from a mid or C-terminal region (i.e., lacking an epitope from within Aβ1-11).

In some methods, patients with two E4 alleles are administered an antibody having an epitope within a mid or C-terminal regions for one or more initial doses and an antibody having an epitope within an N-terminal region for subsequent doses. Such an antibody can be a humanized 266 antibody, a humanized 2H6 antibody, a deglycosylated humanized 2H6 antibody or RN1219. Such an antibody can also be a humanized antibody that specifically binds to an epitope within Aβ28-40 or Aβ33-40. The initial doses preferably consist of 1, 2 or 3 doses. Patients having zero alleles can be administered an antibody having an epitope within an N-terminal region.

The different regimes administered to different patients depending on their E4 status can be maintained indefinitely. However, such is not usually necessary. It has been found that the vasogenic edema side effect associated with the E4 allele usually occurs by the third dose, if at all. Thus, once patients have received about 2-3 doses of treatment, patients having one or two ApoE4 alleles who have not developed vasogenic edema probably will not develop it, and can thereafter, if desired, be treated by the same regime as patients having zero E4 alleles. Likewise patients with one or two ApoE4 alleles who do develop vasogenic edema notwithstanding the present differential treatment regime usually resolve this condition and can thereafter, if desired, be treated in similar fashion to patients having zero E4 alleles. Optionally, the dose is titrated up after recovering from vasogenic edema to that used for non-carriers.

Vasogenic edema typically resolves of its own accord. However, resolution can be facilitated if desired by administration of a corticosteroid.

Agents can be packaged with labels indicating differential treatment procedures dependent on ApoE4 status consistent with any of the above regimes or combinations thereof.

B. Different Monitoring Regimes

Alternatively or additionally, the invention provides different monitoring regimes for patients depending on their E4 status. Vasogenic edema is an increase in brain volume from leakage of plasma into the interstitial space. Once extravasated, fluid is retained outside the vasculature, mostly in the white matter of the brain. Vasogenic edema can be monitored by brain imaging particularly by MRI, Positron Emission Tomography (PET Imaging) or Fluid Attenuated Inversion Recovery (FLAIR) sequence imaging (See *Pediatric Neurology*, 20(3):241-243; *AJNR*, 26:825-830; *NEJM*, 334(8):494-500; *Pediatr Nephrol*, 18:1161-1166; *Internal Medicine Journal*, 35:83-90; *JNNP*, 68:790-79 1; *AJNR*, 23:1038-1048; *Pak J Med Sci*, 21(2):149-154 and, *AJNR*, 21:1199-1209). Vasogenic edema presents with a high signal intensity in white matter. The vasogenic edema observed is often asymptomatic but can also be accompanied by headache, nausea, vomiting, confusion, seizures, visual abnormalities, altered mental functioning, ataxia, frontal symptoms, parietal symptoms, stupor, and focal neurological signs.

According to the present methods, patients with two E4 alleles can be subjected to brain imaging more frequently than patients having zero E4 alleles. For example, patients with two copies of E4 can be imaged before beginning treatment and quarterly thereafter, whereas patients with zero E4 alleles can be imaged before beginning treatment and annually or biannually thereafter. Alternatively, brain imaging can be omitted altogether in patients having zero E4 alleles. Patients having one E4 allele can be imaged with intermediate frequency between patients having zero and two E4 alleles, or can be grouped with patients having either zero or two E4 alleles. It follows that patients with one E4 allele can be monitored differently (e.g., more frequently) than patients with zero E4 alleles and patients with two E4 alleles can be monitored differently (e.g., more frequently) than patients with one E4 allele.

In patients developing vasogenic edema, monitoring can be continued during the vasogenic edema and for about a year after symptoms resolve. Thereafter, assuming no neurologic findings, monitoring can optionally be performed six monthly or annually.

Agents can be packaged with labels indicating differential monitoring procedures dependent on ApoE4 status consistent with any of the above regimes or combinations thereof.

C. Universal Treatment or Monitoring Regimes

Although ApoE4 carriers and non-carriers can have different responses to treatment as discussed above, and some treatment regimes that are safe and effective in ApoE4 carriers are also safe and effective, although not necessarily optimal, in non-ApoE4 carriers and can be used in both types of patients without regard to ApoE status of the patients. In some such regimes, the agent is an antibody that binds to an N-terminal epitope of Aβ having mutation(s) in its constant region that reduce binding to an Fcγ receptor and/or C1q. AAB-003 is an example of such an antibody. In other regimes, the dose and/or frequency and/or the maximal serum concentration and/or mean serum concentration of an administered or induced antibody are constrained within limits as described in PCT/US2007/009499 and further summarized below to reduce the risk of vasogenic edema.

IV. Agents

A. Antibodies

A variety of antibodies to Aβ have been described in the patent and scientific literature for use in immunotherapy of Alzheimer's disease, some of which are in clinical trials (see, e.g., U.S. Pat. No. 6,750,324). Such antibodies can specifically bind to an N-terminal epitope, a mid (i.e., central)-epitope or a C-terminal epitope as defined above. Some antibodies are N-terminal specific (i.e., such antibodies specifically bind to the N-terminus of Aβ without binding to APP). As noted above antibodies binding to epitopes within residues 1-10, 1-3, 1-4, 1-5, 1-6, 1-7 or 3-7 of Aβ42 or within residues 2-4, 5, 6, 7 or 8 of Aβ, or within residues 3-5, 6, 7, 8 or 9 of Aβ, or within residues 4-7, 8, 9 or 10 of Aβ42 can be used. Some antibodies are C-terminal specific (i.e., specifically bind to a C-terminus of Aβ without binding to APP) Antibodies can be polyclonal or monoclonal. Polyclonal sera typically contain mixed populations of antibodies specifically binding to several epitopes along the length of APP. However, polyclonal sera can be specific to a particular segment of Aβ such as Aβ1-11) without specifically binding to other segments of Aβ. Preferred antibodies are chimeric, humanized (including veneered antibodies) (see Queen et al., *Proc. Natl. Acad. Sci. USA* 86:10029-10033 (1989) and WO 90/07861, U.S. Pat. Nos. 5,693,762, 5,693,761, 5,585,089, 5,530,101 and Winter, U.S. Pat. No. 5,225,539), or human (Lonberg et al., WO 93/12227 (1993); U.S. Pat. Nos. 5,877,397, 5,874,299, 5,814,318, 5,789,650, 5,770,429, 5,661,016, 5,633,425, 5,625,126, 5,569,825, 5,545,806, *Nature* 148, 1547-1553 (1994), *Nature Biotechnology* 14, 826 (1996), Kucherlapati, WO 91/10741 (1991)) EP1481008, Bleck, Bioprocessing Journal 1 (September/October 2005), US 2004132066, US 2005008625, WO 04/072266, WO 05/065348, WO 05/069970, and WO 06/055778.

3D6 antibody, 10D5 and variants thereof are examples of antibodies that can be used. Both are described in US 20030165496, US 20040087777, WO 02/46237, and WO 04/080419, WO 02/088306 and WO 02/088307. 10D5 antibodies are also described in US 20050142131. Additional 3D6 antibodies are described in US 20060198851 and PCT/US05/45614. 3D6 is a monoclonal antibody (mAb) that specifically binds to an N-terminal epitope located in the human β-amyloid peptide, specifically, residues 1-5. By comparison, 10D5 is a mAb that specifically binds to an N-terminal epitope located in the human β-amyloid peptide, specifically, residues 3-6. A cell line producing the 3D6 monoclonal antibody (RB96 3D6.32.2.4) was deposited with the American Type Culture Collection (ATCC), Manassas, Va. 20108, USA on Apr. 8, 2003 under the terms of the Budapest Treaty and assigned accession number PTA-5130. A cell line producing the 10D5 monoclonal antibody (RB44 10D5.19.21) was deposited with the ATCC on Apr. 8, 2003 under the terms of the Budapest Treaty and assigned accession number PTA-5129.

Bapineuzumab (International Non-Proprietary Name designated by the World Health Organization) means a humanized 3D6 antibody comprising a light chain having a mature variable region having the amino acid sequence designated SEQ ID NO: 2 and a heavy chain having a mature variable region having the amino acid sequence designated SEQ ID NO: 3. (The heavy and light chain constant regions of the antibody designated bapineuzumab by WHO are human IgG1 and human kappa respectively.) A humanized light chain including variable and constant regions is designated SEQ ID NO: 48 below, and a humanized heavy chain including variable and constant regions is designated SEQ ID NO: 66 or 67 (SEQ ID NO: 66 having an additional C-terminal lysine relative to SEQ ID NO: 67).

```
Humanized 3D6 Light Chain Variable Region
                                     (SEQ ID NO: 2)
Asp Val Val Met Thr Gln Ser Pro Leu Ser Leu Pro
Val Thr Pro Gly Glu Pro Ala Ser Ile Ser Cys Lys
Ser Ser Gln Ser Leu Leu Asp Ser Asp Gly Lys Thr
Tyr Leu Asn Trp Leu Leu Gln Lys Pro Gly Gln Ser
Pro Gln Arg Leu Ile Tyr Leu Val Ser Lys Leu Asp
Ser Gly Val Pro Asp Arg Phe Ser Gly Ser Gly Ser
Gly Thr Asp Phe Thr Leu Lys Ile Ser Arg Val Glu
Ala Glu Asp Val Gly Val Tyr Tyr Cys Trp Gln Gly
Thr His Phe Pro Arg Thr Phe Gly Gln Gly Thr Lys
Val Glu Ile Lys
```

-continued
Humanized 3D6 Heavy Chain Variable Region
(SEQ ID NO: 3)
```
Glu Val Gln Leu Leu Glu Ser Gly Gly Gly Leu Val
Gln Pro Gly Gly Ser Leu Arg Leu Ser Cys Ala Ala
Ser Gly Phe Thr Phe Ser Asn Tyr Gly Met Ser Trp
Val Arg Gln Ala Pro Gly Lys Gly Leu Glu Trp Val
Ala Ser Ile Arg Ser Gly Gly Gly Arg Thr Tyr Tyr
Ser Asp Asn Val Lys Gly Arg Phe Thr Ile Ser Arg
Asp Asn Ser Lys Asn Thr Leu Tyr Leu Gln Met Asn
Ser Leu Arg Ala Glu Asp Thr Ala Val Tyr Tyr Cys
Val Arg Tyr Asp His Tyr Ser Gly Ser Ser Asp Tyr
Trp Gly Gln Gly Thr Leu Val Thr Val Ser Ser
```

A second version of humanized 3D6 antibody comprising a light chain having a mature variable region having the amino acid sequence designated SEQ ID NO: 4 and a heavy chain having a mature variable region having the amino acid sequence designated SEQ ID NO: 5 is shown below.

Humanized 3D6 Light Chain Variable Region
(SEQ ID NO: 4)
```
Tyr Val Val Met Thr Gln Ser Pro Leu Ser Leu Pro
Val Thr Pro Gly Glu Pro Ala Ser Ile Ser Cys Lys
Ser Ser Gln Ser Leu Leu Asp Ser Asp Gly Lys Thr
Tyr Leu Asn Trp Leu Leu Gln Lys Pro Gly Gln Ser
Pro Gln Arg Leu Ile Tyr Leu Val Ser Lys Leu Asp
Ser Gly Val Pro Asp Arg Phe Ser Gly Ser Gly Ser
Gly Thr Asp Phe Thr Leu Lys Ile Ser Arg Val Glu
Ala Glu Asp Val Gly Val Tyr Tyr Cys Trp Gln Gly
Thr His Phe Pro Arg Thr Phe Gly Gln Gly Thr Lys
Val Glu Ile Lys
```

Humanized 3D6 Heavy Chain Variable Region
(SEQ ID NO: 5)
```
Glu Val Gln Leu Leu Glu Ser Gly Gly Gly Leu Val
Gln Pro Gly Gly Ser Leu Arg Leu Ser Cys Ala Ala
Ser Gly Phe Thr Phe Ser Asn Tyr Gly Met Ser Trp
Val Arg Gln Ala Pro Gly Lys Gly Leu Glu Trp Val
Ala Ser Ile Arg Ser Gly Gly Gly Arg Thr Tyr Tyr
Ser Asp Asn Val Lys Gly Arg Phe Thr Ile Ser Arg
Asp Asn Ala Lys Asn Ser Leu Tyr Leu Gln Met Asn
Ser Leu Arg Ala Glu Asp Thr Ala Leu Tyr Tyr Cys
Val Arg Tyr Asp His Tyr Ser Gly Ser Ser Asp Tyr
Trp Gly Gln Gly Thr Leu Val Thr Val Ser Ser
```

A third version of humanized 3D6 antibody comprising a light chain having the amino acid sequence designated SEQ ID NO: 6 and a heavy chain having the amino acid sequence designated SEQ ID NO: 7 is described in US 2005/0090648 A1 published on Apr. 28, 2005 issued as U.S. Pat. No. 7,318,923, which is incorporated herein by reference for all purposes.

Humanized 3D6 Light Chain
(SEQ ID NO: 6)
```
Asp Val Val Met Thr Gln Ser Pro Leu Ser Leu Pro
Val Thr Leu Gly Gln Pro Ala Ser Ile Ser Cys Lys
Ser Ser Gln Ser Leu Leu Asp Ser Asp Gly Lys Thr
Tyr Leu Asn Trp Leu Gln Gln Arg Pro Gly Gln Ser
Pro Arg Arg Leu Ile Tyr Leu Val Ser Lys Leu Asp
Ser Gly Val Pro Asp Arg Phe Ser Gly Ser Gly Ser
Gly Thr Asp Phe Thr Leu Lys Ile Ser Arg Val Glu
Ala Glu Asp Val Gly Val Tyr Tyr Cys Trp Gln Gly
Thr His Phe Pro Arg Thr Phe Gly Gly Gly Thr Lys
Val Glu Ile Lys Arg Thr Val Ala Ala Pro Ser Val
Phe Ile Phe Pro Pro Ser Asp Glu Gln Leu Lys Ser
Gly Thr Ala Ser Val Val Cys Leu Leu Asn Asn Phe
Tyr Pro Arg Glu Ala Lys Val Gln Trp Lys Val Asp
Asn Ala Leu Gln Ser Gly Asn Ser Gln Glu Ser Val
Thr Glu Gln Asp Ser Lys Asp Ser Thr Tyr Ser Leu
Leu Ser Ser Thr Leu Thr Leu Ser Lys Ala Asp Tyr
Glu Lys His Lys Val Tyr Ala Cys Glu Val Thr His
Gln Gly Leu Ser Ser Pro Val Thr Lys Ser Phe Asn
Arg Gly Glu Cys
```

-continued
Humanized 3D6 Heavy Chain
(SEQ ID NO: 7)
```
Glu Val Gln Leu Val Glu Ser Gly Gly Gly Leu Val
Gln Pro Gly Gly Ser Leu Arg Leu Ser Cys Ala Gly
Ser Gly Phe Thr Phe Ser Asn Tyr Gly Met Ser Trp
Val Arg Gln Ala Pro Gly Lys Gly Leu Glu Trp Val
Ala Ser Ile Arg Ser Gly Gly Gly Arg Thr Tyr Tyr
Ser Asp Asn Val Lys Gly Arg Phe Thr Ile Ser Arg
Glu Asn Ala Lys Asn Ser Leu Tyr Leu Gln Met Asn
Ser Leu Arg Ala Glu Asp Thr Ala Val Tyr Tyr Cys
Val Arg Tyr Asp His Tyr Ser Gly Ser Ser Asp Tyr
Trp Gly Gln Gly Thr Leu Val Thr Val Ser Ser Ala
Ser Thr Lys Gly Pro Ser Val Phe Pro Leu Ala Pro
Ser Ser Lys Ser Thr Ser Gly Gly Thr Ala Ala Leu
Gly Cys Leu Val Lys Asp Tyr Phe Pro Glu Pro Val
Thr Val Ser Trp Asn Ser Gly Ala Leu Thr Ser Gly
Val His Thr Phe Pro Ala Val Leu Gln Ser Ser Gly
Gly Leu Tyr Ser Leu Ser Ser Val Val Thr Val Pro
Ser Ser Ser Leu Gly Thr Gln Thr Tyr Ile Cys Asn
Val Asn His Lys Pro Ser Asn Thr Lys Val Asp Lys
Lys Val Glu Pro Lys Ser Cys Asp Lys Thr His Thr
Cys Pro Pro Cys Pro Ala Pro Glu Leu Leu Gly Gly
Pro Ser Val Phe Leu Phe Pro Pro Lys Pro Lys Asp
Thr Leu Met Ile Ser Arg Thr Pro Glu Val Thr Cys
Val Val Val Asp Val Ser His Glu Asp Pro Glu Val
Lys Phe Asn Trp Tyr Val Asp Gly Val Glu Val His
Asn Ala Lys Thr Lys Pro Arg Glu Glu Gln Tyr Asn
Ser Thr Tyr Arg Val Val Ser Val Leu Thr Val Leu
His Gln Asp Tip Leu Asn Gly Lys Glu Tyr Lys Cys
Lys Val Ser Asn Lys Ala Leu Pro Ala Pro Ile Glu
Lys Thr Ile Ser Lys Ala Lys Gly Gln Pro Arg Glu
Pro Gln Val Tyr Thr Leu Pro Pro Ser Arg Asp Glu
Leu Thr Lys Asn Gln Val Ser Leu Thr Cys Leu Val
Lys Gly Phe Tyr Pro Ser Asp Ile Ala Val Glu Trp
Glu Ser Asn Gly Gln Pro Glu Asn Asn Tyr Lys Thr
Thr Pro Pro Val Leu Asp Ser Asp Gly Ser Phe Phe
Leu Tyr Ser Lys Leu Thr Val Asp Lys Ser Arg Trp
Gln Gln Gly Asn Val Phe Ser Cys Ser Val Met His
Glu Ala Leu His Asn His Tyr Thr Gln Lys Ser Leu
Ser Pro Gly Lys.
```

A version of humanized 10D5 antibody comprising a light chain having a mature variable region having the amino acid sequence designated SEQ ID NO: 8 and a heavy chain having a mature variable region having the amino acid sequence designated SEQ ID NO: 9 is shown below.

Humanized 10D5 Light Chain Variable Region
(SEQ ID NO: 8)
```
Asp Val Leu Met Thr Gln Thr Pro Leu Ser Leu Pro
Val Ser Leu Gly Asp Gln Ala Ser Ile Ser Cys Arg
Ser Ser Gln Asn Ile Ile His Ser Asn Gly Asn Thr
Tyr Leu Glu Trp Tyr Leu Gln Lys Pro Gly Gln Ser
Pro Lys Leu Leu Ile Tyr Lys Val Ser Asn Arg Phe
Ser Gly Val Pro Asp Arg Phe Ser Gly Ser Gly Ser
Gly Thr Asp Phe Thr Leu Lys Ile Lys Lys Val Glu
Ala Glu Asp Leu Gly Ile Tyr Tyr Cys Phe Gln Gly
Ser His Val Pro Leu Thr Phe Gly Ala Gly Thr Lys
Leu Glu Leu Glu
```

Humanized 10D5 Heavy Chain Variable Region
(SEQ ID NO: 9)
```
Gln Ala Thr Leu Lys Glu Ser Gly Pro Gly Ile Leu
Gln Ser Ser Gln Thr Leu Ser Leu Thr Cys Ser Phe
Ser Gly Phe Ser Leu Ser Thr Ser Gly Met Gly Val
Ser Trp Ile Arg Gln Pro Ser Gly Lys Gly Leu Glu
Trp Leu Ala His Ile Tyr Trp Asp Asp Asp Lys Arg
Tyr Asn Pro Ser Leu Lys Ser Arg Leu Thr Ile Ser
Lys Asp Thr Ser Arg Lys Gln Val Phe Leu Lys Ile
Thr Ser Val Asp Pro Ala Asp Thr Ala Thr Tyr Tyr
Cys Val Arg Arg Pro Ile Thr Pro Val Leu Val Asp
Ala Met Asp Tyr Trp Gly Gln Gly Thr Ser Val Thr
Val Ser Ser
```

12A11 or a chimeric or humanized or nanobody form thereof is a preferred antibody. The 12A11 antibody or a variant thereof, is described in US 20050118651, US 20060198851, WO 04/108895, and WO 06/066089, all of which are incorporated by reference in their entirety herein for all purposes.

12A11 is a mAb that specifically binds to an N-terminal epitope located in the human β-amyloid peptide, specifically, residues 3-7. A cell line producing the 12A11 monoclonal antibody was deposited at the ATCC (American Type Culture Collection, 10801 University Boulevard, Manassas, Va. 20110-2209) on Dec. 12, 2005 and assigned ATCC accession number PTA-7271.

A preferred version of the humanized 12A11 antibody is version 1 comprising a light chain having the amino acid sequence designated SEQ ID NO: 10 and a heavy chain having the amino acid sequence designated SEQ ID NO: 11. Version 1 of humanized 12A11 is described in US 20050118651 A1 published on Jun. 2, 2005, which is incorporated herein by reference for all purposes.

```
Humanized 12A11 Light Chain
                                    (SEQ ID NO: 10)
Asp Val Val Met Thr Gln Ser Pro Leu Ser Leu Pro
Val Thr Pro Gly Glu Pro Ala Ser Ile Ser Cys Arg
Ser Ser Gln Ser Ile Val His Ser Asn Gly Asn Thr
Tyr Leu Glu Trp Tyr Leu Gln Lys Pro Gly Gln Ser
Pro Gln Leu Leu Ile Tyr Lys Val Ser Asn Arg Phe
Ser Gly Val Pro Asp Arg Phe Ser Gly Ser Gly Ser
Gly Thr Asp Phe Thr Leu Lys Ile Ser Arg Val Glu
Ala Glu Asp Val Gly Val Tyr Tyr Cys Phe Gln Ser
Ser His Val Pro Leu Thr Phe Gly Gln Gly Thr Lys
Leu Glu Ile Lys Humanized 12A11 Heavy Chain Variable Region
(version 1)
                                    (SEQ ID NO: 11)
Gln Val Gln Leu Val Glu Ser Gly Gly Gly Val Val
Gln Pro Gly Arg Ser Leu Arg Leu Ser Cys Ala Phe
Ser Gly Phe Ser Leu Ser Thr Ser Gly Met Ser Val
Gly Trp Ile Arg Gln Ala Pro Gly Lys Gly Leu Glu
Trp Leu Ala His Ile Trp Trp Asp Asp Asp Lys Tyr
Tyr Asn Pro Ser Leu Lys Ser Arg Leu Thr Ile Ser
Lys Asp Thr Ser Lys Asn Thr Val Tyr Leu Gln Met
Asn Ser Leu Arg Ala Glu Asp Thr Ala Val Tyr Tyr
Cys Ala Arg Arg Thr Thr Thr Ala Asp Tyr Phe Ala
Ala Tyr Trp Gly Gln Gly Thr Thr Val Thr Val Ser
Ser
```

A second version of the humanized 12A11 antibody comprising a light chain having the amino acid sequence designated SEQ ID NO: 10 and a heavy chain having the amino acid sequence designated SEQ ID NO: 12 (version 2) is described in US 20050118651 A1 published on Jun. 2, 2005, which is incorporated herein by reference for all purposes.

```
Humanized 12A11 Heavy Chain Variable Region
(version 2)
                                    (SEQ ID NO: 12)
Gln Val Gln Leu Val Glu Ser Gly Gly Gly Val Val Gln Pro Gly Arg Ser Leu Arg Leu Ser Cys Ala Phe Ser Gly Phe Thr Leu Ser Thr Ser Gly Met Ser Val Gly Trp Ile Arg Gln Ala Pro Gly Lys Gly Leu Glu Trp Val Ala His Ile Trp Trp Asp Asp Asp Lys Tyr Tyr Asn Pro Ser Leu Lys Ser Arg Phe Thr Ile Ser Lys Asp Thr Ser Lys Asn Thr Leu Tyr Leu Gln Met Asn Ser Leu Arg Ala Glu Asp Thr Ala Val Tyr Tyr Cys Ala Arg Arg Thr Thr Thr Ala Asp Tyr Phe Ala Tyr Trp Gly Gln Gly Thr Thr Val Thr Val Ser Ser
```

A third version of the humanized 12A11 antibody comprising a light chain having the amino acid sequence designated SEQ ID NO: 10 and a heavy chain having the amino acid sequence designated SEQ ID NO: 13 (version 2.1) is described in US 20050118651 A1 published on Jun. 2, 2005, which is incorporated herein by reference for all purposes.

```
Humanized 12A11 Heavy Chain Variable Region
(version 2.1)
                                    (SEQ ID NO: 13)
Gln Val Gln Leu Val Glu Ser Gly Gly Gly Val Val Gln Pro Gly Arg Ser Leu Arg Leu Ser Cys Ala Phe Ser Gly Phe Thr Leu Ser Thr Ser Gly Met Ser Val Gly Trp Ile Arg Gln Ala Pro Gly Lys Gly Leu Glu Trp Val Ala His Ile Trp Trp Asp Asp Asp Lys Tyr Tyr Asn Pro Ser Leu Lys Ser Arg Phe Thr Ile Ser Lys Asp Asn Ser Lys Asn Thr Leu Tyr Leu Gln Met Asn Ser Leu Arg Ala Glu Asp Thr Ala Val Tyr Tyr Cys Ala Arg Arg Thr Thr Thr Ala Asp Tyr Phe Ala Tyr Trp Gly Gln Gly Thr Thr Val Thr Val Ser Ser
```

A fourth version of the humanized 12A11 antibody comprising a light chain having the amino acid sequence designated SEQ ID NO: 10 and a heavy chain having the amino acid sequence designated SEQ ID NO: 14 (version 3) is described in WO 02/088306 published on Jun. 2, 2005, which is incorporated herein by reference for all purposes.

```
Humanized 12A11 Heavy Chain Variable Region
(version 3)
                                    (SEQ ID NO: 14)
Gln Val Gln Leu Val Glu Ser Gly Gly Gly Val Val Gln Pro Gly Arg Ser Leu Arg Leu Ser Cys Ala Phe Ser Gly Phe Thr Leu Ser Thr Ser Gly Met Ser Val Gly Trp Ile Arg Gln Ala Pro Gly Lys Gly Leu Glu Trp Val Ala His Ile Trp Trp Asp Asp Asp Lys Tyr Tyr Asn Pro Ser Leu Lys Ser Arg Phe Thr Ile Ser Arg Asp Asn Ser Lys Asn Thr Leu Tyr Leu Gln Met Asn Ser Leu Arg Ala Glu Asp Thr Ala Val Tyr Tyr Cys Ala Arg Arg Thr Thr Thr Ala Asp Tyr Phe Ala Tyr Trp Gly Gln Gly Thr Thr Val Thr Val Ser Ser
```

A fifth version of the humanized 12A11 antibody comprising a light chain having the amino acid sequence designated SEQ ID NO: 10 and a heavy chain having the amino acid sequence designated SEQ ID NO: 15 (version 4.1) is described in US 20050118651 A1 published on Jun. 2, 2005, which is incorporated herein by reference for all purposes.

Humanized 12A11 Heavy Chain Variable Region
(version 4.1)
(SEQ ID NO: 15)
Gln Val Gln Leu Val Glu Ser Gly Gly Gly Val Val Gln Pro Gly Arg Ser Leu Arg Leu Ser Cys Ala Phe Ser Gly Phe Thr Leu Ser Thr Ser Gly Met Ser Val Gly Trp Ile Arg Gln Ala Pro Gly Lys Gly Leu Glu Trp Leu Ala His Ile Trp Trp Asp Asp Asp Lys Tyr Tyr Asn Pro Ser Leu Lys Ser Arg Leu Thr Ile Ser Lys Asp Thr Ser Lys Asn Thr Val Tyr Leu Gln Met Asn Ser Leu Arg Ala Glu Asp Thr Ala Val Tyr Tyr Cys Ala Arg Arg Thr Thr Thr Ala Asp Tyr Phe Ala Tyr Trp Gly Gln Gly Thr Thr Val Thr Val Ser Ser A sixth version of the humanized 12A11 antibody comprising a light chain having the amino acid sequence designated SEQ ID NO: 10 and a heavy chain having the amino acid sequence designated SEQ ID NO: 16 (version 4.2) is described in US 20050118651 A1 published on Jun. 2, 2005, which is incorporated herein by reference for all purposes.

Humanized 12A11 Heavy Chain Variable Region
(version 4.2)
(SEQ ID NO: 16)
Gln Val Gln Leu Val Glu Ser Gly Gly Gly Val Val Gln Pro Gly Arg Ser Leu Arg Leu Ser Cys Ala Phe Ser Gly Phe Ser Leu Ser Thr Ser Gly Met Ser Val Gly Trp Ile Arg Gln Ala Pro Gly Lys Gly Leu Glu Trp Val Ala His Ile Trp Trp Asp Asp Asp Lys Tyr Tyr Asn Pro Ser Leu Lys Ser Arg Leu Thr Ile Ser Lys Asp Thr Ser Lys Asn Thr Val Tyr Leu Gln Met Asn Ser Leu Arg Ala Glu Asp Thr Ala Val Tyr Tyr Cys Ala Arg Arg Thr Thr Thr Ala Asp Tyr Phe Ala Tyr Trp Gly Gln Gly Thr Thr Val Thr Val Ser Ser An seventh version of the humanized 12A11 antibody comprising a light chain having the amino acid sequence designated SEQ ID NO: 10 and a heavy chain having the amino acid sequence designated SEQ ID NO: 17 (version 4.3) is described in US 20050118651 A1 published on Jun. 2, 2005, which is incorporated herein by reference for all purposes.

Humanized 12A11 Heavy Chain Variable Region
(version 4.3)
(SEQ ID NO: 17)
Gln Val Gln Leu Val Glu Ser Gly Gly Gly Val Val Gln Pro Gly Arg Ser Leu Arg Leu Ser Cys Ala Phe Ser Gly Phe Ser Leu Ser Thr Ser Gly Met Ser Val Gly Trp Ile Arg Gln Ala Pro Gly Lys Gly Leu Glu Trp Leu Ala His Ile Trp Trp Asp Asp Asp Lys Tyr Tyr Asn Pro Ser Leu Lys Ser Arg Phe Thr Ile Ser Lys Asp Thr Ser Lys Asn Thr Val Tyr Leu Gln Met Asn Ser Leu Arg Ala Glu Asp Thr Ala Val Tyr Tyr Cys Ala Arg Arg Thr Thr Thr Ala Asp Tyr Phe Ala Tyr Trp Gly Gln Gly Thr Thr Val Thr Val Ser Ser A eighth version of the humanized 12A11 antibody comprising a light chain having the amino acid sequence designated SEQ ID NO: 10 and a heavy chain having the amino acid sequence designated SEQ ID NO: 18 (version 4.4) is described in US 20050118651 A1 published on Jun. 2, 2005, which is incorporated herein by reference for all purposes.

Humanized 12A11 Heavy Chain Variable Region
(version 4.4)
(SEQ ID NO: 18)
Gln Val Gln Leu Val Glu Ser Gly Gly Gly Val Val Gln Pro Gly Arg Ser Leu Arg Leu Ser Cys Ala Phe Ser Gly Phe Ser Leu Ser Thr Ser Gly Met Ser Val Gly Trp Ile Arg Gln Ala Pro Gly Lys Gly Leu Glu Trp Leu Ala His Ile Trp Trp Asp Asp Asp Lys Tyr Tyr Asn Pro Ser Leu Lys Ser Arg Leu Thr Ile Ser Lys Asp Thr Ser Lys Asn Thr Leu Tyr Leu Gln Met Asn Ser Leu Arg Ala Glu Asp Thr Ala Val Tyr Tyr Cys Ala Arg Arg Thr Thr Thr Ala Asp Tyr Phe Ala Tyr Trp Gly Gln Gly Thr Thr Val Thr Val Ser Ser A ninth version of the humanized 12A11 antibody comprising a light chain having the amino acid sequence designated SEQ ID NO: 10 and a heavy chain having the amino acid sequence designated SEQ ID NO: 19 (version 5.1) is described in US 20050118651 A1 published on Jun. 2, 2005, which is incorporated herein by reference for all purposes.

Humanized 12A11 Heavy Chain Variable Region
(version 5.1)
(SEQ ID NO: 19)
Gln Val Gln Leu Val Glu Ser Gly Gly Gly Val Val Gln Pro Gly Arg Ser Leu Arg Leu Ser Cys Ala Phe Ser Gly Phe Thr Leu Ser Thr Ser Gly Met Ser Val Gly Trp Ile Arg Gln Ala Pro Gly Lys Gly Leu Glu Trp Val Ala His Ile Trp Trp Asp Asp Asp Lys Tyr Tyr Asn Pro Ser Leu Lys Ser Arg Leu Thr Ile Ser Lys Asp Thr Ser Lys Asn Thr Val Tyr Leu Gln Met Asn Ser Leu Arg Ala Glu Asp Thr Ala Val Tyr Tyr Cys Ala Arg -continued
```
Arg Thr Thr Thr Ala Asp Tyr Phe Ala Tyr Trp Gly Gln Gly Thr Thr Val Thr Val Ser Ser
```

A tenth version of the humanized 12A11 antibody comprising a light chain having the amino acid sequence designated SEQ ID NO: 10 and a heavy chain having the amino acid sequence designated SEQ ID NO: 20 (version 5.2) is described in US 20050118651 A1 published on Jun. 2, 2005, which is incorporated herein by reference for all purposes.

```
Humanized 12A11 Heavy Chain Variable Region
(version 5.2)
                                       (SEQ ID NO: 20)
Gln Val Gln Leu Val Glu Ser Gly Gly Gly Val Val Gln Pro Gly Arg Ser Leu Arg Leu Ser Cys Ala Phe Ser Gly Phe Thr Leu Ser Thr Ser Gly Met Ser Val Gly Trp Ile Arg Gln Ala Pro Gly Lys Gly Leu Glu Trp Leu Ala His Ile Trp Trp Asp Asp Asp Lys Tyr Tyr Asn Pro Ser Leu Lys Ser Arg Phe Thr Ile Ser Lys Asp Thr Ser Lys Asn Thr Val Tyr Leu Gln Met Asn Ser Leu Arg Ala Glu Asp Thr Ala Val Tyr Tyr Cys Ala Arg Arg Thr Thr Thr Ala Asp Tyr Phe AlaTyr Trp Gly Gln Gly Thr Thr Val Thr Val Ser Ser
```

An eleventh version of the humanized 12A11 antibody comprising a light chain having the amino acid sequence designated SEQ ID NO: 10 and a heavy chain having the amino acid sequence designated SEQ ID NO: 21 (version 5.3) is described in US 20050118651 A1 published on Jun. 2, 2005, which is incorporated herein by reference for all purposes.

```
Humanized 12A11 Heavy Chain Variable Region
(version 5.3)
                                       (SEQ ID NO: 21)
Gln Val Gln Leu Val Glu Ser Gly Gly Gly Val Val Gln Pro Gly Arg Ser Leu Arg Leu Ser Cys Ala Phe Ser Gly Phe Thr Leu Ser Thr Ser Gly Met Ser Val Gly Trp Ile Arg Gln Ala Pro Gly Lys Gly Leu Glu Trp Leu Ala His Ile Trp Trp Asp Asp Asp Lys Tyr Tyr Asn Pro Ser Leu Lys Ser Arg Leu Thr Ile Ser Lys Asp Thr Ser Lys Asn Thr Leu Tyr Leu Gln Met Asn Ser Leu Arg Ala Glu Asp Thr Ala Val Tyr Tyr Cys Ala Arg Arg Thr Thr Thr Ala Asp Tyr Phe Ala Tyr Trp Gly Gln Gly Thr Thr Val Thr Val Ser Ser Val
```

A twelfth version of the humanized 12A11 antibody comprising a light chain having the amino acid sequence designated SEQ ID NO: 10 and a heavy chain having the amino acid sequence designated SEQ ID NO: 22 (version 5.4) is described in US 20050118651 A1 published on Jun. 2, 2005, which is incorporated herein by reference for all purposes.

```
Humanized 12A11 Heavy Chain Variable Region
(version 5.4)
                                       (SEQ ID NO: 22)
Gln Val Gln Leu Val Glu Ser Gly Gly Gly Val Val Gln Pro Gly Arg Ser Leu Arg Leu Ser Cys Ala Phe Ser Gly Phe Ser Leu Ser Thr Ser Gly Met Ser Val Gly Trp Ile Arg Gln Ala Pro Gly Lys Gly Leu Glu Trp Val Ala His Ile Trp Trp Asp Asp Asp Lys Tyr Tyr Asn Pro Ser Leu Lys Ser Arg Phe Thr Ile Ser Lys Asp Thr Ser Lys Asn Thr Val Tyr Leu Gln Met Asn Ser Leu Arg Ala Glu Asp Thr Ala Val Tyr Tyr Cys Ala Arg Arg Thr Thr Thr Ala Asp Tyr Phe Ala Tyr Trp Gly Gln Gly Thr Thr Val Thr Val Ser Ser Val
```

A thirteenth version of the humanized 12A11 antibody comprising a light chain having the amino acid sequence designated SEQ ID NO: 10 and a heavy chain having the amino acid sequence designated SEQ ID NO: 23 (version 5.5) is described in US 20050118651 A1 published on Jun. 2, 2005, which is incorporated herein by reference for all purposes.

```
Humanized 12A11 Heavy Chain Variable Region
(version 5.5)
                                       (SEQ ID NO: 23)
Gln Val Gln Leu Val Glu Ser Gly Gly Gly Val Val Gln Pro Gly Arg Ser Leu Arg Leu Ser Cys Ala Phe Ser Gly Phe Ser Leu Ser Thr Ser Gly Met Ser Val Gly Trp Ile Arg Gln Ala Pro Gly Lys Gly Leu Glu Trp Val Ala His Ile Trp Trp Asp Asp Asp Lys Tyr Tyr Asn Pro Ser Leu Lys Ser Arg Leu Thr Ile Ser Lys Asp Thr Ser Lys Asn Thr Leu Tyr Leu Gln Met Asn Ser Leu Arg Ala Glu Asp Thr Ala Val Tyr Tyr Cys Ala Arg Arg Thr Thr Thr Ala Asp Tyr Phe Ala Tyr Trp Gly Gln Gly Thr Thr Val Thr Val Ser Ser
```

A fourteenth version of the humanized 12A 11 antibody comprising a light chain having the amino acid sequence designated SEQ ID NO: 10 and a heavy chain having the amino acid sequence designated SEQ ID NO: 24 (version 5.6) is described in US 20050118651 A1 published on Jun. 2, 2005, which is incorporated herein by reference for all purposes.

```
Humanized 12A11 Heavy Chain Variable Region
(version 5.6)
                                       (SEQ ID NO: 24)
Gln Val Gln Leu Val Glu Ser Gly Gly Gly Val Val Gln Pro Gly Arg Ser Leu Arg Leu Ser Cys Ala Phe Ser Gly Phe Ser Leu Ser Thr Ser Gly
```

```
Met Ser Val Gly Trp Ile Arg Gln Ala Pro Gly

Lys Gly Leu Glu Trp Leu Ala His Ile Trp Trp

Asp Asp Asp Lys Tyr Tyr Asn Pro Ser Leu Lys

Ser Arg Phe Thr Ile Ser Lys Asp Thr Ser Lys

Asn Thr Leu Tyr Leu Gln Met Asn Ser Leu Arg

Ala Glu Asp Thr Ala Val Tyr Tyr Cys Ala Arg

Arg Thr Thr Thr Ala Asp Tyr Phe Ala Tyr Trp

Gly Gln Gly Thr Thr Val Thr Val Ser Ser
```

A fifteenth version of the humanized 12A11 antibody comprising a light chain having the amino acid sequence designated SEQ ID NO: 10 and a heavy chain having the amino acid sequence designated SEQ ID NO: 25 (version 6.1) is described in US 20050118651 A1 published on Jun. 2, 2005, which is incorporated herein by reference for all purposes.

```
Humanized 12A11 Heavy Chain Variable Region
(version 6.1)
                                    (SEQ ID NO: 25)
Gln Val Gln Leu Val Glu Ser Gly Gly Gly Val Val Gln Pro Gly Arg Ser Leu Arg Leu Ser Cys Ala Phe Ser Gly Phe Thr Leu Ser Thr Ser Gly Met Ser Val Gly Trp Ile Arg Gln Ala Pro Gly Lys Gly Leu Glu Trp Val Ala His Ile Trp Trp Asp Asp Asp Lys Tyr Tyr Asn Pro Ser Leu Lys Ser Arg Phe Thr Ile Ser Lys Asp Thr Ser Lys Asn Thr Val Tyr Leu Gln Met Asn Ser Leu Arg Ala Glu Asp Thr Ala Val Tyr Tyr Cys Ala Arg Arg Thr Thr Thr Ala Asp Tyr Phe Ala Tyr Trp Gly Gln Gly Thr Thr Val Thr Val Ser Ser
```

A sixteenth version of the humanized 12A11 antibody comprising a light chain having the amino acid sequence designated SEQ ID NO: 10 and a heavy chain having the amino acid sequence designated SEQ ID NO: 26 (version 6.2) is described in US 20050118651 A1 published on Jun. 2, 2005, which is incorporated herein by reference for all purposes.

```
Humanized 12A11 Heavy Chain Variable Region
(version 6.2)
                                    (SEQ ID NO: 26)
Gln Val Gln Leu Val Glu Ser Gly Gly Gly Val Val Gln Pro Gly Arg Ser Leu Arg Leu Ser Cys Ala Phe Ser Gly Phe Thr Leu Ser Thr Ser Gly Met Ser Val Gly Trp Ile Arg Gln Ala Pro Gly Lys Gly Leu Glu Trp Val Ala His Ile Trp Trp Asp Asp Asp Lys Tyr Tyr Asn Pro Ser Leu Lys Ser Arg Leu Thr Ile Ser Lys Asp Thr Ser Lys Asn Thr Leu Tyr Leu Gln Met Asn Ser Leu Arg Ala Glu Asp Thr Ala Val Tyr Tyr Cys Ala Arg Arg Thr Thr Thr Ala Asp Tyr Phe Ala Tyr Trp Gly Gln Gly Thr Thr Val Thr Val Ser Ser
```

A seventeenth version of the humanized 12A11 antibody comprising a light chain having the amino acid sequence designated SEQ ID NO: 10 and a heavy chain having the amino acid sequence designated SEQ ID NO: 27 (version 6.3) is described in US 20050118651 A1 published on Jun. 2, 2005, which is incorporated herein by reference for all purposes.

```
Humanized 12A11 Heavy Chain Variable Region
(version 6.3)
                                    (SEQ ID NO: 27)
Gln Val Gln Leu Val Glu Ser Gly Gly Gly Val Val Gln Pro Gly Arg Ser Leu Arg Leu Ser Cys Ala Phe Ser Gly Phe Thr Leu Ser Thr Ser Gly Met Ser Val Gly Trp Ile Arg Gln Ala Pro Gly Lys Gly Leu Glu Trp Leu Ala His Ile Trp Trp Asp Asp Asp Lys Tyr Tyr Asn Pro Ser Leu Lys Ser Arg Phe Thr Ile Ser Lys Asp Thr Ser Lys Asn Thr Leu Tyr Leu Gln Met Asn Ser Leu Arg Ala Glu Asp Thr Ala Val Tyr Tyr Cys Ala Arg Arg Thr Thr Thr Ala Asp Tyr Phe Ala Tyr Trp Gly Gln Gly Thr Thr Val Thr Val Ser Ser
```

A eighteenth version of the humanized 12A11 antibody comprising a light chain having the amino acid sequence designated SEQ ID NO: 10 and a heavy chain having the amino acid sequence designated SEQ ID NO: 28 (version 6.4) is described in US 20050118651 A1 published on Jun. 2, 2005, which is incorporated herein by reference for all purposes.

```
Humanized 12A11 Heavy Chain Variable Region
(version 6.4)
                                    (SEQ ID NO: 28)
Gln Val Gln Leu Val Glu Ser Gly Gly Gly Val Val Gln Pro Gly Arg Ser Leu Arg Leu Ser Cys Ala Phe Ser Gly Phe Ser Leu Ser Thr Ser Gly Met Ser Val Gly Trp Ile Arg Gln Ala Pro Gly Lys Gly Leu Glu Trp Val Ala His Ile Trp Trp Asp Asp Asp Lys Tyr Tyr Asn Pro Ser Leu Lys Ser Arg Phe Thr Ile Ser Lys Asp Thr Ser Lys Asn Thr Leu Tyr Leu Gln Met Asn Ser Leu Arg Ala Glu Asp Thr Ala Val Tyr Tyr Cys Ala Arg Arg Thr Thr Thr Ala Asp Tyr Phe Ala Tyr Trp Gly Gln Gly Thr Thr Val Thr Val Ser Ser
```

A nineteenth version of the humanized 12A11 antibody comprising a light chain having the amino acid sequence designated SEQ ID NO: 10 and a heavy chain having the amino acid sequence designated SEQ ID NO: 29 (version 7) is described in US 20050118651 A1 published on Jun. 2, 2005, which is incorporated herein by reference for all purposes.

```
Humanized 12A11 Heavy Chain Variable Region
(version 7)
                                    (SEQ ID NO: 29)
Gln Val Gln Leu Val Glu Ser Gly Gly Val Val Gln Pro Gly Arg Ser Leu Arg Leu Ser Cys Ala Phe Ser Gly Phe Thr Leu Ser Thr Ser Gly Met Ser Val Gly Trp Val Arg Gln Ala Pro Gly Lys Gly Leu Glu Trp Leu Ala His Ile Trp Trp Asp Asp Asp Lys Tyr Tyr Asn Pro Ser Leu Lys Ser Arg Leu Thr Ile Ser Lys Asp Thr Ser Lys Asn Thr Val Tyr Leu Gln Met Asn Ser Leu Arg Ala Glu Asp Thr Ala Val Tyr Tyr Cys Ala Arg Arg Thr Thr Thr Ala Asp Tyr Phe Ala Tyr Trp Gly Gln Gly Thr Thr Val Thr Val Ser Ser
```

A twentieth version of the humanized 12A11 antibody comprising a light chain having the amino acid sequence designated SEQ ID NO: 10 and a heavy chain having the amino acid sequence designated SEQ ID NO: 30 (version 8) is described in US 20050118651 A1 published on Jun. 2, 2005, which is incorporated herein by reference for all purposes.

```
Humanized 12A11 Heavy Chain Variable Region
(version 8)
                                    (SEQ ID NO: 30)
Gln Val Gln Leu Val Glu Ser Gly Gly Val Val Gln Pro Gly Arg Ser Leu Arg Leu Ser Cys Ala Phe Ser Gly Phe Ser Leu Ser Thr Ser Gly Met Ser Val Gly Trp Ile Arg Gln Ala Pro Gly Lys Gly Leu Glu Trp Leu Ala His Ile Trp Trp Asp Asp Asp Lys Tyr Tyr Asn Pro Ser Leu Lys Ser Arg Leu Thr Ile Ser Lys Asp Asn Ser Lys Asn Thr Val Tyr Leu Gln Met Asn Ser Leu Arg Ala Glu Asp Thr Ala Val Tyr Tyr Cys Ala Arg Arg Thr Thr Thr Ala Asp Tyr Phe Ala Tyr Trp Gly Gln Gly Thr Thr Val Thr Val Ser Ser
```

Other exemplary antibodies include 12B4 antibody or variant thereof, as described in US 20040082762A1 and WO 03/077858. 12B4 is a mAb that specifically binds to an N-terminal epitope located in the human β-amyloid peptide, specifically, residues 3-7. The light (SEQ ID NO: 31) and heavy chain (SEQ ID NO: 32) of 12B4 have the following variable regions (not including signal sequences).

```
                                    (Seq ID NO: 31)
Asp Val Leu Met Thr Gln Thr Pro Leu Ser Leu

Pro Val Ser Leu Gly Asp Gln Ala Ser Ile Ser

Cys Arg Ser Ser Gln Asn Ile Val His Ser Asn

Gly Asn Thr Tyr Leu Glu Trp Tyr Leu Gln Lys

Pro Gly Gln Ser Pro Lys Leu Leu Ile Tyr Lys

Val Ser Asn Arg Phe Ser Gly Val Pro Asp Arg

Phe Ser Gly Ser Gly Ser Gly Thr Asp Phe Thr

Leu Lys Ile Ser Arg Val Glu Ala Glu Asp Leu

Gly Val Tyr Tyr Cys Phe Gln Gly Ser His Val

Pro Leu Thr Phe Gly Ala Gly Thr Lys Leu Glu

Leu Lys (SEQ ID NO: 32)
Gln Val Thr Leu Lys Glu Ser Gly Pro Gly Ile

Leu Gln Pro Ser Gln Thr Leu Ser Leu Thr Cys

Ser Phe Ser Gly Phe Ser Leu Ser Thr Asn Gly

Met Gly Val Ser Trp Ile Arg Gln Pro Ser Gly

Lys Gly Leu Glu Trp Leu Ala His Ile Tyr Trp

Asp Glu Asp Lys Arg Tyr Asn Pro Ser Leu Lys

Ser Arg Leu Thr Ile Ser Lys Asp Thr Ser Asn

Asn Gln Val Phe Leu Lys Ile Thr Asn Val Asp

Thr Ala Asp Thr Ala Thr Tyr Tyr Cys Ala Arg

Arg Arg Ile Ile Tyr Asp Val Glu Asp Tyr Phe

Asp Tyr Trp Gly Gln Gly Thr Thr Leu Thr Val

Ser Ser
```

Other exemplary antibodies are 6C6 antibody, or a variant thereof, as described in a US 20060165682 and WO 06/06604. 6C6 is a mAb that specifically binds to an N-terminal epitope located in the human β-amyloid peptide, specifically, residues 3-7. A cell line producing the antibody 6C6 was deposited on Nov. 1, 2005, with the ATCC under the terms of the Budapest Treaty and assigned accession number PTA-7200.

Other exemplary antibodies are 2H3 antibody and variants thereof as described in US 20060257396. 2H3 is a mAb that specifically binds to an N-terminal epitope located in the human β-amyloid peptide, specifically, residues 2-7. A cell line producing the antibody 2H3 was deposited on Dec. 13, 2005, with the ATCC under the terms of the Budapest Treaty and assigned accession number PTA-7267.

Other exemplary antibodies include 3A3 and variants thereof as described in US 20060257396. 3A3 is a mAb that specifically binds to an N-terminal epitope located in the human β-amyloid peptide, specifically, residues 3-7. A cell line producing the antibody 3A3 was deposited on Dec. 13, 2005, with the ATCC under the terms of the Budapest Treaty and assigned accession number PTA-7269.

Other exemplary antibodies are 2B1, 1C2 or 9G8. Cell lines producing the antibodies 2B1, 1C2 and 9G8 were deposited on Nov. 1, 2005, with the ATCC under the terms of the Budapest Treaty and were assigned accession numbers PTA-7202, PTA-7199 and PTA-7201, respectively.

Another exemplary antibody is a humanized 266 antibody or variant thereof. The 266 antibody binds to an epitope between residues 13-28 of Aβ. A cell line producing the antibody 266 antibody was deposited on Jul. 20, 2004 with the ATCC under the terms of the Budapest Treaty and assigned accession number PTA-6123. Humanized forms of the 266 antibody are described in US 20040265308, US 20040241164, WO 03/016467, and U.S. Pat. No. 7,195,761. The light (SEQ ID NO: 33) and heavy chain (SEQ ID NO: 34) of the 266 antibody have the following variable region sequences (not including signal sequences).

```
                                              (SEQ ID NO: 33)
Asp Xaa Val Met Thr Gln Xaa Pro Leu Ser Leu

Pro Val Xaa Xaa Gly Gln Pro Ala Ser Ile Ser

Cys Arg Ser Ser Gln Ser Leu Xaa Tyr Ser Asp

Gly Asn Ala Tyr Leu His Trp Phe Leu Gln Lys

Pro Gly Gln Ser Pro Xaa Leu Leu Ile Tyr Lys

Val Ser Asn Arg Phe Ser Gly Val Pro Asp Arg

Phe Ser Gly Ser Gly Ser Gly Thr Asp Phe Thr

Leu Lys Ile Ser Arg Val Glu Ala Glu Asp Xaa

Gly Val Tyr Tyr Cys Ser Gln Ser Thr His Val

Pro Trp Thr Phe Gly Xaa Gly Thr Xaa Xaa Glu

Ile Lys Arg
``` wherein: Xaa at position 2 is Val or Ile; Xaa at position 7 is Ser or Thr; Xaa at position 14 is Thr or Ser; Xaa at position 15 is Leu or Pro; Xaa at position 30 is Ile or Val; Xaa at position 50 is Arg, Gln, or Lys; Xaa at position 88 is Val or Leu; Xaa at position 105 is Gln or Gly; Xaa at position 108 is Lys or Arg; and Xaa at position 109 is Val or Leu; and

```
                                              (SEQ ID NO: 34)
Xaa Val Gln Leu Val Glu Xaa Gly Gly Gly Leu

Val Gln Pro Gly Gly Ser Leu Arg Leu Ser Cys

Ala Ala Ser Gly Phe Thr Phe Ser Arg Tyr Ser

Met Ser Trp Val Arg Gln Ala Pro Gly Lys Gly

Leu Xaa Leu Val Ala Gln Ile Asn Ser Val Gly

Asn Ser Thr Tyr Tyr Pro Asp Xaa Val Lys Gly

Arg Phe Thr Ile Ser Arg Asp Asn Xaa Xaa Asn

Thr Leu Tyr Leu Gln Met Asn Ser Leu Arg Ala

Xaa Asp Thr Ala Val Tyr Tyr Cys Ala Ser Gly

Asp Tyr Trp Gly Gln Gly Thr Xaa Val Thr Val

Ser Ser
``` wherein: Xaa at position 1 is Glu or Gln; Xaa at position 7 is Ser or Leu; Xaa at position 46 is Glu, Val, Asp, or Ser; Xaa at position 63 is Thr or Ser; Xaa at position 75 is Ala, Ser, Val or Thr; Xaa at position 76 is Lys or Arg; Xaa at position 89 is Glu or Asp; and Xaa at position 107 is Leu or Thr.

An exemplary humanized 266 antibody comprises the following light chain (SEQ ID NO: 35) and heavy chain (SEQ ID NO: 36) sequences (not including signal sequences).

```
                                              (SEQ ID NO: 35)
Asp Val Val Met Thr Gln Ser Pro Leu Ser Leu

Pro Val Thr Leu Gly Gln Pro Ala Ser Ile Ser

Cys Arg Ser Ser Gln Ser Leu Ile Tyr Ser Asp

Gly Asn Ala Tyr Leu His Trp Phe Leu Gln Lys

Pro Gly Gln Ser Pro Arg Leu Leu Ile Tyr Lys

Val Ser Asn Arg Phe Ser Gly Val Pro Asp Arg

Phe Ser Gly Ser Gly Ser Gly Thr Asp Phe Thr

Leu Lys Ile Ser Arg Val Glu Ala Glu Asp Val

Gly Val Tyr Tyr Cys Ser Gln Ser Thr His Val

Pro Trp Thr Phe Gly Gln Gly Thr Lys Val Glu

Ile Lys Arg Thr Val Ala Ala Pro Ser Val Phe

Ile Phe Pro Pro Ser Asp Glu Gln Leu Lys Ser

Gly Thr Ala Ser Val Val Cys Leu Leu Asn Asn

Phe Tyr Pro Arg Glu Ala Lys Val Gln Trp Lys

Val Asp Asn Ala Leu Gln Ser Gly Asn Ser Gln

Glu Ser Val Thr Glu Gln Asp Ser Lys Asp Ser

Thr Tyr Ser Leu Ser Ser Thr Leu Thr Leu Ser

Lys Ala Asp Tyr Glu Lys His Lys Val Tyr Ala

Cys Glu Val Thr His Gln Gly Leu Ser Ser Pro

Val Thr Lys Ser Phe Asn Arg Gly Glu Cys (SEQ ID NO: 36)
Glu Val Gln Leu Val Glu Ser Gly Gly Gly Leu

Val Gln Pro Gly Gly Ser Leu Arg Leu Ser Cys

Ala Ala Ser Gly Phe Thr Phe Ser Arg Tyr Ser

Met Ser Trp Val Ary Gln Ala Pro Gly Lys Gly

Leu Glu Leu Val Ala Gln Ile Asn Ser Val Gly

Asn Ser Thr Tyr Tyr Pro Asp Thr Val Lys Gly

Arg Phe Thr Ile Ser Arg Asp Asn Ala Lys Asn

Thr Leu Tyr Leu Gln Met Asn Ser Leu Arg Ala

Glu Asp Thr Ala Val Tyr Tyr Cys Ala Ser Gly

Asp Tyr Trp Gly Gln Gly Thr Leu Val Thr Val

Ser Ser Ala Ser Thr Lys Gly Pro Ser Val Phe

Pro Leu Ala Pro Ser Ser Lys Ser Thr Ser Gly

Gly Thr Ala Ala Leu Gly Cys Leu Val Lys Asp

Tyr Phe Pro Glu Pro Val Thr Val Ser Trp Asn

Ser Gly Ala Leu Thr Ser Gly Val His Thr Phe

Pro Ala Val Leu Gln Ser Ser Gly Leu Tyr Ser

Leu Ser Ser Val Val Thr Val Pro Ser Ser Ser

Leu Gly Thr Gln Thr Tyr Ile Cys Asn Val Asn

His Lys Pro Ser Asn Thr Lys Val Asp Lys Lys

Val Glu Pro Lys Ser Cys Asp Lys Thr His Thr

Cys Pro Pro Cys Pro Ala Pro Glu Leu Leu Gly

Gly Pro Ser Val Phe Leu Phe Pro Pro Lys Pro
```

-continued

```
Lys Asp Thr Leu Met Ile Ser Arg Thr Pro Glu

Val Thr Cys Val Val Val Asp Val Ser His Glu

Asp Pro Glu Val Lys Phe Asn Trp Tyr Val Asp

Gly Val Glu Val His Asn Ala Lys Thr Lys Pro

Arg Glu Glu Gln Tyr Asn Ser Thr Tyr Arg Val

Val Ser Val Leu Thr Val Leu His Gln Asp Trp

Leu Asn Gly Lys Glu Tyr Lys Cys Lys Val Ser

Asn Lys Ala Leu Pro Ala Pro Ile Glu Lys Thr

Ile Ser Lys Ala Lys Gly Gln Pro Arg Glu Pro

Gln Val Tyr Thr Leu Pro Pro Ser Arg Asp Glu

Leu Thr Lys Asn Gln Val Ser Leu Thr Cys Leu

Val Lys Gly Phe Tyr Pro Ser Asp Ile Ala Val

Glu Trp Glu Ser Asn Gly Gln Pro Glu Asn Asn

Tyr Lys Thr Thr Pro Pro Val Leu Asp Ser Asp

Gly Ser Phe Phe Leu Tyr Ser Lys Leu Thr Val

Asp Lys Ser Arg Trp Gln Gln Gly Asn Val Phe

Ser Cys Ser Val Met His Glu Ala Leu His Asn

His Tyr Thr Gln Lys Ser Leu Ser Leu Ser Pro

Gly Lys
```

The antibody can also be 15C11 or a humanized form thereof (see US 20060165682), which specifically binds to an epitope within Aβ15-24.

The antibody can also be a humanized form of 20C2 or a variant thereof. Such antibodies are described, e.g., in US 2007081998. The core linear epitope for 20C2 corresponds to amino acid residues 3-8 of Aβ1-42, with a conformational epitope that is dependent upon elements from within residues 17-42 of Aβ. The light (SEQ ID NO: 37) and heavy chain (SEQ ID NO: 38) of humanized 20C2 antibody (version 1) have the following variable region sequences (not including signal sequences).

```
                                   (SEQ ID NO: 37)
Asp Val Val Met Thr Gln Ser Pro Leu Ser Leu

Pro Val Thr Pro Gly Glu Pro Ala Ser Ile Ser

Cys Arg Ser Ser Gln Ser Ile Leu His Ser Asn

Gly Asn Thr Tyr Leu Glu Trp Tyr Leu Gln Lys

Pro Gly Gln Ser Pro Gln Leu Leu Ile Tyr Lys

Val Ser Asn Arg Phe Ser Gly Val Pro Asp Arg

Phe Ser Gly Ser Gly Ser Gly Thr Asp Phe Thr

Leu Lys Ile Ser Arg Val Glu Ala Glu Asp Val

Gly Val Tyr Tyr Cys Phe Gln Gly Ser Leu Val

Pro Leu Thr Phe Gly Gln Gly Thr Lys Leu Glu

Ile Lys (SEQ ID NO: 38)
Gln Val Thr Leu Lys Glu Ser Gly Pro Ala Leu

Val Lys Pro Thr Gln Thr Leu Thr Leu Thr Cys

Thr Phe Ser Gly Phe Ser Leu Ser Thr Ser Gly

Met Gly Val Gly Trp Ile Arg Gln Pro Pro Gly

Lys Ala Leu Glu Trp Leu Ala His Ile Trp Trp

Asp Asp Asp Lys Ser Tyr Asn Pro Ser Leu Lys

Ser Arg Leu Thr Ile Ser Lys Asp Thr Ser Lys

Asn Gln Val Val Leu Thr Met Thr Asn Met Asp

Pro Val Asp Thr Ala Thr Tyr Tyr Cys Ala Arg

Arg Gln Leu Gly Leu Arg Ser Ile Asp Ala Met

Asp Tyr Trp Gly Gln Gly Thr Thr Val Thr Val

Ser Ser
```

An additional humanized 20C2 antibody (version 2) comprises the light chain variable region sequence of SEQ ID NO: 37 and the heavy chain variable region sequence of SEQ ID NO: 39 (not including signal sequence).

```
                                   (SEQ ID NO: 39)
Gln Val Thr Leu Lys Glu Ser Gly Pro Ala Leu

Val Lys Pro Thr Gln Thr Leu Thr Leu Thr Cys

Thr Leu Ser Gly Phe Ser Leu Ser Thr Ser Gly

Met Gly Val Gly Trp Ile Arg Gln Pro Pro Gly

Lys Ala Leu Glu Trp Leu Ala His Ile Trp Trp

Asp Asp Asp Lys Ser Tyr Asn Pro Ser Leu Lys

Ser Arg Leu Thr Ile Ser Lys Asp Thr Ser Lys

Asn Gln Val Val Leu Thr Met Thr Asn Met Asp

Pro Val Asp Thr Ala Thr Tyr Tyr Cys Ala Arg

Arg Gln Leu Gly Leu Arg Ser Ile Asp Ala Met

Asp Tyr Trp Gly Gln Gly Thr Thr Val Thr Val

Ser
```

Another antibody that can be used according to the invention is C705 or a variant thereof, which binds an epitope comprising amino acids 7-12 of the Aβ peptide, as described in WO 05/028511. The C705 antibody comprises the light chain variable region sequence of SEQ ID NO: 40 and heavy chain variable region of SEQ ID NO: 41, signal sequence underlined.

```
                                   (SEQ ID NO: 40)
Met Lys Leu Pro Val Arg Leu Leu Val Leu Met

Phe Trp Ile Pro Gly Ser Ser Ser Asp Val Met

Met Thr Gln Thr Pro Leu Ser Leu Pro Val Ser

Leu Gly Asp Gln Ala Ser Ile Ser Cys Arg Ser

Ser Gln Ser Leu Val His Ser Asn Gly Asn Thr

Tyr Leu Glu Trp Tyr Met Gln Lys Pro Gly Gln

Ser Pro Met Leu Leu Ile Tyr Lys Val Ser Asn

Arg Phe Ser Gly Val Pro Asp Arg Phe Ser Gly
```

```
Ser Gly Ser Gly Thr Asp Phe Thr Leu Lys Ile

Ser Ser Val Glu Ala Glu Asp Leu Gly Val Phe

Tyr Cys Phe Gln Gly Ser Arg Val Pro Leu Thr

Phe Gly Ala Gly Thr Lys Leu Glu Leu Lys Arg (SEQ ID NO: 41)
Met Asp Arg Leu Thr Ser Ser Phe Leu Leu Leu

Ile Val Pro Ala Tyr Val Leu Ser Gln Val Thr

Leu Lys Glu Ser Gly Pro Gly Ile Leu Gln Pro

Ser Gln Thr Leu Ser Leu Thr Cys Ser Phe Ser

Gly Phe Ser Leu Ser Thr Ser Gly Met Gly Val

Ser Trp Ile Arg Gln Pro Ser Gly Lys Gly Leu

Glu Trp Leu Ala His Ile Tyr Trp Asp Asp Asp

Lys Arg Tyr Asn Pro Ser Leu Lys Ser Arg Leu

Thr Ile Ser Lys Asp Thr Ser Arg Asn Gln Val

Phe Leu Lys Ile Thr Ser Val Asp Thr Thr Asp

Thr Ala Thr Tyr Tyr Cys Thr Arg Ser Ser Gly

Ser Ile Val Ile Ala Thr Gly Phe Ala Tyr Trp

Gly Gln Gly Thr Leu Val Thr Val Ser Ala
```

Another antibody that can be used according to the invention is C706 or a variant thereof, which binds to an epitope comprising amino acids 6-11 of the Aβ peptide, as described in WO 05/028511. The C706 antibody comprises the light chain variable region sequence of SEQ ID NO: 42, and the heavy chain variable region sequence of SEQ ID NO: 43. Signal sequences are underlined.

```
                                      (SEQ ID NO: 42)
Met Asp Phe Gln Val Gln Ile Phe Ser Phe Leu

Leu Ile Ser Ala Ser Val Ile Ile Ser Arg Gly

Gln Ile Val Leu Thr Gln Ser Pro Ala Ile Met

Ser Ala Ser Pro Gly Glu Lys Val Thr Met Thr

Cys Ser Ala Ser Ser Ser Val Ser Tyr Met His

Trp Tyr Gln Gln Lys Ser Gly Thr Ser Pro Lys

Arg Trp Ile Tyr Asp Ser Ser Arg Leu Ala Ser

Gly Val Pro Ser Arg Phe Ser Gly Gly Gly Ser

Gly Thr Ser Tyr Ser Pro Thr Ile Ser Asn Met

Glu Ala Glu Asp Ala Ala Thr Tyr Phe Cys Gln

Asn Trp Arg Ser Ser Pro Thr Phe Gly Ala Gly

Thr Lys Leu Glu Leu Lys Arg (SEQ ID NO: 43)
Met Glu Trp Thr Trp Val Phe Leu Phe Leu Leu

Ser Val Thr Ala Gly Val His Ser Gln Val Gln

Leu Gln Gln Ser Gly Pro Glu Leu Met Lys Pro

Gly Ala Ser Val Lys Ile Ser Cys Lys Ala Thr

Gly Tyr Thr Phe Ser Thr Ser Trp Ile Glu Trp

Ile Lys Gln Arg Pro Gly His Gly Leu Glu Trp

Ile Gly Glu Val Leu Pro Gly Ser Gly Lys Ser

Asn His Asn Ala Asn Phe Lys Gly Arg Ala Thr

Phe Thr Ala Asp Thr Ala Ser Asn Thr Ala Tyr

Met Gln Leu Ser Ser Leu Thr Ser Glu Asp Ser

Ala Val Tyr Tyr Cys Ala Arg Glu Gly Ser Asn

Asn Asn Ala Leu Ala Tyr Trp Gly Gln Gly Thr

Leu Val Thr Val Ser Ala
```

Other antibodies that can be used according to the invention include humanized 2286 antibodies and variants thereof. These antibodies recognize an epitope comprising amino acids 28-40 of the Aβ peptide, as described in US 20070160616. A humanized 2286 antibody (version 1) comprises the light chain variable region of SEQ ID NO: 44 and the heavy chain variable region of SEQ ID NO: 45 (not including signal sequences).

```
                                      (SEQ ID NO: 44)
DIQMTQSPSSLSASVGDRVTITCSASQGISNYLNWYQQKPGKAPKLLI

YYTSSLHSGVPSRFSGSGSGTDFTFTISSLQPEDIATYYCQQYRKLPY

TFGGGTKVEIKR
                                      (SEQ ID NO: 45)
EVQLVESGGGLVQPGGSLRLSCAASGFDFSRYWMNWVRQAPGKGLEWV

SEINPDSSTINYTPSLKDRFTISRDNAKNTLYLQMNSLRAEDTAVYYC

ARQMGYWGQGTTLTVSS
```

Another version of humanized 2286 comprises the light chain variable region of SEQ ID NO: 44 and the heavy chain variable region of SEQ ID NO: 46 (not including signal sequences).

```
                                      (SEQ ID NO: 46)
QVQLQESGPGLVKPSETLSLTCTVSGFDFSRYWMNWIRQPPGKGLEWI

GEINPDSSTINYTPSLKDRVTISKDTSKNQFSLKLSSVTAADTAVYYC

ARQMGYWGQGTLVTVSS
```

Additional antibodies that can be used according to the invention are a fourth version of humanized 3D6 and a second version of humanized 10D5, as disclosed in U.S. Pat. Nos. 7,318,923 and 7,320,790, respectively. These antibodies bind to the N-terminus of the Aβ peptide, as explained above. The humanized 3D6 (version 4) comprises the light chain variable region sequence of SEQ ID NO: 71 and the heavy chain variable region sequence of SEQ ID NO: 72.

```
                                      (SEQ ID NO: 71)
Asp Val Val Met Thr Gln Ser Pro Leu Ser Leu Pro

Val Thr Leu Gly Gln Pro Ala Ser Ile Ser Cys Lys

Ser Ser Gln Ser Leu Leu Asp Ser Asp Gly Lys Thr

Tyr Leu Asn Trp Leu Gln Gln Arg Pro Gly Gln Ser

Pro Arg Arg Leu Ile Tyr Leu Val Ser Lys Leu Asp
```

```
Ser Gly Val Pro Asp Arg Phe Ser Gly Ser Gly Ser

Gly Thr Asp Phe Thr Leu Lys Ile Ser Arg Val Glu

Ala Glu Asp Val Gly Val Tyr Tyr Cys Trp Gln Gly

Thr His Phe Pro Arg Thr Phe Gly Gly Gly Thr Lys

Val Glu Ile Lys Arg (SEQ ID NO: 72)
Glu Val Gln Leu Val Glu Ser Gly Gly Gly Leu Val

Gln Pro Gly Gly Ser Leu Arg Leu Ser Cys Ala Gly

Ser Gly Phe Thr Phe Ser Asn Tyr Gly Met Ser Trp

Val Arg Gln Ala Pro Gly Lys Gly Leu Glu Trp Val

Ala Ser Ile Arg Ser Gly Gly Gly Arg Thr Tyr Tyr

Ser Asp Asn Val Lys Gly Arg Phe Thr Ile Ser Arg

Glu Asn Ala Lys Asn Ser Leu Tyr Leu Gln Met Asn

Ser Leu Arg Ala Glu Asp Thr Ala Val Tyr Tyr Cys

Val Arg Tyr Asp His Tyr Ser Gly Ser Ser Asp Tyr

Trp Gly Gln Gly Thr Leu Val Thr Val Ser Ser
```

The humanized 10D5 antibody (version 2) comprises the light chain variable region sequence of SEQ ID NO: 73 and the heavy chain variable region sequence of SEQ ID NO: 74.

```
                                        (SEQ ID NO: 73)
Asp Val Val Met Thr Gln Ser Pro Leu Ser Leu Pro

Val Thr Leu Gly Gln Pro Ala Ser Ile Ser Cys Arg

Ser Ser Gln Asn Ile Ile His Ser Asn Gly Asn Thr

Tyr Leu Glu Trp Tyr Leu Gln Lys Pro Gly Gln Ser

Pro Arg Leu Leu Ile Tyr Lys Val Ser Asn Arg Phe

Ser Gly Val Pro Asp Arg Phe Ser Gly Ser Gly Ser

Gly Thr Asp Phe Thr Leu Lys Ile Ser Arg Val Glu

Ala Glu Asp Val Gly Val Tyr Tyr Cys Phe Gln Gly

Ser His Val Pro Leu Thr Phe Gly Gly Gly Thr Lys

Val Glu Ile Lys Arg (SEQ ID NO: 74)
Gln Val Thr Leu Lys Glu Ser Gly Pro Val Leu Val

Lys Pro Thr Glu Thr Leu Thr Leu Thr Cys Thr Phe

Ser Gly Phe Ser Leu Ser Thr Ser Gly Met Gly Val

Ser Trp Ile Arg Gln Pro Pro Gly Lys Ala Leu Glu

Trp Leu Ala His Ile Tyr Trp Asp Asp Asp Lys Arg

Tyr Asn Pro Ser Leu Lys Ser Arg Leu Thr Ile Ser

Lys Asp Thr Ser Lys Ser Gln Val Val Leu Thr Met

Thr Asn Met Asp Pro Val Asp Thr Ala Thr Tyr Tyr

Cys Val Arg Arg Pro Ile Thr Pro Val Leu Val Asp

Ala Met Asp Tyr Trp Gly Gln Gly Thr Leu Val Thr

Val Ser Ser
```

Another exemplary antibody is humanized 2E7, as disclosed in WO 07/113,172. The 2E7 antibody binds residues 1-12 of Aβ peptide, but not 2-13, or longer variants of the peptide. Humanized 2E7 antibody (version 1) comprises light chain variable region sequence of SEQ ID NO: 75 and heavy chain variable region sequence of SEQ ID NO: 76.

```
                                        (SEQ ID NO: 75)
DIVMTQSPLSLPVTPGEPASISCRVSQSLLHSNGYTYLHWYLQKPGQSP

QLLIYKVSNRFSGVPDRFSGSGSGTDFTLKISRVEAEDVGVYYCSQTRH

VPYTFGGGTKVEIK (SEQ ID NO: 76)
EVQLVESGGGLVQPGGSLRLSCAASGFTFSDNGMAWVRQAPGKGLEWVS

FISNLAYSIDYADTVTGRFTISRDNAKNSLYLQMNSLRAEDTAVYYCVS

GTWFAYWGQGTLVTVSS
```

A second version of humanized 2E7 antibody comprises the light chain variable region of SEQ ID NO: 75 and the heavy chain variable region sequence of SEQ ID NO: 77 (see, e.g., WO 07/113,172).

```
                                        (SEQ ID NO: 77)
EVQLVESGGGLVQPGGSLRLSCAVSGFTFSDNGMAWVRQAPGKGLEW

VSFISNLAYSIDYADTVTGRFTISRDNAKNSLYLQMNSLRAEDTAVY

YCVSGTWFAYWGQGTLVTVSS
```

Humanized 2E7 antibody (version 3) comprises the light chain variable region sequence of SEQ ID NO: 75 and the heavy chain variable region sequence of SEQ ID NO: 78 (see, e.g., WO 07/113,172).

```
                                        (SEQ ID NO: 78)
EVQLVESGGGLVQPGGSLRLSCAASGFTFSDNGMAWVRQAPGKGLEW

ISFISNLAYSIDYADTVTGRFTISRDNAKNSLYLQMNSLRAEDTAVY

YCVSGTWFAYWGQGTLVTVSS
```

An additional antibody that can be used according to the invention includes humanized 9TL antibody (ATCC accession numbers PTA-6124 and PTA-6125), as described in WO 06/036291. The heavy and light chain variable regions, without signal sequences, are shown as SEQ ID NO: 79 and SEQ ID NO: 80, respectively.

```
                                        (SEQ ID NO: 79)
QVQLVQSGAEVKKPGASVKVSCKASGYYTEAYYIHWVRQAPGQGLEW

MGRIDPATGNTKYAPRLQDRVTMTRDTSTSTVYMELSSLRSEDTAVY

YCASLYSLPVYWGQGTTVTVSS (SEQ ID NO: 80)
DVVMTQSPLSLPVTLGQPASISCKSSQSLLYSDAKTYLNWFQQRPGQ

SPRRLIYQISRLDPGVPDRFSGSGSGTDFTLKISRVEAEDVGVYYCL

QGTHYPVLFGQGTRLEIKRT
```

Humanized versions of the 6G antibody can also be used according to the invention. The heavy and light chain variable regions, without signal sequences, are shown as SEQ ID NOs:81 and 82, respectively.

(SEQ ID NO: 81)
QVQLVQSGAEVKKPGASVKVSCKASGYTFTTYAIHWVRQAPGQGLEW

MGFTSPYSGVSNYNQKFKGRVTMTRDTSTSTVYMELSSLRSEDTAVY

YCARFDNYDRGYVRDYWGQGTLV (SEQ ID NO: 82)
DIVMTQSPDSLAVSLGERATINCRASESVDNDRISFLNWYQQKPGQP

PKLLIYAATKQGTGVPDRFSGSGSGTDFTLTISSLQAEDVAVYYCQQ

SKEFPWSFGGGTKVEIKRTV

Additional antibodies that can be used according to the invention are humanized versions of the 2.1 antibody, as described in WO 06/081171. These antibodies rely on the CDRs of the murine 2.1 antibody and substitute residues from the human VKII A19/JK4 light chain variable framework region. The heavy chain variable framework region used for substitution is roughly based on VH 2-70. An exemplary humanized 2.1 antibody comprises the heavy and light chain variable regions, without signal sequences, shown as SEQ ID NOs: 83 and 84, respectively.

(SEQ ID NO: 83)
QVTLKESGPALVKPTQTLTLTCTFSGFSLRTSGMGVGWIRQPPGKAL

EWLAHIWWDDDKSYNPSLKS QLTISKDTSKNQVVLTMTNMDPVDTA

TYYCARRNYYYDDYFAYWGQGTLVTVSS (SEQ ID NO: 84)
DVLMTQSPLSLPVTLGQPASISCRSSQSIVHSNGNTYLEWYLQRPGQ

SPKLLIYKVSNRFSGVPDRFSGSGSGTDFTLKISRVEAEDVGVYYCF

QGSHVPLTFGAGTKLEIK

Other antibodies that can be used according to the invention include CW1181 and CW1185 antibodies. These antibodies specifically bind to two regions of the Aβ peptide, as described in WO 03/070760 and US 20050196399. The first region comprises AEFRHDSGY (SEQ ID NO: 85) or a fragment thereof (e.g., AEFRHD (SEQ ID NO: 86), or EFRHDSG (SEQ ID NO: 87), EFRHD (SEQ ID NO: 88)) and second region comprises the amino acid sequence YEVHHQKLVFFAEDVG (SEQ ID NO: 89) or a fragment thereof (e.g., VFFA (SEQ ID NO: 90), or QKLFFAEDV (SEQ ID NO: 91)).

An additional antibody that can be used according to the invention is the monoclonal NAB61 antibody. NAB61 binds Aβ1-11, but does not bind to full length APP or C99, as disclosed in WO 07/062,088. Similarly, the monoclonal 82E1 antibody can be used according to the invention. 82E1 binds the N-terminus of the Aβ peptide, but not full length APP, as disclosed in US 20080025988.

Other antibodies of the invention are anti-ADDL antibodies. Such antibodies have been generated and selected for the ability to bind ADDLs specifically, without binding to Aβ monomer or amyloid fibrils. See e.g., WO 04/031400.

Other antibodies that can be used include (i) the catalytic antibody ABP 102 (Abzyme, from Abiogen Pharma); (ii) ACI-01 Ab7 C2 (AC Immune Genentech); (iii) AZD-3102 (AstraZeneca/Dyax); (iv) IVIg (Gammagard S/D Immune Globulin Intravenous (Human), from Baxter Bioscience); (v) BAN 2401 (BioArctic Neuroscience AB/Eisai Co. Ltd.; (vi) R1450 (Hoffman-La Roche/MorphoSys); (vii) LY2062430 (Eli Lilly); (viii) h3D6 (Eli Lilly); (ix) ACU-5A5 (αADDL mAb from Merck/Acumen); α-amyloid-spheroid (ASPD) antibody (Mitsubishi Pharma Corp.); (xi) the antibody derived from PBMCs of an AN1792 patient (Neurimmune Therapeutics AG); (xii) BC05 (Takeda); (xiii) the CEN701-CEN706 antibodies (Centocor/Johnson & Johnson); and (xiv) PF-04360365 (also called RN-1219 (h2286), from Pfizer/Rinat Neurosciences). Each of these antibodies can be used according to any of the methods of the invention.

The ABP 102 antibody cleaves aggregated Aβ as described, e.g., in U.S. Pat. No. 6,387,674 and WO 99/06536. The ACI-01 Ab7 C2 antibody binds the Aβ peptide between residues 10-20 and is described in US 20070166311. The IVIg Gammagard SD Immune Globulin antibody is described, e.g., on the Baxter Bioscience website at Baxter.com. The BAN 2401 antibody is a humanized antibody that binds Aβ protofibrils, and is described, e.g., in WO 05/123775. The human R-1450 HuCAL antibody has a dual 266/3D6 epitope. The humanized LY2062430 antibody (IgG) binds the Aβ peptide between residues 16-23, and is described, e.g., in U.S. Pat. No. 7,195,761. The humanized h3D6 antibody binds the Aβ peptide at residues 1-5, and is described, e.g., in U.S. Pat. No. 7,318,923. The BC05 antibody binds a C terminal Aβ epitope, as described by Asami-Odaka et al. (2005) Neurodegenerative Diseases 2:36-43. The CEN701-CEN706 antibodies are described, e.g., in WO 05/028511. The humanized PF-04360365 antibody binds the Aβ peptide between residues 28-40 and is described, e.g., in WO 04/032868.

Any of the antibodies or antibody fragments described herein can be designed or prepared using standard methods, as disclosed, e.g., in US 20040038304, US 20070020685, US 200601660184, US 20060134098, US 20050255552, US 20050130266, US 2004025363, US 20040038317, US 20030157579, and U.S. Pat. No. 7,335,478.

Any of the antibodies described above can be produced with different isotypes or mutant isotypes to control the extent of binding to different Fcγ receptors. Antibodies lacking an Fc region (e.g., Fab fragments) lack binding to Fcγ receptors. Selection of isotype also affects binding to Fcγ receptors. The respective affinities of various human IgG isotypes for the three Fcγ receptors, FcγRI, FcγRII, and FcγRIII, have been determined. (See Ravetch & Kinet, Annu. Rev. Immunol. 9, 457 (1991)). FcγRI is a high affinity receptor that binds to IgGs in monomeric form, and the latter two are low affinity receptors that bind IgGs only in multimeric form. In general, both IgG1 and IgG3 have significant binding activity to all three receptors, IgG4 to FcγRI, and IgG2 to only one type of FcγRII called IIa$_{LR}$ (see Parren et al., J. Immunol. 148, 695 (1992). Therefore, human isotype IgG1 is usually selected for stronger binding to Fcγ receptors is desired, and IgG2 is usually selected for weaker binding.

Mutations on, adjacent, or close to sites in the hinge link region (e.g., replacing residues 234, 235, 236 and/or 237 with another residue) in all of the isotypes reduce affinity for Fcγ receptors, particularly FcγRI receptor (see, e.g., U.S. Pat. No. 6,624,821). Optionally, positions 234, 236 and/or 237 are substituted with alanine and position 235 with glutamine. (See, e.g., U.S. Pat. No. 5,624,821.) Position 236 is missing in the human IgG2 isotype. Exemplary segments of amino acids for positions 234, 235 and 237 for human IgG2 are Ala Ala Gly, Val Ala Ala, Ala Ala Ala, Val Glu Ala, and Ala Glu Ala. A preferred combination of mutants is L234A, L235A, and G237A for human isotype IgG1. A particular preferred antibody is bapineuzumab having human isotype IgG and these three mutations of the Fc region. Other substitutions that decrease binding to Fcγ receptors are an E233P mutation (particularly in mouse IgG1) and D265A (particularly in mouse IgG2a). Other examples of mutations and combinations of mutations reducing Fc and/or C1q binding are described in the Examples (E318A/K320A/R322A (particularly in mouse IgG1), L235A/E318A/K320A/K322A (particularly in mouse IgG2a). Similarly, residue 241 (Ser) in human IgG4 can be replaced, e.g., with proline to disrupt Fc binding.

Additional mutations can be made to the constant region to modulate effector activity. For example, mutations can be made to the IgG2a constant region at A330S, P331S, or both. For IgG4, mutations can be made at E233P, F234V and L235A, with G236 deleted, or any combination thereof. IgG4 can also have one or both of the following mutations S228P and L235E. The use of disrupted constant region sequences to modulate effector function is further described, e.g., in WO 06/118,959 and WO 06/036291.

Additional mutations can be made to the constant region of human IgG to modulate effector activity (see, e.g., WO 06/03291). These include the following substitutions: (i) A327G, A330S, P331S; (ii) E233P, L234V, L235A, G236 deleted; (iii) E233P, L234V, L235A; (iv) E233P, L234V, L235A, G236 deleted, A327G, A330S, P331S; and (v) E233P, L234V, L235A, A327G, A330S, P331S to human IgG1.

The affinity of an antibody for the FcR can be altered by mutating certain residues of the heavy chain constant region. For example, disruption of the glycosylation site of human IgG1 can reduce FcR binding, and thus effector function, of the antibody (see, e.g., WO 06/036291). The tripeptide sequences NXS, NXT, and NXC, where X is any amino acid other than proline, are the enzymatic recognition sites for glycosylation of the N residue. Disruption of any of the tripeptide amino acids, particularly in the CH2 region of IgG, will prevent glycosylation at that site. For example, mutation of N297 of human IgG1 prevents glycosylation and reduces FcR binding to the antibody.

The sequences of several exemplary humanized 3D6 antibodies and their components parts are shown below. Human constant regions show allotypic variation and isoallotypic variation between different individuals, that is, the constant regions can differ in different individuals at one or more polymorphic positions. Isoallotypes differ from allotypes in that sera recognizing an isoallotype binds to a non-polymorphic region of a one or more isotypes. The allotype of the IgG1 constant region shown below is 3D6 (AAB-001) is G1mz which has Glu at position 356 and Met at position 358. The allotype of the kappa constant region shown below is Km3, which has an Ala at position 153 and a Val at position 191. A different allotye Km(1) has Val and Leu at positions 153 and 191 respectively. Allotypic variants are reviewed by J Immunogen 3: 357-362 (1976) and Loghem, Monogr Allergy 19: 40-51 (1986). Other allotypic and isoallotypic variants of the illustrated constant regions are included. Also included are constant regions having any permutation of residues occupying polymorphic positions in natural allotypes. Examples of other heavy chain IgG1 allotypes include: G1m(f), G1m(a) and G1m(x). G1m(f) differs from G1m(z) in that it has an Arg instead of a Lys at position 214. G1m(a) has amino acids Arg, Asp, Glu, Leu at positions 355-358.

Humanized 3D6 Full Length Light Chain (signal sequence underlined) (bapineuzumab and AAB-003)

(SEQ ID NO: 47)
MDMRVPAQLLGLLMLWVSGSSGDVVMTQSPLSLPVTPGEPASISCKSS
SQSLLDSDGKTYLNWLLQKPGQSPQRLIYLVSKLDSGVPDRFSGSGS
GTDFTLKISRVEAEDVGVYYCWQGTHFPRTFGQGTKVEIKRTVAAPS
VFIFPPSDEQLKSGTASVVCLLNNFYPREAKVQWKVDNALQSGNSQE
SVTEQDSKDSTYSLSSTLTLSKADYEKHKVYACEVTHQGLSSPVTKS
FNRGEC

Humanized 3D6 Full Length Light Chain, Not Including Signal Sequence (bapineuzumab and AAB-003)

(SEQ ID NO: 48)
DVVMTQSPLSLPVTPGEPASISCKSSQSLLDSDGKTYLNWLLQKPGQ
SPQRLIYLVSKLDSGVPDRFSGSGSGTDFTLKISRVEAEDVGVYYCW
QGTHFPRTFGQGTKVEIKRTVAAPSVFIFPPSDEQLKSGTASVVCLL
NNFYPREAKVQWKVDNALQSGNSQESVTEQDSKDSTYSLSSTLTLSK
ADYEKHKVYACEVTHQGLSSPVTKSFNRGEC

DNA encoding humanized 3D6 Light Chain Coding Sequence (signal sequence underlined) (bapineuzumab and AAB-003)

(SEQ ID NO: 49)
ATGGACATGCGCGTGCCCGCCCAGCTGCTGGGCCTGCTGATGCTGTG
GGTGTCCGGCTCCTCCGGCGACGTGGTGATGACCCAGTCCCCCCTGT
CCCTGCCCGTGACCCCCGGCGAGCCCGCCTCCATCTCCTGCAAGTCC
TCCCAGTCCCTGCTGGACTCCGACGGCAAGACCTACCTGAACTGGCT
GCTGCAGAAGCCCGGCCAGTCCCCCCAGCGCCTGATCTACCTGGTGT
CCAAGCTGGACTCCGGCGTGCCCGACCGCTTCTCCGGCTCCGGCTCC
GGCACCGACTTCACCCTGAAGATCTCCCGCGTGGAGGCCGAGGACGT
GGGCGTGTACTACTGCTGGCAGGGCACCCACTTCCCCCGCACCTTCG
GCCAGGGCACCAAGGTGGAGATCAAGCGTACTGTGGCTGCACCATCT
GTCTTCATCTTCCCGCCATCTGATGAGCAGTTGAAATCTGGAACTGC
CTCTGTTGTGTGCCTGCTGAATAACTTCTATCCCAGAGAGGCCAAAG
TACAGTGGAAGGTGGATAACGCCCTCCAATCGGGTAACTCCCAGGAG
AGTGTCACAGAGCAGGACAGCAAGGACAGCACCTACAGCCTCAGCAG
CACCCTGACGCTGAGCAAAGCAGACTACGAGAAACACAAAGTCTACG
CCTGCGAAGTCACCCATCAGGGCCTGAGCTCGCCCGTCACAAAGAGC
TTCAACAGGGGAGAGTGTTAG

Human Heavy Chain Constant Region, IgG1 Isotype, L234A/G237A (SEQ ID NO: 50)
ASTKGPSVFPLAPSSKSTSGGTAALGCLVKDYFPEPVTVSWNSGAL
TSGVHTFPAVLQSSGLYSLSSVVTVPSSSLGTQTYICNVNHKPSNT
KVDKKVEPKSCDKTHTCPPCPAPEALGAPSVFLFPPKPKDTLMISR
TPEVTCVVVDVSHEDPEVKFNWYVDGVEVHNAKTKPREEQYNSTYR
VVSVLTVLHQDWLNGKEYKCKVSNKALPAPIEKTISKAKGQPREPQ
VYTLPPSREEMTKNQVSLTCLVKGFYPSDIAVEWESNGQPENNYKT
TPPVLDSDGSFFLYSKLTVDKSRWQQGNVFSCSVMHEALHNHYTQK
SLSLSPGK The C-terminal K residue can be absent, as indicated below.

```
                                       (SEQ ID NO: 51)
ASTKGPSVFPLAPSSKSTSGGTAALGCLVKDYFPEPVTVSWNSGAL

TSGVHTFPAVLQSSGLYSLSSVVTVPSSSLGTQTYICNVNHKPSNT

KVDKKVEPKSCDKTHTCPPCPAPEALGAPSVFLFPPKPKDTLMISR

TPEVTCVVVDVSHEDPEVKFNWYVDGVEVHNAKTKPREEQYNSTYR

VVSVLTVLHQDWLNGKEYKCKVSNKALPAPIEKTISKAKGQPREPQ

VYTLPPSREEMTKNQVSLTCLVKGFYPSDIAVEWESNGQPENNYKT

TPPVLDSDGSFFLYSKLTVDKSRWQQGNVFSCSVMHEALHNHYTQK

SLSLSPG.
```

Humanized 3D6 Full Length Heavy Chain (IgG1 Isotype, L234A/G237A) including signal sequence (underlined)

```
                                       (SEQ ID NO: 52)
MEFGLSWLFLVAILKGVQCEVQLLESGGGLVQPGGSLRLSCAASGF

TFSNYGMSWVRQAPGKGLEWVASIRSGGGRTYYSDNVKGRFTISRD

NSKNTLYLQMNSLRAEDTAVYYCVRYDHYSGSSDYWGQGTLVTVSS

ASTKGPSVFPLAPSSKSTSGGTAALGCLVKDYFPEPVTVSWNSGAL

TSGVHTFPAVLQSSGLYSLSSVVTVPSSSLGTQTYICNVNHKPSNT

KVDKKVEPKSCDKTHTCPPCPAPEALGAPSVFLFPPKPKDTLMISR

TPEVTCVVVDVSHEDPEVICFNWYVDGVEVHNAKTKPREEQYNSTY

RVVSVLTVLHQDWLNGKEYKCKVSNKALPAPIEKTISKAKGQPREP

QVYTLPPSREEMTKNQVSLTCLVKGFYPSDIAVEWESNGQPENNYK

TTPPVLDSDGSFFLYSKLTVDKSRWQQGNVFSCSVMHEALHNHYTQ

KSLSLSPGK
```

The C-terminal K residue can be absent, as indicated below.

```
                                       (SEQ ID NO: 53)
MEFGLSWLFLVAILKGVQCEVQLLESGGGLVQPGGSLRLSCAASGF

TFSNYGMSWVRQAPGKGLEWVASIRSGGGRTYYSDNVKGRFTISRD

NSKNTLYLQMNSLRAEDTAVYYCVRYDHYSGSSDYWGQGTLVTVSS

ASTKGPSVFPLAPSSKSTSGGTAALGCLVKDYFPEPVTVSWNSGAL

TSGVHTFPAVLQSSGLYSLSSVVTVPSSSLGTQTYICNVNHKPSNT

KVDKKVEPKSCDKTHTCPPCPAPEALGAPSVFLFPPKPKDTLMISR

TPEVTCVVVDVSHEDPEVKFNWYVDGVEVHNAKTKPREEQYNSTYR

VVSVLTVLHQDWLNGKEYKCKVSNKALPAPIEKTISKAKGQPREPQ

VYTLPPSREEMTKNQVSLTCLVKGFYPSDIAVEWESNGQPENNYKT

TPPVLDSDGSFFLYSKLTVDKSRWQQGNVFSCSVMHEALHNHYTQK

SLSLSPG.
```

Humanized 3D6 Full Length Heavy Chain Not Including Signal Sequence (IgG1 Isotype, L234A/G237A)

```
                                       (SEQ ID NO: 54)
EVQLLESGGGLVQPGGSLRLSCAASGFTFSNYGMSWVRQAPGKGLE

WVASIRSGGGRTYYSDNVKGRFTISRDNSKNTLYLQMNSLRAEDTA

VYYCVRYDHYSGSSDYWGQGTLVTVSSASTKGPSVFPLAPSSKSTS

GGTAALGCLVKDYFPEPVTVSWNSGALTSGVHTFPAVLQSSGLYSL

SSVVTVPSSSLGTQTYICNVNHKPSNTKVDKKVEPKSCDKTHTCPP

CPAPEALGAPSVFLFPPKPKDTLMISRTPEVTCVVVDVSHEDPEVI

CFNWYVDGVEVHNAKTKPREEQYNSTYRVVSVLTVLHQDWLNGKEY

KCKVSNKALPAPIEKTISKAKGQPREPQVYTLPPSREEMTKNQVSL

TCLVKGFYPSDIAVEWESNGQPENNYKTTPPVLDSDGSFFLYSKLT

VDKSRWQQGNVFSCSVMHEALHNHYTQKSLSLSPGK
```

The C-terminal K residue can be absent, as indicated below.

```
                                       (SEQ ID NO: 55)
EVQLLESGGGLVQPGGSLRLSCAASGFTFSNYGMSWVRQAPGKGLE

WVASIRSGGGRTYYSDNVKGRFTISRDNSKNTLYLQMNSLRAEDTA

VYYCVRYDHYSGSSDYWGQGTLVTVSSASTKGPSVFPLAPSSKSTS

GGTAALGCLVKDYFPEPVTVSWNSGALTSGVHTFPAVLQSSGLYSL

SSVVTVPSSSLGTQTYICNVNHKPSNTKVDKKVEPKSCDKTHTCPP

CPAPEALGAPSVFLFPPKPKDTLMISRTPEVTCVVVDVSHEDPEVK

FNWYVDGVEVHNAKTKPREEQYNSTYRVVSVLTVLHQDWLNGKEYK

CKVSNKALPAPIEKTISKAKGQPREPQVYTLPPSREEMTKNQVSLT

CLVKGFYPSDIAVEWESNGQPENNYKTTPPVLDSDGSFFLYSKLTV

DKSRWQQGNVFSCSVMHEALHNHYTQKSLSLSPG.
```

Human Heavy Chain Constant Region, IgG4 Isotype, S241P (Kabat numbering); S228P (EU numbering)

```
                                       (SEQ ID NO: 56)
ASTKGPSVFPLAPCSRSTSESTAALGCLVKDYFPEPVTVSWNSGAL

TSGVHTFPAVLQSSGLYSLSSVVTVPSSSLGTKTYTCNVDHKPSNT

KVDKRVESKYGPPCPPCPAPEFLGGPSVFLFPPKPKDTLMISRTPE

VTCVVVDVSQEDPEVQFNWYVDGVEVHNAKTKPREEQFNSTYRVVS

VLTVLHQDWLNGKEYKCKVSNKGLPSSIEKTISKAKGQPREPQVYT

LPPSQEEMTKNQVSLTCLVKGFYPSDIAVEWESNGQPENNYKTTPP

VLDSDGSFFLYSRLTVDKSRWQEGNVFSCSVMHEALHNHYTQKSLS

LSLGK
```

The C-terminal K residue can be absent, as indicated below.

```
                                       (SEQ ID NO: 57)
ASTKGPSVFPLAPCSRSTSESTAALGCLVKDYFPEPVTVSWNSGALT

GVHTFPAVLQSSGLYSLSSVVTVPSSSLGTKTYTCNVDHKPSNTKVD
```

DKRVESKYGPPCPPCPAPEFLGGPSVFLFPPKPKDTLMISRTPEVTC

VVVDVSQEDPEVQFNWYVDGVEVHNAKTKPREEQFNSTYRVVSVLTV

LHQDWLNGKEYKCKVSNKGLPSSIEKTISKAKGQPREPQVYTLPPSQ

EEMTKNQVSLTCLVKGFYPSDIAVEWESNGQPENNYKTTPPVLDSDG

SFFLYSRLTVDKSRWQEGNVFSCSVMHEALHNHYTQKSLSLSLG

Humanized 3D6 Full Length Heavy Chain (IgG4 Isotype, S241P), Including Signal Sequence (underlined)

(SEQ ID NO: 58)
MEFGLSWLFLVAILKGVQCEVQLLESGGGLVQPGGSLRLSCAASGFT

FSNYGMSWVRQAPGKGLEWVASIRSGGGRTYYSDNVKGRFTISRDNS

KNTLYLQMNSLRAEDTAVYYCVRYDHYSGSSDYWGQGTLVTVSSAST

KGPSVFPLAPCSRSTSESTAALGCLVKDYFPEPVTVSWNSGALTSGV

HTFPAVLQSSGLYSLSSVVTVPSSSLGTKTYTCNVDHKPSNTKVDKR

VESKYGPPCPPCPAPEFLGGPSVFLFPPKPKDTLMISRTPEVTCVVV

DVSQEDPEVQFNWYVDGVEVHNAKTKPREEQFNSTYRVVSVLTVLHQ

DWLNGKEYKCKVSNKGLPSSIEKTISKAKGQPREPQVYTLPPSQEEM

TKNQVSLTCLVKGFYPSDIAVEWESNGQPENNYKTTPPVLDSDGSFF

LYSRLTVDKSRWQEGNVFSCSVMHEALHNHYTQKSLSLSLGK

The C-terminal K residue can be absent, as indicated below.

(SEQ ID NO: 59)
MEFGLSWLFLVAILKGVQCEVQLLESGGGLVQPGGSLRLSCAASGFT

FSNYGMSWVRQAPGKGLEWVASIRSGGGRTYYSDNVKGRFTISRDNS

KNTLYLQMNSLRAEDTAVYYCVRYDHYSGSSDYWGQGTLVTVSSAST

KGPSVFPLAPCSRSTSESTAALGCLVKDYFPEPVTVSWNSGALTSGV

HTFPAVLQSSGLYSLSSVVTVPSSSLGTKTYTCNVDHKPSNTKVDKR

VESKYGPPCPPCPAPEFLGGPSVFLFPPKPKDTLMISRTPEVTCVVV

DVSQEDPEVQFNWYVDGVEVHNAKTKPREEQFNSTYRVVSVLTVLHQ

DWLNGKEYKCKVSNKGLPSSIEKTISKAKGQPREPQVYTLPPSQEEM

TKNQVSLTCLVKGFYPSDIAVEWESNGQPENNYKTTPPVLDSDGSFF

LYSRLTVDKSRWQEGNVFSCSVMHEALHNHYTQKSLSLSLG.

Humanized 3D6 Heavy Chain, Not Including Signal Sequence (IgG4 Isotype, S241P)

(SEQ ID NO: 60)
EVQLLESGGGLVQPGGSLRLSCAASGFTFSNYGMSWVRQAPGKGLEW

VASIRSGGGRTYYSDNVKGRFTISRDNSKNTLYLQMNSLRAEDTAVY

YCVRYDHYSGSSDYWGQGTLVTVSSASTKGPSVFPLAPCSRSTSEST

AALGCLVKDYFPEPVTVSWNSGALTSGVHTFPAVLQSSGLYSLSSVV

TVPSSSLGTKTYTCNVDHKPSNTKVDKRVESKYGPPCPPCPAPEFLG

GPSVFLFPPKPKDTLMISRTPEVTCVVVDVSQEDPEVQFNWYVDGVE

VHNAKTKPREEQFNSTYRVVSVLTVLHQDWLNGKEYKCKVSNKGLPS

SIEKTISKAKGQPREPQVYTLPPSQEEMTKNQVSLTCLVKGFYPSDI

AVEWESNGQPENNYKTTPPVLDSDGSFFLYSRLTVDKSRWQEGNVFS

CSVMHEALHNHYTQKSLSLSLGK

The C-terminal K residue can be absent, as indicated below.

(SEQ ID NO: 61)
EVQLLESGGGLVQPGGSLRLSCAASGFTFSNYGMSWVRQAPGKGLEW

VASIRSGGGRTYYSDNVKGRFTISRDNSKNTLYLQMNSLRAEDTAVY

YCVRYDHYSGSSDYWGQGTLVTVSSASTKGPSVFPLAPCSRSTSEST

AALGCLVKDYFPEPVTVSWNSGALTSGVHTFPAVLQSSGLYSLSSVV

TVPSSSLGTKTYTCNVDHKPSNTKVDKRVESKYGPPCPPCPAPEFLG

GPSVFLFPPKPKDTLMISRTPEVTCVVVDVSQEDPEVQFNWYVDGVE

VHNAKTKPREEQFNSTYRVVSVLTVLHQDWLNGKEYKCKVSNKGLPS

SIEKTISKAKGQPREPQVYTLPPSQEEMTKNQVSLTCLVKGFYPSDI

AVEWESNGQPENNYKTTPPVLDSDGSFFLYSRLTVDKSRWQEGNVFS

CSVMHEALHNHYTQKSLSLSLG.

Human Heavy Chain Constant Region, IgG1 Isotype (AAB-003), L234A/L235A/G237A (SEQ ID NO: 62)
ASTKGPSVFPLAPSSKSTSGGTAALGCLVKDYFPEPVTVSWNSGALT

SGVHTFPAVLQSSGLYSLSSVVTVPSSSLGTQTYICNVNHKPSNTKV

DKKVEPKSCDKTHTCPPCPAPEAAGAPSVFLFPPKPKDTLMISRTPE

VTCVVVDVSHEDPEVICFNWYVDGVEVHNAKTKPREEQYNSTYRVVS

VLTVLHQDWLNGKEYKCKVSNKALPAPIEKTISKAKGQPREPQVYTL

PPSREEMTKNQVSLTCLVKGFYPSDIAVEWESNGQPENNYKTTPPVL

DSDGSFFLYSKLTVDKSRWQQGNVFSCSVMHEALHNHYTQKSLSLSP

GK

The C-terminal K residue can be absent, as indicated below.

(SEQ ID NO: 63)
ASTKGPSVFPLAPSSKSTSGGTAALGCLVKDYFPEPVTVSWNSGALT

SGVHTFPAVLQSSGLYSLSSVVTVPSSSLGTQTYICNVNHKPSNTKV

DKKVEPKSCDKTHTCPPCPAPEAAGAPSVFLFPPKPKDTLMISRTPE

VTCVVVDVSHEDPEVKFNWYVDGVEVHNAKTKPREEQYNSTYRVVSV

LTVLHQDWLNGKEYKCKVSNKALPAPIEKTISKAKGQPREPQVYTLP

PSREEMTKNQVSLTCLVKGFYPSDIAVEWESNGQPENNYKTTPPVLD

SDGSFFLYSKLTVDKSRWQQGNVFSCSVMHEALHNHYTQKSLSLSPG.

Humanized 3D6 Full Length Heavy Chain Including Signal Sequence (IgG1 isotone. L234A/L235A/G237A1: AAB-003

(SEQ ID NO: 64)
MEFGLSWLFLVAILKGVQCEVQLLESGGGLVQPGGSLRLSCAASGFT

FSNYGMSWVRQAPGKGLEWVASIRSGGGRTYYSDNVKGRFTISRDNS

KNTLYLQMNSLRAEDTAVYYCVRYDHYSGSSDYWGQGTLVTVSSAST

KGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKK

VEPKSCDKTHTCPPCPAPEAAGAPSVFLFPPKPKDTLMISRTPEVTC

VVVDVSHEDPEVKFNWYVDGVEVHNAKTKPREEQYNSTYRVVSVLTV

LHQDWLNGKEYKCKVSNKALPAPIEKTISKAKGQPREPQVYTLPPSR

EEMTKNQVSLTCLVKGFYPSDIAVEWESNGQPENNYKTTPPVLDSDG

SFFLYSKLTVDKSRWQQGNVFSCSVMHEALHNHYTQKSLSLSPGK

The C-terminal K residue can be absent, as indicated below.

(SEQ ID NO: 65)
MEFGLSWLFLVAILKGVQCEVQLLESGGGLVQPGGSLRLSCAASGFT

FSNYGMSWVRQAPGKGLEWVASIRSGGGRTYYSDNVKGRFTISRDNS

KNTLYLQMNSLRAEDTAVYYCVRYDHYSGSSDYWGQGTLVTVSSAST

KGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKK

VEPKSCDKTHTCPPCPAPEAAGAPSVFLFPPKPKDTLMISRTPEVTC

VVVDVSHEDPEVKFNWYVDGVEVHNAKTKPREEQYNSTYRVVSVLTV

LHQDWLNGKEYKCKVSNKALPAPIEKTISKAKGQPREPQVYTLPPSR

EEMTKNQVSLTCLVKGFYPSDIAVEWESNGQPENNYKTTPPVLDSDG

SFFLYSKLTVDKSRWQQGNVFSCSVMHEALHNHYTQKSLSLSPG.

Humanized 3D6 Heavy Chain, Not Including Signal Sequence (IgG1 isotype, L234A/L235A/G237A): AAB-003

(SEQ ID NO: 66)
EVQLLESGGGLVQPGGSLRLSCAASGFTFSNYGMSWVRQAPGKGLE

WVASIRSGGGRTYYSDNVKGRFTISRDNSKNTLYLQMNSLRAEDTA

VYYCVRYDHYSGSSDYWGQGTLVTVSSASTKGPSVFPLAPSSKSTS

GGTAALGCLVKDYFPEPVTVSWNSGALTSGVHTFPAVLQSSGLYSL

SSVVTVPSSSLGTQTYICNVNHKPSNTKVDKKVEPKSCDKTHTCPP

CPAPEAAGAPSVFLFPPKPKDTLMISRTPEVTCVVVDVSHEDPEVK

FNWYVDGVEVHNAKTKPREEQYNSTYRVVSVLTVLHQDWLNGKEYK

CKVSNKALPAPIEKTISKAKGQPREPQVYTLPPSREEMTKNQVSLT

CLVKGFYPSDIAVEWESNGQPENNYKTTPPVLDSDGSFFLYSKLTV

DKSRWQQGNVFSCSVMHEALHNHYTQKSLSLSPGK

The C-terminal K residue can be absent, as indicated below.

(SEQ ID NO: 67)
EVQLLESGGGLVQPGGSLRLSCAASGFTFSNYGMSWVRQAPGKGLE

WVASIRSGGGRTYYSDNVKGRFTISRDNSKNTLYLQMNSLRAEDTA

VYYCVRYDHYSGSSDYWGQGTLVTVSSASTKGPSVFPLAPSSKSTS

GGTAALGCLVKDYFPEPVTVSWNSGALTSGVHTFPAVLQSSGLYSL

SSVVTVPSSSLGTQTYICNVNHKPSNTKVDKKVEPKSCDKTHTCPP

CPAPEAAGAPSVFLFPPKPKDTLMISRTPEVTCVVVDVSHEDPEVK

FNWYVDGVEVHNAKTKPREEQYNSTYRVVSVLTVLHQDWLNGKEYK

CKVSNKALPAPIEKTISKAKGQPREPQVYTLPPSREEMTKNQVSLT

CLVKGFYPSDIAVEWESNGQPENNYKTTPPVLDSDGSFFLYSKLTV

DKSRWQQGNVFSCSVMHEALHNHYTQKSLSLSPG.

DNA encoding humanized 3D6 Heavy Chain Coding Region including Signal Sequence (underlined) (IgG1 isotype, L234A/L235A/G237A): AAB-003

(SEQ ID NO: 68)
ATGGAGTTTGGGCTGAGCTGGCTTTTTCTTGTGGCTATTTTAAAAG

GTGTCCAGTGTGAGGTGCAGCTGCTGGAGTCCGGCGGCGGCCTGGT

GCAGCCCGGCGGCTCCCTGCGCCTGTCCTGCGCCGCCTCCGGCTTC

ACCTTCTCCAACTACGGCATGTCCTGGGTGCGCCAGGCCCCCGGCA

AGGGCCTGGAGTGGGTGGCCTCCATCCGCTCCGGCGGCGCCGCAC

CTACTACTCCGACAACGTGAAGGGCCGCTTCACCATCTCCCGCGAC

AACTCCAAGAACACCCTGTACCTGCAGATGAACTCCCTGCGCGCCG

AGGACACCGCCGTGTACTACTGCGTGCGCTACGACCACTACTCCGG

CTCCTCCGACTACTGGGGCCAGGGCACCCTGGTGACCGTGTCCTCC

GCGTCGACCAAGGGCCCATCGGTCTTCCCCCTGGCACCCTCCTCCA

AGAGCACCTCTGGGGGCACAGCGGCCCTGGGCTGCCTGGTCAAGGA

CTACTTCCCCGAACCGGTGACGGTGTCGTGGAACTCAGGCGCCCTG

ACCAGCGGCGTGCACACCTTCCCGGCTGTCCTACAGTCCTCAGGAC

TCTACTCCCTCAGCAGCGTGGTGACCGTGCCCTCCAGCAGCTTGGG

CACCCAGACCTACATCTGCAACGTGAATCACAAGCCCAGCAACACC

AAGGTGGACAAGAAAGTTGAGCCCAAATCTTGTGACAAAACTCACA

CATGCCCACCGTGCCCAGCACCTGAAGCCGCTGGGGCACCGTCAGT

CTTCCTCTTCCCCCCAAAACCCAAGGACACCCTCATGATCTCCCGG

ACCCCTGAGGTCACATGCGTGGTGGTGGACGTGAGCCACGAAGACC

CTGAGGTCAAGTTCAACTGGTACGTGGACGGCGTGGAGGTGCATAA

TGCCAAGACAAAGCCGCGGGAGGAGCAGTACAACAGCACGTACCGT

GTGGTCAGCGTCCTCACCGTCCTGCACCAGGACTGGCTGAATGGCA

AGGAGTACAAGTGCAAGGTCTCCAACAAAGCCCTCCCAGCCCCCAT

CGAGAAAACCATCTCCAAAGCCAAAGGGCAGCCCCGAGAACCACAG

GTGTACACCCTGCCCCCATCCCGGGAGGAGATGACCAAGAACCAGG

TCAGCCTGACCTGCCTGGTCAAAGGCTTCTATCCCAGCGACATCGC

CGTGGAGTGGGAGAGCAATGGGCAGCCGGAGAACAACTACAAGACC

ACGCCTCCCGTGCTGGACTCCGACGGCTCCTTCTTCCTCTATAGCA

AGCTCACCGTGGACAAGAGCAGGTGGCAGCAGGGGAACGTCTTCTC

ATGCTCCGTGATGCATGAGGCTCTGCACAACCACTACACGCAGAAG

AGCCTCTCCCTGTCCCCGGGTAAATGA

Full-length heavy chain of bapineuzumab, not including signal sequence, IgG1 isotype, no Fc mutations (SEQ ID NO: 69)
EVQLLESGGGLVQPGGSLRLSCAASGFTFSNYGMSWVRQAPGKGLE

WVASIRSGGGRTYYSDNVKGRFTISRDNSKNTLYLQMNSLRAEDTA

VYYCVRYDHYSGSSDYWGQGTLVTVSSASTKGPSVFPLAPSSKSTS

GGTAALGCLVKDYFPEPVTVSWNSGALTSGVHTFPAVLQSSGLYSL

SSVVTVPSSSLGTQTYICNVNHICPSNTKVDKKVEPKSCDKTHTCP

PCPAPELLGGPSVFLFPPKPKDTLMISRTPEVTCVVVDVSHEDPEV

KFNWYVDGVEVHNAKTKPREEQYNSTYRVVSVLTVLHQDWLNGKEY

KCKVSNKALPAPIEKTISKAKGQPREPQVYTLPPSREEMTKNQVSL

TCLVKGFYPSDIAVEWESNGQPENNYKTTPPVLDSDGSFFLYSKLT

VDKSRWQQGNVFSCSVMHEALHNHYTQKSLSLSPGK

The C-terminal K residue can be absent, as indicated below.

(SEQ ID NO: 70)
EVQLLESGGGLVQPGGSLRLSCAASGFTFSNYGMSWVRQAPGKGLE

WVASIRSGGGRTYYSDNVKGRFTISRDNSKNTLYLQMNSLRAEDTA

VYYCVRYDHYSGSSDYWGQGTLVTVSSASTKGPSVFPLAPSSKSTS

GGTAALGCLVKDYFPEPVTVSWNSGALTSGVHTFPAVLQSSGLYSL

SSVVTVPSSSLGTQTYICNVNHKPSNTKVDKKVEPKSCDKTHTCPP

CPAPELLGGPSVFLFPPKPKDTLMISRTPEVTCVVVDVSHEDPEVK

FNWYVDGVEVHNAKTKPREEQYNSTYRVVSVLTVLHQDWLNGKEYK

CKVSNKALPAPIEKTISKAKGQPREPQVYTLPPSREEMTKNQVSLT

CLVKGFYPSDIAVEWESNGQPENNYKTTPPVLDSDGSFFLYSKLTV

DKSRWQQGNVFSCSVMHEALHNHYTQKSLSLSPG

In some antibodies, positions 234, 235, and 237 of a human IgG heavy chain constant region can be AAA respectively, LLA respectively, LAG respectively, ALG respectively, AAG respectively, ALA respectively, or LAA respectively. As shown above, AAB-003 is an L234A, L235A, and G237A variant of bapineuzumab (i.e., having identical amino acid sequences to bapineuzumab except for the L234A, L235A, and G237A mutations, alanine (A) being the variant amino acid). Like bapineuzumab, AAB-003 has a full-length human kappa light chain constant region and a full-length human IgG1 heavy chain constant region (in either bapineuzumab or AAB-003, a C-terminal lysine residue is sometimes cleaved intracellularly and is sometimes missing from the final product).

Although the three mutations in AAB-003 are close to the hinge region rather than the complement binding region, AAB-003 has reduced binding to both Fcγ receptors and to C1q, relative to bapineuzumab. Thus, the AAB-003 antibody has reduced capacity to induce both phagocytosis and the complement cascade. Furthermore, AAB-003 displays less binding to human FcγRII than an otherwise identical antibody with fewer than the three mutations present in AAB-003 (e.g., one with substitutions at residues 234 and 237), indicating that all three mutations in the AAB-003 Fc region contribute to reducing effector function. Mutation of the heavy chain constant region to reduce interaction with Fcγ receptor(s) and or C1q can reduce microhemorrhaging in a mouse model without eliminating useful activities. Microhemorraghing in mice is one factor that may contribute to vasogenic edema occurring in humans. Antibodies bearing such mutations retain the ability to inhibit cognitive decline as well as ability to clear amyloid deposits.

Similarly heavy chain constant region mutants can also be combined with the variable region sequences described above, e.g., for humanized 12A11 and 12B4 antibodies. The following table shows exemplary combinations of heavy chain variable regions and heavy chain constant regions with mutation(s) for antibodies described above. The heavy chains shown in the table for a particular antibody e.g., 12A11, can be paired with any of the light chain variable regions described above for that antibody linked to a light chain constant region (e.g., a human kappa light chain constant region as follows:

(SEQ ID NO: 85)
RTVAAPSVFIFPPSDEQLKSGTASVVCLLNNFYPREAKVQWKVDNA

LQSGNSQESVTEQDSKDSTYSLSSTLTLSKADYEKHKVYACEVTHQ

GLSSPVTKSFNRGEC or an allotype or isoallotype thereof.

TABLE 1

Correlation of Full Length Heavy Chain SEQ ID NOS with Respective Variable and Constant Region SEQ ID NOS

| Antibody | Heavy Chain Variable region | Heavy Chain Constant region |
|---|---|---|
| 10D5 (version 1) | 9 | 50 |
|  | 9 | 51 |
|  | 9 | 56 |
|  | 9 | 57 |
|  | 9 | 62 |
|  | 9 | 63 |
| 12B4 | 32 | 50 |
|  | 32 | 51 |
|  | 32 | 56 |
|  | 32 | 57 |
|  | 32 | 62 |
|  | 32 | 63 |
| 12A11 (version 1) | 11 | 50 |
|  | 11 | 51 |
|  | 11 | 56 |
|  | 11 | 57 |
|  | 11 | 62 |
|  | 11 | 63 |
| 12A11 (version 2) | 12 | 50 |
|  | 12 | 51 |
|  | 12 | 56 |
|  | 12 | 57 |
|  | 12 | 62 |
|  | 12 | 63 |
| 12A11 (version 2.1) | 13 | 50 |
|  | 13 | 51 |
|  | 13 | 56 |
|  | 13 | 57 |
|  | 13 | 62 |
|  | 13 | 63 |
| 12A11 (version 3) | 14 | 50 |
|  | 14 | 51 |
|  | 14 | 56 |
|  | 14 | 57 |
|  | 14 | 62 |
|  | 14 | 63 |
| 12A11 (version 4.1) | 15 | 50 |
|  | 15 | 51 |
|  | 15 | 56 |
|  | 15 | 57 |
|  | 15 | 62 |
|  | 15 | 63 |

TABLE 1-continued

Correlation of Full Length Heavy Chain SEQ ID NOS with Respective Variable and Constant Region SEQ ID NOS

| Antibody | Heavy Chain Variable region | Heavy Chain Constant region |
| --- | --- | --- |
| 12A11 (version 4.2) | 16 | 50 |
|  | 16 | 51 |
|  | 16 | 56 |
|  | 16 | 57 |
|  | 16 | 62 |
|  | 16 | 63 |
| 12A11 (version 4.3) | 17 | 50 |
|  | 17 | 51 |
|  | 17 | 56 |
|  | 17 | 57 |
|  | 17 | 62 |
|  | 17 | 63 |
| 12A11 (version 4.4) | 18 | 50 |
|  | 18 | 51 |
|  | 18 | 56 |
|  | 18 | 57 |
|  | 18 | 62 |
|  | 18 | 63 |
| 12A11 (version 5.1) | 19 | 50 |
|  | 19 | 51 |
|  | 19 | 56 |
|  | 19 | 57 |
|  | 19 | 62 |
|  | 19 | 63 |
| 12A11 (version 5.2) | 20 | 50 |
|  | 20 | 51 |
|  | 20 | 56 |
|  | 20 | 57 |
|  | 20 | 62 |
|  | 20 | 63 |
| 12A11 (version 5.3) | 21 | 50 |
|  | 21 | 51 |
|  | 21 | 56 |
|  | 21 | 57 |
|  | 21 | 62 |
|  | 21 | 63 |
| 12A11 (version 5.4) | 22 | 50 |
|  | 22 | 51 |
|  | 22 | 56 |
|  | 22 | 57 |
|  | 22 | 62 |
|  | 22 | 63 |
| 12A11 (version 5.5) | 23 | 50 |
|  | 23 | 51 |
|  | 23 | 56 |
|  | 23 | 57 |
|  | 23 | 62 |
|  | 23 | 63 |
| 12A11 (version 5.6) | 24 | 50 |
|  | 24 | 51 |
|  | 24 | 56 |
|  | 24 | 57 |
|  | 24 | 62 |
|  | 24 | 63 |
| 12A11 (version 6.1) | 25 | 50 |
|  | 25 | 51 |
|  | 25 | 56 |
|  | 25 | 57 |
|  | 25 | 62 |
|  | 25 | 63 |
| 12A11 (version 6.2) | 26 | 50 |
|  | 26 | 51 |
|  | 26 | 56 |
|  | 26 | 57 |
|  | 26 | 62 |
|  | 26 | 63 |
| 12A11 (version 6.3) | 27 | 50 |
|  | 27 | 51 |
|  | 27 | 56 |
|  | 27 | 57 |
|  | 27 | 62 |
|  | 27 | 63 |
| 12A11 (version 6.4) | 28 | 50 |
|  | 28 | 51 |
|  | 28 | 56 |
|  | 28 | 57 |
|  | 28 | 62 |
|  | 28 | 63 |
| 12A11 (version 7) | 29 | 50 |
|  | 29 | 51 |
|  | 29 | 56 |
|  | 29 | 57 |
|  | 29 | 62 |
|  | 29 | 63 |
| 12A11 (version 8) | 30 | 50 |
|  | 30 | 51 |
|  | 30 | 56 |
|  | 30 | 57 |
|  | 30 | 62 |
|  | 30 | 63 |
| 12B4 | 32 | 50 |
|  | 32 | 51 |
|  | 32 | 56 |
|  | 32 | 57 |
|  | 32 | 62 |
|  | 32 | 63 |
| 266 | 34 | 50 |
|  | 34 | 51 |
|  | 34 | 56 |
|  | 34 | 57 |
|  | 34 | 62 |
|  | 34 | 63 |
| 20C2 (version 1) | 38 | 50 |
|  | 38 | 51 |
|  | 38 | 56 |
|  | 38 | 57 |
|  | 38 | 62 |
|  | 38 | 63 |
| 20C2 (version 2) | 39 | 50 |
|  | 39 | 51 |
|  | 39 | 56 |
|  | 39 | 57 |
|  | 39 | 62 |
|  | 39 | 63 |
| C705 | 41 | 50 |
|  | 41 | 51 |
|  | 41 | 56 |
|  | 41 | 57 |
|  | 41 | 62 |
|  | 41 | 63 |
| C706 | 43 | 50 |
|  | 43 | 51 |
|  | 43 | 56 |
|  | 43 | 57 |
|  | 43 | 62 |
|  | 43 | 63 |
| 2286 (version 1) | 45 | 50 |
|  | 45 | 51 |
|  | 45 | 56 |
|  | 45 | 57 |
|  | 45 | 62 |
|  | 45 | 63 |
| 2286 (version 2) | 46 | 50 |
|  | 46 | 51 |
|  | 46 | 56 |
|  | 46 | 57 |
|  | 46 | 62 |
|  | 46 | 63 |
| 3D6 (version 4) | 72 | 50 |
|  | 72 | 51 |
|  | 72 | 56 |
|  | 72 | 57 |
|  | 72 | 62 |
|  | 72 | 63 |

TABLE 1-continued

Correlation of Full Length Heavy Chain SEQ ID NOS
with Respective Variable and Constant Region SEQ ID NOS

| Antibody | Heavy Chain Variable region | Heavy Chain Constant region |
|---|---|---|
| 10D6 (version 2) | 74 | 50 |
| | 74 | 51 |
| | 74 | 56 |
| | 74 | 57 |
| | 74 | 62 |
| | 74 | 63 |
| 2E7 (version 1) | 76 | 50 |
| | 76 | 51 |
| | 76 | 56 |
| | 76 | 57 |
| | 76 | 62 |
| | 76 | 63 |
| 2E7 (version 2) | 77 | 50 |
| | 77 | 51 |
| | 77 | 56 |
| | 77 | 57 |
| | 77 | 62 |
| | 77 | 63 |
| 2E7 (version 3) | 78 | 50 |
| | 78 | 51 |
| | 78 | 56 |
| | 78 | 57 |
| | 78 | 62 |
| | 78 | 63 |
| 9TL | 79 | 50 |
| | 79 | 51 |
| | 79 | 56 |
| | 79 | 57 |
| | 79 | 62 |
| | 79 | 63 |
| 6G | 81 | 50 |
| | 81 | 51 |
| | 81 | 56 |
| | 81 | 57 |
| | 81 | 62 |
| | 81 | 63 |
| 2.1 | 82 | 50 |
| | 82 | 51 |
| | 82 | 56 |
| | 82 | 57 |
| | 82 | 62 |
| | 82 | 63 |

Amino acids in the constant region are numbered by alignment with the human antibody EU (see Cunningham et al., *J. Biol. Chem.*, 9, 3161 (1970)). That is, the heavy and light chains of an antibody are aligned with the heavy and light chains of EU to maximize amino acid sequence identity and each amino acid in the antibody is assigned the same number as the corresponding amino acid in EU. The EU numbering system is conventional (see generally, Kabat et al., *Sequences of Protein of Immunological Interest*, NIH Publication No. 91-3242, US Department of Health and Human Services (1991)).

The affinity of an antibody for complement component C1q can be altered by mutating at least one of the amino acid residues 318, 320, and 322 of the heavy chain to a residue having a different side chain. Other suitable alterations for altering, e.g., reducing or abolishing, specific C1q-binding to an antibody include changing any one of residues 318 (Glu), 320 (Lys) and 322 (Lys), to Ala. C1q binding activity can be abolished by replacing any one of the three specified residues with a residue having an inappropriate functionality on its side chain. It is not necessary to replace the ionic residues only with Ala to abolish C1q binding. It is also possible to use other alkyl-substituted non-ionic residues, such as Gly, Ile, Leu, or Val, or such aromatic non-polar residues as Phe, Tyr, Trp and Pro in place of any one of the three residues in order to abolish C1q binding. In addition, it is also be possible to use such polar non-ionic residues as Ser, Thr, Cys, and Met in place of residues 320 and 322, but not 318, to abolish C1q binding activity. Replacement of the 318 (Glu) residue by a polar residue may modify but not abolish C1q binding activity. Replacing residue 297 (Asn) with Ala results in removal of lytic activity while only slightly reducing (about three fold weaker) affinity for C1q. This alteration destroys the glycosylation site and the presence of carbohydrate that is required for complement activation. Any other substitution at this site also destroys the glycosylation site.

Additional mutations that can affect C1q binding to the constant region of human IgG1 include those described, e.g., in WO 06/036291. In this case, at least one of the following substitutions can be made to reduce C1q binding: D270A, K322A, P329A, and P311S. Each of these mutations, including those at residues 297, 318, and 320 can be made individually or in combination.

Antibodies with heavy chain constant region mutations that reduce binding to Fcγ receptor(s) and/or C1q can be used in any of the methods of the invention. Preferably, such antibodies have reduced binding relative to an otherwise identical antibody lacking the mutation of at least 50% to at least one Fcγ receptor and/or to C1q.

B. Aβ Fragments

Numerous fragments of Aβ have been now been described in the scientific and patent literature as agents for active immunotherapy (see, e.g., U.S. Pat. No. 6,750,324, US 20040213800; US 20070134762). In general, fragments including an epitope within residues 1-11 of Aβ induce antibodies that bind Fcγ receptors and induce a clearing response against amyloid deposits, whereas fragments lacking an epitope within residues 1-11 of Aβ induce antibodies that bind preferentially or exclusively to soluble forms of Aβ rather than plaques and induces little if any clearing response against amyloid deposits.

Preferred fragment for inducing antibodies that bind to amyloid deposits and induce a clearing response are N-terminal fragments beginning at residues 1-3 of Aβ and ending at residues 7-11 of Aβ. Exemplary N-terminal fragments include Aβ1-5, 1-6, 1-7, 1-10, 3-7, 1-3, and 1-4 with 1-7 being particularly preferred. A class of exemplary fragments includes fragments beginning at a residue between 1-3 (inclusive) and ending at a residue between 7-11 (inclusive).

Preferred fragments for inducing antibodies to soluble Aβ, which induce little, if any, clearing response against amyloid deposits include Aβ15-21, Aβ16-22, Aβ17-23, Aβ18-24, Aβ19-25, Aβ15-22, Aβ16-23, Aβ17-24, Aβ18-25, Aβ15-23, Aβ16-24, Aβ17-25, Aβ18-26, Aβ15-24, Aβ16-25, and Aβ15-25. Aβ16-23 is particularly preferred meanings a fragment including residues 16-23 of Aβ and lacking other residues of Aβ. Also preferred are C-terminal fragments of Aβ42 or 43 of 5-10 and preferably 7-10 contiguous amino acids. Analogous C-terminal fragments of Aβ40, or 39 can also be used. These fragments can generate an antibody response that includes end-specific antibodies. Fragments preferably lack T-cell epitopes that would induce T-cells against Aβ. Generally, T-cell epitopes are greater than 10 contiguous amino acids. Therefore, preferred fragments of Aβ are of size 5-10 or preferably 7-10 contiguous amino acids; i.e., sufficient length to generate an antibody response without generating a T-cell response. Absence of T-cell epitopes is preferred because these epitopes are not needed for immunogenic activity of fragments, and may cause an undesired inflammatory response in a subset of patients.

Agents to induce antibodies to Aβ that can be used in the methods of the invention also include (i) ACI-24 (AC Immune); (ii) Affitopes AD02 and AD02 (Affiris GmbH); (iii) Arctic Immunotherapeutic KLVFFAGDV (SEQ ID NO: 92) (BioArctic Neuroscience/Eisai); (iv) Aβ1-15-K-K-Aβ1-15 (Brigham & Women's Hospital); (v) 13-Vax™ and Recall-Vax™ (Intellect Neurosciences); (vi) K6-Aβ1-30 (Intellect Neurosciences/NYU); (vii) V-950 (Merck); (viii) CAD106 (Novartis/Cytos); (ix) Aβ DCtag™ nanoparticle adjuvant (Prana Biotechnology/PRIMABioMed); (x) PX106 (also 2Aβ1-11-PADRE, from Pharmexa/Lundbeck); (xi) Aβ4-10 conjugated to a T cell epitope (U. Toronto); and (xii) p3102 and p3075 (United Biomedical).

ACI-24 is an Aβ1-15 liposome construct with Aβ1-15-K-K-16C palmitic acid inserted into a liposomal bilayer. These compounds are described in US 2004/0242845, WO 05/081872, US 2007/0281006, and US 2006/0073158. Affitopes AD01 and AD02 are mimotopes from the N-terminus of Aβ, as described in WO 06/005707. The Arctic Immunotherapeutic is derived from Aβ22 of E692G, as described in US 20020162129 and US 20070248606. Aβ1-15-K-K-Aβ1-15 represents two linked N-terminal Aβ fragments, as described in WO 05/012330 and WO 02/0123553. β-Vax™, Recall-Vax™ and K6-Aβ1-30 are Aβ fragments linked to a T cell epitope, as described in WO 01/42306. V-950 is an 8-mer Aβ peptide linked to a multivalent linear peptide with at least one spacer and a multivalent branched multiple antigen peptide, as described in WO 06/121656. CAD106 is a Q13 carrier (an RNA VLP) linked to an N-terminal Aβ peptide, as described in WO 04/016282. The Aβ DCtag™ nanoparticle adjuvant is described, e.g., in WO 02/00245. PX106 is a Aβ1-11 peptide linked to a T cell epitope called a "pan DR epitope peptide (PADRE)," as described in U.S. Pat. No. 7,135,181. p3102 and p3075 are Aβ1-14 peptides linked by a spacer to a T cell epitope (e.g., measles epitope), as described in US 20030068325 US 20040247612, U.S. Pat. No. 6,906,169, and WO 02/096350.

Fragments are usually natural Aβ peptides but can include unnatural amino acids or modifications of N or C terminal amino acids at a one, two, five, ten or even all positions. For example, the natural aspartic acid residue at position 1 and/or 7 of Aβ can be replaced with iso-aspartic acid. Examples of unnatural amino acids are D, alpha, alpha-disubstituted amino acids, N-alkyl amino acids, lactic acid, 4-hydroxyproline, γ-carboxyglutamate, epsilon-N,N,N-trimethyllysine, epsilon-N-acetyllysine, O-phosphoserine, N-acetylserine, N-formylmethionine, 3-methylhistidine, 5-hydroxylysine, omega-N-methylarginine, β-alanine, ornithine, norleucine, norvaline, hydroxproline, thyroxine, β-amino butyric acid, homoserine, citrulline, and isoaspartic acid. Some therapeutic agents of the invention are all-D peptides, e.g., all-D Aβ or all-D Aβ fragment, and all-D peptide analogs. Fragments can be screened for prophylactic or therapeutic efficacy in transgenic animal models in comparison with untreated or placebo controls.

Fragments are typically conjugated to carrier molecules, which provide a T-cell epitope, and thus promote an immune response against the fragment conjugated to the carrier. A single agent can be linked to a single carrier, multiple copies of an agent can be linked to multiple copies of a carrier, which are in turn linked to each other, multiple copies of an agent can be linked to a single copy of a carrier, or a single copy of an agent can be linked to multiple copies of a carrier, or different carriers. Suitable carriers include serum albumins, keyhole limpet hemocyanin, immunoglobulin molecules, thyroglobulin, ovalbumin, tetanus toxoid, or a toxoid from other pathogenic bacteria, such as diphtheria (e.g., CRM197), E. coli, cholera, or H. pylori, or an attenuated toxin derivative. T cell epitopes are also suitable carrier molecules. Some conjugates can be formed by linking agents of the invention to an immunostimulatory polymer molecule (e.g., tripalmitoyl-5-glycerine cysteine (Pam₃Cys), mannan (a mannose polymer), or glucan (a β1→2 polymer)), cytokines (e.g., IL-1, IL-1 alpha and β peptides, IL-2, γ-INF, IL-10, GM-CSF), and chemokines (e.g., MIP1-α and β, and RANTES). Immunogenic agents can also be linked to peptides that enhance transport across tissues, as described in O'Mahony, WO 97/17613 and WO 97/17614. Immunogens may be linked to the carries with or with out spacers amino acids (e.g., gly-gly).

Additional carriers include virus-like particles. Virus-like particles (VLPs), also called pseudovirions or virus-derived particles, represent subunit structures composed of multiple copies of a viral capsid and/or envelope protein capable of self assembly into VLPs of defined spherical symmetry in vivo. (Powilleit, et al., (2007) *PLoS ONE* 2(5):e415.) These particles have been found to be useful as antigen delivery systems. VLPs can be produced and readily purified in large quantities and due to their particulate nature and high molecular weights. VLPs induce an immune response without additional application of an adjuvant. (Ulrich et al., (1996) *Intervirology* 39:126-132.) Exemplary chimeric particles useful as VLP antigen delivery systems include those based on hepatitis B virus, human immunodeficiency virus (HIV), yeast retrotransposon Ty, yeast totivirus L-A, parvovirus, influenza virus, Norwalk virus, rotavirus, adeno-associated virus, bluetongue virus, hepatitis A virus, human papillomavirus, measles virus, polyoma virus and RNA phage virus, as well as those based on various retroviruses and lentiviruses. For review, see Lechner, et al. (2002) *Intervirology* 45:212-217.

The core protein of hepatitis B virus (HBcAg) is a common VLP used for carrying foreign antigens (see Koletzki et al., (1997) *J Gen Vir* 78:2049-2053). Briefly, HBcAg can be used as a core to construct VLPs that present extended foreign protein segments. The method employs a construct having a linker sequence between the a C-terminally truncated HBcAg and a foreign protein sequence that contains a stop codon. Truncated HBcAg/foreign protein chimera is expressed utilizing a read through mechanism based on the opal TGA-Trp mutation for expression in an *E. coli* suppressor strain. The method described by Koletzki et al. allows for incorporation of long foreign protein sequences into VLPs, allowing for a greater variety of antigens to be carried by the VLP.

The HIV virus Gag protein can be used as an antigen carrier system (see Griffiths et al., (1993) *J. Virol.* 67(6): 3191-3198). Griffiths utilized the V3 loop of HIV, which is the principle neutralizing determinant of the HIV envelope. The Gag:V3 fusion proteins assembled in vivo into hybrid Gag particles, designated virus-derived particles (VDPs). The VDPs induce both humoral and cellular responses. As the V3 loop contains a CTL epitope, immunization with Gag:V3 induces a CTL response to the V3 protein portion of the VLP.

A hybrid HIV:Ty VLP can also be used (see Adams et al., (1987) *Nature* 329(3):68-70). The HIV:Ty VLP employs the p1 protein of the yeast transposon Ty. The first 381 amino acids of p1 are sufficient for VLP formation. The HIV:Ty fusion proteins are capable of assembling into VLPs in vivo, as well as inducing an immune response to the HIV antigen carried by the VLP. VLPs using the Ty p1 protein can also contain p1 fused to the whole of an alpha2-interferon, the product of the bovine papilloma virus E1 and E2 genes, and a portion of an influenza hemagglutinin. Each of these Ty fusions formed VLPs and were capable of inducing production of antisera to the non-Ty VLP component.

VLPs can also be designed from variants of the yeast totivirus L-A (see Powilleit et al. (2007) PLOS One 2(5): e415). The Pol gene of the L-A virus can be replaced with an appropriate antigen to induce a specific immune response, demonstrating that yeast VLPs are effective antigen carriers.

Recombinant, nonreplicative parvovirus-like particles can also be used as antigen carriers. (Sedlik, et al. (1997) PNAS 94:7503-7508.) These particles allow the carried antigens into the cytosol so they enter the class I-restricted immunological pathway, thus stimulating cytotoxic T-lymphocyte (CTL) mediated responses. Sedlik specifically used PPV: VLP, which contained the VP2 capsid protein of the parvovirus and residues 118-132 from the lymphocytic choriomeningitis virus (LCMV) was inserted into the VP2 capsid protein. The PPV:VLP containing LCMV was capable of inducing an immune response to LCMV and elicited immunological protection against lethal viral doses in pre-immunized mice.

VLPs can also comprise replication incompetent influenza that lack the influenza NS2 gene, the gene essential for viral replication. (Watanabe, et al. (1996) J. Virol. 76(2): 767-773.) These VLPs infect mammalian cells and allow expression of foreign proteins.

Norwalk virus (NV)-based VLPs can also be used as vehicles for immunogen delivery. (Ball, et al. (1999) Gastroenterology 117:40-48.) The NV genome has three open reading frames (ORFs 1-3). Recombinant baculovirus expression of ORFs 2 and 3 allows for spontaneous assembly of high yields of recombinant Norwalk virus (rNV) VLPs.

Some conjugates can be formed by linking agents of the invention to at least one T cell epitope. Some T cell epitopes are promiscuous whereas other T cell epitopes are universal. Promiscuous T cell epitopes are capable of enhancing the induction of T cell immunity in a wide variety of subjects displaying various HLA types. In contrast to promiscuous T cell epitopes, universal T cell epitopes are capable of enhancing the induction of T cell immunity in a large percentage, e.g., at least 75%, of subjects displaying various HLA molecules encoded by different HLA-DR alleles.

A large number of naturally occurring T-cell epitopes exist, such as, tetanus toxoid (e.g., the P2 and P30 epitopes), Hepatitis B surface antigen, pertussis, toxoid, measles virus F protein, Chlamydia trachomatis major outer membrane protein, diphtheria toxoid, Plasmodium falciparum circumsporozoite T, Plasmodium falciparum CS antigen, Schistosoma mansoni triose phosphate isomerase, Escherichia coli TraT, and Influenza virus hemagglutinin (HA). The immunogenic peptides of the invention can also be conjugated to the T-cell epitopes described in Sinigaglia F. et al., Nature, 336:778-780 (1988); Chicz R. M. et al., J. Exp. Med., 178:27-47 (1993); Hammer J. et al., Cell 74:197-203 (1993); Falk K. et al., Immunogenetics, 39:230-242 (1994); WO 98/23635; and, Southwood S. et al. J. Immunology, 160: 3363-3373 (1998).

Carriers also include virus-like particles (see US 20040141984).

Fragments are often administered with pharmaceutically acceptable adjuvants. The adjuvant increases the titer of induced antibodies and/or the binding affinity of induced antibodies relative to the situation if the peptide were used alone. A variety of adjuvants can be used in combination with an immunogenic fragment of Aβ, to elicit an immune response. Preferred adjuvants augment the intrinsic response to an immunogen without causing conformational changes in the immunogen that affect the qualitative form of the response. Preferred adjuvants include aluminum hydroxide and aluminum phosphate, 3 De-O-acylated monophosphoryl lipid A (MPL™) (see GB 2220211 (RIBI ImmunoChem Research Inc., Hamilton, Mont., now part of Corixa). Stimulon™ QS-21 is a triterpene glycoside or saponin isolated from the bark of the Quillaja Saponaria Molina tree found in South America (see Kensil et al., in Vaccine Design: The Subunit and Adjuvant Approach (eds. Powell & Newman, Plenum Press, NY, 1995); U.S. Pat. No. 5,057,540), (Aquila BioPharmaceuticals, Framingham, Mass.; now Antigenics, Inc., New York, N.Y.). Other adjuvants are oil in water emulsions (such as squalene or peanut oil), optionally in combination with immune stimulants, such as monophosphoryl lipid A (see Stoute et al., N. Engl. J. Med. 336, 86-91 (1997)), pluronic polymers, and killed mycobacteria. Another adjuvant is CpG (WO 98/40100). Adjuvants can be administered as a component of a therapeutic composition with an active agent or can be administered separately, before, concurrently with, or after administration of the therapeutic agent.

A preferred class of adjuvants is aluminum salts (alum), such as alum hydroxide, alum phosphate, alum sulfate. Such adjuvants can be used with or without other specific immunostimulating agents such as MPL or 3-DMP, QS-21, polymeric or monomeric amino acids such as polyglutamic acid or polylysine. Another class of adjuvants is oil-in-water emulsion formulations. Such adjuvants can be used with or without other specific immunostimulating agents such as muramyl peptides (e.g., N-acetylmuramyl-L-threonyl-D -isoglutamine (thr-MDP), N-acetyl-normuramyl-L-alanyl-D-isoglutamine (nor-MDP), N-acetylmuramyl-L-alanyl-D -isoglutaminyl-L-alanine-2-(1'-2'dipalmitoyl-sn-glycero-3-hydroxyphosphoryloxy)-ethylamine (MTP-PE), N-acetylglucsaminyl-N-acetylmuramyl-L-A1-D-isoglu-L-Ala-di-palmitoxy propylamide (DTP-DPP) Theramide™), or other bacterial cell wall components. Oil-in-water emulsions include (a) MF59 (WO 90/14837), containing 5% Squalene, 0.5% Tween 80, and 0.5% Span 85 (optionally containing various amounts of MTP-PE) formulated into submicron particles using a microfluidizer such as Model 110Y microfluidizer (Microfluidics, Newton Mass.), (b) SAF, containing 10% Squalene, 0.4% Tween 80, 5% pluronic-blocked polymer L121, and thr-MDP, either microfluidized into a submicron emulsion or vortexed to generate a larger particle size emulsion, and (c) Ribi™ adjuvant system (RAS), (Ribi ImmunoChem, Hamilton, Mont.) containing 2% squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™).

Another class of preferred adjuvants is saponin adjuvants, such as Stimulon™ (QS-21, Aquila, Framingham, Mass.) or particles generated therefrom such as ISCOMs (immunostimulating complexes) and ISCOMATRIX. Other adjuvants include RC-529, GM-CSF and Complete Freund's Adjuvant (CFA) and Incomplete Freund's Adjuvant (IFA). Other adjuvants include cytokines, such as interleukins (e.g., IL-1a and 13 peptides, IL-2, IL-4, IL-6, IL-12, IL13, and IL-15), macrophage colony stimulating factor (M-CSF), granulocyte-macrophage colony stimulating factor (GM-CSF), tumor necrosis factor (TNF), chemokines, such as MIP1α and β and RANTES. Another class of adjuvants is glycolipid analogues including N-glycosylamides, N-glycosylureas and N-glycosylcarbamates, each of which is substituted in the sugar residue by an amino acid, as immuno-modulators or adjuvants (see U.S. Pat. No. 4,855,283). Heat shock proteins, e.g., HSP70 and HSP90, may also be used as adjuvants.

An adjuvant can be administered with an immunogen as a single composition, or can be administered before, concurrent with or after administration of the immunogen. Immunogen and adjuvant can be packaged and supplied in the same vial or can be packaged in separate vials and mixed before use. Immunogen and adjuvant are typically packaged with a label indicating the intended therapeutic application. If immunogen and adjuvant are packaged separately, the packaging typically includes instructions for mixing before use. The choice of an adjuvant and/or carrier depends on the stability of the immunogenic formulation containing the adjuvant, the route of administration, the dosing schedule, the efficacy of the adjuvant for the species being vaccinated, and, in humans, a pharmaceutically acceptable adjuvant is one that has been approved or is approvable for human administration by pertinent regulatory bodies. For example, Complete Freund's adjuvant is not suitable for human administration. Alum, MPL and QS-21 are preferred. Optionally, two or more different adjuvants can be used simultaneously. Preferred combinations include alum with MPL, alum with QS-21, MPL with QS-21, MPL or RC-529 with GM-CSF, and alum, QS-21 and MPL together. Also, Incomplete Freund's adjuvant can be used (Chang et al., *Advanced Drug Delivery Reviews* 32, 173-186 (1998)), optionally in combination with any of alum, QS-21, and MPL and all combinations thereof.

V. Patients Amenable to Treatment

The present regimes are useful for treatment of any disease characterized by amyloid deposits of Aβ in the brain. As well as Alzheimer's disease, such diseases include Down's syndrome, Parkinson's disease, mild-cognitive impairment, and vascular amyloid disease. Patients amenable to treatment include individuals at risk of disease but not showing symptoms, as well as patients presently showing symptoms. In the case of Alzheimer's disease, virtually anyone is at risk of suffering from Alzheimer's disease if he or she lives long enough. Therefore, the present methods can be administered prophylactically to the general population without the need for any assessment of the risk of the subject patient. The present methods can also be useful for individuals who have a known genetic risk of Alzheimer's disease. Such individuals include those having relatives who have experienced this disease, and those whose risk is determined by analysis of genetic or biochemical markers. Genetic markers of risk toward Alzheimer's disease include mutations in the APP gene, particularly mutations at position 717 and positions 670 and 671 referred to as the Hardy and Swedish mutations respectively (see Hardy, supra). Other markers of risk are mutations in the presenilin genes, PS1 and PS2, and ApoE4, family history of AD, hypercholesterolemia or atherosclerosis. Individuals presently suffering from Alzheimer's disease can be recognized from characteristic dementia, as well as the presence of risk factors described above. In addition, a number of diagnostic tests are available for identifying individuals who have AD. These include measurement of CSF tau and Aβ42 levels. Elevated tau and decreased Aβ42 levels signify the presence of AD. Individuals suffering from Alzheimer's disease can also be diagnosed by ADRDA criteria as discussed in the Examples section.

In asymptomatic patients, treatment can begin at any age (e.g., 10, 20, 30). Usually, however, it is not necessary to begin treatment until a patient reaches 40, 50, 60 or 70 years of age. Treatment typically entails multiple dosages over a period of time. Treatment can be monitored by assaying antibody levels over time. If the response falls, a booster dosage is indicated. In the case of potential Down's syndrome patients, treatment can begin antenatally by administering therapeutic agent to the mother or shortly after birth.

Patients amenable to treatment include patients 50 to 87 years of age, patients suffering from mild to moderate Alzheimer's disease, patients having an MMSE score of 14-26, patients having a diagnosis of probable Alzheimer's disease based on Neurological and Communicative Disorders and Stroke-Alzheimer's disease Related Disorders (NINCDS-ADRDA) criteria, and/or patients having an Rosen Modified Hachinski Ischemic score less than or equal to 4. Patients with MRI an scan consistent with the diagnosis of Alzheimer's disease, i.e., that there are no other abnormalities present on the MRI that could be attributed to other diseases, e.g. stroke, traumatic brain injury, arachnoid cysts, tumors, etc are also amendable to treatment.

VI. Treatment Regimes

In prophylactic applications, agents or pharmaceutical compositions or medicaments containing the same are administered to a patient susceptible to, or otherwise at risk of, Alzheimer's disease in an amount sufficient to eliminate or reduce the risk, lessen the severity, or delay the outset of the disease, including biochemical, histologic and/or behavioral symptoms of the disease, its complications and intermediate pathological phenotypes presenting during development of the disease. In therapeutic applications, compositions or medicaments are administered to a patient suspected of, or already suffering from such a disease in an amount sufficient to cure, or at least partially arrest, the symptoms of the disease (biochemical, histologic and/or behavioral), including its complications and intermediate pathological phenotypes in development of the disease.

Effective doses of the compositions of the present invention, for the treatment of the above described conditions vary depending upon many different factors, including means of administration, target site, physiological state of the patient, whether the patient is human or an animal, other medications administered, and whether treatment is prophylactic or therapeutic.

Optionally, antibodies are administered to achieve a mean serum concentration of administered antibody of 0.1-60, 0.4-20, or 1-15 µg/ml in a patient. These ranges bracket the demonstrated effective concentrations in mice and humans allowing some margin for error in measurement and individual patient variation. The serum concentration can be determined by actual measurement or predicted from standard pharmacokinetics (e.g., WinNonline Version 4.0.1 (Pharsight Corporation, Cary, USA)) based on the amount of antibody administered, frequency of administration, route of administration and antibody half-life.

The mean antibody concentration in the serum is optionally within a range of 1-10, 1-5 or 2-4 µg/ml. It is also optional to maintain a maximum serum concentration of the antibody in the patient less than about 28 µg antibody/ml serum for maximizing therapeutic benefit relative to the occurrence of possible side effects, particularly vascular edema. A preferred maximum serum concentration is within a range of about 4-28 µg antibody/ml serum. The combination of maximum serum less than about 28 µg antibody/ml serum and an mean serum concentration of the antibody in the patient is below about 7 µg antibody/ml serum is particularly beneficial. Optionally, the mean concentration is within a range of about 2-7 µg antibody/ml serum.

The concentration of Aβ in plasma following antibody administration changes roughly in parallel with changes of antibody serum concentration. In other words, plasma concentration of Aβ is highest after a dose of antibody and then declines as the concentration of antibody declines between doses. The dose and regime of antibody administration can be varied to obtain a desired level of Aβ in plasma. In such methods, the mean plasma concentration of antibody can be at least 450 pg/ml or for example, within a range of 600-30000 pg/ml or 700-2000 pg/ml or 800-1000 pg/ml.

The preferred dosage ranges for antibodies are from about 0.01 to 5 mg/kg, and more usually 0.1 to 3 mg/kg or 0.15-2 mg/kg or 0.15-1.5 mg/kg, of the host body weight. Subjects can be administered such doses daily, on alternative days, weekly, biweekly, monthly, quarterly, or according to any other schedule determined by empirical analysis. An exemplary treatment entails administration in multiple dosages over a prolonged period, for example, of at least six months. Additional exemplary treatment regimes entail administration once per every two weeks or once a month or once every 3 to 6 months.

For intravenous administration, doses of 0.1 mg/kg to 2 mg/kg, and preferably 0.5 mg/kg or 1.5 mg/kg administered intravenously quarterly are suitable. Preferred doses of antibody for monthly intravenous administration occur in the range of 0.1-1.0 mg/kg antibody or preferably 0.5-1.0 mg/kg antibody.

For more frequent dosing, e.g., from weekly to monthly dosing, subcutaneous administration is preferred. Subcutaneous dosing is easier to administer and can reduce maximum serum concentrations relative to intravenous dosing. The doses used for subcutaneous dosing are usually in the range of 0.01 to 0.6 mg/kg or 0.01-0.35 mg/kg, preferably, 0.05-0.25 mg/kg. For weekly or biweekly dosing, the dose is preferably in the range of 0.015-0.2 mg/kg, or 0.05-0.15 mg/kg. For weekly dosing, the dose is preferably 0.05 to 0.07 mg/kg, e.g., about 0.06 mg/kg. For biweekly dosing, the dose is preferably 0.1 to 0.15 mg/kg. For monthly dosing, the dose is preferably 0.1 to 0.3 mg/kg or about 0.2 mg/kg. Monthly dosing includes dosing by the calendar month or lunar month (i.e., every four weeks). Here as elsewhere in the application, dosages expressed in mg/kg can be converted to absolute mass dosages by multiplying by the mass of a typical patient (e.g., 70 or 75 kg) typically rounding to a whole number. Other regimes are described by e.g., PCT/US2007/009499. The dosage and frequency can be varied within these guidelines based on the ApoE status of the patient as discussed above.

The amount of an agent for active administration varies from 1-500 μg per patient and more usually from 5-100 μg per injection for human administration. Exemplary dosages per injection are 3, 10, 30, or 90 μg for each human injection. The mass of immunogen also depends on the mass ratio of immunogenic epitope within the immunogen to the mass of immunogen as a whole. Typically, $10^{-3}$ to $10^{-5}$ micromoles of immunogenic epitope are used for each immunization of immunogen. The timing of injections can vary significantly from once a day, to once a year, to once a decade. On any given day that a dosage of immunogen is given, the dosage is greater than 1 μg/patient and usually greater than 10 μg/patient if adjuvant is also administered, and greater than 10 μg/patient and usually greater than 100 μg/patient in the absence of adjuvant. A typical regimen consists of an immunization followed by booster injections at time intervals, such as 6 week intervals. Another regimen consists of an immunization followed by booster injections 1, 2 and 12 months later. Another regimen entails an injection every two months for life Alternatively, booster injections can be on an irregular basis as indicated by monitoring of immune response. The dosage and frequency can be varied such that antibodies induced by an active agent have mean serum concentrations within a range of 0.1-60, 0.4-20, or 1-15 or 2-7 μg/ml as in passive administration. The dosage and frequency can be varied within these guidelines based on the ApoE status of the patient as discussed above.

VII. Exemplary Regimes Depending on Carrier Status

The invention provides methods of treating non-carrier patients having Alzheimer's disease (e.g., mild or moderate) in which an effective regime of an antibody that specifically binds to an N-terminal epitope of Aβ is administered to such a patient. The antibody can for example bind to an epitope within residues 1-11, 1-7, 1-5, or 3-7 of Aβ. Optionally, the antibody is bapineuzumab. The dosage of the antibody can be within a range of about 0.15 mg/kg to 2 mg/kg administered by intravenous infusion. Optionally, the dosage is about 0.5 mg/kg to about 1 mg/kg The dosage can be administered for example every 8-16 weeks, every 1-14 weeks or every 13 weeks.

The invention also provides methods of reducing cognitive decline in a non-carrier patient having been diagnosed with mild or moderate Alzheimer's disease. The method entails administering an effective regime of an antibody that specifically binds to an N-terminal epitope of Aβ to such a patient. The antibody can for example bind to an epitope within residues 1-11, 1-7, 1-5, or 3-7 of Aβ. Optionally, the antibody is bapineuzumab. The dosage of the antibody can be within a range of about 0.15 mg/kg to 2 mg/kg administered by intravenous infusion. Optionally, the dosage is about 0.5 mg/kg to about 1 mg/kg The dosage can be administered for example every 8-16 weeks, every 1-14 weeks or every 13 weeks. Cognitive decline can be measured by comparing the patient being treated with the cognitive decline in a population of control patients also of non-carrier status and having mild or moderate Alzheimer's disease (e.g., a control population in a clinical trial). Cognitive ability can be measured by scales such as ADAS-COG, NTB, MMSE or CDR-SB. The rate of change in such a scale (points over time) in a patient can be compared with the mean decline in a population of control patients as described above.

The invention also provides methods of reducing brain volume decline in a non-carrier patient having been diagnosed with mild or moderate Alzheimer's disease. The method entails administering an effective regime of an antibody that specifically binds to an N-terminal epitope of Aβ to such a patient. The antibody can for example bind to an epitope within residues 1-11, 1-7, 1-5, or 3-7 of Aβ. Optionally, the antibody is bapineuzumab. The dosage of the antibody can be within a range of about 0.15 mg/kg to 2 mg/kg administered by intravenous infusion. Optionally, the dosage is about 0.5 mg/kg to about 1 mg/kg The dosage can be administered for example every 8-16 weeks, every 1-14 weeks or every 13 weeks. Brain volume can be measured by MRI. Change in brain volume in a patient can be compared with the mean decline in brain volume in a population of control patients also of non-carrier status and having mild or moderate Alzheimer's disease (e.g., a control population in a clinical trial).

The invention also provides methods of treating non-carrier patients having Alzheimer's disease (e.g., mild or moderate) in which a regime of an antibody that specifically binds to an N-terminal epitope of Aβ is administered to such a patient. The regime is effective to maintain a mean serum concentration of the antibody in the range of about 0.1 μg/ml to about 60 μg/ml, optionally 0.4-20 or 1-5 μg/ml. Additionally or alternatively, the regime is administered to maintain a mean plasma concentration of Aβ of 600-3000 pg/ml, 700-2000 pg/ml or 800-100 pg/ml. Optionally, the antibody in such methods is bapineuzumab.

The invention also provides methods of treating a patient who is an ApoE4 carrier and has Alzheimer's disease in which the antibody administered has a constant region mutation that reduces binding to C1q and/or and Fcγ receptor(s). Optionally, the antibody is an antibody that binds to an epitope within an N-terminal region of Aβ. Optionally, the antibody is AAB-003. Optionally, the patients are monitored, e.g., quarterly, by MRI for vasogenic edema. If vasogenic edema develops the frequency or dose can be reduced or eliminated. Vasogenic edema can optionally be treated with a corticosteroid. After resolution of vasogenic edema, administration of treatment can be resumed. Optionally, the dose is increased over time.

The invention also provides methods of treating a patient diagnosed with probable Alzheimer's disease, irrespective of ApoE4 status. In such methods, an effective regime of an antibody that specifically binds to an N-terminal region of Aβ is administered. The antibody has a constant region mutation that reduces binding to C1q and/or and Fcγ receptor relative to an otherwise identical antibody without the mutation. Optionally, the antibody is an antibody that binds to an epitope within an N-terminal region of Aβ. Optionally, the antibody is AAB-003. Optionally, the patients are monitored, e.g., quarterly, by MRI for vasogenic edema. If vasogenic edema develops the frequency or dose can be reduced or eliminated. Vasogenic edema can optionally be treated with a corticosteroid. After resolution of vasogenic edema, administration of treatment can be resumed. Optionally, the dose is increased over time after resolution of vasogenic edema.

The invention provides methods of treating an ApoE carrier patient with Alzheimer disease comprising subcutaneously administering to a patient having the disease an antibody that specifically binds to an N-terminal epitope of Aβ. Optionally, the antibody is administered at a dose of 0.01-0.6 mg/kg and a frequency of between weekly and monthly. Optionally, the antibody is administered at a dose of 0.05-0.5 mg/kg. Optionally, the antibody is administered at a dose of 0.05-0.25 mg/kg. Optionally, the antibody is administered at a dose of 0.015-0.2 mg/kg weekly to biweekly. Optionally, the antibody is administered at a dose of 0.05-0.15 mg/kg weekly to biweekly. Optionally, the antibody is administered at a dose of 0.05-0.07 mg/kg weekly. Optionally, the antibody is administered at a dose of 0.06 mg/kg weekly. Optionally, the antibody is administered at a dose of 0.1 to 0.15 mg/kg biweekly. Optionally, the antibody is administered at a dose of 0.1 to 0.3 mg/kg monthly. Optionally, the antibody is administered at a dose of 0.2 mg/kg monthly.

The invention also provides methods of treating an ApoE4 carrier patient having Alzheimer disease comprising subcutaneously administering to a patient having the disease an antibody that specifically binds to an N-terminal fragment of Aβ, wherein the antibody is administered at a dose of 1-40 mg and a frequency of between weekly and monthly. Optionally, the antibody is administered at a dose of 5-25 mg. Optionally, the antibody is administered at a dose of 2.5-15 mg. Optionally, the antibody is administered at a dose of 1-12 mg weekly to biweekly. Optionally, the antibody is administered at a dose of 2.5-10 mg weekly to biweekly. Optionally, the antibody is administered at a dose of 2.5-5 mg weekly. Optionally, the antibody is administered at a dose of 4-5 mg weekly. Optionally, the antibody is administered at a dose of 7-10 mg biweekly.

VIII. Pharmaceutical Compositions

Agents of the invention are often administered as pharmaceutical compositions comprising an active therapeutic agent, i.e., and a variety of other pharmaceutically acceptable components. See Remington's Pharmaceutical Science (15th ed., Mack Publishing Company, Easton, Pa. (1980)). The preferred form depends on the intended mode of administration and therapeutic application. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

Pharmaceutical compositions can also include large, slowly metabolized macromolecules such as proteins, polysaccharides such as chitosan, polylactic acids, polyglycolic acids and copolymers (such as latex functionalized Sepharose™, agarose, cellulose, and the like), polymeric amino acids, amino acid copolymers, and lipid aggregates (such as oil droplets or liposomes). Additionally, these carriers can function as immunostimulating agents (i.e., adjuvants).

Agents are typically administered parenterally. Antibodies are usually administered intravenously or subcutaneously. Agents for inducing an active immune response are usually administered subcutaneously or intramuscularly. For parenteral administration, agents of the invention can be administered as injectable dosages of a solution or suspension of the substance in a physiologically acceptable diluent with a pharmaceutical carrier that can be a sterile liquid such as water oils, saline, glycerol, or ethanol. Additionally, auxiliary substances, such as wetting or emulsifying agents, surfactants, pH buffering substances and the like can be present in compositions. Other components of pharmaceutical compositions are those of petroleum, animal, vegetable, or synthetic origin, for example, peanut oil, soybean oil, and mineral oil. In general, glycols such as propylene glycol or polyethylene glycol are preferred liquid carriers, particularly for injectable solutions. Antibodies can be administered in the form of a depot injection or implant preparation, which can be formulated in such a manner as to permit a sustained release of the active ingredient.

Some preferred formulations are described in US 20060193850. A preferred formulation has a pH of about 5.5 to about 6.5, comprises i. at least one Aβ antibody at a concentration of about 1 mg/ml to about 30 mg/ml; ii. mannitol at a concentration of about 4% w/v or NaCl at a concentration of about 150 mM; iii. about 5 mM to about 10 mM histidine or succinate; and iv. 10 mM methionine. Optionally, the formulation also includes polysorbate 80 at a concentration of about 0.001% w/v to about 0.01% w/v. Optionally, the formulation has a pH of about 6.0 to about 6.5 and comprises about 10 mg/ml Aβ antibody, about 10 mM histidine and about 4% w/v mannitol and about 0.005% w/v polysorbate 80 Optionally, the formulation has a pH of about 6.0 to about 6.2 and comprises about 20 mg/ml Aβ antibody, about 10 mM histidine, about 4% w/v mannitol and about 0.005% w/v polysorbate 80. Optionally, the formulation has a pH of about 6.0 to about 6.2 and comprises about 30 mg/ml Aβ antibody, about 10 mM histidine, about 4% w/v mannitol and about 0.005% w/v polysorbate 80.

Typically, compositions are prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above (see Langer, Science 249: 1527 (1990) and Hanes, Advanced Drug Delivery Reviews 28:97 (1997)). The agents of this invention can be administered in the form of a depot injection or implant preparation, which can be formulated in such a manner as to permit a sustained or pulsatile release of the active ingredient.

Additional formulations suitable for other modes of administration include oral, intranasal, and pulmonary formulations, suppositories, and transdermal applications. For suppositories, binders and carriers include, for example, polyalkylene glycols or triglycerides; such suppositories can be formed from mixtures containing the active ingredient in the range of 0.5% to 10%, preferably 1%-2%. Oral formulations include excipients, such as pharmaceutical grades of mannitol, lactose, starch, magnesium stearate, sodium saccharine, cellulose, and magnesium carbonate. These compositions take the form of solutions, suspensions, tablets, pills, capsules, sustained release formulations or powders and contain 10%-95% of active ingredient, preferably 25%-70%.

IX. Kits and Labels

The invention provides kits containing an antibody binding to an N-terminal epitope of Aβ. The antibody is typically provided in lyophilized or solution form in a vial, optionally in a single-dose form. The antibody in the vial is typically sterile and manufactured under GMP conditions. The kits can also include diluents, syringes, needles, intravenous or subcutaneous drips and the like. The kits typically contain instructions (e.g., a package insert or label) for use. In some kits, the instructions specify whether the antibody is to be provided to ApoE4 carriers or non-carriers or can be provided to both. The instructions can also specify that the antibody is not to be provided to ApoE4 carriers. In some kits, the instructions can provide information or sources for ApoE testing.

In some kits, the instructions specify results that can be achieved by administering the antibody. The results can include an inhibition of cognitive decline. The instructions can also include a measure of cognitive decline in a control patient (typically a mean value from a population of such patients) for purposes of comparison. Cognitive decline can be measured, by for example, ADAS-COG, NTB, MMSE or CDR-SB Likewise, the instructions can refer to inhibition of decrease in brain volume or inhibition of ventricular volume. The instructions can also include a measure of decrease in brain volume or inhibition of ventricular volume in a control patient (typically a mean value from a population of such patients for purposes of comparison).

In some kits, the instructions specify potential side effects including vasogenic edema. The instructions can also specify a monitoring regime, such as performing MRI at quarterly, six monthly or annual intervals. The instructions can specify different monitoring regimes for ApoE4 non-carriers and carriers as discussed above. The instructions can also specify altered dosing schedules on occurrence and/or resolution of vasogenic edema and treatment measures for vasogenic edema, such as corticosteroids.

The kits can also include instructions for patients for whom treatment is contraindicated such as prior brain injury, CVA, brain tumor, multiple lacunes, venothrombotic disease, anticoagulation (heparin/coumadin) or atrial fibrillation. The kits can also provide instructions for route (e.g., subcutaneous), dosage amount or frequency of dosing.

X. Antibodies with Mutated IgG1 Constant Region

The invention provides a human IgG1 constant region, in which amino acids at positions 234, 235, and 237 (EU numbering) are each alanine, and isolated antibodies or fusion proteins containing such a constant region. Such antibodies include human antibodies, humanized antibodies and chimeric antibodies as described above. Examples of such antibodies include antibodies to Aβ, antibodies to the Lewis Y antigen and the 5T4 tumor antigen, such as described in the Examples. Fusion proteins include the extracellular domains of receptors (e.g., TNF-alpha receptor) linked to a constant region. Methods for fusing or conjugating polypeptides to the constant regions of antibodies are described by, e.g., U.S. Pat. Nos. 5,336,603, 5,622,929, 5,359,046, 5,349,053, 5,447,851, 5,723,125, 5,783,181, 5,908,626, 5,844,095, 5,112,946; EP 0 307 434; EP 0 367 166; EP 0 394 827).

Antibodies or fusion proteins incorporating these mutations can offer advantages of the IgG1 isotype including pharmacokinetics and ease of manufacture, but also have reduced or eliminated effector function relative to an otherwise identical antibody lacking these mutations. Effector function is typically impaired in binding to one or more Fc gamma receptors, binding to C1Q, antibody-dependent cellular cytotoxicity and/or antibody-dependent complement activity. In some antibodies, all of these activities are reduced or eliminated. An activity is considered eliminated if there is no detectable difference beyond experimental error in that activity between an antibody having the above three mutations and an otherwise identical control antibody without the mutations.

Typically, a mutated constant region includes CH1, hinge, CH2 and CH3 domains. However, the CH1 domain is sometimes replaced particularly in fusion proteins with a synthetic linker. Some constant regions contain a full-length IgG1 constant region with the possible exception of a C-terminal lysine residue. Exemplary sequences of a mutated constant region are provided by SEQ ID NOS: 62 and 63. These sequences differ in the 62 contains a C-terminal lysine not present in 63.

The sequences 62 and 63 represent the G1mz allotype of human IgG1. Other examples of allotypes have been provided above. Allotypes are natural polymorphic variations in the human IgG1 constant region that differ between different individuals at the polymorphic position. The G1mz allotype has Glu at position 356 and Met at position 358.

Other allotypic variants of SEQ ID NOS. 62 and 63 are included. Also included are human IgG1 constant regions having alanine residues at positions 234, 235 and 237 any permutation of residues occupying polymorphic positions in natural allotypes.

Mutated IgG1 constant regions having alanine at positions 234, 235 and 237 can have additional mutations present relative to a natural human IgG1 constant region. As an example in which additional mutations can be present, alanine mutations at positions 234, 235 and 237 can be combined with mutations at positions 428 and/or 250 as described in U.S. Pat. No. 7,365,168. Mutations at positions 428 and 250 can result in increased half life. Additional mutations that can be combined with mutations at positions 234, 235 and 237 have been described in Section IV A in connection with antibodies that bind Aβ. Some such constant regions have no additional mutations present. Some such constant regions have no additional mutations present in and around regions of the IgG1 constant region affecting Fc gamma receptor and/or complement binding (e.g., residues 230-240 and 325-325 by EU numbering). The omission of a C-terminal lysine residue by intracellular processing is not considered to be a mutation. Likewise, naturally occurring amino acids occupying polymorphic sites differing between allotypes are considered natural rather than mutant amino acids.

XI. Experimental Models, Assays and Diagnostics

A. Animal Models

Such models include, for example, mice bearing a 717 (APP770 numbering) mutation of APP described by Games et al., supra, and mice bearing a 670/671 (APP770 numbering) Swedish mutation of APP such as described by McConlogue et al., U.S. Pat. No. 5,612,486 and Hsiao et al., *Science*, 274, 99 (1996); Staufenbiel et al., *Proc. Natl. Acad. Sci. USA*, 94:13287-13292 (1997); Sturchler-Pierrat et al., *Proc. Natl. Acad. Sci. USA*, 94:13287-13292 (1997); Borchelt et al., *Neuron*, 19:939-945 (1997)); Richards et al., *J. Neurosci.* 23:8989-9003, 2003; Cheng, Nat. Med. 10(11): 1190-2, 2004 Hwang et al., Exp Neurol. 2004 Mar. Mutations of APP suitable for inclusion in transgenic animals include conversion of the wild-type Val717 (APP770 numbering) codon to a codon for Ile, Phe, Gly, Tyr, Leu, Ala, Pro, Trp, Met, Ser, Thr, Asn, or Gln. A preferred substitution for Val717 is Phe. Another suitable mutation is the arctic mutation E693G (APP 770 numbering). The PSAPP mouse, which has both amyloid precursor protein and presenilin transgenes, is described by Takeuchi et al., American Journal of Pathology. 2000; 157:331-339. A triple transgenic mouse having amyloid precursor protein, presenilin and tau transgenes is described by LaFerla, (2003), Neuron 39, 409-421. Another useful transgenic mouse has both APP and TGF-β transgenes. Protein encoding sequences in transgenes are in operable linkage with one or more suitable regulatory elements for neural expression. Such elements include the PDGF, prion protein and Thy-1 promoters. Another useful transgenic mouse has an APP transgene with both a Swedish and 717 mutation. Another useful transgenic mouse has an APP transgene with an arctic mutation (E693G).

B. Assays to Detect Amyloid Related Pathologies

Contextual fear conditioning assays. Contextual fear conditioning (CFC) is a common form of learning that is exceptionally reliable and rapidly acquired in most animals, for example, mammals. Test animals learn to fear a previously neutral stimulus and/or environment because of its association with an aversive experience. (see, e.g., Fanselow, *Anim. Learn. Behav.* 18:264-270 (1990); Wehner et al., *Nature Genet.* 17:331-334. (1997); Caldarone et al., *Nature Genet.* 17:335-337 (1997)).

Contextual fear conditioning is especially useful for determining cognitive function or dysfunction, e.g., as a result of disease or a disorder, such as a neurodegenerative disease or disorder, an Aβ-related disease or disorder, an amyloidogenic disease or disorder, the presence of an unfavorable genetic alteration effecting cognitive function (e.g., genetic mutation, gene disruption, or undesired genotype), and/or the efficacy of an agent, e.g., an Aβ conjugate agent, on cognitive ability. Accordingly, the CFC assay provides a method for independently testing and/or validating the therapeutic effect of agents for preventing or treating a cognitive disease or disorder, and in particular, a disease or disorder affecting one or more regions of the brains, e.g., the hippocampus, subiculum, cingulated cortex, prefrontal cortex, perirhinal cortex, sensory cortex, and medial temporal lobe (see US 2008145373).

C. Phagocytosis Assays to Determine Antibody Effector Function

Antibodies can be screened for clearing an amyloid deposit in an ex vivo assay. A tissue sample from a brain of a patient with Alzheimer's disease or an animal model having characteristic Alzheimer's pathology is contacted with phagocytic cells bearing an Fcγ receptor, such as microglial cells, and the antibody under test in a medium in vitro. The phagocytic cells can be a primary culture or a cell line, such as BV-2, C8-B4, or THP-1. A series of measurements is made of the amount of amyloid deposit in the reaction mixture, starting from a baseline value before the reaction has proceeded, and one or more test values during the reaction. The antigen can be detected by staining, for example, with a fluorescently labelled antibody to Aβ or other component of amyloid plaques. A reduction relative to baseline during the reaction of the amyloid deposits indicates that the antibody under test has clearing activity.

Generally, isotype controls are added to ensure that the appropriate Fc-Fcγ receptor interaction is being observed. Additional controls include use of non-specific antibodies, and/antibodies with a known affinity for the Fγc receptors on the phagocytic cells. Such assays can be carried out with human or non-human tissues and phagocytic cells, and human, non-human, or humanized antibodies.

A variation on the ex vivo phagocytosis assay eliminates the need for an Aβ-containing tissue, although still allowing detection of the interaction between a particular antibody and Fcγ receptors. In this case, the assay relies on a solid matrix which is coated with antibody. The solid matrix is generally in a form that can be engulfed by a phagocytic cell, e.g., a bead or particle on the order of nanometers to several microns in size. The solid matrix can be conjugated to a detectable moiety, e.g., a fluorophore, so that the particle can be traced. Kits and materials for phagocytosis assays of this sort are commercially available, e.g., from Beckman Coulter (Fullerton, Calif.) and Molecular Probes (Eugene, Oreg.). An example of such an assay is provided in the Examples section.

D. Complement Binding Assays

Antibody effector function can also be determined by detecting the ability of an antibody to interact with complement, in particular, the C1q polypeptide (see, e.g., Mansouri et al. (1999) *Infect. Immun.* 67:1461). In the case of Aβ-specific antibody, a solid matrix (e.g., a multiwell plate) can be coated with Aβ, and exposed to antibody, and, in turn, exposed to labelled C1q. Alternatively, C1q can be attached to the matrix, and labelled antibody added. Alternatively, the antibody can be attached to the matrix and exposed to C1q, followed by detection of C1q. Such in vitro binding assays are common in the art and are amenable to modification and optimization as necessary.

E. Diagnostic Methods

Cognitive function assessment tools. A number of tools exist to quantify the cognition and mental function of dementia patients. These include the NTB, DAD, ADAS, MMSE, CDR-SOB, NINCDS-ADRDA criteria, and the RMHI (Rosen Modified Hachinski Ischemic) score. These tools are generally known in the art.

The NTB (Neuropsychological Test Battery) is composed of nine well-accepted tests of memory and executive function. The test battery is acceptable in the most recent EMEA guidance. Patients are generally assessed in the following memory tests periodically: Weschsler Memory Scale Visual Paired Associates; Weschsler Memory Scale Verbal Paired Associates; and Rey Auditory Verbal Learning Test. The Executive function tests include: Wechsler Memory Scale Digit Span; Controlled Word Association Test; and Category Naming Test. This test is sensitive to change in mild AD patients and clinical effects of amyloid lowering agents.

The DAD (Disability Assessment for Dementia) test was developed and validated to measure the functional disability of patients with Alzheimer's disease (Gelinas et al. (1999) *Am J Occup Ther* 53:471-81.) Caregivers answer questions about the patients' ability to perform both instrumental and basic activities of daily living that had been attempted in the preceding two weeks. The proportion of DAD activities successfully completed out of those attempted is then determined and reported as a percentage.

The ADAS-Cog refers to the cognitive portion of the Alzheimer's Disease Assessment Scale (see Rosen, et al. (1984) *Am J Psychiatry* 141:1356-64.) The test consists of eleven tasks that measure disturbances in memory, language, praxis, attention and other cognitive abilities.

The NINCDS-ADRDA (Neurological and Communicative Disorders and Stroke-Alzheimer's disease Related Disorders Assessment) measures eight criteria affected in Alzheimer's: memory, language, perceptual skills, attention, constructive abilities, orientation, problem solving, and functional abilities (McKhann et al. (1984) *Neurology* 34: 939-44)

The MMSE (Mini Mental State Exam), CDR-SOB (Clinical Dementia Rating-Sum of Boxes, and RMHI (Rosen Modified Hachinki Ischemic) score are also known in the art (see, e.g., Folstein et al. (1975) *J Psych Res* 12: 189-198; Morris (1993) *Neurology* 43: 2412-2414; and Rosen et al. (1980) *Ann Neurol.* 17:486-488).

Biomarkers. Biomarkers for Alzheimer's symptomology in humans can be measured using MRI volumetrics, blood and CSF protein levels, and PET (positron emission topography). For example, biomarkers to support antibody-Aβ engagement include Aβ40 and Aβ42 in the CSF and plasma, and amyloid plaque imaging, e.g., by PET. Biomarkers pointing to disease modification include brain morphology (MRI), CSF tau and phosphotau levels, and again, amyloid plaque imaging.

XII. Examples

Example 1: Phase 1 Trial 111 patients with a diagnosis of probable Alzheimer's disease (mild to moderate) were administered the humanized antibody bapineuzumab at doses ranging from 0.15 to 2.0 mg/kg in a multiple ascending dose study (MAD). Antibody was administered by intravenous infusion every thirteen weeks until the dosing regime is complete. Patients were also classified for ApoE4 status. Table 2 shows that eleven patients in the study experienced vasogenic edema detected by MRI. Table 2 also shows symptoms experienced in some of these patients; in other patients the vasogenic edema was asymptomatic. Table 3 shows the risk of vasogenic edema stratified by genotype irrespective of dose. The risk is only 2% in patients lacking an E4 allele but is 35% in patients with two E4 alleles. Table 4 shows the risk of vasogenic edema in only the highest dose group (2 mg/kg). The risk of vasogenic edema for patients with two E4 alleles is 60% and that for patients with one allele is 35%.

Table 5 shows the risk of vasogenic edema at different dosages. The risk of vasogenic edema is very low for all genotypes for doses between 0.15-0.5 mg/ml but starts to become significant for patients with two E4 alleles at a dose of 1 mg/kg and for patients with one E4 allele at 2 mg/kg.

These data indicate that the risk of vasogenic edema is dependent on both ApoE genotype and dose and patients.

TABLE 2

| Study | Dose (mg/kg) | Dose # | E4 status | Symptoms |
|---|---|---|---|---|
| SAD | 5 | 1 | ND | — |
| SAD | 5 | 1 | ND | — |
| SAD | 5 | 1 | ND | dizziness, confusion |
| MAD | 0.15 | 2 | 4/4 | abn gait, confusion |
| MAD | 1 | 1 | 4/4 | visual |
| MAD | 1 | 1 | 4/4 | — |
| MAD | 1 | 2 | 3/4 | — |
| MAD | 2 | 1 | 4/4 | — |
| MAD | 2 | 1 | 3/4 | — |
| MAD | 2 | 1 | 4/4 | confusion |
| MAD | 2 | 1 | 3/4 | — |

TABLE 2

| Study | Dose (mg/kg) | Dose # | E4 status | Symptoms |
|---|---|---|---|---|
| MAD | 2 | 1 | 3/4 | HA, lethargy, confusion |
| MAD | 2 | 2 | 3/4 | — |
| PET | 2 | 1 | 3/4 | — |
| MAD | 2 | 3 | 4/4 | — |

TABLE 3

| ApoE$_4$ genotype (alleles) | VE cases genotype/ total VE cases | % of VE cases | VE cases/patients exposed | % of patients exposed |
|---|---|---|---|---|
| 2 | 6/11 | 55% | 6/17 | 35% |
| 1 | 4/11 | 36% | 4/52 | 8% |
| 0 | 1/11 | 9% | 1/42 | 2% |

TABLE 4

| ApoE$_4$ genotype (alleles) | VE cases genotype/ total VE cases | % of VE cases | VE cases/patients exposed | % of patients exposed |
|---|---|---|---|---|
| 2 | 3/7 | 43% | 3/5 | 60% |
| 1 | 3/7 | 43% | 3/9 | 33% |
| 0 | 1/7 | 14% | 1/14 | 7% |

TABLE 5

Number of patients (number developing vasogenic edema)

| ApoE4 copy # | 0.15 mg/kg | 0.5 mg/kg | 1.0 mg/kg | 2.0 mg/kg |
|---|---|---|---|---|
| 0 | 13 (0) | 11 (0) | 9 (0) | 14 (1) |
| 1 | 15 (0) | 14 (0) | 14 (1) | 9 (3) |
| 2 | 3 (1) | 4 (0) | 5 (2) | 5 (3) |

Example 2: Phase 2 Trial

A randomized double-blind placebo-controlled multiple ascending dose study was conducted on a population of 234 patients randomized from an initial population of 317 screened patients. Patients were assessed for ApoE4 carrier status, but carriers (homozygous and heterozygous) and non-carriers received the same treatment. Inclusion criteria were: probable AD diagnosis; aged 50-85 years; MMSE score 16-26; Rosen Modified Hachinski Ischemic score≤4; Living at home or in a community dwelling with a capable caregiver; MRI consistent with diagnosis of AD; MRI scan of sufficient quality for volumetric analysis; stable doses of medication for treatment of non-excluded conditions; stable doses of AchEIs and/or memantine for 120 days prior to screen. The main exclusion criteria were: current manifestation of a major psychiatric disorder (e.g., major depressive disorder); current systemic illness likely to result in deterioration of the patient's condition; history or evidence of a clinically important auto-immune disease or disorder of the immune system; history of any of the following: clinically evident stroke, clinically important carotid or vertebrobasilar stenosis/plaque, seizures, cancer within the last 5 years, alcohol/drug dependence within last 2 years, myocardial infarction within the last 2 years, a significant neurologic disease (other than AD) that might affect cognition. Kits of the invention and their accompanying labels or package inserts can provide exclusions for patients meeting any of the above exclusion criteria and any subcombinations thereof.

Four dose levels were employed (0.15, 0.5, 1.0 and 2.0 mg/kg) together with a placebo. 124 patients received bapineuzumab and 110 received a placebo. Of those patients, 122 and 107, respectively, were analyzed for efficacy. Bapineuzumab was supplied as a sterile aqueous solution in 5 ml vials containing: 100 mg of bapineuzumab (20 mg/mL), 10 mM histidine, 10 mM methionine, 4% mannitol, 0.005% polysorbate-80 (vegetable-derived), pH of 6.0. The placebo was supplied in matching vials containing the same constituents except for bapineuzumab. The study medication was diluted in normal saline and administered as a 100 ml intravenous (IV) infusion over ~1 hour The treatment period was for 18 months with 6 intravenous infusions at 13 week intervals. Safety follow-up visits, including MRI scans occurred 6 weeks following each dose. Following the treatment period patients were either monitored with a 1 year safety follow up for continued treatment in open label extension. The primary objective of the trial was to evaluate the safety and tolerability of bapineuzumab in patients with mild to moderate Alzheimer's disease. The primary endpoints for the study were (Alzheimer Disease Assessment Scale-Cognitive Subscale (ADAS-Cog), Disability Assessment Scale for Dementia (DAD) together with safety and tolerability). The ADAS-Cog 12 contains an additional test involving delayed recall of a ten item word list relative to the ADAS-Cog 11. The secondary objective of the study was to evaluate the efficacy of bapineuzumab in patients with mild to moderate Alzheimer's disease. Other end points were neuropsychological test battery (NTB), neuropsychiatric inventory (NPI), clinical dementia rating sum of boxes (CDR-SB), MRI brain volumetrics, and CSF measures.

A summary of the total population, the populations broken down by dosage group and populations broken down by carrier status is provided is the following tables.

TABLE 6

| | Demographics and Patient Characteristics | |
|---|---|---|
| | All Placebo N = 107 | All Bapineuzumab N = 122 |
| Age | 67.9 | 70.1 |
| Gender (% F) | 59.8 | 50.0 |
| Ethnicity (% Caucasian) | 95.3 | 96.7 |
| Years Since Onset | 3.7 | 3.5 |
| ApoE4 (% carrier) | 69.8 | 60.5 |
| Screening MMSE | 20.7 | 20.9 |
| % Cholinesterase or Memantine Use | 96.3 | 95.1 |

TABLE 7

| Bapineuzumab | Avg MMSE | Avg Age | Disease Duration | Disease Severity Mild | Disease Severity Moderate | % APOE Carrier | Con Alz Meds | # of patients Baseline | Wk 78 |
|---|---|---|---|---|---|---|---|---|---|
| 0.15 mg/kg | 20 | 70 | 4 | 29% | 71% | 64% | 100% | 31 | 24 |
| Placebo | 20 | 64 | 4 | 33% | 65% | 46% | 96% | 26 | 17 |
| 0.5 mg/kg | 21 | 71 | 4 | 48% | 51% | 58% | 91% | 33 | 17 |
| Placebo | 21 | 69 | 4 | 43% | 57% | 86% | 93% | 28 | 21 |
| 1.0 mg/kg | 21 | 69 | 3 | 43% | 55% | 69% | 97% | 29 | 25 |
| Placebo | 21 | 69 | 4 | 36% | 69% | 75% | 93% | 26 | 21 |
| 2.0 mg/kg | 2 | 70 | 3 | 63% | 34% | 53% | 90% | 29 | 17 |
| Placebo | 21 | 69 | 3 | 56% | 44% | 70% | 100% | 27 | 22 |
| All Bapineuzumab | 21 | 70 | 4 | 46% | 53% | 61% | 95% | 122 | 83 |
| All Placebo | 21 | 68 | 4 | 42% | 59% | 69% | 96% | 107 | 81 |

TABLE 8

| | Carrier | | Non-carrier | |
|---|---|---|---|---|
| | Placebo N = 74 | Bapineuzumab N = 72 | Placebo N = 32 | Bapineuzumab N = 47 |
| Age | 68.6 | 71.2 | 66.1 | 69.1 |
| Gender (% F) | 59.5 | 48.6 | 62.5 | 51.1 |
| Ethnicity (% Caucasian) | 97.3 | 97.2 | 90.6 | 95.7 |
| Years Since Onset | 3.8 | 3.7 | 3.5 | 3.0 |
| Screening MMSE | 21.0 | 20.6 | 19.8 | 21.4 |
| % Cholinesterase or Memantine Use | 95.9 | 98.6 | 96.9 | 89.4 |

Comparison of the various dosage cohorts with placebo using a linear model of cognitive decline on ADAS-COG and DAD scales did not achieve statistical significance for any of the dosage cohorts or the combined dosage cohorts population.

The data were reanalyzed using a statistical model not assuming linear decline (a) based on all of the patients in whom efficacy was determined and (b) based only on patients who had received all six dosages ("completers") and not including patients who had dropped out for various reasons. The non-linear model is believed to be more accurate because the cognitive abilities do not necessarily decline linearly with time.

The results using the non-linear decline model for all of the patients in whom efficacy was determined (ApoE4 carriers and non-carriers combined) are shown in FIG. 1. MITT (modified intent to treat) analysis was done using the repeated measures model without assumption of linearity. Bars above the X-axis represent a favorable result (i.e., inhibited decline) relative to placebo. Although statistical significance was not obtained, a trend was observed for the combined dosage cohorts using the ADAS-cog and NTB scales($0.1 \geq p \geq 0.05$).

Figure 2:
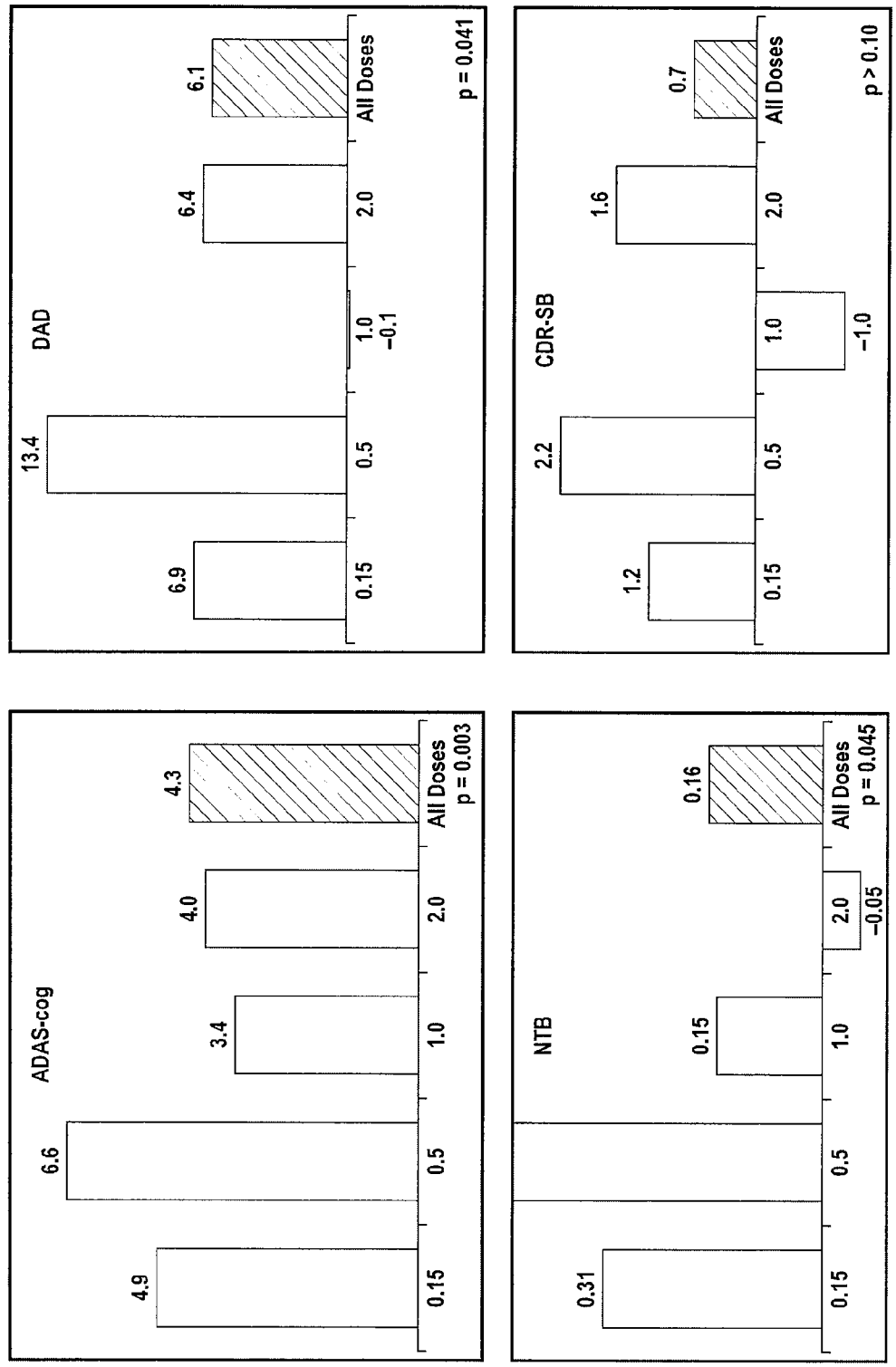
FIG. 2 shows changes in ADAS-Cog, DAD, NTB and CDR-SB in treated patients who completed the trials ("completers") relative to placebo patients using a repeated measures statistical model without assumption of linearity. Bars above zero indicate improvement relative to placebo.

The results for the completer populations (ApoE4 carriers and non-carriers combined) are shown in FIG. 2. Completers were defined as patients who received all 6 infusions and an efficacy assessment at week 78. Bars above the axis indicate improvement relative to placebo. Statistical significance was obtained for the combined dosage cohorts for ADAS-cog and DAD measurements and a positive trend ($0.1 \geq p \geq 0.05$) was found for NTB measurement.

Separate analyses were performed for ApoE4 carriers and non-carriers using the non-linear model and (a) all treated patients in whom efficacy was determined and (b) completers.

Figure 3:
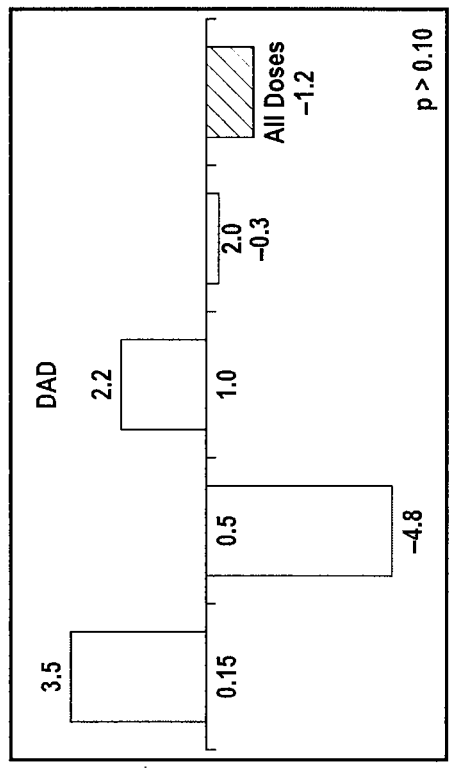
FIG. 3 shows changes in ADAS-Cog, DAD, NTB and CDR-SB in ApoE4 carrier treated patients relative to placebo patients using a repeated measures statistical model without assumption of linearity. Bars above zero indicate improvement relative to placebo.
Figure 3:
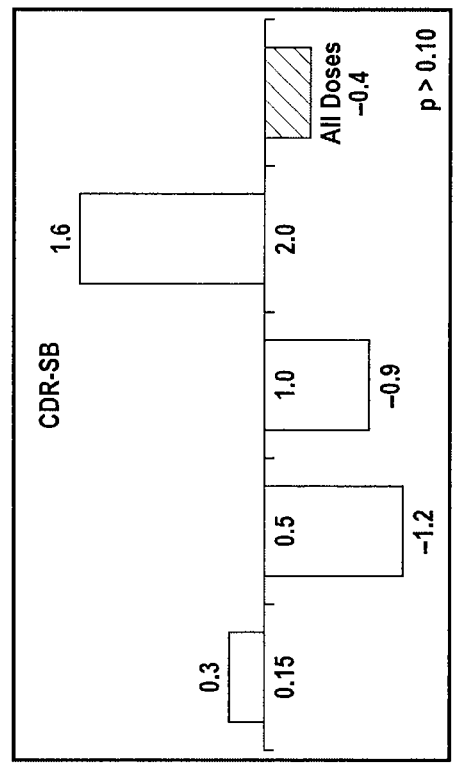
Figure 3:
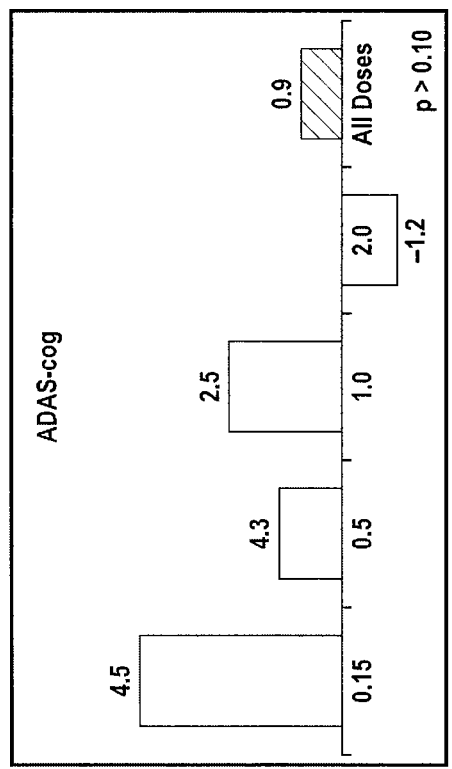
Figure 3:
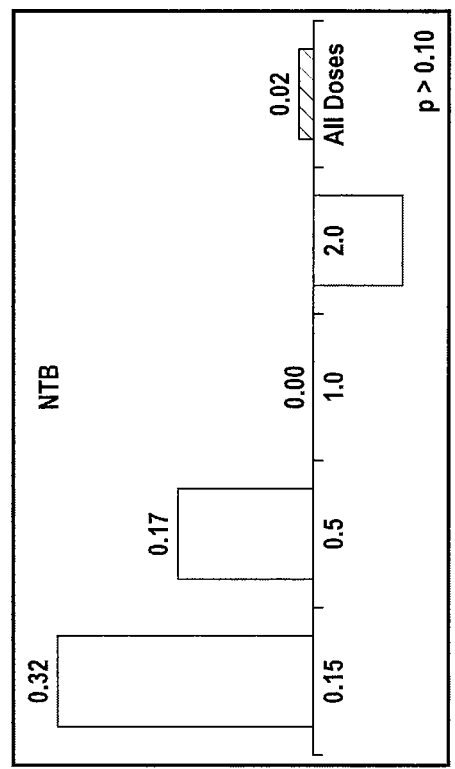
Figure 4:
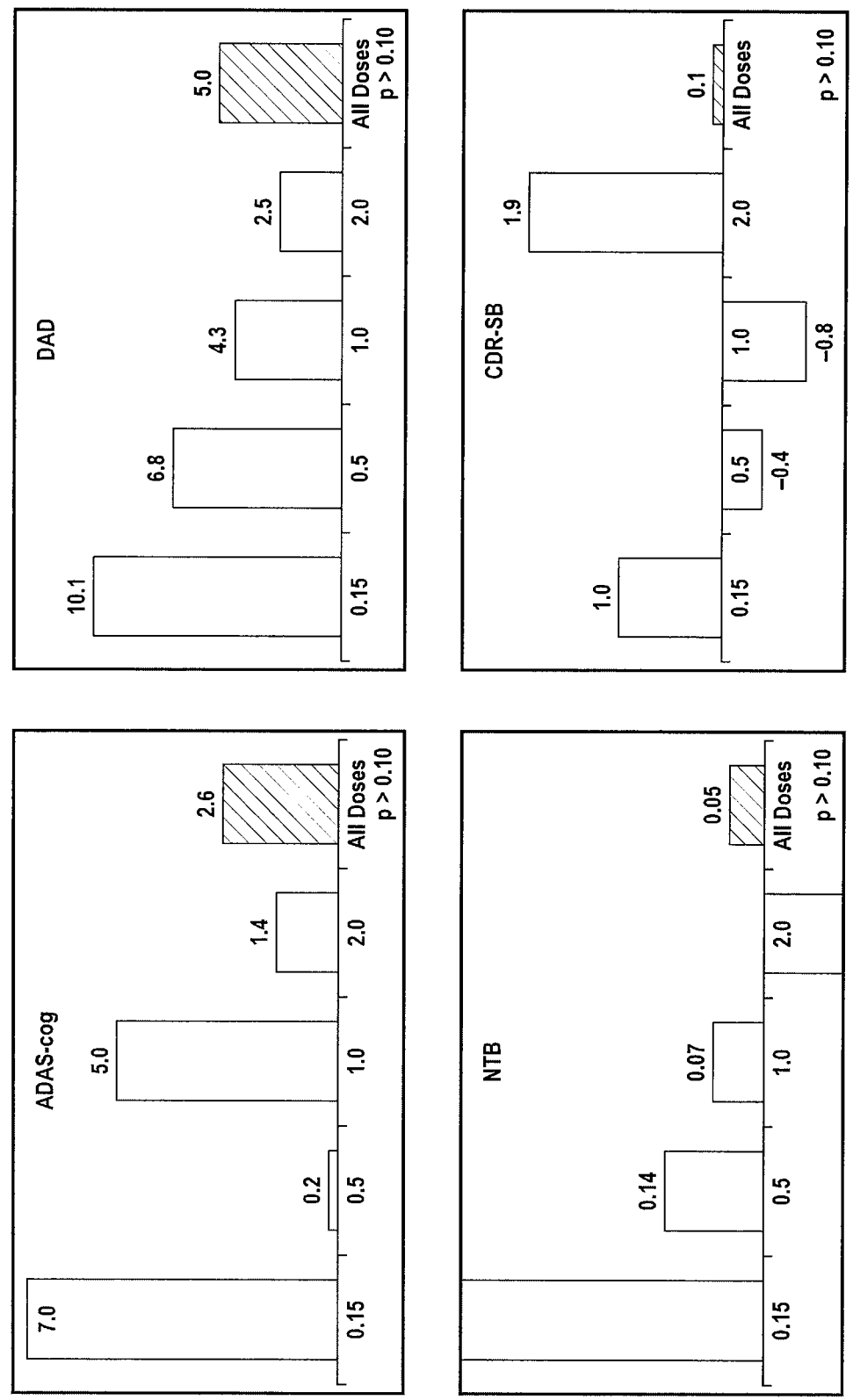
FIG. 4 shows changes in ADAS-Cog, DAD, NTB and CDR-SB in ApoE4 carrier treated patients who completed the trial relative to placebo patients using a repeated measures statistical model without assumption of linearity. Bars above zero indicate improvement relative to placebo.

FIG. 3 shows the results for all ApoE4 carrier patients in which efficacy was measured. Statistical significance was not found for any of the cognitive scales. Again, MITT analysis used repeated measures model without assumption of linearity. FIG. 4 shows the analysis for ApoE4 carrier completers, as defined above. Again, statistical significance was not found by any of the scales (ADAS-cog, DAD, NTB, and CDR-SB). However, favorable directional changes (bars above the axis) were found particularly for the ADAS-cog and DAD measurements.

Figure 5:
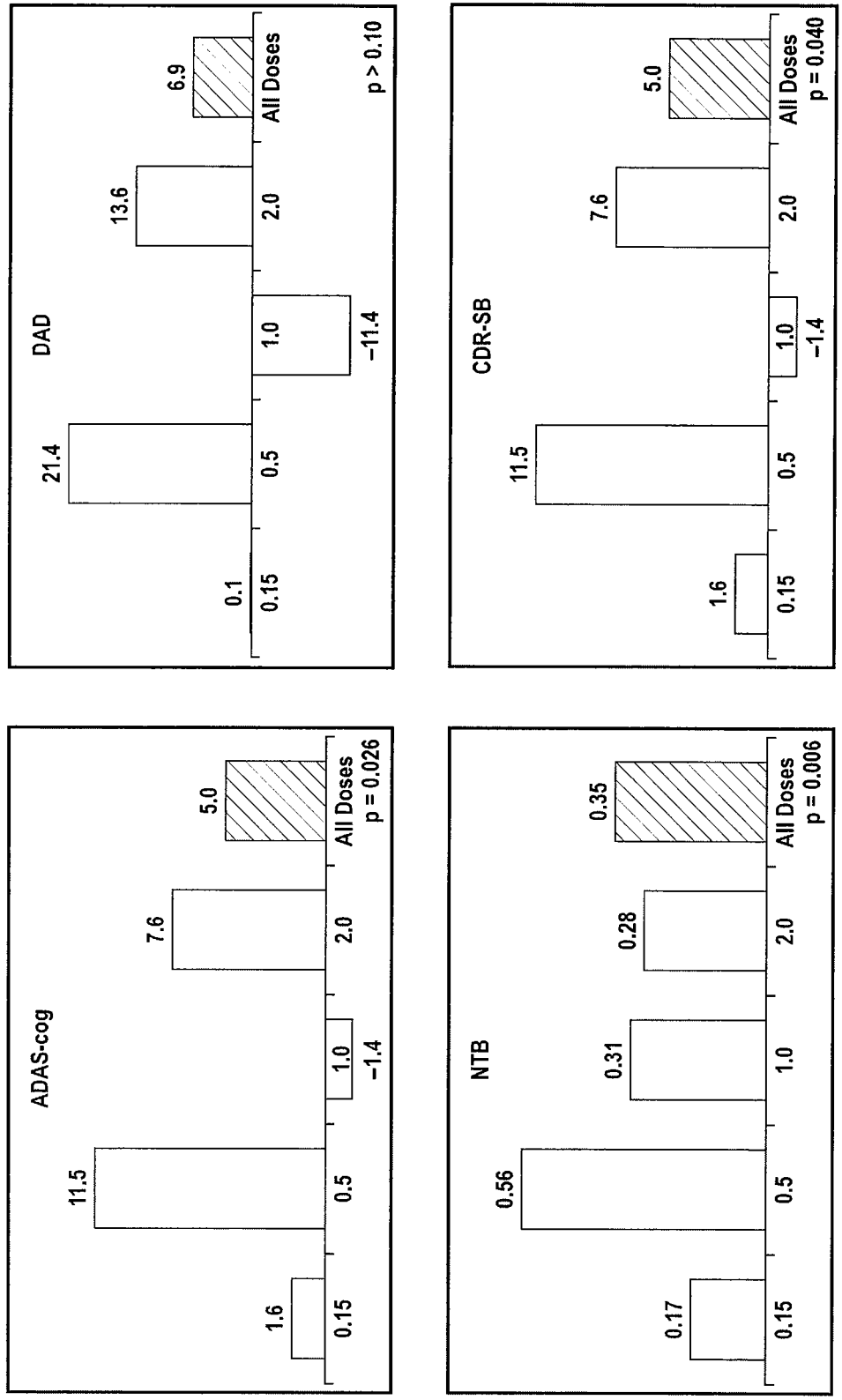
FIG. 5 shows changes in ADAS-Cog, DAD, NTB and CDR-SB in ApoE4 non-carrier treated patients relative to placebo patients using a repeated measures statistical model without assumption of linearity. Bars above zero indicate improvement relative to placebo.
Figure 6:
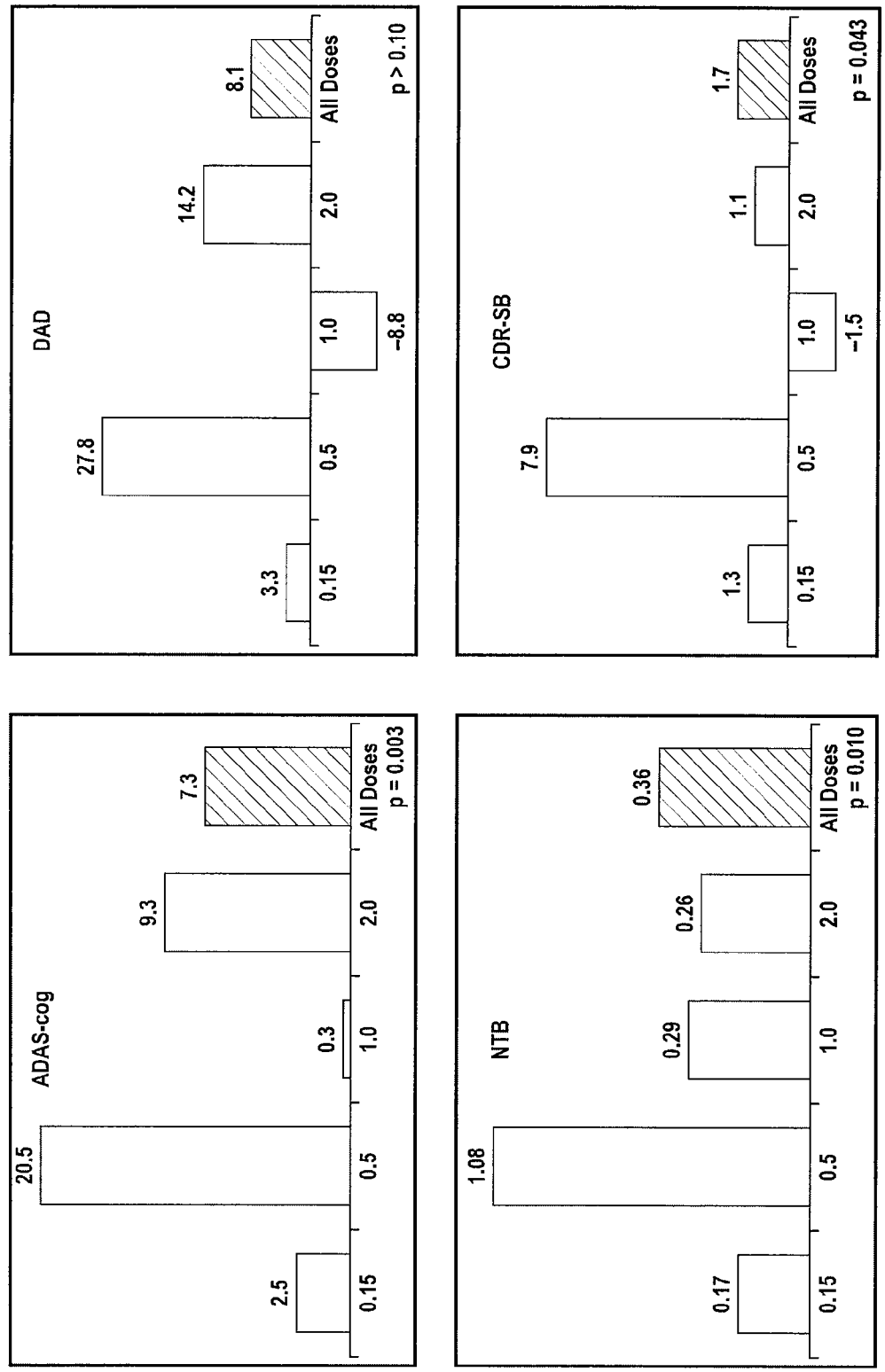
FIG. 6 provides similar information to FIG. 5 except that FIG. 6 shows changes based on the MMSE scale relative to placebo.
Figure 7:
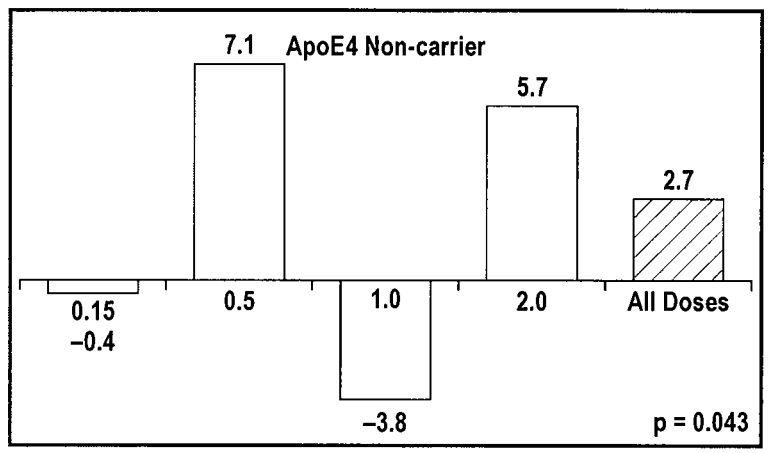
FIG. 7 shows changes in ADAS-Cog, DAD, NTB and CDR-SB in ApoE4 non-carrier treated patients who completed the trial relative to placebo patients using a repeated measures statistical model without assumption of linearity. Bars above zero indicate improvement relative to placebo.
Figure 8:
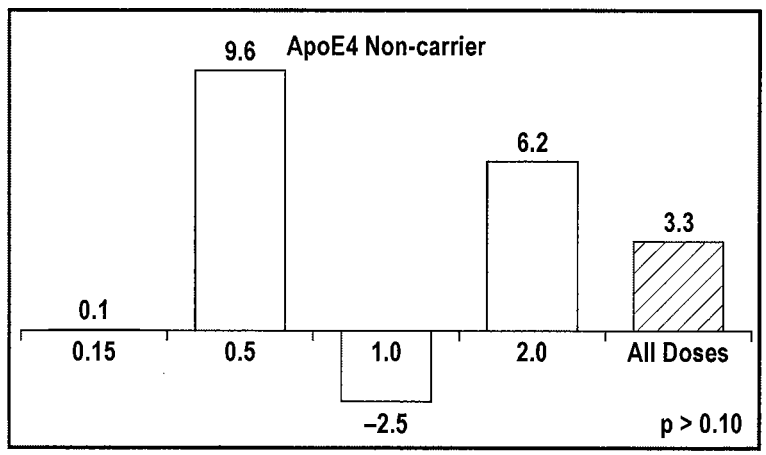
FIG. 8 shows similar information to FIG. 7 except that FIG. 8 shows changed based on the MMSE scale relative to placebo.
Figure 9:
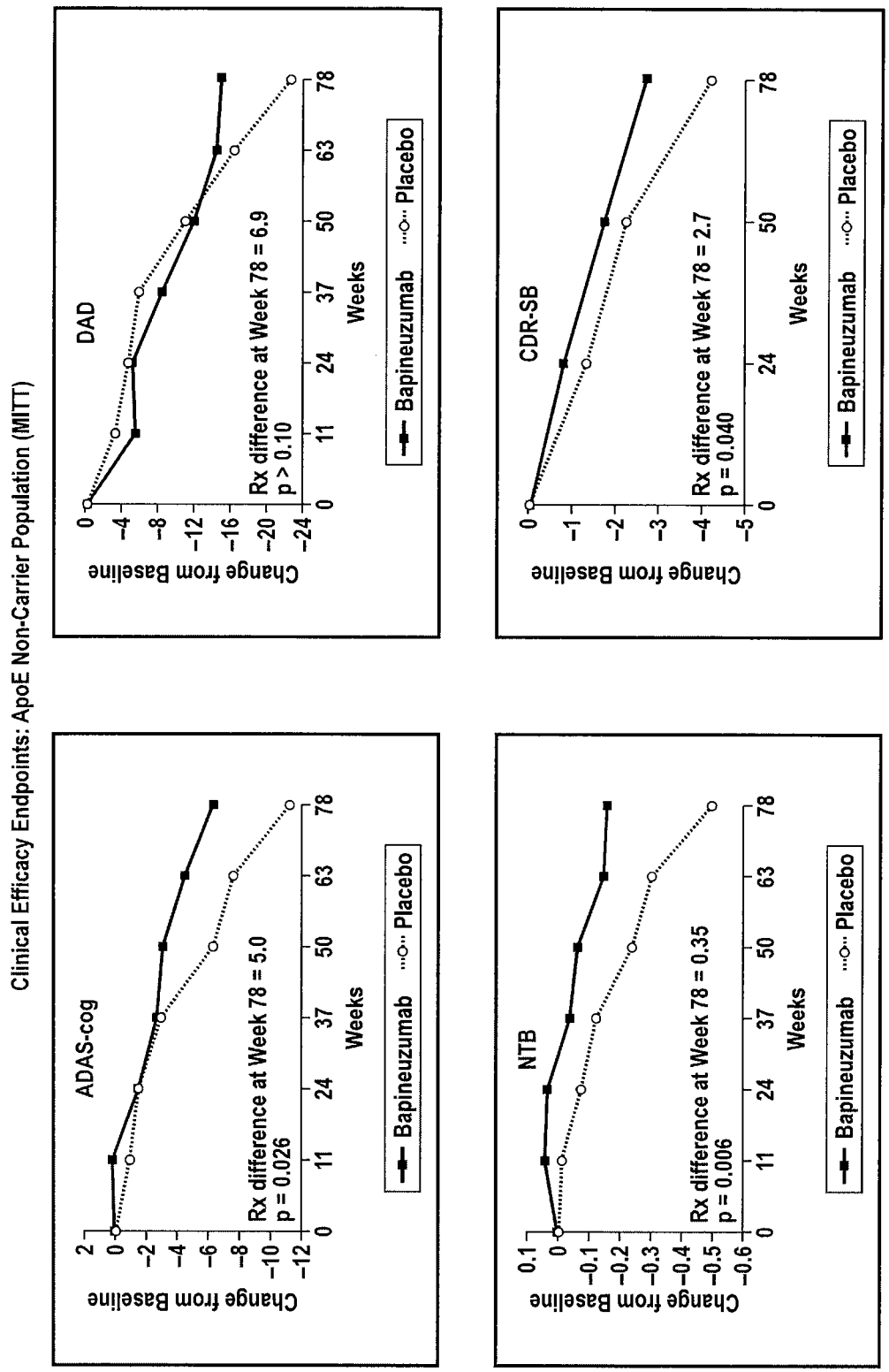
FIG. 9 shows changes in ADAS-cog, DAS, NTB and CDR-SB over time in treated patients compared with placebos in an ApoE4 non-carrier population.

FIGS. 5 and 6 show the results for all ApoE4 non-carrier patients in whom efficacy was measured. Statistical significance was obtained for ADAS-cog, NTB, CDR-SB and MMSE measurements for the combined dosage cohorts. Bars above the axis indicate improvement relative to placebo. FIG. 9 shows time course analysis of these parameters (ADAS-cog, upper left, DAD, upper right, NTB, lower left, CDR-SB, lower right). The decline in cognitive performance for treated patients was less than that of placebo at all time points on the ADAS-cog, NTB and CDR-SB scales. FIGS. 7 and 8 show the analysis for ApoE4 non-carrier completers, as defined above. Statistical significance was again obtained for ADAS-cog, NTB, CDR-SB and MMSE measurements. Again, bars above the axis indicate improvement relative to placebo.

MRI was performed up to seven times per patient during the study six weeks after each infusion. Changes in the brain were assessed by brain volume, ventricular volume, brain boundary shift integral and ventricular boundary shift integral. The boundary shift integral (BSI) as a measure of cerebral volume changes derived from registered repeat three-dimensional magnetic resonance scans. The BSI determines the total volume through which the boundaries of a given cerebral structure have moved and, hence, the volume change, directly from voxel intensities. The ventricular shift integral is a similar measurement of ventricular space changes. Both of these parameters increase as Alzheimer's disease progresses. Thus, inhibition of the increase in these parameters relative to placebo shows a positive (i.e., desired) effect of treatment.

In the total treated population (carriers and non-carriers) no significant differences were found for changes in brain volume measured by brain boundary shift integral or ventricular volume measured by ventricular boundary shift integral over 78 weeks compared with the placebo population.

In the treated non-ApoE4 carrier population brain volume decline was significantly lower than the non-ApoE4 placebo population (mean −10.7 cc; 95% CI: −18.0 to −3.4; p=0.004). The increase in ventricular volume compared to placebo was also reduced but the change did not reach statistical significance. There was no significant change in brain volume compared with the ApoE4 placebo population. However, the ventricular volume increased significantly compared to placebo (mean 2.5 cc; 95% CI: 0.1 to 5.1; p=0.037).

Figure 10:
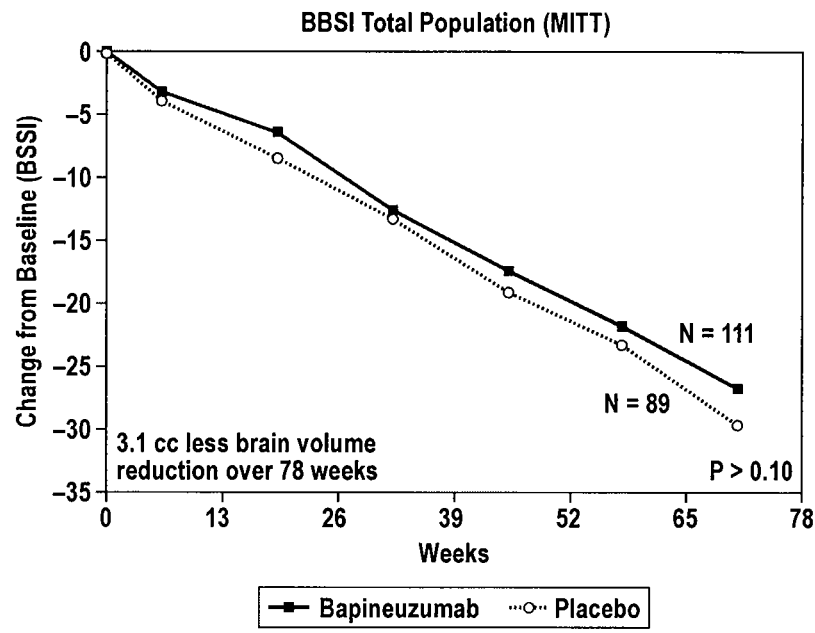
FIGS. 10, 11 and 12 show changes in BBSI in total population (ApoE4 carriers and non-carriers), ApoE4 carriers and ApoE4 non-carriers respectively compared with placebo populations.
Figure 11:
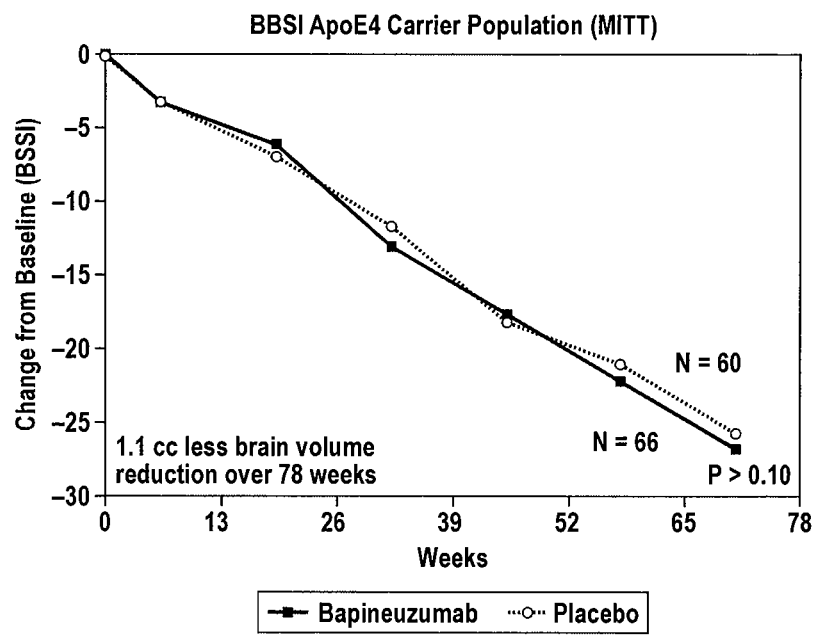
Figure 12:
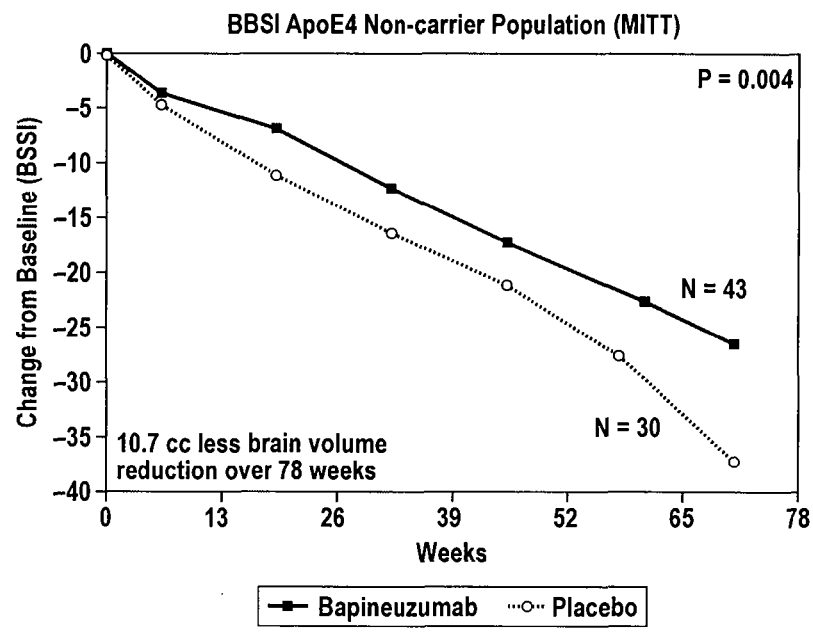

The changes of BBSI in the total population, ApoE4 carrier population and ApoE4 non-carrier population are shown in FIGS. 10-12. FIG. 12 (ApoE4 non-carriers) shows a statistically significant separation between the lines for treated patients and placebo. The change in brain volume was reduced in the treated population relative to placebo at all measured time points. FIG. 10 (combined ApoE4 carriers and non-carriers) shows separation of the lines for treated and placebo patients but the results did not reach statistical significance. FIG. 11 (ApoE4 carriers) shows the lines for treated and placebo patients are virtually superimposed. Analysis used repeated measures model with time as categorical, adjusting for APOE4 carrier status. Baseline was whole brain volume and MMSE stratum.

Figure 13:
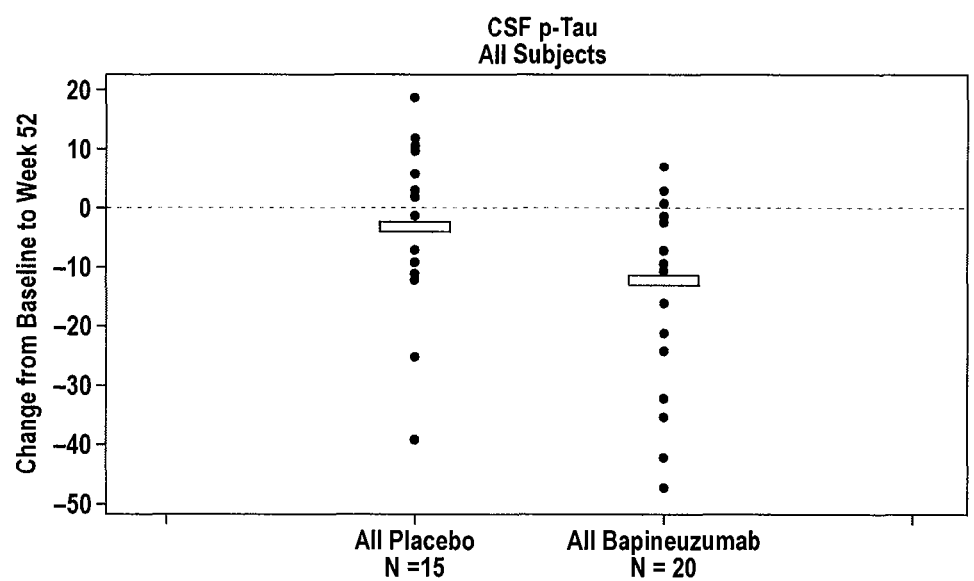
FIG. 13 shows CSF concentration of phospho-tau in treated patients compared with placebo patients (without distinguishing between ApoE4 genotypes).

A trend was observed for reduction in CSF phospho-tau in the bapineuzumab treated patient population relative to the placebo treated population at 52 weeks into the trials (FIG. 13). Phospho-tau is a biomarker associated with Alzheimer's disease. No significant differences were found between CSF levels of tau and Aβ42 between all treated patients and controls. The figure is based on ANCOVA analysis, adjusted for baseline value. One outlier was excluded in the 0.15 mg/kg placebo dose cohort.

Treatment was generally safe and well tolerated. Vasogenic edema (VE) occurred only in bapineuzumab treated patients. VE occurred with greater frequency in ApoE4 carriers (10) than non-carriers (2) and at greater frequency with increasing dose, there being 8, 3, 0 and 1 episodes at doses of 2.0, 1.0, 0.5 and 0.15 mg/kg respectively. All VE episodes occurred after the first or second dose. Most episodes of VE were detected only by MRI and had no detected clinical symptoms. The VE episodes resolved over weeks to months. In one patient, the VE was treated with steroids. Excluding VE, and excluding the 0.15 mg/kg cohort (which contained patients with more advanced disease than other cohorts), serious adverse events were similar between treated and placebo groups. Adverse events were generally mild to moderate, transient, considered unrelated to study drug, occurred in relatively small proportion of patients and did not appear to be dose-related.

Figure 14:
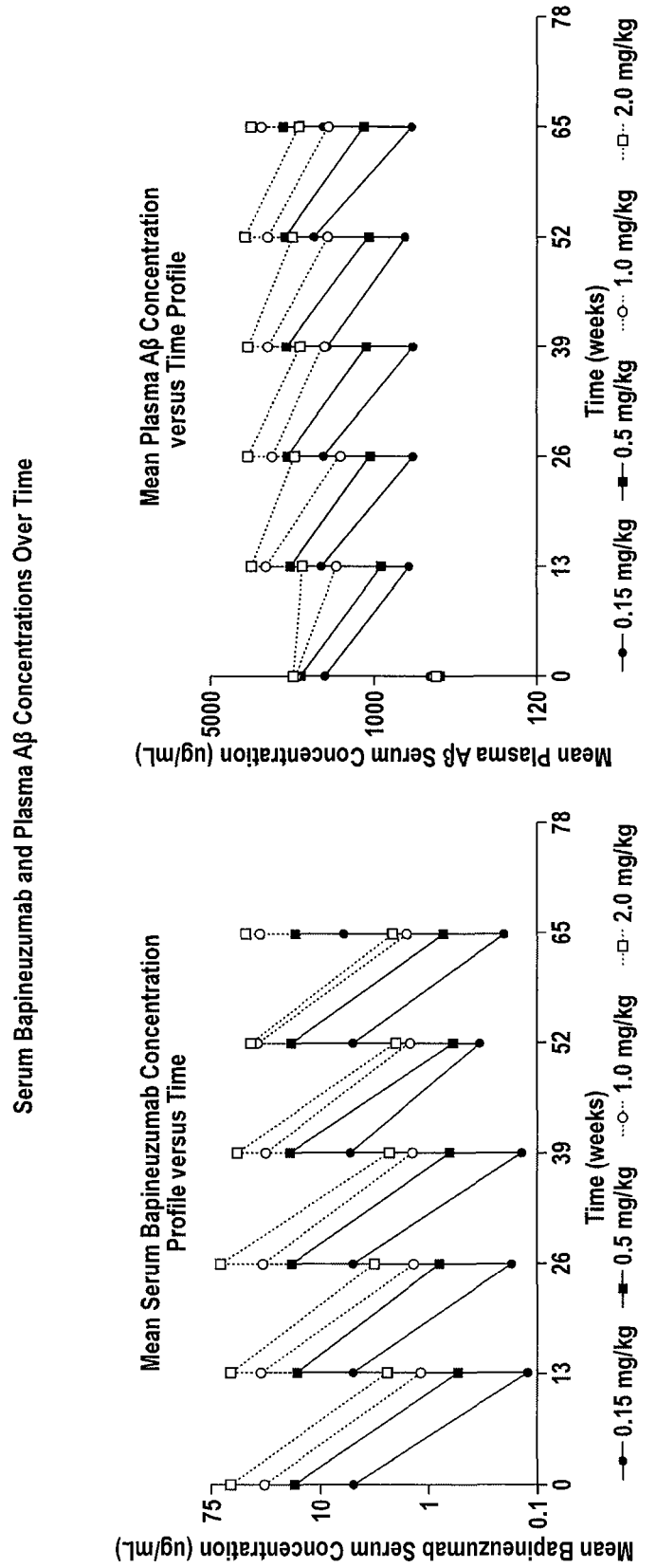
FIG. 14 shows changes in serum concentration of bapineuzuab in serum over time (left) and concentration of Aβ in plasma over time.

Serum concentration of bapineuzumab and plasma concentration of Aβ were measured in treated patients over time for the different dosage cohorts as shown in FIG. 14. The Cmax for serum bapineuzumab ranged from about 3.5-50 µg/ml in the different dosage cohorts from 0.15 mg/kg to 2.0 mg/kg. The profile of mean plasma concentration of Aβ mirrored that of mean serum bapineuzumab with the concentration of plasma Aβ rising on dosing with bapineuzumab and declining as the concentration of bapineuzumab declined. The concentration of plasma Aβ ranged from about 500-3000 pg/ml. The variation of plasma concentration of Aβ between different dosage cohorts showed less variation than the variation between doses. For example, increasing the dose from 0.15 mg/kg to 2 mg/kg increases plasma Aβ by about a factor of 2.

The PK parameters after the first infusion of bapineuzumab are summarized in Table 9 below.

TABLE 9

| Dose (mg/kg) | Cmax (μg/mL) | Cavg (μg/mL) | Cmin (μg/mL) | Tmax (days) | AUCinf (μg · h/mL) | CL/F (mL/hr/kg) | Vz/F (mL/kg) | T½ (days) |
|---|---|---|---|---|---|---|---|---|
| 0.15 | 4.6 | 0.7 | 0.1‡ | 0.1 | 1794 | 0.09 | 76.2 | 26.7 |
| 0.5* | 17.7 | 3.0 | 1.1‡ | 0.4 | 7165 | 0.07 | 63.7 | 26.4 |
| 1.0 | 28.0 | 5.5 | 1.8‡ | 0.1 | 13499 | 0.08 | 75.4 | 28.4 |
| 2.0 | 56.3 | 9.5* | 1.7‡ | 0.1 | 21802* | 0.09* | 65.8* | 20.5* |

N = 6 unless otherwise specified;
*n = 5
‡trough values of 2nd infusion; all values below limit of quantification for trough of 1st infusion
Abbreviations:
Cavg- Average concentration over 13 weeks;
Cmin - Minimum concentration ("trough");
Tmax - Time of maximum concentration;
AUC inf - Area under Concentration vs. time curve extrapolated to infinity;
CLss/F - ratio of the extravascular clearance at steady state (CLss) and extent of bioavailability (F);
Vz/F - ratio of apparent volume of distribution at steady state (Vz) and F;
t½ - elimination (or terminal) half-life in days.

Conclusions

1. The trial provides evidence that ApoE4 carriers and non-carriers react differently to immunotherapy.
2. The trial provides evidence that vasogenic edema occurs more frequently in ApoE4 carriers and at higher dosages.
3. The trial provides statistically significant evidence of efficacy in non-ApoE4 carriers and in patients receiving at least 6 doses of bapineuzumab (ApoE4 carriers and non-carriers).
4. The trial provides evidence of trends or favorable directional changes in a total population (ApoE4 carriers and non-carriers) and ApoE4-carrier population by some measures. Statistical significance might be shown with larger populations. Alternative treatment regimes in these patients such as discussed above are likely to improve efficacy as discussed above.
5. The trial provides evidence that the treatment is generally safe and well tolerated.

Example 3: Clinical Study of Subcutaneous Administration of Bapineuzumab in Alzheimer's Patients Subcutaneous injections are generally easier to administer, which can be a consideration for patients with impaired mental function and coordination, or caregivers administering to an uncooperative patient. It is also easier to do at home, which is less upsetting to the patient, as well as less expensive. Finally, subcutaneous administration usually results in a lower peak concentration of the composition (Cmax) in the patient's system than intravenous. The reduced peak can reduce the likelihood of vasogenic edema.

For these reasons, a clinical study was designed for subcutaneous administration of bapineuzumab. The primary endpoints for the initial study are safety and bioavailability. Once these are established for subcutaneous administration, the cognitive tests described above will be administered to determine efficacy.

Under the initial regime, bapineuzumab is administered subcutaneously to patients every 13 weeks for 24 months, for a total of 9 doses. All patients receive a dose of 0.5 mg/kg. Patients are screened and periodically monitored as described in the above examples, e.g., for blood levels of the antibody, heart function, and vasogenic edema.

Example 4: Design of Specific Mouse and Human Antibodies

Variants of humanized and mouse 3D6 antibodies differing in isotype and or constant region mutations were constructed to test effects of reducing effector function on amyloid deposit clearing, cognitive function and microhemorrhaging. Mice treated with antibodies to Aβ proteins often exhibit signs of microhemorrhage in cerebral vessels, which is one factor that my be related to the vasogenic edema observed in human patients undergoing similar treatment.

Figure 15:
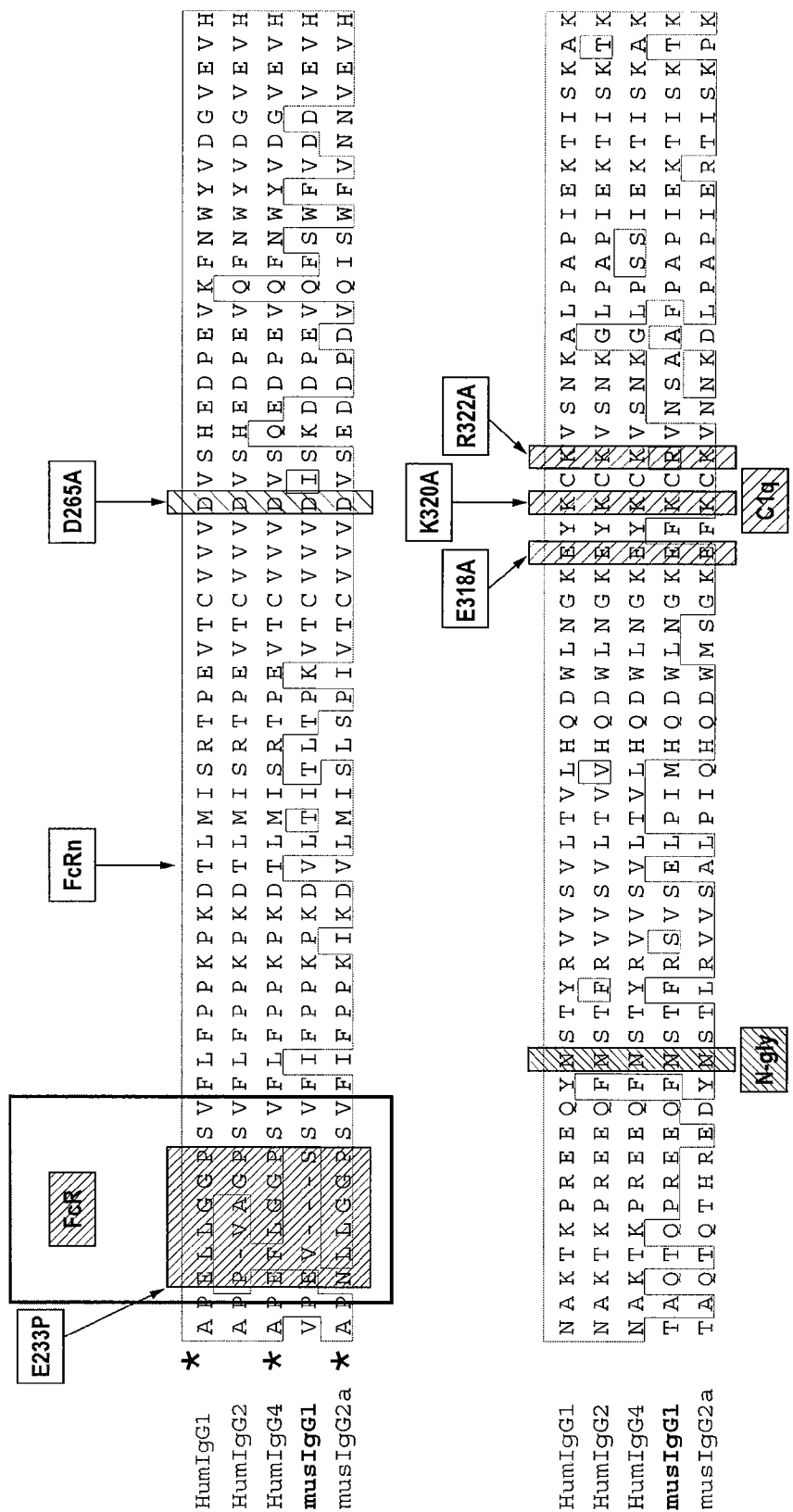
FIG. 15 shows an alignment of the CH2 domains of human IgG1 (SEQ ID NO: 95), IgG2 (SEQ ID NO: 96), and IgG4 (SEQ ID NO: 97) with mouse IgG1 (SEQ ID NO: 98) and IgG2a (SEQ ID NO: 99).

An alignment of the CH2 domains of human IgG1, IgG2, and IgG4 with mouse IgG1 and IgG2a are shown in FIG. 15. The alignment highlights the residues responsible for FcR and C1q binding. The C1q binding motif is conserved across species and isotypes. The FcR binding motif is conserved in human IgG1, IgG4, and murine IgG2a.

The following table discloses the particular modifications made to the CH2 region of the heavy chain. The amino acid numbering is by the EU system. The format is wildtype residue, position, mutant residue.

TABLE 10

3D6 Derivative Antibodies

| 3D6 Derivative Antibody | Isotype (species) | Mutated Residues |
|---|---|---|
| Bapineuzumab Control AAB-001 | IgG1 (human) | — |
| Humanized 3D6 2m (FcγR) | IgG1 (human) | L234A/G237A (EU numbering) |
| Humanized 3D6 3m (FcγR) AAB-003 | IgG1 (human) | L234A/L235A/G237A (EU numbering) |
| Humanized 3D6 1m (hinge region) | IgG4 (human) | S241P (Kabat numbering) |
| 3D6 Control | IgG1 (mouse) | — |
| 3D6 1m (FcγR) | IgG1 (mouse) | E233P |
| 3D6 3m (C1q) | IgG1 (mouse) | E318A/K320A/R322A |
| 3D6 4m (C1q) | IgG1 (mouse) | E318A/K320A/R322A/E233P |
| 3D6 Control | IgG2a (mouse) | — |
| 3D6 1m (FcγR) | IgG2a (mouse) | D265A |
| 3D6 4m (FcγR, C1q) | IgG2a (mouse) | L235A/E318A/K320A/K322A |

The epitope-binding regions of 3D6 derivative antibodies are the same, and the kinetics of Aβ binding are comparable. Table 11 discloses the kinetics of the Fc receptor binding to the 3D6 derivative antibodies listed in Table 10. These values were generated as follows.

For the humanized 3D6 derivative antibodies, the following assay conditions were used. A Biacore 3000 and CM5 chip coated with penta-His (SEQ ID NO: 93) antibody (Qiagen, Cat # 34660) was used in combination with His-tagged domains of human FcγRI, FcγRII, and FcγRIII (R&D Systems, Cat # 1257-Fc, 1330-CD, 1597-Fc). Each receptor was separately captured in one flow cell of the sensor chip by the penta-His (SEQ ID NO: 93) antibody. A solution of the antibody to be tested was injected to enable measurements of association and dissociation rates to the captured receptor. After measurements were completed, the receptors and experimental antibodies were removed by injection of buffer at pH2.5. The flow cell was then ready for the next cycle. Each cycle was carried out in duplicate, and the same conditions (e.g., concentrations, flow rates, and timing) were used for each sample.

As indicated by the values in Table 11, bapineuzumab (unmodified Fc region) bound to all of the human FcγR receptors with relatively high affinity. $K_D$ for FcγRI was in the nm range, while $K_D$ for FcγRII and III were in the μm range. For the latter two, the sensorgrams showed typical fast-on, fast-off kinetics. IgG4 isotype had similar binding to FcγRI, but did not bind FcγRIII, as expected. The two IgG1 derivatives, Hu 3D6 2m and 3m, did not show detectable binding to either FcγRI or FcγRIII.

For the mouse 3D6 derivative antibodies, similar methods were used to determine binding to mouse FcγRI, II, and III. FcγRI and III are activating receptors, while FcγRII is generally considered to be inhibitory. The antibodies tested were 3D6 IgG2a, 3D6 IgG1, and the IgG1 mutants, 3D6 1m, 3m and 4m. Results are expressed as a relative percentage of 3D6 IgG2a binding. As shown in Table 11, 3D6 IgG2a was the only antibody with detectable FcγRI binding ability. 3D6 IgG1 and the 3D6 3m IgG1 had similar FcγRII and III binding profiles.

TABLE 11

Fc Receptor Binding Ability of 3D6 Antibodies

| | Relative Binding Capability* (%) | | |
|---|---|---|---|
| 3D6 Derivative | Human FcγRI** | Human FcγRII** | Human FcγRIII** |
| Bapineuzumab Control | 100 | 100 | 100 |
| Humanized 3D6 1m | 85-95 | 40-50 | 0 |
| Humanized 3D6 2m | 0 | 40-50 | 0 |
| Humanized 3D6 3m AAB-003 | 0 | 8-12 | 0 |

| | Mouse FcγRI** | Mouse FcγRII** | Mouse FcγRIII** |
|---|---|---|---|
| 3D6 Control IgG2a | 100*** | 100 | 100 |
| 3D6 Control IgG1 | 0 | 180 | 70 |
| 3D6 1m IgG1 | 0 | 15 | 10 |
| 3D6 3m IgG1 | 0 | 180 | 70 |
| 3D6 4m IgG1 | 0 | 25 | 15 |

*Defined as the amount of binding in (RU) relative to that of IgG2a control at the steady state
**The mFcγRI and mFcγRIII are activating receptors, mFcγRII is an inhibitory receptor. Another potent activating receptor, mFcγRIV, is not commercially available.
***A steady-state binding was not reached. Kinetic fitting led to an estimate of $K_D$ in the nanomolar range.

The above results show that that the Hu 3D6 3m (AAB-003) antibody has the most reduced Fc gamma receptor binding of the three tested. Of those tested, the 3D6 1m IgG1 mouse mutant antibody was the most similar to AAB-003, in that its FcγR binding was reduced to near 10% of normal.

Example 5: Mouse Studies of 3D6 Derivative Antibodies

Study Design

One-year old PDAPP mice were exposed to a 6 month treatment paradigm with control or the 3D6 derivative antibodies described in Table 10. The negative control was a mouse IgG2a antibody to an irrelevant, non-amyloid epitope. The mice were injected IP with 3 mg/kg of the indicated antibody each week.

Serum antibody concentrations were tested over the course of the study by ELISA. Levels were comparable in all groups. After six months, the mice were sacrificed and perfused. Brain sections and tissues were prepared according to known methods (Johnson-Wood et al. (1997) *Proc. Natl. Acad. Sci., USA* 94:1550-55).

Amyloid burden was measured in the cortex and hippocampus of transgenic mice. Results in Table 12A and 12B are indicated as percentage reduction of area with amyloid (p values indicate significant difference compared to IgG2a control antibody).

TABLE 12A

Cortical Amyloid Burden (% reduction)

| | Control IgG2a | 3D6 Control IgG2a | 3D6 Control IgG1 | 3D6 1 m IgG1 (FcγR) | 3D6 3 m IgG1 (C1q) |
|---|---|---|---|---|---|
| Median % Area | 6.25076 | 0.757259 | 1.24205 | 2.06056 | 1.50084 |
| Range | 0.069-17.073 | 0-9.646 | 0-17.799 | 0-24.531 | 0-17.069 |
| % Change Control IgG2a | — | 88 p < 0.0001 | 80 p < 0.0001 | 67 p < 0.003 | 76 p < 0.0001 |
| % Change 3D6 IgG1 | — | — | — | 165.9 | 120.8 |
| Number | 32 | 34 | 36 | 36 | 34 |

TABLE 12B

Hippocampal Amyloid Burden (% reduction)

|  | Control IgG2a | 3D6 Control IgG2a | 3D6 Control IgG1 | 3D6 1 m IgG1 (FcγR) | 3D6 3 m IgG1 (C1q) |
|---|---|---|---|---|---|
| Median % Area | 20.36 | 8.462 | 12.29 | 12.18 | 8.435 |
| Range | 4.707-35.79 | 1.467-17.59 | 0.2449-18.61 | 0-26.99 | 0.8445-18.61 |
| % Change Control IgG2a | — | 58 p < 0.0001 | 40 p < 0.0001 | 40 p < 0.0001 | 59 p < 0.0001 |
| % Change 3D6 IgG1 | — | — | — | 0.895 | 31.4 |
| number | 34 | 34 | 37 | 37 | 34 |

The above results indicate that all of the 3D6 antibodies (IgG2a, IgG1 and mutants) significantly reduced amyloid burden relative to negative controls. Differences between the tested antibodies were not statistically significant.

The effect of the 3D6 derivative antibodies was then tested on vascular amyloid ratings. Table 13 shows the number of mice with the indicated vascular amyloid rating and the percentage of animals with a rating of 4 or greater (p values indicate significant difference compared to 3D6 IgG2a antibody).

TABLE 13

% of Mice Having Vascular Amyloid

|  | None-little (0-3) | Moderate (4+) | Percentage with moderate rating |  |
|---|---|---|---|---|
| Control IgG2a | 11 | 24 | 69 | p < 0.0001 |
| 3D6 Control IgG2a | 27 | 7 | 21 | — |
| 3D6 Control IgG1 | 12 | 25 | 68 | p < 0.0001 |
| 3D6 1m (FcγR) IgG1 | 15 | 21 | 58 | p < 0.0016 |
| 3D6 3m (C1q) IgG1 | 20 | 17 | 46 | <0.0434 |

The above data show that the positive control 3D6 IgG2a significantly reduced vascular amyloid relative to the irrelevant IgG2a antibody. The reduction with 3D6 IgG2a was also statistically significant relative to that with 3D6 IgG1, 3D6 1 m IgG1 and 3D6 3 m IgG1. Differences between 3D6 IgG1, 3D6 1 m IgG1 and 3D6 3 m IgG1 and control IgG2a were not statistically significant.

To determine whether the 3D6 antibody derivatives cause microhemorrhage in mice, hemosiderin levels, a marker for microhemorrhage, were examined in brain sections of mice treated with 3 mg/kg antibody. Staining was carried out with 2% potassium ferrocyanide in 2% hydrochloric acid, followed by a counterstain in a 1% neutral red solution. Table 14 indicates the percentage and absolute number of mice with the indicated level of hemosiderin staining. The results demonstrate that 3D6 1m IgG1 (FcγR) and 3D6 3m IgG1 (C1q), which are shown above to be effective in clearing amyloid plaques, reduce microhemorrhage levels relative to 3D6 IgG2a. Differences between 3D6 IgG1, 3D6 1m IgG1 and 3D6 3m IgG1 did not reach statistical significance, although the difference between 3D6 1m IgG1 and 3D6 IgG1 showed a trend. (p values indicate significant difference compared to 3D6 IgG2a antibody).

TABLE 14

|  | Microhemorrhage level: | | | |
|---|---|---|---|---|
|  | 0 | 1 | 2 | 3 |
| Control IgG2a p < 0.0001 | 68% (23) | 32% (11) | 0% (0) | 0% (0) |
| 3D6 Control IgG2a | 9% (3) | 42% (14) | 27% (9) | 21% (7) |
| 3D6 Control IgG1 p < 0.0023 | 38% (14) | 46% (17) | 3% (1) | 13% (5) |
| 3D6 1m IgG1 (FcγR) p < 0.0001 | 51% (19) | 49% (18) | 0% (0) | 0% (0) |
| 3D6 3m IgG1 (C1q) p < 0.0001 | 53% (19) | 42% (15) | 0% (0) | 5% (2) |

Example 6: Phagocytosis Assays

Materials and Methods

Ex vivo plaque phagocytosis assays: Frozen brain sections from PDAPP mice were pre-incubated with 3D6 IgG1 and the effector function mutants described in Table 10 (3D6 1m (FcγR1) and 3D6 3m (C1q), both mouse IgG1 isotype). 3D6 IgG2a was used as a positive control and irrelevant IgG1 and IgG2a antibodies were used as isotype controls. Sections were treated with 0.3 or 3 µg/ml antibody for 30 minutes prior to addition of mouse microglia, at 5% $CO_2$ at 37C. The co-cultures were extracted the next day. Remaining Aβ was measured by ELISA (266 antibody for capture, and 3D6-B for reporter) to assess Aβ clearance.

Phagocytosis of murine IgG2a derivatives was tested. These experiments included: 3D6 IgG2a (positive control); non-specific IgG2a (negative control); 3D6 1m (FcγR1, IgG2a isotype); and 3D6 4m (FcγR1/C1q) antibodies. Conditions were similar to those described above.

Non-plaque phagocytosis was additionally determined for humanized 3D6 (Hu 3D6 IgG1) and the effector mutants described in Table 10 (Hu 3D6 2m IgG1, Hu 3D6 3m IgG1, and Hu 3D6 1m IgG4). The negative control was an irrelevant human IgG1 antibody. Assay and detection conditions were otherwise the same.

In vitro assays: For the mouse antibody assays of fluorescently conjugated bead phagocytosis, 10 µM Fluoro-Sphere particles (5×10$_6$) were opsonized with 1 mg/ml of mouse F(ab'2), 3D6 IgG2a, 3D6 IgG1, or the 3D6 FcγR mutant for 2 hrs at RT with rotation. Following 2 hrs, beads were washed with 1 ml of PBS 3 times to remove unbound IgG. Opsonized particles were added (1:10) to mouse microglia for the murine 3D6 Ig2a (3D62a) experiments. Beads were incubated with the cells for 90 min at 37 C. Unbound particles were then washed away with PBS. Cells were stained with DiffQuick for 30 sec for each stain and phagocytosis was visualized by light microscopy. Controls for this assay were un-opsonized beads (unlabelled) (to detect non-specific engulfment) and pre-treatment with human Fc-fragments (3D62a+FC) (to block FcγR1).

For humanized antibody assays, conditions and detection were the same. However, the antibodies were: no antibody (unlabelled; negative control), irrelevant human IgG1 (Human IgG1; positive control), Hu 3D6 IgG1, Hu 3D6 2m IgG1, Hu 3D6 3m IgG1, and Hu 3D6 1m IgG4. The phagocytic cells were human THP-1 cells (differentiated with PMA).

Results

Figure 16:
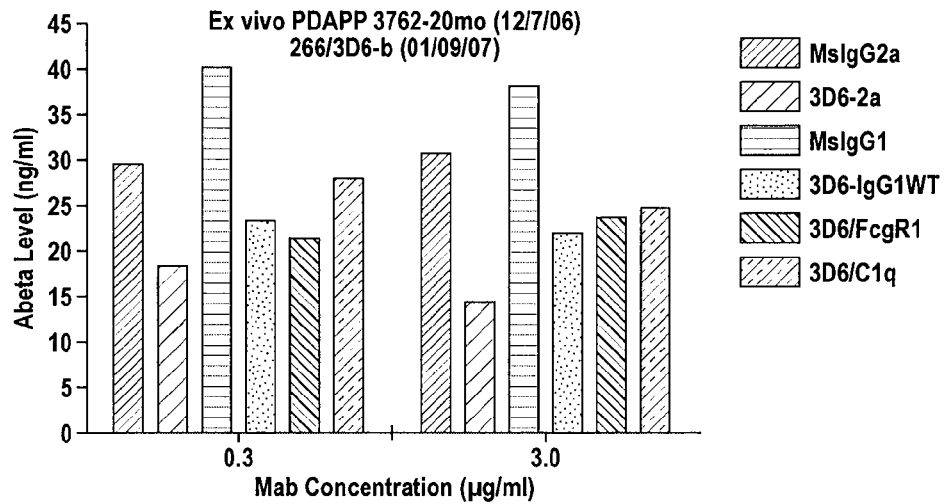
FIG. 16 shows Aβ plaque clearance by mouse microglia of murine 3D6 IgG1 derivatives. MsIgG1 and MsIgG2a are murine antibodies against irrelevant antigens. The 3D6 antibodies have the variable region described herein. 3D6/FcγR1 indicates the single E233P mutant in the Fc binding region of the IgG1 constant region. 3D6/C1q indicates the triple mutant in the C1q binding region. See, e.g., Example 6 and Table 10.

Ex vivo plague phagocytosis assays: The murine 3D6 IgG1 antibody and its effector mutants (3D6 1m (FcγR1) and 3D6 3m (C1q)) were assayed to assess their ability to facilitate amyloid clearance (see FIG. 16). The 3D6 IgG2a antibody stimulated more robust clearance than 3D6 IgG1, 3D6 1m (FcγR1) and 3D6 3m (C1q). Stimulation of phagocytosis by 3D6 IgG1, 3D6 1m (FcγR1) and 3D6 3m (C1q) was greater than the negative control. Mutations to the Fc domain of 3D6 IgG1 do not appear to significantly dampen its ability to stimulate clearance in the ex vivo clearance assay.

Figure 17A:
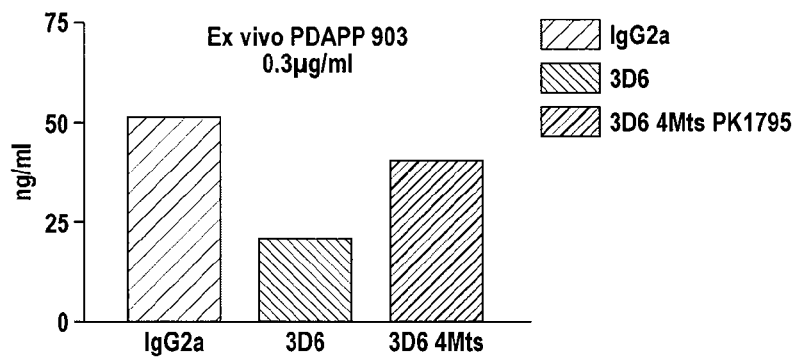
FIG. 17 shows Aβ plaque clearance by mouse microglia of murine 3D6 IgG2a derivatives. IgG2a is a murine antibody against an irrelevant antigen. The remaining antibodies and conditions are described, e.g., in Example 6 and Table 10.
Figure 17B:
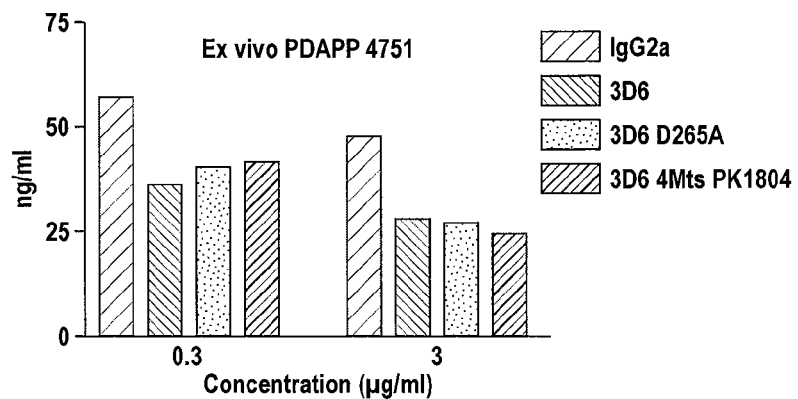

For the IgG2a 3D6 derivatives, the mutants stimulated clearance equivalent to wild-type 3D6 IgG2a and to a greater degree relative to an irrelevant IgG2 isotype matched control (see FIG. 17). Thus, neither of the mutants completely inhibited Aβ phagocytosis.

Figure 18:
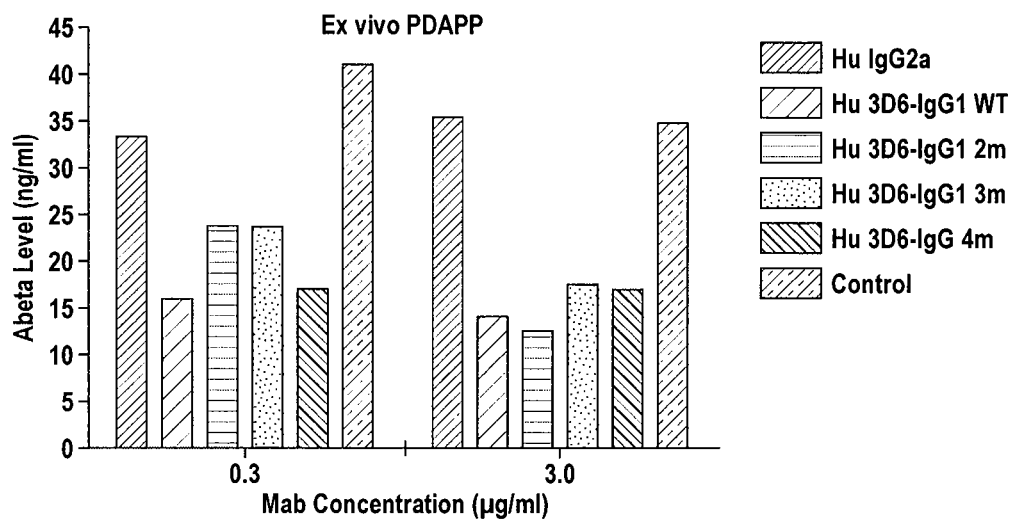
FIG. 18 shows Aβ plaque clearance by mouse microglia of humanized 3D6 derivatives (AAB). The antibodies and conditions are described e.g., in Example 6 and Table 10.

In the humanized antibody assays, mutations to the effector region of the Hu 3D6 IgG1 retained significant clearing activity relative to the negative control. Hu 3D6 IgG1 stimulated clearance in the ex vivo Aβ plaque clearance assay, and the effector region mutants had moderately impaired function. Hu 3D6 IgG4 induced phagocytosis to the same extent as Hu 3D6 IgG1, and mutation to the IgG4 hinge region of 3D6 did not appear to change its effector function (see FIG. 18).

Figure 19:
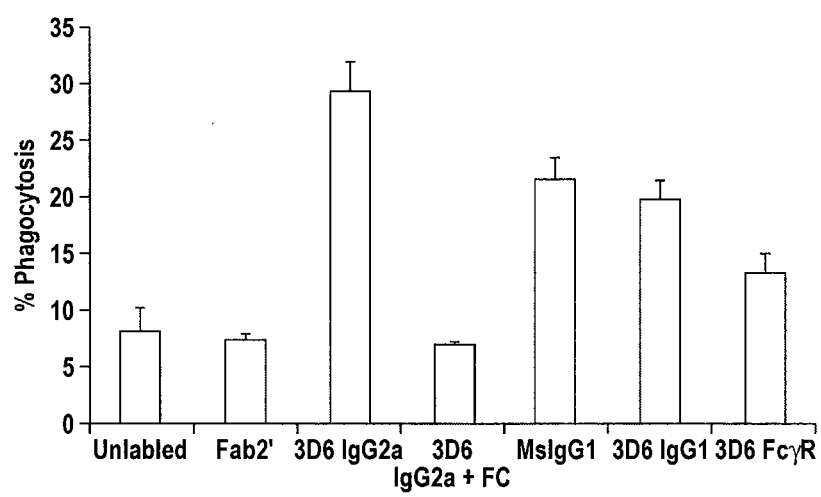
FIG. 19 shows results of an in vitro assay measuring engulfment of murine IgG-coated beads by mouse microglial cells. Conditions are described in Example 6.

In vitro bead phagocytosis assays: To determine if the ex vivo results were specific for Aβ clearance and whether the Fc mutation in the 3D6 IgG1 altered its effector function, non-specific Fc-mediated bead phagocytosis assays were performed. In the mouse antibody bead phagocytosis assay, the 3D6 IgG2a isotype antibody mediated more efficient phagocytosis than 3D6 IgG1 (see FIG. 19). The Fc mutation in 3D6 IgG1 did not significantly diminish the ability to stimulate phagocytosis, as compared to the positive control 3D6 IgG2a, indicating that the Fc mutation in 3D6 IgG1 was moderately effective in reducing phagocytosis.

Figure 20:
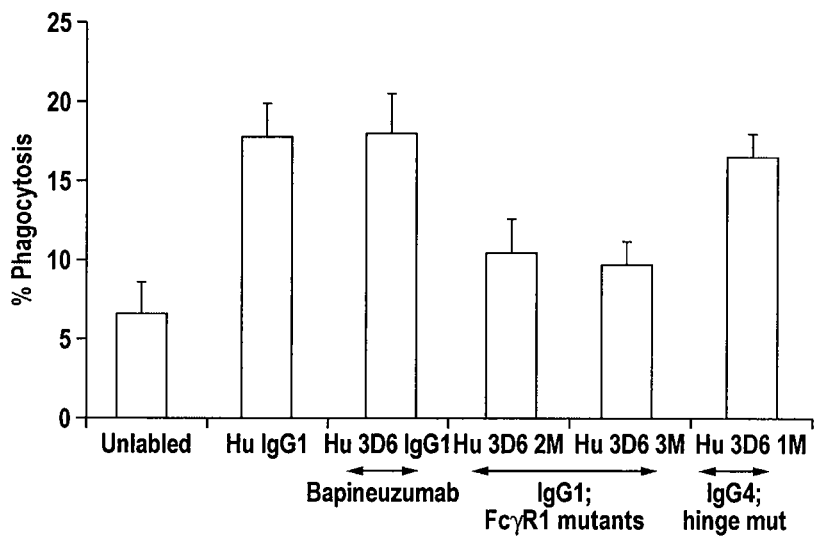
FIG. 20 shows a similar assay using the indicated humanized antibodies. Conditions are described in Example 6.

In the humanized antibody assay, the effect of the Fc mutation seen in the ex vivo plaque phagocytosis assay was verified on Fc-mediated bead phagocytosis. Again, the mutations in the Fc portion of humanized 3D6 diminished its ability to mediate phagocytosis of fluorescent beads and there was no significant difference between the 2m and 3m mutants. Again, the theoretically ineffective IgG4 isotype mediated removal to the same extent as the IgG1 isotype (see FIG. 20). Mutation to the IgG4 hinge region of 3D6 does not appear to change its effector function.

Example 7: C1q Binding Ability of Humanized 3D6 Derivatives

The humanized 3D6 derivatives were tested for ability to bind C1q and induce a complement response. A standard C1q dilution series protocol was followed, as described below. Similar protocols are described, e.g., in Idusogie et al. (2000) J. Immunol. 164: 4178-4184.

Figure 21:
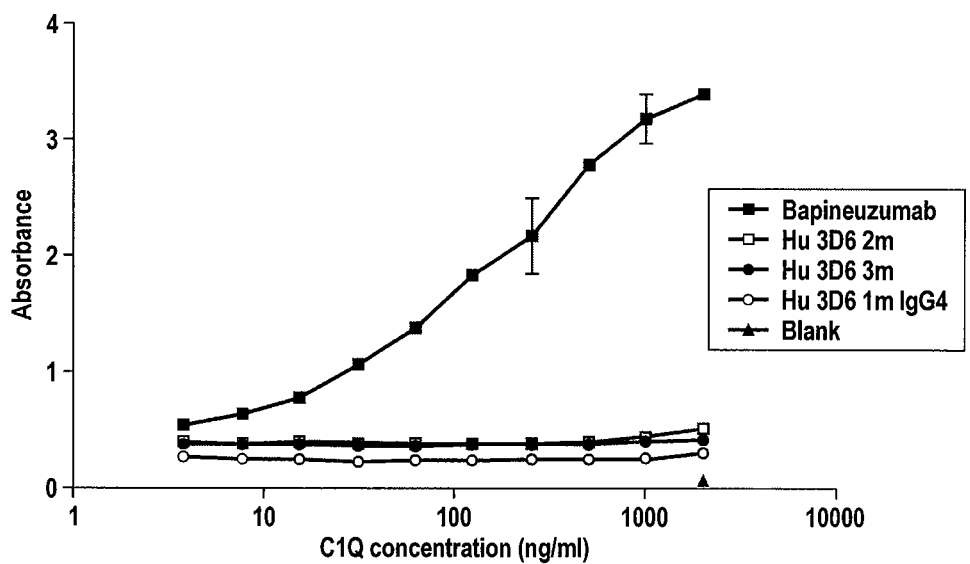
FIG. 21 shows results of an ELISA assay measuring C1q binding by the indicated humanized antibodies. See Example 7.

Purified Aβ was coated on to ELISA plates and exposed to one of the following humanized 3D6 antibodies at the concentrations indicated in FIG. 21: Hu 3D6 2m (IgG1), Hu 3D6 3m (IgG1), Hu 3D6 1m (IgG4), and unmodified Hu 3D6 (IgG1). The ELISA plates were washed and then blocked with 0.02% Casein solution in PBS for 3 to 24 hours with slow agitation. The blocking solution was removed with another step of washing.

Next, purified human C1q (191391, MP Biomedicals) was added to the ELISA plates, with 2 ug C1q/ml assay buffer starting the 2× dilution series. C1q was allowed to bind for 2 hours with agitation. Following another wash step, 100 μl/well anti-C1q antibody (Rb anti human C1q FITC conjugated cat# F010 DBS (dbiosys.com)) used at 1:200 was added for 1 hour with agitation. Results were compared to a blank with no anti-C1q antibody.

As shown in FIG. 21, the humanized 3D6 derivative antibodies did not significantly interact with C1q. This is in contrast to bapineuzumab, which does not have mutations in the Fc region.

The derivative antibodies were tested for ability to induce complement-mediated lysis of HEK 293 cells expressing Aβ on the surface. A standard $^{51}$Cr release assay was used, as described in Phillips et al. (2000) Cancer Res. 60:6977-84; Aprile et al. (1981) Clin. Exp. Immunol. 46:565-76.

The target cells were HEK293 cells (ATCC, CRL-1573) that expressed a fusion protein with the Aβ epitope detected by 3D6 (DAEFR (SEQ ID NO: 94)) on the surface. The Aβ-containing sequence was inserted into the pDisplay vector (Invitrogen). The pDisplay vector was altered to remove the HA tag and instead start with the Aβ-containing peptide after leader sequence. A stable pool of HEK 293 was moved forward to the ADCC assay.

For labeling, $10^7$ cells were suspended in 2 ml RPMI 10% FCS and added 250 uCi of $^{51}$Cr (NEN catalog #NEZ-030; sodium$^{51}$ chromate in saline). Cells were incubated for 1 hour at 37 C with occasional agitation. At the end of the incubation, 10 ml RPMI with 10% FCS was added. Cells were spun down so the supernatant could be removed, and resuspended in 10 ml RPMI containing 10% FCS. Cells were again incubated, at room temperature for 1.5 hours with occasional agitation, to allow excess $^{51}$Cr to bleed from the cells. Target cells were washed 3 times with 10 ml RPMI, and a final time in 10 ml RPMI containing 10% FCS. Cells were resuspended in RPMI with 10% FCS to a concentration of $10^6$ cells/ml.

Effector cells were collected from human blood. Briefly, blood was diluted 1:1 with PBS and layered over Ficoll (Sigma Histopaque 1077). The column was spun for 20 min, 1200×g, with no brake at 20C. Cells at the interface were collected; washed once with 2-3 volumes PBS, and twice with RPMI containing 10% FCS. NK enrichment is detected with antibodies to CD3 and CD56.

Effector cells and target cells were added to 96 well plates at a ratio of 25:1 (effector:target) in a total volume of 200 μl. The following control samples were included: Spontaneous lysis (containing target cells with no effectors) and Total lysis (leave wells empty) was included. The cells were incubated for 5 hours at 37 C. Just before harvest, 100 μl 0.1% Triton X-100 was added to the Total lysis sample to release $^{51}$Cr. The reactions were harvested onto filter units with a Skatron harvester (Molecular Devices) and total $^{51}$Cr was detected.

To calculate % lysis, the average cpm and standard deviation was determined for each sample. The % Maximum $^{51}$Cr Release is determined with the following formula:

$$\frac{(\text{Experimental} - \text{Spontaneous}) \times 100}{(\text{Total} - \text{Spontaneous})}$$

Figure 22:
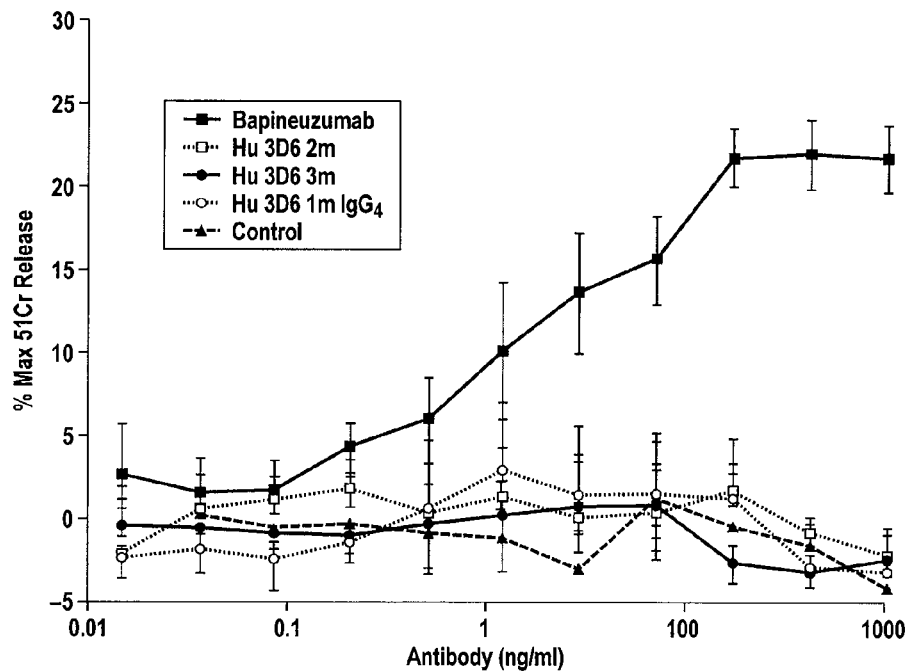
FIG. 22 shows the results of an antibody dependent complement cytotoxicity assay using the indicated humanized antibodies. Results are expressed as described in Example 7.

Consistent with the results of the C1q binding assay, the humanized 3D6 effector function mutant derivative antibodies were not effective at inducing complement lysis of the Aβ-expressing HEK 293 cells (see FIG. 22).

Example 8: ELISA Assay Measuring C1q Binding Ability of Murine 3D6 Derivatives

Materials and Methods

A 96-well fluorescent plate was coated with 1, 3, or 6 µg/ml of various antibodies in 100 µl well coating buffer overnight at 4 C. After coating, plates were washed and blocked with 200 µl Casein Elisa Block for 1 hr at RT. Plates were washed and 100 µl of 2 µg/ml human C1q in diluent buffer was added for 2 hrs at RT. After 2 hrs, plates were washed and FITC-labelled rabbit anti-C1q (1:1000) was added for 1 hr. Plates were washed twice and read at 494/517 on the fluorescent plate reader in PBS. The following mouse antibody samples were tested: IgG2a, IgG2b, 3D6 IgG2a, IgG1, 3D6 IgG1, and the 3D6 IgG1 C1q mutant.

Results

Figure 23:
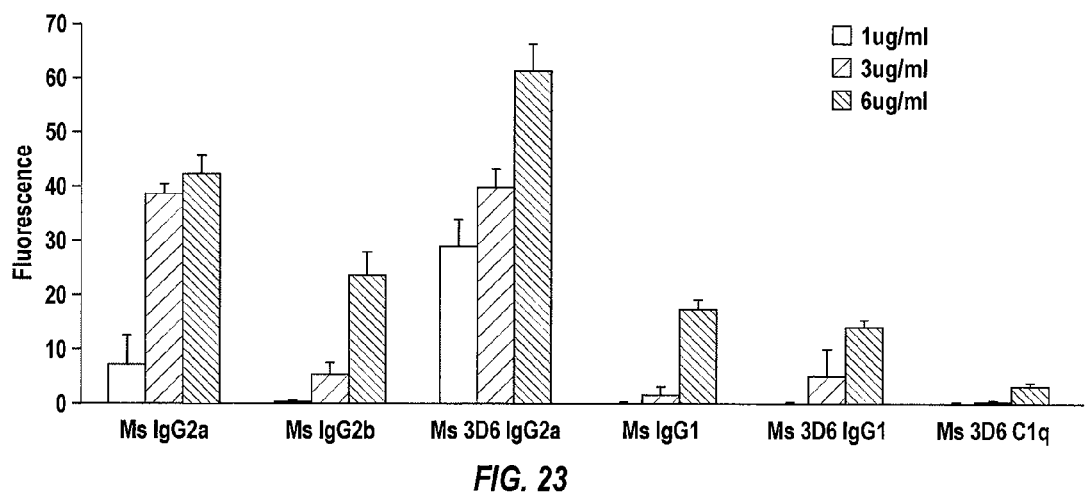
FIG. 23 shows results of an ELISA assay measuring C1q binding by the indicated murine antibodies. See Example 8.

The highest level of C1q binding was observed for IgG2a and 3D6 IgG2a (see FIG. 23). C1q binding to IgG1 and 3D6 IgG1 was significantly lower than IgG2a. The mutation in 3D6 IgG1 C1q binding domain suppressed this binding further.

Example 9: Contextual Fear Conditioning (CFC) Assay

Tg2576 transgenic mice and wild-type littermate controls were individually housed for at least 2 weeks prior to any testing and allowed ad libitum access to food and water. CFC occurred in operant chambers (Med Associates, Inc.) constructed from aluminum sidewalls and PLEXIGLAS ceiling, door and rear wall. Each chamber was equipped with a floor through which a foot shock could be administered. In addition, each chamber had 2 stimulus lights, one house light and a solenoid. Lighting, the footshock (US) and the solenoid (CS) were all controlled by a PC running MED-PC software. Chambers were located in a sound isolated room in the presence of red light.

Mice (n=8-12/genotype/treatment) were trained and tested on two consecutive days. The Training Phase consisted of placing mice in the operant chambers, illuminating both the stimulus and house lights and allowing them to explore for 2 minutes. At the end of the two minutes, a footshock (US; 1.5 mAmp) was administered for 2 seconds. This procedure was repeated and 30 seconds after the second foot shock the mice were removed from the chambers and returned to their home cages.

Twenty hours after training, animals were returned to the chambers in which they had previously been trained. Freezing behavior, in the same environment in which they had received the shock ("Context"), was then recorded using time sampling in 10 seconds bins for 5 minutes (30 sample points). Freezing was defined as the lack of movement except that required for respiration. At the end of the 5 minute Context test mice were returned to their home cages.

Approximately 20-week old wild-type mice and Tg2576 transgenic mice were administered a single dose of treatment antibody by intraperitoneal injection at 24 hours prior to the training phase of the CFC. Treatment antibodies were: (i) non-specific IgG1 antibody; (ii) Hu 3D6 3m (FcγR) (also called AAB-003); and (iii) bapineuzumab (also called AAB-001).

Figure 24:
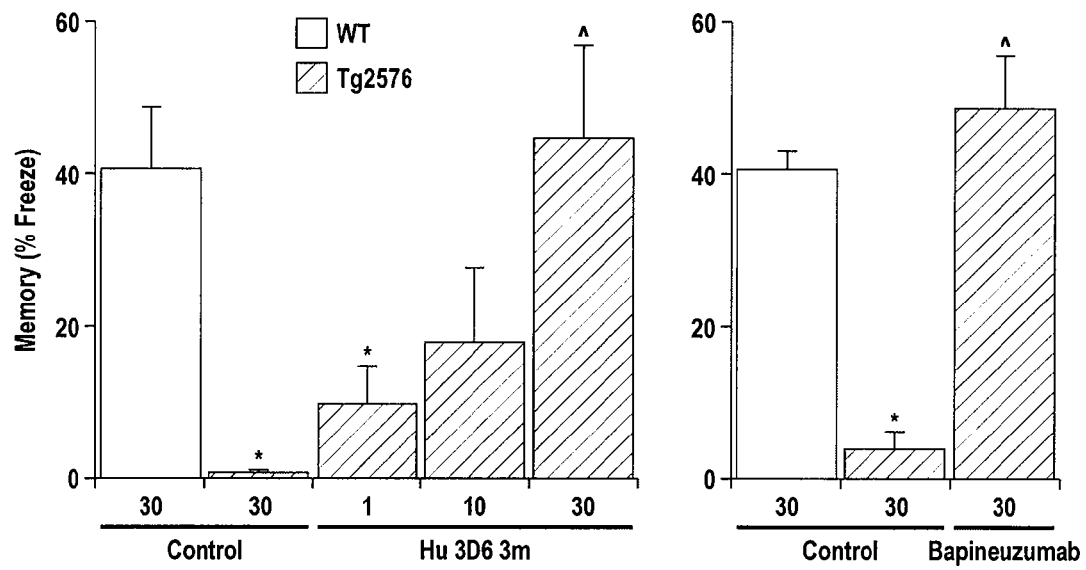
FIGS. 24-25 show the results of a contextual fear assay in mice treated with the indicated humanized antibodies. Results are compared between wild type and Tg2576 mice, as described in Example 9.

FIG. 24 demonstrates the results. Control-treated wild type mice showed about 40% freeze, while in comparison, control-treated transgenic mice exhibited a severe deficit in contextual memory. When administered at 30 mg/kg, the Hu 3D6 3m antibody restored cognitive function to wild type levels. Furthermore, the effector function mutant had the same effect on contextual memory as the parent antibody, bapineuzumab.

Figure 25:
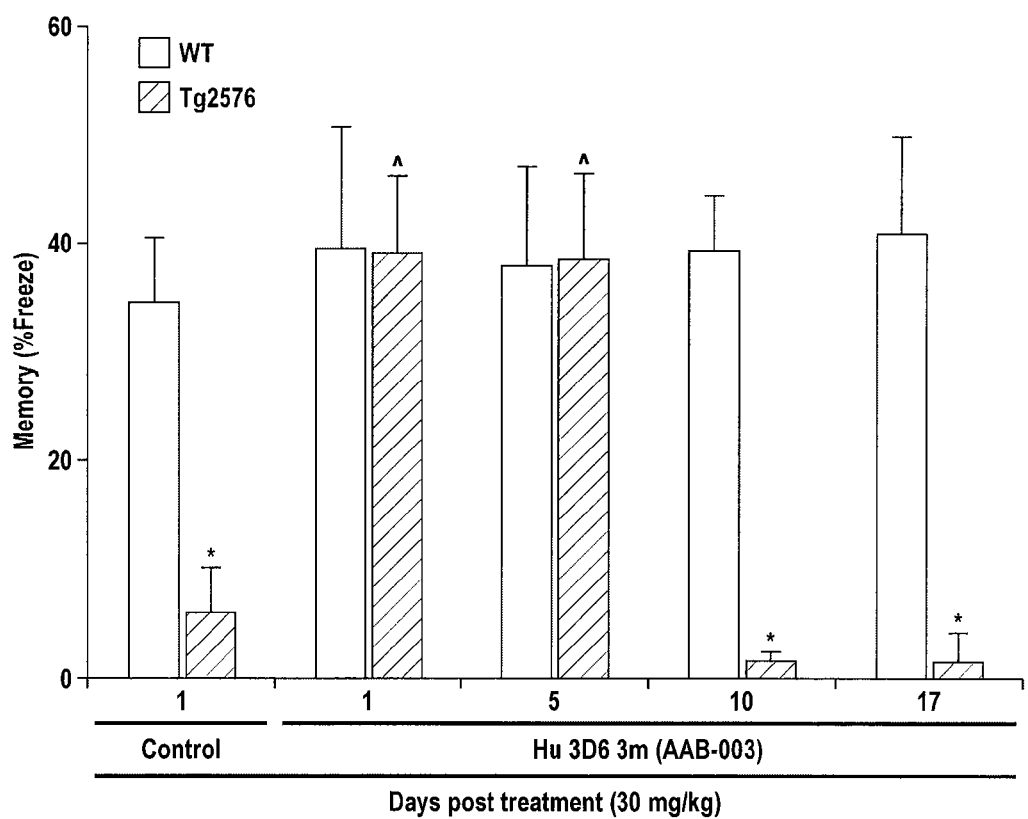

The effect of the Hu 3D6 3m antibody on contextual memory was observed over time. FIG. 25 illustrates that treatment with 30 mg/kg Hu 3D6 3m antibody provided wild type levels of cognition at least 5 days post-administration.

In summary, the above examples show that Hu 3D6 3m results in similar cognition improvements as bapineuzumab. This is despite the fact that the derivative antibody does not significantly bind to Fc receptors or C1q, or induce phagocytosis or ADCC activity.

Example 10: Mouse Studies with 3D6 4m (FcγR/C1q) IgG2a and Hu 3D6 3m IgG1 (AAB-003)

Study Design

One-year old PDAPP mice are exposed to a 6 month treatment paradigm with control; 3D6 4m (FcγR/C1q) IgG2a; or Hu 3D6 3m IgG1 (see Table 10). Negative controls include a mouse IgG2a antibody and a human IgG1 antibody to an irrelevant, non-amyloid epitope. Positive controls include 3D6 IgG2a and Hu 3D6 IgG1. The mice are split into dosage cohorts and injected IP at weekly intervals with 3, 30, or 300 mg/kg of the indicated antibody. Experimental conditions are as described in Example 5.

After 6 months, the mice are sacrificed and brain tissue harvested as described above. Tissues are examined for cortical and hippocampal Ab and amyloid burden, vascular amyloid, and microhemorrhage.

Example 11: Cynomolgus Monkey Studies with Hu 3D6 3m IgG1 (AAB-003)

Study Design

Cynomolgus monkeys are treated with Hu 3D6 3m IgG1 (AAB-003). The negative control includes a human IgG1 antibody to an irrelevant, non-amyloid epitope. The positive control include Hu 3D6 IgG1 (Bapineuzumab). Monkeys are split into dosage cohorts receiving either 15, 50, or 150 mg/kg of the indicated antibody. Each cohort is further split into IV and SC administration groups.

Monkeys are injected weekly for 13 weeks, with a 2 month observation period. At the end of the study, the monkeys are sacrificed and brain tissue harvested. Tissues are examined for cortical and hippocampal Aβ and amyloid burden, vascular amyloid, and microhemorrhage.

Example 12: Single Ascending Dose (SAD) Study in Humans of Hu 3D6 3m (AAB-003) Antibody Mild to moderate Alzheimer's patients, including ApoE4 carriers and non-carriers, are divided into cohorts for intravenous (IV) or subcutaneous (SC) injection with AAB-003 antibody. The cohorts are given a single dose with a 12 month follow up, and monitored throughout by an independent safety monitoring committee.

The goal of the study is to increase the exposure equivalent to at least 5 mg/kg of intravenous Bapineuzumab (unless signs of vasogenic edema are observed). At this dose of Bapineuzumab, VE was observed in 3 of 10 patients.

The SC cohorts include at least two subcutaneous dosage levels. These patients are be observed for bioavailability of the antibody and linearity thereof.

All patients are screened (e.g., for ApoE status) and monitored as described in Example 1. For all cohorts, safety monitoring includes MRI monitoring. MRI results are compared to those from the Bapineuzumab study described in the above examples. Efficacy is measured by cognitive metrics (e.g., NTB, DAD, ADAS-Cog); plasma Aβ levels; CSF levels of amyloid, tau, and phosphotau; and amyloid imaging.

Certain biomarkers are tracked in each patient during the study. Biomarkers to support Aβ binding by the antibody include Aβ40 and Aβ42 in the CSF and plasma, and amyloid plaque imaging, e.g., by PET. Biomarkers pointing to disease modification include MRI, CSF tau and phosphotau levels, and again, amyloid plaque imaging.

Example 13: Pharmacokinetic Profiles of Hu 3D6 3m (AAB-003) in Tg2576 and Wild Type Mice Tg2576 transgenic mice and wild type controls were dosed with AAB-003 subcutaneously (SC) or intraperitoneally (IP) to determine bioavailability of the antibody. The profile was typical for therapeutic antibody.

AAB-003 was eliminated slowly, with a $T_{1/2}$ of 66-160 hours. There was low volume distribution (71-96) and good exposure (as measured by AUC).

Some differences between the wild type and transgenic mice were apparent. For example, wild type mice had higher AUC and $T_{1/2}$. The transgenic mice had slightly higher levels of anti-AAB-003 antibodies.

Example 14: Pharmacokinetic Profiles of Hu 3D6 3m (AAB-003) in Cynomolgus Monkeys 10 mg/kg Hu 3D6 3m or bapineuzumab were administered intravenously (IV) to cynomolgus monkeys (3 animals/antibody treatment) to compare the pharmacokinetic profiles and determine whether the effector function mutation had any effect. The results were comparable between the two antibodies, and typical for therapeutic antibodies in general. There was low clearance (0.16±0.06 ml/hr/kg), small volume of distribution (~62 ml/kg), and long elimination half-life (309±226 hours). One of the three animals tested positive for antibodies against AAB-003.

The same antibody doses were administered subcutaneously (SC). Bioavailability was good, approximating 69%, and the half-life ranged from 21-445 hours. Two of the three animals tested positive for antibodies against AAB-003.

Example 15: Effect of Fc Mutations on the Effector Function of an Anti-Lewis Y Antibody To determine the effect of mutations in the low hinge region of human IgG1 on the effector function of antibodies with different antigen specificity, we designed antibodies to the Lewis Y (LeY) antigen. LeY is a type 2 blood group related difucosylated oligosaccharide that is mainly expressed in epithelial cancers, including breast, pancreas, colon, ovary, gastric, and lung. LeY does not appear to be expressed on tumors of neuroectodermal or mesodermal origin.

The anti-LeY Ab02 antibody was generated with one of three heavy chain constant regions: (i) wild type human IgG1; (ii) wild type human IgG4; and (iii) human IgG1 with two effector region mutations, L234A and G237A (see SEQ ID NOs:50 and 51). IgG4 has been shown to have reduced effector function in other systems.

Figure 26:
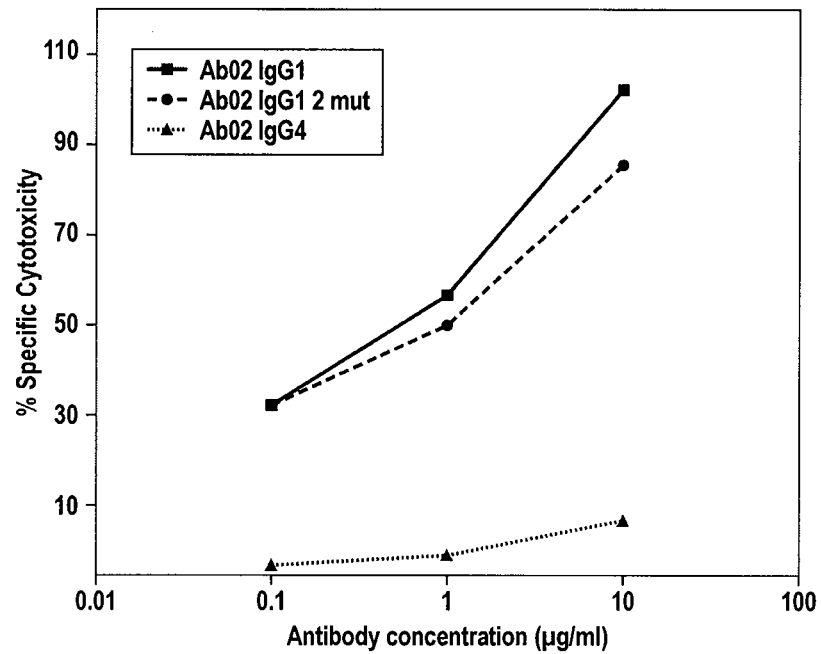
FIG. 26 shows the results of the ADCC activities of anti-Lewis Y Ab02 antibodies. See Example 15.

For the ADCC (antibody-dependent complement cytotoxicity) assay, LeY-overexpressing N87 human gastric adenocarcinoma cells were used as target cells, and freshly isolated human PBMC were used as effector cells. Effector and target cells were plated at a ratio of 50:1 in 96 well plates. Antibody was applied at varying concentrations (0.1, 1 and 10 μg/ml) in triplicate with medium, effector and target cell controls, and antibody controls. The ADCC activities of anti-Lewis Y Ab02 versions are presented in FIG. 26.

For the CDC (complement dependent cytotoxicity) assay, LeY positive tumor cells (A431 LeY) were plated in 96 well plates with varying amount of antibody (0.1, 1 and 10 μg/ml). Diluted human complement (1:100), was added to each well. Tests were done in triplicate at a final volume of 100 μl/ml with medium, cells alone, and antibody and complement controls. After 4 hours incubation at 37 C, plates were removed and equilibrated to 22 C.

Figure 27:
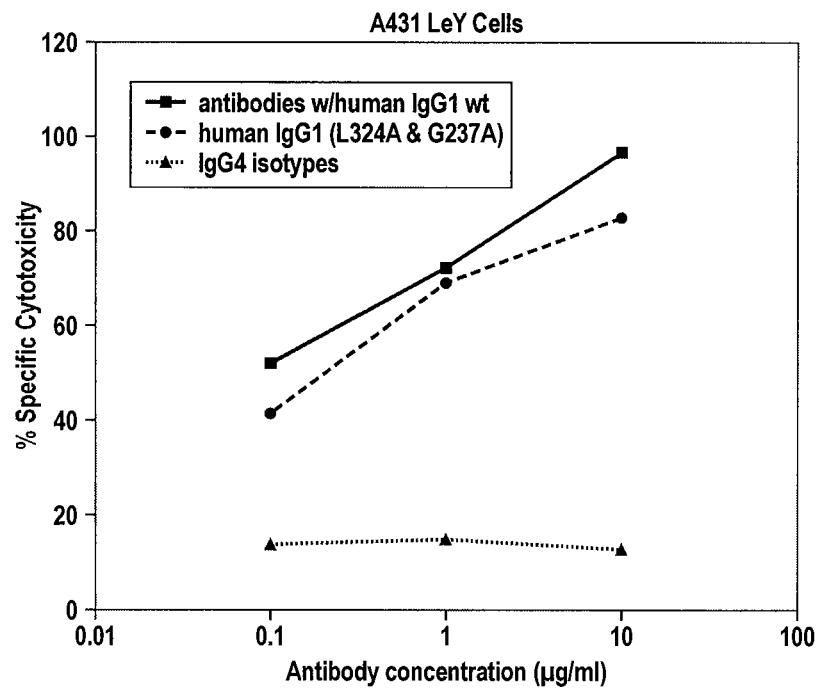
FIG. 27 shows the results of the CDC (complement dependent cytotoxicity) activities of anti-Lewis Y Ab02 antibodies. See Example 15.

An equal volume of CytoTox-One™ was added to each well, and incubated for 10 minutes at 22 C. As a positive control, 2 μl of lysis buffer per well (in triplicate) was added to generate a maximum LDH (lactate dehydrogenase) release in control wells. The enzymatic reaction was stopped by adding 50 μl of stop solution. The resulting fluorescence was recorded with an excitation wavelength of 560 nm and an emission wavelength of 590 nm. The % of complement-related cell lysis was calculated as % of total LDH release (FIG. 27).

In spite of the L234A and G237A mutations in IgG1, the mutant antibody fully retained its capacity to mediate both ADCC and CDC against Lewis Y expressing tumor cells, as compared to wild type IgG1.

Example 16: Effect of Fc Mutations on the Effector Function of Anti-5T4 Antibody To investigate further the effect of Fc mutations in human IgG1 on the effector function of antibodies with different antigen specificity, we designed antibodies to the oncofetal protein 5T4. 5T4 is a tumor-associated protein displayed on the cell membrane of various carcinomas, and is a promising target for anti-tumor vaccine development and for antibody directed therapies.

The anti-5T4 antibody was generated with different combinations of mutations in the heavy chain constant region. The heavy chains used were: (i) wild type human IgG1; (ii) wild type human IgG4; (iii) human IgG1, L234A and L235A; (iv) human IgG1, L234A and G237A; (v) human IgG1, L235A and G237A; and (vi) human IgG1 with three effector region mutations, L234A, L235A, and G237A (see SEQ ID NOs:62 and 63).

Human breast carcinoma cell line MDAMB435, stably transfected with 5T4 antigen, was used for the ADCC and CDC assays. The ADCC assay of anti-5T4 antibodies was as described in Example 15, using freshly isolated human PBMC as effector cells at an effector:target cell ratio 50:1. MDAMB435-Neo transfected cells were used as a negative control. The results of ADCC activity (maximum specific cytotoxicity at the antibody concentration 10 ug/ml) are summarized in Table 15.

TABLE 15

ADCC activity of anti-5T4 antibodies against 5T4 positive and negative human breast carcinoma cell line MDAMB435

| Antibody | MDAMB345-5T4 % specific cytotoxicity | MDAMB-Neo % specific cytotoxicity |
|---|---|---|
| 5T4-IgG1wt | 81 | 3 |
| 5T4-IgG1 L234A/G237A | 78 | 2 |
| 5T4-IgG1 L234A/L235A | 15 | 2 |
| 5T4-IgG1 L235A/G237A | 27 | 2 |
| 5T4-IgG1 L234A/L235A/G237A | 2 | 2 |
| 5T4-IgG1 N297A | 5 | 3 |
| 5T4-IgG4 | 2 | 2 |

To evaluate an effect of Fc mutations on the complement induced cytotoxicity, human breast carcinoma MDAMB435-5T4 cells were incubated with diluted human complement as described in the Example 15. The results of CDC assays are presented in the Table 16.

TABLE 16

CDC activity of anti-5T4 antibodies against 5T4 positive and negative human breast carcinoma cell line MDAMB435

| Antibody | MDAMB345-5T4 % specific cytotoxicity | MDAMB-Neo % specific cytotoxicity |
|---|---|---|
| 5T4-IgG1wt | 90 | 2 |
| 5T4-IgG1 L234A/G237A | 72 | 2 |
| 5T4-IgG1 L3234A/L235A | 5 | 2 |
| 5T4-IgG1 L235A/G237A | 19 | 2 |
| 5T4-IgG1 L234A/L235A/G237A | 1 | 1 |
| 5T4-IgG1 N297A | 1 | 1 |
| 5T4-IgG4 | 1 | 1 |

The introduction of two mutations in the low hinge region of human IgG1 in any of the combinations tried (L234A/L235; L234A/G237A; L235A/G237A) only partially reduced ADCC and CDC activity with L235A/G237A showing the higher residual effector function capabilities. However, anti-5T4 antibody with three mutations in the IgG1 low hinge region (L234A/L235A/G237A) demonstrated completely abolished ADCC and CDC activities.

Conclusions

The Examples provide a number of comparisons of Fc region mutant antibodies with different antigen specificities. Example 6 describes an ADCC assay using Aβ-specific antibodies with IgG1 Fc mutations at either L234A and G237A (double mutant), or L234, L235A, and G237A (triple mutant). Both the double and triple mutants had significantly reduced function (see FIG. 22). Example 15 describes ADCC and CDC assays using LeY-specific antibodies with IgG1 mutations at L234A and G237A. In this case, the mutant antibody retained effector function (see FIGS. 26 and 27). Finally, Example 16 compares IgG1 Fc mutants of 5T4-specific antibodies. Each of the double mutants (L234A/L235; L234A/G237A; L235A/G237A) retained more effector activity than the triple mutant (L234A/L235A/G237A) (see Tables 15 and 16). The effector activity of the L234A/L235 double mutant, however, was reduced to nearly the same level as that of the triple mutant.

The above results demonstrate that the effect of the hinge-region mutations can depend on a number of factors, including target antigen density on the cell surface. However, the data indicate that disruptions at all three positions are necessary to eliminate effector activity.

The above examples are illustrative only and do not define the invention; other variants will be readily apparent to those of ordinary skill in the art. The scope of the invention is encompassed by the claims of any patent(s) issuing herefrom. The scope of the invention should, therefore, be determined not with reference to the above description, but instead should be determined with reference to the issued claims along with their full scope of equivalents. All publications, references, accession numbers, and patent documents cited in this application are incorporated by reference in their entirety for all purposes to the same extent as if each individual publication or patent document were so individually denoted.

What is claimed is:

1. A method of treating a disease characterized by Aβ deposits in the brain of patient comprising intravenously or subcutaneously administering an effective regime of a humanized antibody to a population of patients suffering from the disease; wherein the humanized antibody comprises a mature light chain variable region sequence of SEQ ID NO:2 and a mature heavy chain variable region sequence of SEQ ID NO:3, and a human heavy chain constant region of IgG1 isotype with L234A, L235A, and G237A mutations, wherein positions are numbered by the EU numbering system, and thereby treating the disease in the patients, wherein the regime administered to different patients in the population does not depend on the number of ApoE4 alleles present in a patient.

2. The method of claim 1, wherein the dose is 0.15-1 mg/kg.

3. The method of claim 1, wherein the dose is 0.15-2 mg/kg.

4. The method of claim 1, wherein the dosage is 10 mg/kg.

5. The method of claim 1, further comprising monitoring the patient by MRI for vasogenic edema.

6. The method of claim 1, wherein the antibody is an L234A, L235A, G237A variant of bapineuzumab.

7. The method of claim 2, wherein the antibody is an L234A, L235A, G237A variant of bapineuzumab.

8. The method of claim 3, wherein the antibody is an L234A, L235A, G237A variant of bapineuzumab.

9. The method of claim 5, wherein the antibody is an L234A, L235A, G237A variant of bapineuzumab.

10. The method of claim 1, wherein the disease is Alzheimer's disease.

11. The method of claim 6, wherein the disease is Alzheimer's disease.

12. The method of claim 7, wherein the disease is Alzheimer's disease.

13. The method of claim 8, wherein the disease is Alzheimer's disease.

14. The method of claim 9, wherein the disease is Alzheimer's disease.

15. A method of reducing the risk, lessening the severity or delaying the outset of a disease characterized by Aβ deposits in the brain of patient comprising administering an effective regime of a humanized antibody to a population of patients susceptible to the disease; wherein the humanized antibody comprises a mature light chain variable region sequence of SEQ ID NO:2 and a mature heavy chain variable region sequence of SEQ ID NO:3, and a human heavy chain constant of IgG1 isotype with L234A, L235A, and G237A mutations, wherein positions are numbered by the EU numbering system, thereby reducing the risk, lessening the severity or delaying the outset of the disease in the patients, wherein the regime administered to different patients in the population does not depend on the number of ApoE4 alleles present in a patient.

16. The method of claim 15, wherein the dose is 0.15-1 mg/kg.

17. The method of claim 15, wherein the dose is 0.15-2 mg/kg.

18. The method of claim 15, further comprising monitoring the patient by MRI for vasogenic edema.

19. The method of claim 15, wherein the antibody is an L234A, L235A, G237A variant of bapineuzumab.

20. The method of claim 16, wherein the antibody is an L234A, L235A, G237A variant of bapineuzumab.

21. The method of claim 17, wherein the antibody is an L234A, L235A, G237A variant of bapineuzumab.

22. The method of claim 18, wherein the antibody is an L234A, L235A, G237A variant of bapineuzumab.

23. The method of claim 15, wherein the disease is Alzheimer's disease.

24. The method of claim 19, wherein the disease is Alzheimer's disease.

25. The method of claim 20, wherein the disease is Alzheimer's disease.

26. The method of claim 21, wherein the disease is Alzheimer's disease.

27. The method of claim 22, wherein the disease is Alzheimer's disease.

* * * * *